(12) United States Patent
Jan et al.

(10) Patent No.: US 7,683,168 B2
(45) Date of Patent: Mar. 23, 2010

(54) COMPOSITIONS OF NOVEL OPIOID COMPOUNDS AND METHOD OF USE THEREOF

(75) Inventors: Shyi-Tai Jan, Cary, NC (US); Kwen-Jen Chang, Chapel Hill, NC (US); Kestutis P. Biciunas, Durham, NC (US); Xin Ma, Carrboro, NC (US)

(73) Assignee: Mount Cook Bio Sciences, Inc., NY, NY (US)

( * ) Notice: Subject to any disclaimer, the term of this patent is extended or adjusted under 35 U.S.C. 154(b) by 500 days.

(21) Appl. No.: 11/404,632

(22) Filed: Apr. 14, 2006

(65) Prior Publication Data

US 2007/0043028 A1 Feb. 22, 2007

Related U.S. Application Data

(60) Provisional application No. 60/671,367, filed on Apr. 14, 2005.

(51) Int. Cl.
*C07D 245/02* (2006.01)

(52) U.S. Cl. .............. 540/470; 540/575; 544/391; 546/245; 548/539

(58) Field of Classification Search ............ 540/470, 540/575; 544/391; 546/245; 548/539
See application file for complete search history.

(56) References Cited

U.S. PATENT DOCUMENTS

| | | | |
|---|---|---|---|
| 5,063,929 A | 11/1991 | Bartlett et al. | |
| 5,151,448 A | 9/1992 | Crenshaw et al. | |
| 5,276,042 A | 1/1994 | Crenshaw et al. | |
| 5,552,404 A | 9/1996 | Chang et al. | |
| 5,574,159 A | 11/1996 | Chang et al. | |
| 5,587,167 A | 12/1996 | Choi et al. | |
| 5,658,908 A | 8/1997 | Chang et al. | |
| 5,681,830 A | 10/1997 | Chang et al. | |
| 5,707,999 A | 1/1998 | Cavallini | |
| 5,807,858 A | 9/1998 | Chang et al. | |
| 5,854,249 A | 12/1998 | Chang et al. | |
| 5,929,054 A | 7/1999 | Baker et al. | |
| 5,985,880 A | 11/1999 | Chang et al. | |
| 6,046,200 A | 4/2000 | Tortella et al. | |
| 6,130,222 A | 10/2000 | Roberts et al. | |
| 6,187,792 B1 | 2/2001 | Delorme et al. | |
| 6,228,864 B1 | 5/2001 | Smith et al. | |
| 6,300,332 B1 | 10/2001 | Chang et al. | |
| 6,514,975 B1 | 2/2003 | Maw et al. | |
| 6,924,288 B2 | 8/2005 | Chang et al. | |
| 7,030,124 B2 | 4/2006 | Chang et al. | |
| 7,189,725 B2 | 3/2007 | Chang et al. | |
| 7,314,880 B2 | 1/2008 | Chang et al. | |
| 2002/0022624 A1 | 2/2002 | Dinnell et al. | |

FOREIGN PATENT DOCUMENTS

WO   WO 03/057223   *   7/2003

OTHER PUBLICATIONS

Calderon, S.N. et al., 2004, SNC 80 and Related Delta Opioid Agonists; Current Pharmaceutical Design, 10, pp. 733-742.

* cited by examiner

*Primary Examiner*—James O Wilson
*Assistant Examiner*—Brian McDowell

(57) ABSTRACT

Diarylmethylpiperazine compounds are described, which are useful as mu and/or delta receptor opioid compounds, without central side effects. Pharmaceutical compositions containing such compounds are variously useful for peripheral or non-centrally mediated indications, including peripherally mediated and neuropathic pain, urogenital tract disorders, overactive bladder, urinary incontinence, sexual disorders, premature ejaculation, cough, lung edema, cardiac disorders, cardioprotection, gastro-intestinal disorders, diarrhea, irritable bowl syndrome, functional distention, immuno-modulation and anti-tumor activity.

1 Claim, No Drawings

COMPOSITIONS OF NOVEL OPIOID COMPOUNDS AND METHOD OF USE THEREOF

CROSS-REFERENCE TO RELATED APPLICATION

The benefit of priority of U.S. Provisional Patent Application 60/671,367 filed Apr. 14, 2005 in the names of Shyi-Tai Jan, Kwer-Jen Chang, Kestutis P. Biciunas and Xin Ma for "COMPOSITIONS OF NOVEL OPIOID COMPOUNDS AND METHOD OF USE THEREOF" is hereby claimed under 35 USC 119.

BACKGROUND OF THE INVENTION

1. Technical Field

This invention relates generally to diarylmethylpiperazine compounds useful as mu and/or delta receptor opioid compounds and pharmaceuticals containing same that may be useful for mediating analgesia, combating drug addiction, alcohol addiction, drug overdose, mental illness, bladder dysfunctions, neurogenic bladder, interstitial cystitis, urinary incontinence, premature ejaculation, inflammatory pain, peripherally mediated and neuropathic pain, cough, lung edema, diarrhea, cardiac disorders, cardioprotection, depression, and cognitive, respiratory, diarrhea, irritable bowel syndrome and gastro-intestinal disorders, immunomodulation, and anti-tumor agents.

2. Background of Related Art

In the study of opioid biochemistry, a variety of endogenous opioid compounds and non-endogenous opioid compounds have been identified. In this effort, significant research has been focused on understanding the mechanism of opioid drug action, particularly as it relates to cellular and differentiated tissue opiate receptors.

Opioid drugs typically are classified by their binding selectivity in respect of the cellular and differentiated tissue receptors to which a specific drug species binds as a ligand. These receptors include mu (µ), delta (δ), sigma (σ) and kappa (κ) receptors.

The well-known narcotic opiates, such as morphine and its analogs, are selective for the opiate mu receptor. Mu receptors mediate analgesia, respiratory depression, and inhibition of gastrointestinal transit. Kappa receptors mediate analgesia and sedation. Sigma receptors mediate various biological activities.

The existence of the opioid delta receptor is a relatively recent discovery that followed the isolation and characterization of endogenous enkephalin peptides that are ligands for the delta receptor. Delta receptors mediate analgesia, but do not appear to inhibit intestinal transit in the manner characteristic of mu receptors.

Opioid agents frequently are characterized as either agonists or antagonists. Agonists and antagonists are agents that recognize and bind to receptors, affecting (either initiating or blocking) biochemical/physiological sequences, a process known as transduction. Agonists inhibit or suppress neurotransmitter outputs in tissues containing receptors, e.g., inhibiting pain responses, or affecting other output-related phenomena. Antagonists also bind to receptors, but do not inhibit neurotransmitter outputs. Thus, antagonists bind to the receptor sites and block the binding of agonist species that are selective for the same receptor.

Various physiological effects of the known peptide-based opioid ligands have been studied, including: analgesia; respiratory depression; gastrointestinal effects; mental, emotional, and cognitive process function; and mediation/modulation of other physiological processes.

There is a continuing need in the art for improved opioid compounds, particularly compounds that are free of addictive character and other adverse side effects of conventional opiates such as morphine.

Previous disclosed diarylmethylpiperazine compounds exhibiting delta receptor agonist activities produced seizure-like convulsion activity in mice and rats after a rapid bolus iv administration through central (central nervous system, CNS) mechanism. Similarly, these compounds including current therapeutic analgesics possessing mu opioid receptor agonist activity produce respiratory depressive, nausea and emesis effects, addictive effects and abuse liability through a central mechanism. Delta and mu opioid receptors are localized in peripheral organs and tissues. Various physiological effects are known for those peripheral organs and tissues: gastro-intestinal tracts disorder such as antidiarrhea, and irritable bowel syndrome, cough, bladder functional modulation, genital organ regulation such as vas deferens contractility, immuno-modulation, and cardioprotection for heart attack. For those peripheral applications, compounds that lack central side effects are desirable.

The present invention described a series of novel opioid compounds, with potent delta and/or mu receptor agonist activities, that produce essentially no central mechanism side effects as evident from the lack of centrally mediated seizure-like convulsion activity and antinociception in tail-pinch assay after a rapid bolus iv injection of a high dose in mice.

SUMMARY OF THE INVENTION

Historically, the opioid compounds reported in the literature have a fixed addressing group, namely the substituent at A ring, such as shown below.

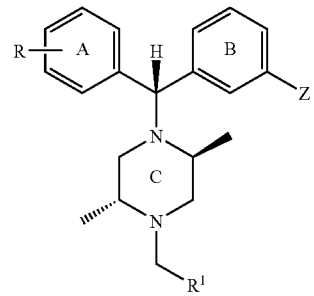

( R = addressing groups)

The compounds presented herein are compounds with changeable or functionalized addressing group(s). Since it is a functionalized addressing group, many modifications may be made at the addressing group to fine-tune the properties of the drug candidate thereby synthesizing many potential compounds for screening.

In one aspect the present invention relates to compounds as shown below in formula 1,

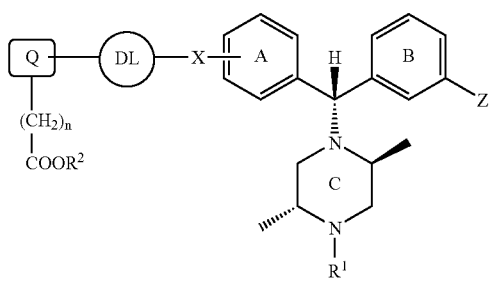

(1)

wherein:

Z is H, O(CH$_2$)nCH$_3$, wherein n=0 to 4, or OH;

X which is C=O or SO$_2$ which is on the meta or para position of the phenyl ring;

DL is di-functional amine linker having a nitrogen that is covalently bonded to the carbon or sulfur atom of group X via an amide bond;

Q is either —CH$_2$— or —(CH$_2$)$_m$—Ar—, wherein m is 1 or 2, wherein the di-functional linker is covalently bonded to the terminal carbon of the group Q;

Ar is a disubstituted 5- or 6-membered carbocyclic or heterocyclic aromatic ring;

n is 0, 1, 2, 3, 4, or 5 wherein any one carbon in the chain may optionally be a carbonyl;

R$^1$ is C$_1$-C$_6$ alkyl, C$_1$-C$_6$ alkenyl, C$_1$-C$_6$ cycloalkylmethyl, arylalkyl having C$_5$-C$_{10}$ aryl and C$_1$-C$_6$ alkyl moieties, benzyl, halobenzyl or carboxybenzyl; and R$^2$ is methyl, ethyl or H. The compounds of formula 1 include all isomers and/or racemic mixture thereof.

In another aspect, the present invention relates to compounds according to formula (2):

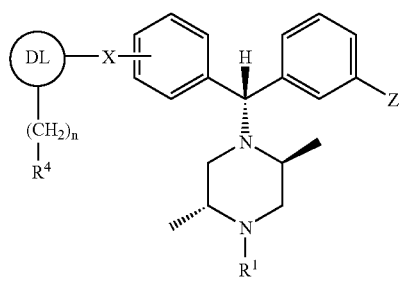

(2)

wherein

Z is H, O(CH$_2$)nCH$_3$, wherein n=0 to 4, or OH;

X which is C=O or SO$_2$ which is on the meta or para position of the phenyl ring;

DL is di-functional amine linker having a nitrogen that is covalently bonded to the carbon or sulfur atom of group X via an amide bond;

R$^1$ is C$_1$-C$_6$ alkyl, C$_1$-C$_6$ alkenyl, C$_1$-C$_6$ cycloalkylmethyl, arylalkyl having C$_5$-C$_{10}$ aryl and C$_1$-C$_6$ alkyl moieties, benzyl, halobenzyl or carboxybenzyl; and R$^4$ is: —OR$^5$, —CO—NR$^6$R$^7$, —O—R$^8$, or —R$^9$COR$^{10}$, wherein R$^5$, R$^6$, R$^7$, R$^8$, R$^9$ and R$^{10}$ is the same or different and selected from the R$^1$ group. The compounds of formula 2 include all isomers and/or racemic mixture thereof.

The amine linker may include one of the following groups, wherein R$^3$ is C$_1$-C$_6$ alkyl, C$_1$-C$_6$ cycloalkyl, or C$_1$-C$_6$ cycloalkylmethyl.

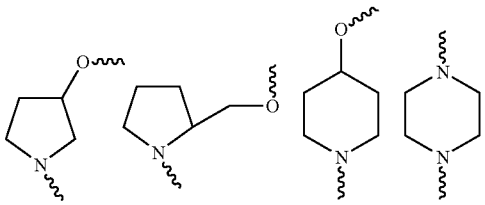

In another aspect, the present invention relates to compounds comprising modifiers to the diethylamide phenyl substituent, wherein an incorporated functional group will be a synthetic entry for introducing property modifiers, as shown in formula 3

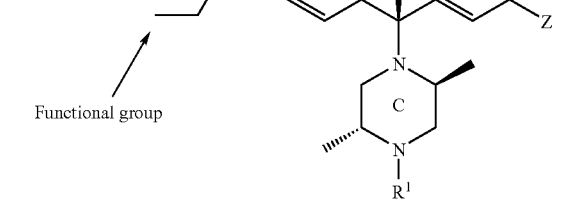

(3)

wherein X which is C=O or SO$_2$ which is on the meta or para position of the phenyl ring;

a di-functional amine linker having a nitrogen that is covalently bonded to the carbon or sulfur atom of group X via an amide bond and functional groups are built into the N,N-diethylamide moiety. Consequently, the added functional group makes the substituent changeable because many new phenyl substituents can be synthesized thru chemical transformations of the incorporated functional groups. Di-functional amines are used as synthetic precursors for the synthesis of new opioid ligands including:

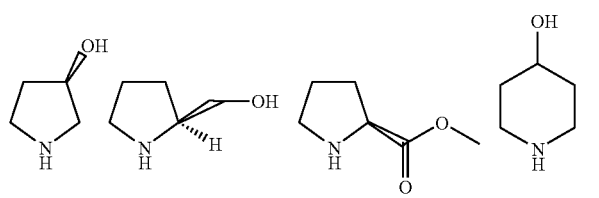
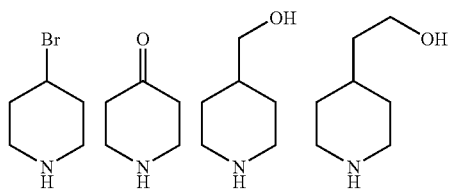
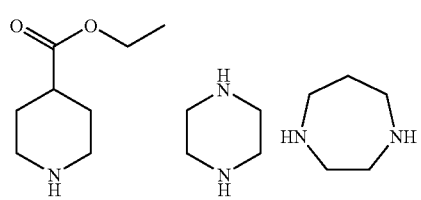

These compounds can be used for making compounds with functionalized amide addressing group or sulfonamide addressing groups.

The compounds presented herein are compounds with functionalized A-ring phenyl substituents in contrast to prior art compounds that are saturated hydrocarbon, and as such, inaccessible for further chemical transformations. Since these are changeable or replaceable phenyl substituents, many chemical transformations can be done at the substituents to produce new opioid ligands with new A-ring phenyl substituents. Applying the methods of modifying the A-ring phenyl substituents, a large number of novel compounds, including racemic mixtures or individual isomers thereof, can be derived from this design.

The following schematic provides an example of an opioid ligand with functionalized substituents:

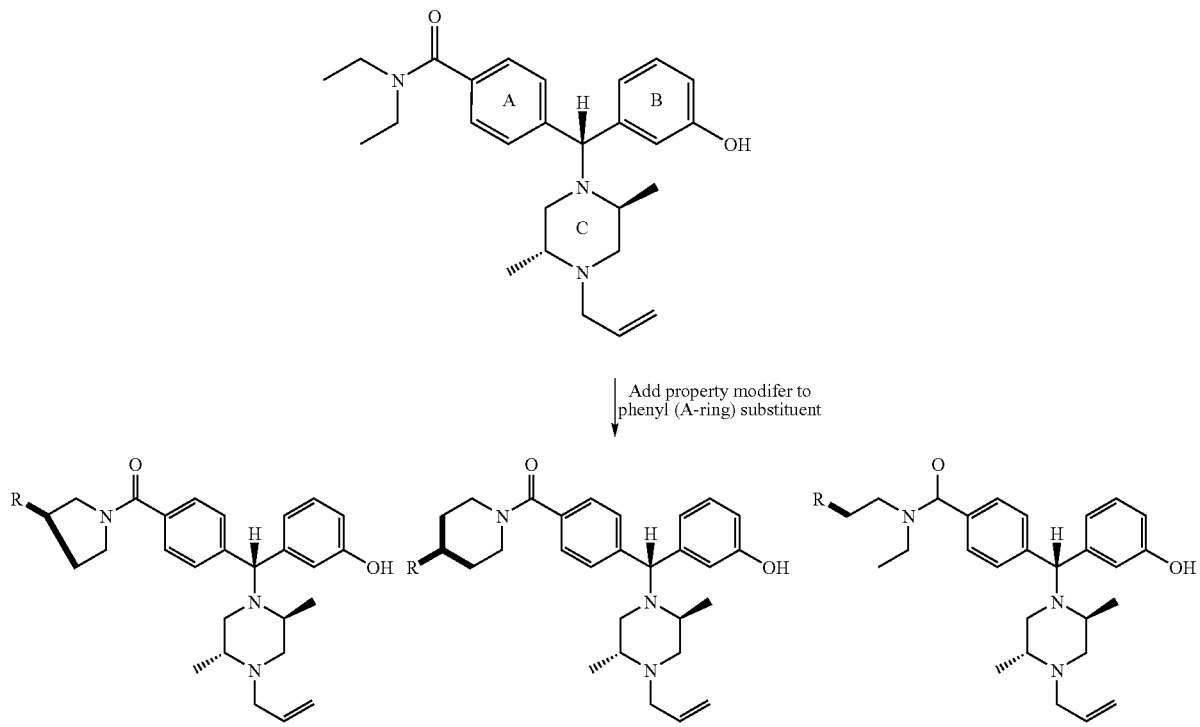

Examples of applicable "R" may include the following:
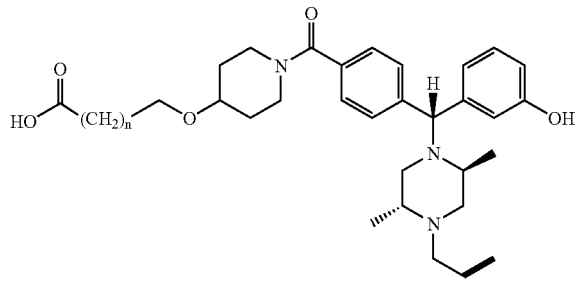
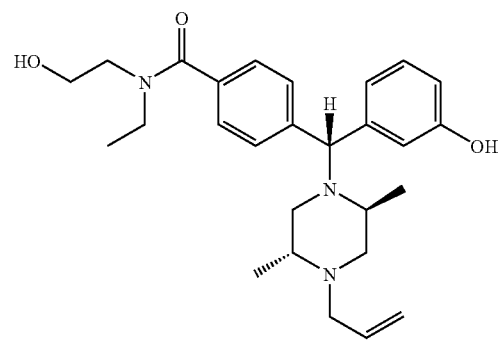
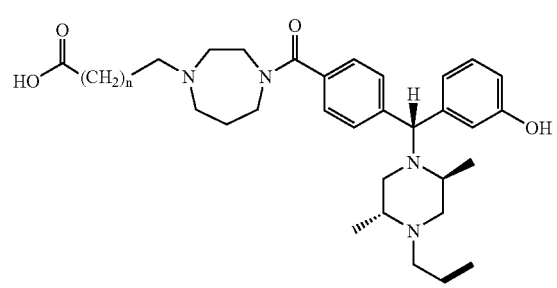
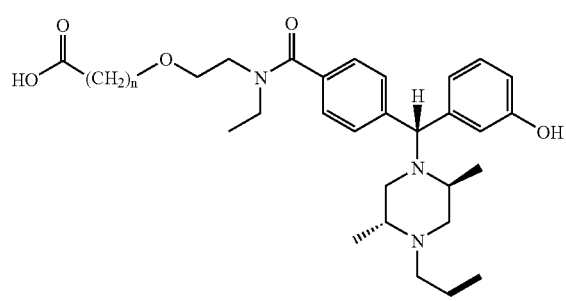
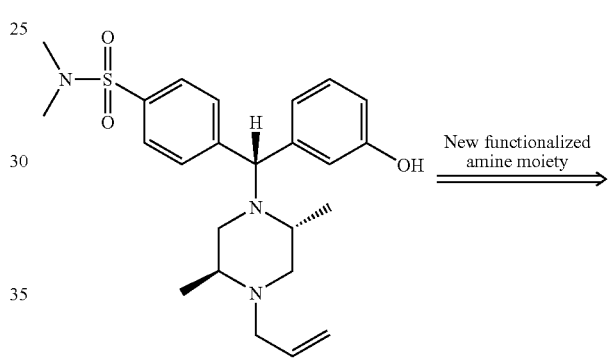
Likewise, functionalized sulfonamide A-ring phenyl substituent may be prepared wherein the sulfonamide may be in either the para or meta position.
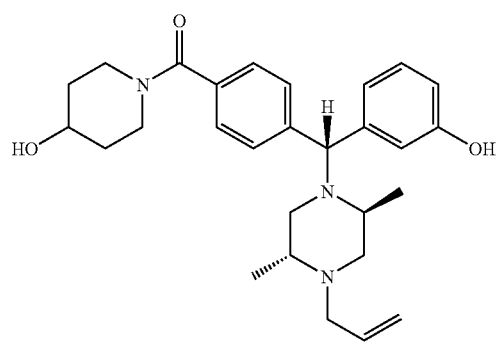
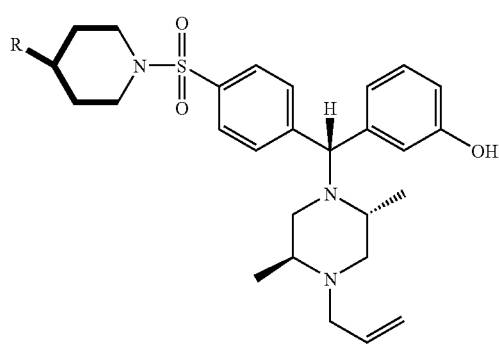
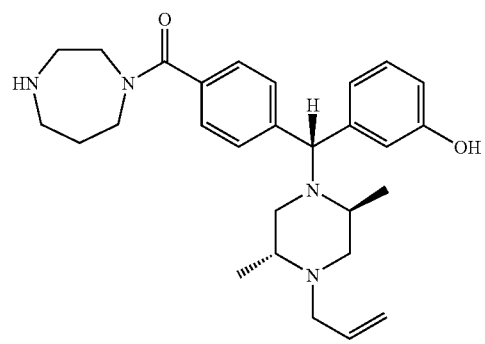
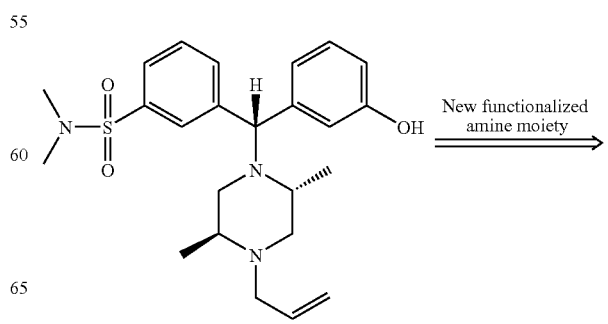

-continued

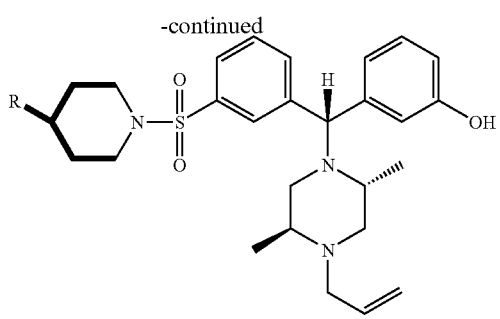

In another aspect, the present invention relates to a method for preventing or treating a disease or condition selected from the group consisting of combating drug addiction, alcohol addiction, drug overdose, mental illness, bladder dysfunctions, neurogenic bladder, interstitial cystitis, urinary incontinence, premature ejaculation, inflammatory pain, peripherally mediated and neuropathic pain, cough, lung edema, diarrhea, cardiac disorders, cardioprotection, depression, and cognitive, respiratory, diarrhea, gastro-intestinal disorders, immunomodulation, anti-tumor agents, arthritis, psoriasis, asthma, inflammatory bowel disease, disorders of respiratory function, gastro-intestinal disorders, functional bowel disease, sexual dysfunctions, functional GI disorders, irritable bowel syndrome, functional distension, functional pain, non-ulcerogenic dyspepisa, disorders of motility or secretion, urogenital tract disorders, non-somatic pain, rejection in organ transplant and skin graft by administering to a mammal a therapeutically effective amount of a compound, salt or solvate of formula 1:

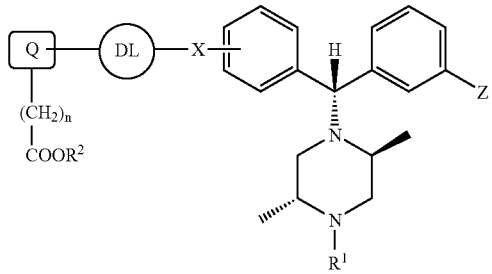
(1)

wherein:

Z is H, $O(CH_2)nCH_3$, or OH;

X which is C=O or $SO_2$ which is on the meta or para position of the phenyl ring;.

DL is di-functional amine linker having a nitrogen that is covalently bonded to the carbon or sulfur atom of group X via an amide bond, and the other function of the di-functional linker (either oxygen or nitrogen) is covalently bonded to the terminal carbon of group Q;

'Q' is either —$CH_2$— or —$(CH_2)_m$—Ar—, wherein m is 1 or 2;

Ar is a disubstituted 5- or 6-membered carbocyclic or heterocyclic aromatic ring;

$R^3$ is $C_1$-$C_6$ alkyl, $C_1$-$C_6$ cycloalkyl, or $C_1$-$C_6$ cycloalkylmethyl;

n is 0, 1, 2, 3, 4, or 5 wherein any one carbon in the chain may optionally be a carbonyl;

$R^1$ is $C_1$-$C_6$ alkyl, $C_1$-$C_6$ alkenyl, $C_1$-$C_6$ cycloalkylmethyl, arylalkyl having $C_5$-$C_{10}$ aryl and $C_1$-$C_6$ alkyl moieties, benzyl, halobenzyl or carboxybenzyl; and $R^2$ is methyl, ethyl or H.

Another aspect of the present invention relates to a compound of the formula

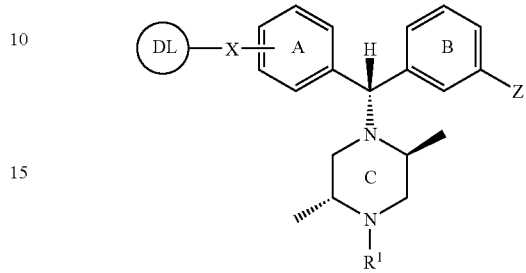

wherein:

Z is H, $O(CH_2)nCH_3$, wherein n=0 to 4, or OH;

X is C=O which is on the meta or para position of the phenyl ring;

DL is a di-functional amine linker having a nitrogen that is covalently bonded to the atom of group X;

$R^1$ is $C_1$-$C_6$ alkyl, $C_1$-$C_6$ alkenyl, $C_1$-$C_6$ cycloalkylmethyl, arylalkyl having $C_5$-$C_{10}$ aryl and $C_1$-$C_6$ alkyl moieties, benzyl, halobenzyl or carboxybenzyl; and wherein the di-functional amine linker is selected from the group consisting of:

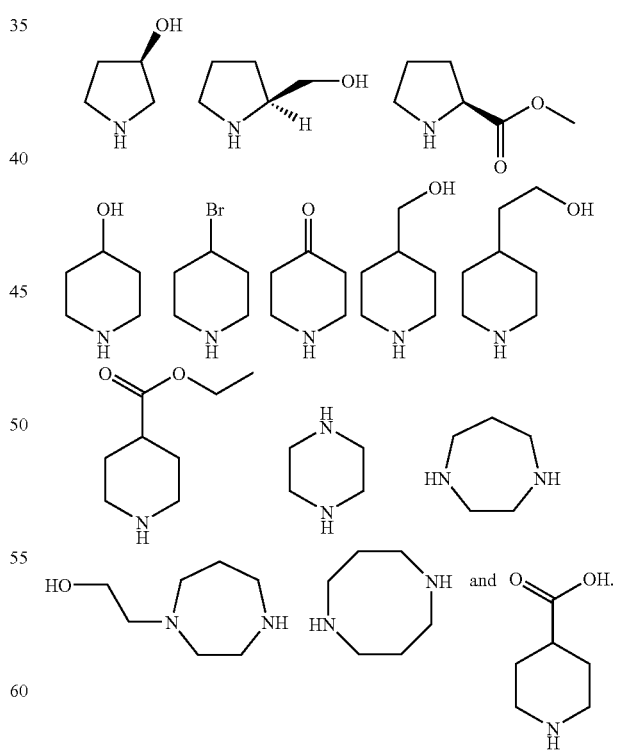

and wherein the bonding nitrogen that is covalently bonded to the carbon atom of group X has lost a hydrogen during the bonding process.

Various other aspects, features and embodiments of the invention will be more fully apparent from the ensuing disclosure and appended claims.

DETAILED DESCRIPTION OF THE INVENTION, AND PREFERRED EMBODIMENTS THEREOF

One broad aspect of the present invention relates to compounds, including inter alia pharmaceutical compositions comprising the same and methods for making and using the same. In particular, the invention relates to cyclic compounds and compositions comprising the same—as well as their preparation—and their use as selective agonists for the delta (δ) and/or mu (μ) receptor and preferably peripheral receptors.

While the compounds of the invention are described hereinafter with primary reference to diarylmethylpiperazines, piperidines and derivatives thereof, including their respective ester and salt forms, it will be recognized that the methods of the invention for treatment or prophylaxis of various disease states and physiological conditions may include use of a wide variety of diarylmethylpiperazines.

The compounds of the invention have utility in treatment or prophylaxis in a variety of non-centrally mediated or peripheral indications, including, without limitation, cough, lung edema, sexual dysfunction, gastro-intestinal disorders, arthritis, psoriasis, asthma, inflammatory bowel disease, disorders of respiratory function, functional bowel disease, irritable bowel syndrome, diarrhea, functional distension, peripherally mediated and neuropathis pain (e.g., functional pain, trauma pain, etc.), non-ulcerogenic dyspepsia, urogenital tract disorders, sexual dysfunctions, urinary tract disorders, organ transplant rejection, skin graft rejection, cardiac disorders, emesis; respiratory depression; acne and skin lesions.

In a particularly preferred method of the invention, treatment or prophylaxis of overactive bladder or urinary incontinence is effected by administering to a subject in need of such treatment or prophylaxis an effective amount of a compound of formula (1) or a pharmaceutically acceptable ester or salt thereof.

Examples of pharmaceutically acceptable esters of the compound of formula (1) include carboxylic acid esters of the hydroxyl group in the compound of formula (1) in which the non-carbonyl moiety of the carboxylic acid portion of the ester grouping is selected from straight or branched chain alkyl (e.g. n-propel, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl) aminocarbonyl); and inorganic esters (e.g. mono-, di- or triphosphate).

Examples of pharmaceutically acceptable salts of the compound of formula (1) include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4{}^+$, or $NR'_4{}^+$ (wherein R' is for example a $C_{1-4}$ alkyl group).

The compounds of formula (1) have utility as exogenous receptor combining or complexing compounds, and may be used for binding with an opioid receptor. Further, the compounds may be used as a conjugate in an agonist/antagonist pair that is employed for transductional assay of neurotransmitter function in appertaining cellular or differentiated tissue systems, as well as for receptor assay, differential binding, and specificity applications for cellular, histological, and corporeal monitoring and assessment purposes.

The compounds of the above formula (1) exhibit specific bioactivity characteristics rendering them useful as therapeutic agents for treatment or prophylaxis of a wide variety of physiological and pathological conditions.

The compounds of formula (1) are particularly useful in mediating analgesia with reduced respiratory depression, as well as for the treatment of various disease states and physiological conditions, including, without limitation, diarrhea, cardiac disorders, cough, lung edema, gastrointestinal disorders, spinal injury, and drug addiction.

The compounds of formula (1) can be administered for therapeutic intervention in a pharmaceutical composition containing the compound and a pharmaceutically acceptable carrier. The invention contemplates the use of any means and/or of modality of administration of the compositions of the invention.

Compounds of the above general formula (1) exhibit binding selectivity for receptor(s). Depending on the structure and stereo-specificity of the particular formula (1) compounds, such compounds may exhibit binding ability to receptor(s) selected from the group consisting of delta receptors, mu receptors, kappa receptors, sigma receptors, and combinations of such receptors.

Various compounds within general formula (1) exhibit delta and mu receptor agonist activity. In the case of delta receptor agonists, activity is generally distinguished and measured by activity in the electrically stimulated mouse vas deferens assay, as well as in mouse brain assay involving the existence of a delta receptor subtype that is different from the delta receptor in the mouse vas deferens.

Various compounds within general formula (1) exhibit mu opioid receptor agonist activity. In the case of mu opioid receptor agonists, activity is generally distinguished and measured by activity in the electrically stimulated guinea pig ileum assay, as well as in rat brain assay involving the existence of a mu receptor subtype that is different from the mu receptor in the guinea pig ileum.

In consequence of the existence of delta receptor subtypes, other receptor binding assays or screening techniques may be employed as a further predictor of agonist or antagonist activity for specific compounds of the present invention.

In addition, to the extent that degeneration or dysfunction of opioid receptors is present or implicated in a disease state involving tissue or discrete cellular loci, isotopically labeled versions of the opioid compounds of the present invention may find utility in diagnostic and imaging applications, e.g., diagnostic techniques involving positron emission tomography (PET) scans of the brain.

For example, a method of diagnosis of degeneration or dysfunction of delta opioid receptors associated with a disease state or physiological condition involving tissue or discrete cellular loci comprising such receptors, may be carried out by administration of a labeled delta opioid receptor-binding compound to a subject to effect binding of the compound to the delta opioid receptors in the subject, followed by determination of the extent of binding of the compound to the delta opioid receptors in the subject, as diagnostic information for the diagnosis.

The opioid receptor-binding compound may for example be labeled by fluorescent, isotopic or reporter group labeling. In one preferred aspect, the extent of binding of the compound to the opioid receptors in the subject, is determined using positron emission tomography.

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethylbenzylpiperazine or piperidine compound for its intended utility (examples of substituents for substituted alkyl groups include halogen (e.g., fluoro, chloro, bromo, and iodo), amino, amido, $C_1$-$C_4$ alkyl, $C_1$-$C_4$ alkoxy, nitro, hydroxy, etc.); (iii) saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethylbenzylpiperazine compound for its intended utility; and (iv) alkyl groups including linking or bridge moieties, e.g., heteroatoms such as nitrogen, oxygen, sulfur, etc.

As used herein, in reference to the present invention, the term "aryl" is intended to be broadly construed as referring to carbocyclic (e.g., phenyl, naphthyl) as well as heterocyclic aromatic groups (e.g., pyridyl, thienyl, furanyl, etc.) and encompassing unsubstituted as well as substituted aryl groups, wherein the substituents of substituted aryl groups may include any sterically acceptable substituents which are compatible with such aryl groups and which do not preclude the efficacy of the diarylmethylbenzylpiperazine compound for its intended utility. Examples of substituents for substituted aryl groups include one or more of halogen (e.g., fluoro, chloro, bromo, and iodo), amino, amido, $C_1$-$C_4$ alkyl, $C_1$-$C_4$ alkoxy, nitro, trifluoromethyl, hydroxy, hydroxyalkyl containing a $C_1$-$C_4$ alkyl moiety, etc.

The compounds contemplated by the invention include those of formula (1) per se, as well as physiologically functional derivatives thereof.

By "physiologically functional derivative" is meant a pharmaceutically acceptable salt, ether, ester or salt of an ether or ester of the compound of formula (1) or any other compound which, upon administration to the recipient, is capable of providing (directly or indirectly) the said compound of formula (1) or an active metabolite or residue thereof. Phenolic $C_1$-$C_6$ alkyl ethers are a sub-class of physiologically functional derivatives of the compounds of formula (1).

The compounds of the present invention may be readily synthesized within the skill of the art and in view of the illustrative synthetic examples hereinafter set forth.

The compounds of the invention when used in pharmaceutical or diagnostic applications desirably are prepared in a racemic mixture or an essentially pure enantiomer form, with an enantiopurity of at least 90% enantiomeric excess (EE), preferably at least 95% EE, more preferably at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered compounds of formula (1) at any suitable therapeutically effective and safe dosage, as may readily be determined within the skill of the art, and without undue experimentation.

In in vitro tests for agonist/antagonist activity, such as receptor binding affinity tests, and inhibition of electrically stimulated muscle twitch tests, compounds of the present invention exhibit potency over a range of from nanomolar to micromolar concentrations, depending on the specific compound employed.

In general, while the effective dosage of compounds of the invention for therapeutic use may be widely varied in the broad practice of the invention, depending on the specific application, condition, or disease state involved, as readily determinable within the skill of the art, suitable therapeutic doses of the compounds of the invention, for each of the appertaining compositions described herein, and for achievement of therapeutic benefit in treatment of each of the conditions described herein, will be in the range of 10 micrograms (μg) to 100 milligrams (mg) per kilogram body weight of the recipient per day, preferably in the range of 50 μg to 75 mg per kilogram body weight per day, and most preferably in the range of 100 μg to 50 mg per kilogram body weight per day. The desired dose is preferably presented as two, three, four, five, six, or more sub-doses administered at appropriate intervals throughout the day. These sub-doses may be administered in unit dosage forms, for example, containing from 10 μg to 1000 mg, preferably from 50 μg to 500 mg, more preferably from 50 μg to 250 mg, and most preferably from 50 μg to 10 mg of active ingredient per unit dosage form. Alternatively, if the condition of the recipient so requires, the doses may be administered as a continuous infusion.

The mode of administration and dosage forms will of course affect the therapeutic amounts of the compounds which are desirable and efficacious for the given treatment application.

For example, orally administered dosages typically are at least twice, e.g., 2-10 times, the dosage levels used in parenteral administration methods, for the same active ingredient. In oral administration, dosage levels for delta receptor binding compounds of the invention may be on the order of 5-200 mg/70 kg body weight/day. In tablet dosage forms, typical active agent dose levels are on the order of 10-100 mg per tablet.

The compounds of formula (1) may be administered per se as well as in the form of pharmaceutically acceptable esters, salts, and ethers, as well as other physiologically functional derivatives of such compounds.

The present invention also contemplates pharmaceutical formulations, both for veterinary and for human medical use, which comprise as the active agent one or more compound(s) of the invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, transdermal, nasal, ophthalmic, subcutaneous, intramuscular, intravenous, transdermal, spinal, intrathecal, intra-articular, intra-arterial, sub-arachnoid, bronchial, lymphatic, and intra-uterine administration. Formulations suitable for parenteral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The disease state or physiological condition involved in such therapeutic intervention may be of any suitable type or kind, e.g., peripherally mediated pain and neuropathic pain, cough, lung edema, gastro-intestinal disorders, arthritis, psoriasis, asthma, inflammatory bowel disease, disorders of respiratory function, functional bowel disease, irritable bowel syndrome, diarrhea, functional distension, pain (e.g., functional pain, trauma pain, etc.), non-ulcerogenic dyspepsia, urogenital tract disorders, premature ejaculation, overactive balder, urinary incontinence, organ transplant rejection, skin graft rejection, cardiac disorders, cardioprotection, emesis, acne and skin lesions.

The invention is further illustrated by the following non-limiting examples.

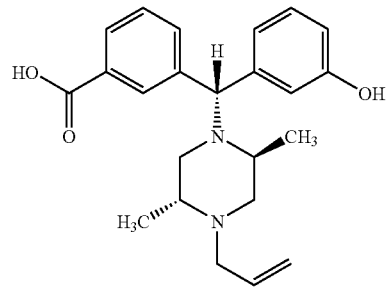

PRECURSOR ACID A

3-[(R)-((2S,5R)-4-Allyl-2,5-dimethylpiperazin-1-yl)(3-hydroxyphenyl)methyl]-benzoic acid 3-Iodophenol (110 g, 0.50 mol, 1 eq) and imidazole (93.6 g, 1.375 mol, 2.75 eq) were placed in a 2000 ml flask with dichloromethane (1150 mL) and cooled in an ice water bath to 15° C. under nitrogen. tert-Butyldimethylchlorosilane (82.9 g, 0.55 mol, 1.1 eq) in dichloromethane (200 mL) was added dropwise through an addition funnel and the reaction mixture was stirred overnight. The reaction solution was washed with 0.5 N sodium hydroxide solution (3×200 mL), water (3×200 mL) and brine (200 ml) and dried over sodium sulfate. The solvent was removed under reduced pressure leaving 166.34 g of crude (3-iodo-phenoxy)-tert-butyl-dimethyl-silane. $^1$H NMR (300 MHz, CDCl$_3$) δ 7.27 (ddd, J=8.0, 2.0, 1.0 Hz), 7.19 (dd, 1H, J=2.0, 2.0 Hz), 6.92 (dd, 1H, J=8.0, 8.0 Hz), 6.77 (ddd, 1H, J=8.0, 2.0, 1.0 Hz).

Methyl 3-formylbenzoate (10 g, 60.91 mmol, 1 eq), benzotriazole (7.25 g, 60.91 mmol, 1 eq) and (2S,5R)-1-allyl-2,5-dimethylpiperazine (Chirotech Division of Dow Pharmaceutical Services, Cambridge, UK, 9.39 g, 60.91 mmol, 1 eq) were placed in a flask with dry toluene (300 mL) and triethylamine (1 mL). The flask was fitted with a Dean-Stark trap and condenser and heated to a gentle reflux in an oil bath (temperature ≦135° C.) for several hours with azeotropic removal of water. Most of the toluene was removed under reduced pressure to give 28 g of crude 3-[(S)-((2S,5R)-4-allyl-2,5-dimethylpiperazin-1-yl)benzotriazol-1-yl-methyl]benzoic acid methyl ester as a dark amber viscous liquid.

(3-Iodo-phenoxy)-tert-butyl-dimethyl-silane (35.63 g, 106.6 mmol) was dissolved in THF (110 mL) at room temperature under nitrogen. Isopropylmagnesium chloride (2.0 M in THF, 53.3 mL, 106.6 mmol) was added dropwise through a dry addition funnel, and the reaction was stirred for an hour to give a pale yellow solution of 3-(tert-butyldimethylsilyloxy)phenyl magnesium iodide.

The freshly prepared benzotriazole adduct (28 g crude, ≦60.91 mmol, 1.0 eq) in THF (100 mL) was added via double ended needle to the above solution of Grignard reagent (1.75 eq) at room temperature under nitrogen and stirred overnight. The reaction was quenched with 12 mL of saturated ammonium chloride solution and stirred for 30 min at room temperature. The resulting suspension was filtered and solvent was removed under vacuum to give a viscous dark liquid. The residue was dissolved in ethyl acetate (700 mL) and washed with 10% sodium hydroxide solution (5×100 mL), water (4×100 mL) and brine (2×100 mL), and dried over sodium sulfate. Solvent was removed under reduced pressure to give a dark viscous residue (31.7 g). The residue was purified by chromatography on silica gel by eluting first with pentane/dichloromethane mixtures of 1:1, 1:2, and 1:4, followed successively by pure dichloromethane and 1.5% and 2% ethanol in dichloromethane, to give 26.9 g (86.8%) of 3-{(R)-((2S,5R)-4-allyl-2,5-dimethylpiperazin-1-yl)[3-(tert-butyl-dimethylsilanyloxy)phenyl]methyl}benzoic acid methyl ester.

A mixture of 3-{(R)-((2S,5R)-4-allyl-2,5-dimethyl-piperazin-1-yl)[3-(tert-butyl-dimethylsilanyloxy)phenyl] methyl}benzoic acid methyl ester (7.4 g, 14.5 mmol) and 18.2 mL of 2.0 N aqueous sodium hydroxide (36.4 mmol, 2.5 eq) in THF (30 mL) was stirred overnight at room temperature. Hydrochloric acid (18.2 mL of 2 N aqueous solution) was added, and the THF was removed under vacuum. The aqueous residue was filtered to collect precipitated solid, which was washed with dichloromethane to remove organic impurities. The aqueous filtrate was concentrated to dryness to give additional solid material. The recovered solids were combined, washed with water to remove sodium chloride, and dried to give 5.5 g (99.4%) of crude 3-[(R)-((2S,5R)-4-allyl-2,5-dimethylpiperazin-1-yl)(3-hydroxyphenyl)methyl]benzoic acid (Acid A).

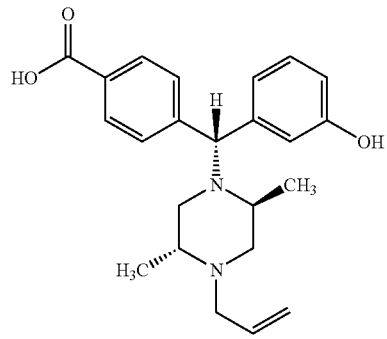

PRECURSOR ACID B

4-[(R)-((2S,5R)-4-Allyl-2,5-dimethyl-piperazin-1-yl)-(3-hydroxy-phenyl)-methyl]-benzoic acid A mixture of 4-cyanobenzaldehyde (9.3 g), benzotriazole (8.45 g), 2R,5S-1-allyl-2,5-dimethylpiperazine (10.94 g), triethylamine (1 mL) and toluene (300 mL) in a round-bottom flask equipped with Dean-Stark trap (azeotropic removal of water) and reflux condenser was refluxed for 4 h under nitrogen. After cooling to room temperature, most of the solvent was removed under vacuum to give a viscous dark brown benzotriazole adduct.

Isopropylmagnesium chloride (124 mL of 2.0 M THF solution) was added to a solution of (3-iodo-phenoxy)-tert-butyl-dimethyl-silane (41.47 g, cf. procedure for Precursor Acid A) in THF (150 mL) at room temperature under nitrogen. The reaction was stirred at room temperature for 1 h to give a solution of 3-(tert-butyldimethylsilyloxy)phenyl magnesium iodide.

Anhydrous THF (50 mL) was added to the viscous dark brown benzotriazole adduct under nitrogen. The resulting solution was added dropwise at room temperature to the solution of 3-(tert-butyldimethylsilyloxy)phenyl magnesium iodide and stirred overnight. The reaction was quenched by the addition of saturated aqueous NH$_4$Cl (14 mL). After stirring for 30 minutes, the mixture was filtered. The filtrate was concentrated to give a dark brown residue, which was re-dissolved in EtOAc (400 mL), washed with 10% NaOH solution (50 mL×5), water (50 mL×3) and brine (50 mL×3). The EtOAc layer was dried over sodium sulfate and concentrated. Hexane (600 mL) was added to the residue. Undissolved solids were removed by filtration. The filtrate was concentrated to give crude 4-{(R)-((2S,5R)-4-allyl-2,5-dimethyl-piperazin-1-yl)-[3-(tert-butyl-dimethylsilanyloxy)-phenyl]-methyl}-benzonitrile (32.1 g), which was used for the next step without further purification. $^1$H NMR (300 MHz, CDCl$_3$) δ 7.55 (s, 4H), 7.17 (dd, 1H, J=8.0, 8.0 Hz), 6.73 (m, 2H), 6.51 (s, 1H), 5.83 (m, 1H), 5.15 (m, 3H), 3.35 (m, 1H), 2.81 (m, 2H), 2.58 (m, 1H), 2.46 (m, 2H), 2.11 (dd, 1H, J=11.0, 9.5 Hz), 1.83 (dd, 1H, J=11.5, 9.5 Hz), 1.15 (d, 3H, J=6.0 Hz), 0.96 (d, 3H, J=6.0 Hz), 0.93 (s, 9H), 0.13 (s, 3H), 0.12 (3H).

Ethanol (240 mL) was added to the above crude product (32.1 g), followed by the addition of NaOH (18.35 g). The reaction was refluxed for 40 h. After being cooled to room temperature, the reaction mixture was concentrated. Water (50 mL) was added to the residue. The resulting solution was neutralized to pH≅5 by 1N HCl solution. The desired product precipitated during neutralization and was collected by filtration. The collected solid was rinsed with ether and dried to give crude product (22.5 g), which was purified by column chromatography to give 4-[(R)-((2S,5R)-4-allyl-2,5-dimethyl-piperazin-1-yl)-(3-hydroxy-phenyl)-methyl]-benzoic acid (Acid B, 10.4 g, 39% from 4-cyanobenzaldehyde). $^1$H NMR (300 MHz, CD$_3$OD) δ 7.90 (d, 2H, J=8.5 Hz), 7.46 (d, 2H, J=8.5 Hz), 7.19 (dd, 1H, J=7.5, 7.5 Hz), 6.73 (m, 3H), 5.94 (m, 1H), 5.47 (m, 2H), 5.25 (s, 1H), 3.72 (m, 1H), 3.40 (m, 1H), 3.20 (m, 1H), 3.11 (m, 1H), 2.85 (m, 2H), 2.68 (m, 1H), 2.14 (m, 1H), 1.26 (d, 3H, J=6.5 Hz), 1.22 (d, 3H, J=6.5 Hz).

See Tables 1-6 for activity data.

Homopiperazine Derivatives

EXAMPLE 1

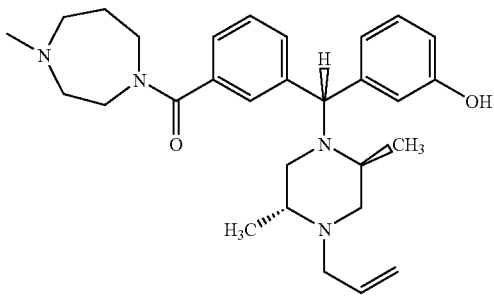

{3-[(R)-((2S,5R)-4-Allyl-2,5-dimethyl-piperazin-1-yl)-(3-hydroxy-phenyl)-methyl]-phenyl}methyl-[1,4]diazepan-1-yl)-methanone Thionyl chloride (210 mg) was added to the mixture of Acid A (560 mg) in CH$_2$Cl$_2$ (40 mL) at room temperature under a drying tube. The reaction mixture was initially a cloudy suspension, but became clear after stirring for 30 min at room temperature. The acid chloride solution was added to the solution of 1-methylhomopiperazine (504 mg), N,N-diisopropylethylamine (571 mg) in CH$_2$Cl$_2$ (20 mL) at room temperature via a syringe. The reaction was stirred at room temperature for 3 h while it was opened to air via a drying tube. The reaction was quenched by the addition of water (30 mL) and saturated NaHCO$_3$ solution (30 mL). The resulting mixture was transferred into a separatory funnel. EtOAc: MeOH=95:5 (100 mL) was used to extract the mixture. Solid was still observed in the mixture floating in both organic and water layers. The mixture was filtered thru a fritted funnel. The filtrate was poured back into separatory funnel. The organic layer and water layer was separated. The water layer was extracted by EtOAc:MeOH=95:5 (20 mL×2). The combined organic layers were washed by water (40 mL×2) and brine (40 mL×1), dried by Na$_2$SO$_4$ and concentrated to give crude product (830 mg), which was purified by silica gel chromatography conducted on CombiFlash™ Sq 16× (gradient: 100% CH$_2$Cl$_2$ to 20% MeOH in CH$_2$Cl$_2$) to give {3-[(R)-((2S,5R)-4-allyl-2,5-dimethyl-piperazin-1-yl)-(3-hydroxy-phenyl)-methyl]-phenyl}-(4-methyl-[1,4]diazepan-1-yl)-methanone (274 mg; 39%). $^1$H NMR (300 MHz, CDCl$_3$) δ 7.51 (m, 1H), 7.38-7.21 (m, 3H), 7.07 (dd, 1H, J=8.0, 8.0 Hz), 6.59 (m, 2H), 6.51(s, 1H), 5.86 (m, 1H), 5.19 (m, 3H), 3.73 (m, 2H), 3.46-3.36 (m, 3H), 2.89-2.73(m, 3H), 2.64-2.30 (m, 9H), 2.13 (dd, 1H, J=10.0, 10.0 Hz), 1.99 (m, 1H), 1.92 (dd, 1H, J=10.5, 10.5 Hz), 1.79 (m, 1H), 1.14 (d, 3H, J=5.5 Hz), 0.98 (d, 3H, J=6.0 Hz); MS (FAB, glycerol) m/z: 477 (M$^+$+1); 323, 209, 153; Found: C, 71.70; H, 8.41; N, 11.36. Calc. (C29H40N4O2 0.13 CH2Cl2): C, 71.74; H, 8.32; N, 11.49.

EXAMLE 2

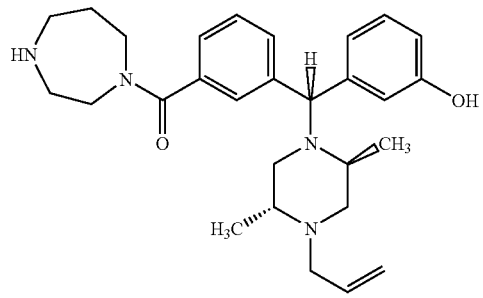

{3-[(R)-((2S,5R)-4-Allyl-2,5-dimethyl-piperazin-1-yl)-(3-hydroxy-phenyl)-methyl]-phenyl}-[1,4]diazepan-1-yl-methanone Thionyl chloride (893 mg) was added to the cloudy mixture of Acid A (2.04 g) in CH$_2$Cl$_2$ (150 mL) at room temperature under a drying tube. The reaction solution became clear after stirring for 40 minutes at room temperature. The acid chloride solution was transferred to an addition funnel and then slowly added to a round bottom flask fitted with a drying tube and containing homopiperazine (3.22 g) and N,N-diisopropylethylamine (2.08 g) in CH$_2$Cl$_2$ (100 mL) over a period of 20 minutes. The reaction was stirred at room temperature for 5 hr. The reaction was worked up by the addition of water (100 mL) and saturated NaHCO$_3$ solution (50 mL). The CH$_2$Cl$_2$ layer and water layer were separated. The water layer was extracted by CH$_2$Cl$_2$ (80 mL×3). The combined CH$_2$Cl$_2$ layer was washed by H$_2$O (100 mL×3) and brine (100 mL×1), dried by Na$_2$SO$_4$ and concentrated to give crude product (2.1 g), which was purified by silica gel chromatography conducted on CombiFlash™ Sq 16× (gradient: 100% CH$_2$Cl$_2$ to 30% MeOH in CH$_2$Cl$_2$) to give {3-[(R)-((2S,5R)-4-allyl-2,5-dimethyl-piperazin-1-yl)-(3-hydroxy-phenyl)-methyl]-phenyl}-[1,4]diazepan-1-yl-methanone (1.341 g; 54%). $^1$H NMR (300 MHz, CDCl$_3$) δ 7.531 (m, 1H), 7.36-7.21 (m, 3H), 7.06 (dd, 1H, J=8.0, 8.0 Hz), 6.61 (d, 1H, J=8.0 Hz), 6.57(d, 1H, J=8.0 Hz), 6.53(s, 1H), 5.86 (m, 1H), 5.18 (m, 3H), 4.63 (bs, 1H), 3.73 (m, 2H), 3.39 (m, 3H), 3.00 (1H), 2.88-2.76 (m, 5H), 2.62 (m, 1H), 2.55 (m, 1H), 2.45 (m, 1H), 2.12 (dd, 1H, J=10.0, 10.0 Hz), 1.92 (m, 2H), 1.65 (m, 1H), 1.14 (d, 3H, J=6.0 Hz), 0.97 (d, 3H, J=6.0 Hz).

EXAMPLE 3

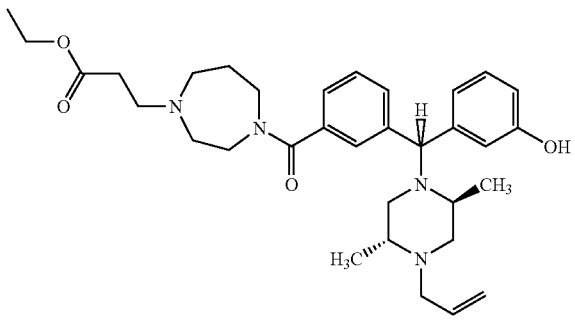

3-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-propionic acid ethyl ester Method A The compound of Example 2 (362 mg) and ethyl acrylate (81 mg) in ethanol (10 mL) was refluxed for 4 h. TLC of reaction solution indicated a new spot and starting material. Additional ethyl acrylate (65 mg) was added to the reaction solution. The reaction was refluxed for another 6 h. After being cooled to room temperature, the reaction solution was dried by rotary evaporator. The remaining residual was purified by silica gel chromatography conducted on CombiFlash™ Sq 16× (gradient: 100% $CH_2Cl_2$ to 10% MeOH in $CH_2Cl_2$) to give 3-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-propionic acid ethyl ester (275 mg; 63%). $^1$H NMR (300 MHz, $CDCl_3$) δ 7.59-7.47 (m, 1H), 7.39-7.22 (m, 3H), 7.09 (m, 1H), 6.63 (m, 3H), 5.89 (m, 1H), 5.21 (m, 3H), 4.14 (q, 2H, J=7.0 Hz), 3.76-3.63 (m, 2H), 3.44-3.34 (m, 3H), 2.95-2.76 (m, 5H), 2.72-2.39 (m, 8H), 2.17 (dd, 1H, J=10.0, 10.0 Hz), 2.00 (dd, 1H, J=11.0, 11.0 Hz), 1.92 (m, 1H), 1.69 (m, 1H), 1.25 (t, 3H, J=7.0 Hz), 1.15 (d, 3H, J=6.0 Hz), 1.02 (d, 3H, J=5.5 Hz); MS (FAB, glycerol) m/z: 563 ($M^+$+1), 409, 209, 153; Found C, 68.59; H, 8.30; N, 9.64. Calc. ($C_{33}H_{46}N_4O_4$ 0.2 CH2Cl2) C, 68.78; H, 8.07; N, 9.66.

Method B

4-[1,4]Diazepan-1-yl-propionic acid ethyl ester $Na_2CO_3$ (2.94 g) was added to the solution of homopiperazine (13.88 g; 5.0 eq.) and ethyl 3-bromopropionate (5.02 g; 1 eq.) in $CH_3CN$ (100 mL). The reaction was stirred at room temperature for overnight. The reaction mixture was filtered thru a celite pad. The filtrate was concentrated. To the resulting residual water (200 mL) was added. The water solution was extracted by $CHCl_3$ (200 mL×3). The combined $CH_3Cl$ layer was washed by $H_2O$ (150 mL×2) and brine (150 mL×1), dried by $Na_2SO4$ and concentrated to give 4-[1,4]diazepan-1-yl-propionic acid ethyl ester (3.49 g), which was carried on for the next step without further purification. $^1$H NMR (300 MHz, $CDCl_3$) δ 4.10 (m, 2H), 2.91-2.78 (m, 6H), 2.67 (m, 4H), 2.43 (m, 2H), 1.81 (bs, 1H), 1.72 (m, 2H), 1.23 (m, 3H).

Thionyl chloride (2.90 g) was added to the cloudy mixture of Acid A (6.63 g) in $CH_2Cl_2$ (200 mL) at room temperature. The reaction was stirred at room temperature for 90 minutes while it was opened to air via a drying tube. The reaction solution became clear. The acid chloride solution was transferred into an additional funnel and then slowly added to a round bottom flask containing 4-[1,4]diazepan-1-yl-propionic acid ethyl ester (3.49 g) and triethylamine (3.88 g) in $CH_2Cl_2$ (100 mL) at room temperature. The reaction was stirred at room temperature overnight while it was opened to air via a drying tube. The reaction was worked up by the addition of water (200 mL). Saturated $NaHCO_3$ solution was used to neutralize the H2O layer to pH≅8. The $CH_2Cl_2$ layer and water layer were separated. The water layer was extracted by $CH_2Cl_2$ (150 mL×3). The combined $CH_2Cl_2$ layer was washed by H2O (150 mL×2) and brine (150 mL×1), dried by $Na_2SO_4$ and concentrated to give crude product, which was purified by silica gel chromatography conducted on CombiFlash™ Sq 16× (gradient: 100% $CH_2Cl_2$ to 10% MeOH in $CH_2Cl_2$) to give 3-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-propionic acid ethyl ester (4.2 g; 43%).

EXAMPLE 4

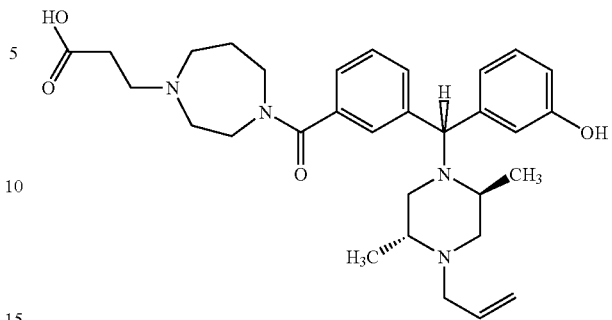

3-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-propionic acid To the compound of Example 3 (540 mg) in THF (3 mL) was added 1N NaOH solution (2.2 mL). The reaction was stirred at room temperature for overnight. The reaction solution was neutralized by the addition of 1 N HCl solution (2.2 mL). The mixture was put under rotary evaporator for the removal of THF. The remaining water layer was diluted by water (2 mL). The water layer was extracted by n-butanol (5 mL×3). The combined n-butanol layer was washed by water (3 mL×2) and concentrated to give crude product (430 mg), which was purified by silica gel chromatography conducted on CombiFlash™ Sq 16× (gradient: 100% $CH_2Cl_2$ to 30% MeOH in $CH_2Cl_2$) to give 3-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-propionic acid (385 mg; 75%). $^1$H NMR (300 MHz, DMSO-$d_6$) δ 9.34 (bs, 1H), 8.31 (s, 1H), 7.36 (m, 3H), 7.18(d, 1H, J=6.5 Hz), 7.12(dd, 1H,J=8.0, 8.0 Hz), 6.66 (m, 3H) 5.77 (m, 1H), 5.18-5.00 (m, 3H), 3.55 (m, 2H), 3.29 (m, 2H), 3.16 (m, 1H), 2.84 (m, 1H), 2.75-2.49 (m, 10H), 2.32 (m, 2H), 2.07 (m, 1H), 1.81 (m, 2H), 1.62 (m, 1H), 1.06 (d, 3H, J=6.50 Hz), 0.92 (d, 3H, J=5.5 Hz).

EXAMPLE 5

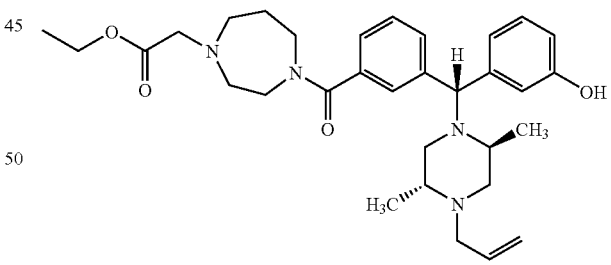

(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-acetic acid ethyl ester Sodium carbonate (1.27 g) was added to a solution of homopiperazine (5.99 g; 5 eq.) and ethyl bromoacetate (2.0 g; 1 eq.) in $CH_3CN$ (120 mL). The reaction was stirred at room temperature for 6 h. The reaction mixture was filtered thru a celite pad. The filtrate was concentrated. The remaining residual was dissolved in $CHCl_3$ (120 mL), washed by $H_2O$ (50 mL×3) and brine (50 mL×1), dried by $Na_2SO4$ and concentrated to give [1,4]diazepan-1-yl-acetic acid ethyl ester (1.794 g), which was carried on for the next step without further purification. $^1$H NMR (300 MHz, CDCl$_3$) δ 4.15 (m, 2H), 3.39 (s, 2H), 2.91 (m, 4H), 2.81 (m, 4H), 1.76 (m, 3H), 1.25 (m, 3H).

Thionyl chloride (1.76 g) was added to the cloudy mixture of Acid A (4.03 g) in CH$_2$Cl$_2$ (250 mL) at room temperature. The reaction was stirred at room temperature for 45 minutes while it was opened to air via a drying tube. The reaction solution became clear light-brown solution. The acid chloride solution was transferred into an additional funnel and then slowly added to a round-bottom flask containing [1,4]diazepan-1-yl-acetic acid ethyl ester (1.79 g) and triethylamine (2.14 g) in CH$_2$Cl$_2$ (100 mL) at 0° C. The reaction system was opened to air via a drying tube. After the addition of acid chloride solution, the cooling ice bath was removed and the reaction was stirred at room temperature for overnight. The reaction was quenched by the addition of water (150 mL). Saturated NaHCO$_3$ solution was used to neutralize the water layer to pH≅7. The CH$_2$Cl$_2$ layer, turbid at this point, and water layer were separated. The CH$_2$Cl$_2$ layer was washed by water (60 mL×2). All the above water layers were combined and extracted by EtOAc:MeOH=95:5 (120 mL×3). The CH$_2$Cl$_2$ layer and EtOAc/MeOH layer were combined, dried by Na$_2$SO$_4$ and concentrated to give crude product (4.9 g), which was purified by silica gel chromatography conducted on CombiFlash™ Sq 16× (gradient: 100% CH$_2$Cl$_2$ to 10% MeOH in CH$_2$Cl$_2$) to give (4-{3-[(R)-((2S,5R)-4-allyl-2,5-dimethyl-piperazin-1-yl)-(3-hydroxy-phenyl)-methyl]-benzoyl}-[1,4]diazepan-1-yl)-acetic acid ethyl ester (1.93 g; 37%). $^1$H NMR (300 MHz, CDCl$_3$) δ 7.53-7.22 (m, 4H), 7.08 (ddd, 1H, J=8.0, 8.0, 3.0 Hz), 6.61 (m, 3H), 5.88 (m, 1H), 5.20 (m, 3H), 4.17 (m, 2H), 3.82-3.68 (m, 2H), 3.47-3.32 (m, 5H), 2.95-2.80 (m, 4H), 2.77-2.50 (m, 5H), 2.15 (dd, 1H, J=10.0, 10.0 Hz), 1.97 (m, 2H), 1.75 (m, 1H), 1.27 (m, 3H), 1.15 (d, 3H, J=5.5 Hz), 1.00 (d, 3H, J=5.5 Hz); MS (FAB, glycerol) m/z: 549 (M$^+$+1), 395, 209, 153; Found C, 68.71; H, 7.97; N, 9.95. Calc.(C$_{32}$H$_{44}$N$_4$O$_4$ 0.15 CH$_2$Cl$_2$) C, 68.78; H, 7.95; N, 9.98.

EXAMPLE 6

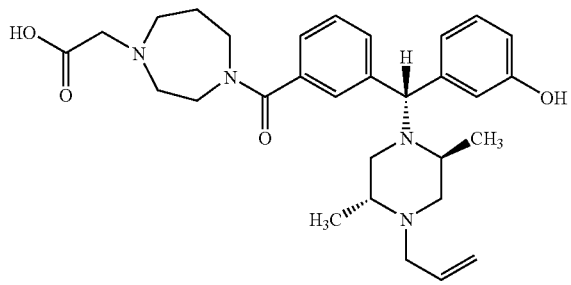

(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-acetic acid To the compound of Example 5 (330 mg) in THF (3 mL) was added 1N NaOH solution (1 mL). The reaction was stirred at room temperature for overnight. TLC of reaction mixture indicated the disappearance of starting material. The reaction solution was neutralized by the addition of 1 N HCl solution (1 mL). The mixture was put under rotary evaporator for the removal of THF.

The remaining water layer was diluted by water (2 mL). The water layer was extracted by EtOAc:MeOH=95:5 (5 mL×3). TLC of the water layer at this point indicated strong UV active spot. Consequently, the water layer was extracted by n-butanol (5 mL×3). The combined n-butanol layer was washed by water (5 mL×1) and concentrated to give crude product (340 mg), which was purified by silica gel chromatography conducted on CombiFlash™ Sq 16× (gradient: 100% CH$_2$Cl$_2$ to 20% MeOH in CH$_2$Cl$_2$) to give (4-{3-[(R)-((2S,5R)-4-allyl-2,5-dimethyl-piperazin-1-yl)-(3-hydroxy-phenyl)-methyl]-benzoyl}-[1,4]diazepan-1-yl)-acetic acid (190 mg; 61%). (Note: The $^1$H NMR and TLC of the sample (12 mg) obtained from EtOAc:MeOH=95:5 layer indicated no desired product.). $^1$H NMR (300 MHz, DMSO-d$_6$) δ 9.40 (bs, 1H) 8.31 (s, 1H), 7.36 (m, 3H), 7.18 (d, 1H, J=7.0 Hz), 7.12 (dd, 1H, J=8.0, 8.0 Hz), 6.66 (m, 3H), 5.77 (m, 1H), 5.18-4.99 (m, 3H), 3.60 (m, 2H), 3.31-3.13 (m, 5H), 2.91-2.69 (m, 6H), 2.52 (m, 3H), 2.07 (dd, 1H, J=10.5, 7.5 Hz), 1.82 (m, 2H), 1.68 (m, 1H), 1.06 (d, 3H, J=6.0 Hz), 0.91 (d, 3H, J=5.5 Hz).

EXAMPLE 7

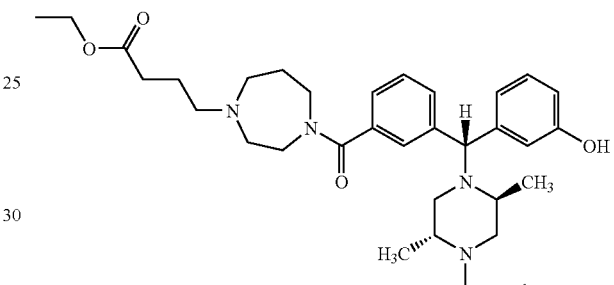

4-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-butyric acid ethyl ester Sodium carbonate (2.12 g) was added to the solution of homopiperazine (10.0 g; 5 eq.) and ethyl 4-bromobutyrate (3.90 g; 1 eq.) in CH$_3$CN (120 mL). The reaction was stirred at room temperature for 6 h. The reaction mixture was filtered thru a celite pad. The filtrate was concentrated. The remaining residual was dissolved in CHCl$_3$ (120 mL), washed by H$_2$O (50 mL×3) and brine (50 mL×1), dried by Na$_2$SO4 and concentrated to give 4-[1,4]diazepan-1-yl-butyric acid ethyl ester (3.8 g), which was carried on for the next step without further purification.

$^1$H NMR (300 MHz, CDCl$_3$) δ 4.09 (q, 2H, J=7.0 Hz), 2.88 (m, 4H), 2.63 (m, 4H), 2.48 (t, 2H, J=7.5 Hz), 2.30 (t, 2H, J=7.5 Hz), 1.99 (s, 1H), 1.74 (m, 4H), 1.22 (t, 3H, J=7.0 Hz).

Thionyl chloride (0.93 g) was added to the cloudy mixture of Acid A (2.13 g) in CH$_2$Cl$_2$ (120 mL) at room temperature. The reaction was stirred at room temperature for 45 minutes while it was opened to air via a drying tube. The reaction solution became clear light-brown solution. The acid chloride solution was transferred into an additional funnel and then slowly added to a round-bottom flask containing 4-[1,4]diazepan-1-yl-butyric acid ethyl ester (1.2 g) and triethylamine (1.25 g) in CH$_2$Cl$_2$ (50 mL) at 0° C. The reaction system was opened to air via a drying tube. After the addition of acid chloride solution, the cooling ice bath was removed and the reaction was stirred at room temperature for overnight. The reaction was quenched by the addition of water (150 mL). Saturated NaHCO$_3$ solution was used to neutralize the water layer to pH≅8. The CH$_2$Cl$_2$ layer and water layer were separated. The water layer was extracted by CH$_2$Cl$_2$ (150 mL×3). The CH$_2$Cl$_2$ layers were combined, washed by H$_2$O (150 mL×2) and saturated NaCl solution (150 mL×1), dried by Na$_2$SO$_4$ and concentrated to give crude product (2.7 g), which was purified by silica gel chromatography conducted on CombiFlash™ Sq 16× (gradient: 100% CH$_2$Cl$_2$ to 10% MeOH in CH$_2$Cl$_2$) to give 4-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-butyric acid ethyl ester (0.97 g; 30%). $^1$H NMR (300 MHz, CDCl$_3$) δ 7.58-7.49 (m, 1H), 7.38-7.22 (m, 3H), 7.07 (m, 1H), 6.60 (m, 3H), 5.87 (m, 1H), 5.19 (m, 3H), 4.13 (q, 2H, J=7.0 Hz), 3.71 (m, 2H), 3.38(m, 3H),2.85 (m, 3H), 2.66-2.40 (m, 8H), 2.31 (m, 2H), 2.14 (dd, 1H, J=10.0, 10.0 Hz), 1.94 (m, 2H), 1.81-1.70 (m, 3H), 1.25 (t, 3H, J=7.0 Hz), 1.15 (d, 3H, J=5.5 Hz), 0.99 (d, 3H, J=5.0 Hz); MS (FAB, glycerol) m/z: 577 (M$^+$+1), 423, 209, 153; Found: C, 69.56; H, 8.36; N, 9.24 (ave. of 2 run). Calc. (C$_{34}$H$_{48}$N$_4$O$_4$ 0.1 CHCl$_3$): C, 69.57; H, 8.24; N, 9.52.

Due to the low yield, all the water layers from the above work-up procedure were combined and extracted by n-butanol (100 mL×3). The n-butanol layers were combined and concentrated to give 750 mg of crude 4-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-butyric acid ethyl ester (indicated by $^1$H NMR), which was treated by ester hydrolysis condition to afford the desired acid according to the following Example 8.

EXAMPLE 8

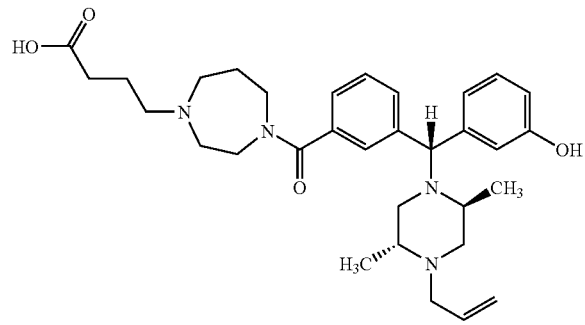

4-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-butyric acid To the compound of Example 7 (750 mg) in THF (10 mL) was added 1N NaOH solution (3.0 mL). The reaction was stirred at room temperature for overnight. The reaction solution was neutralized by the addition of 1 N HCl solution (3.0 mL). The mixture was put under rotary evaporator for the removal of THF. The remaining water layer was diluted by water (5 mL). The water layer was extracted by n-butanol (6 mL×3). The combined n-butanol layer was washed by water (5 mL×2) and concentrated to give crude product, which was purified by silica gel chromatography conducted on CombiFlash™ Sq 16× (gradient: 100% CH$_2$Cl$_2$ to 30% MeOH in CH$_2$Cl$_2$) to give 4-(4-{3-[(R)-((2S,5R)-4-allyl-2,5-dimethyl-piperazin-1-yl)-(3-hydroxy-phenyl)-methyl]-benzoyl}-[1,4] diazepan-1-yl)-butyric acid (202 mg, 28%). $^1$H NMR (300 MHz, DMSO-d$_6$) δ 9.36 (bs, 1H), 8.31 (s, 1H), 7.35 (m, 3H), 7.18 (m, 1H), 7.11 (m, 1H), 6.64 (m, 3H), 5.77 (m, 1H), 5.19-5.00 (m, 3H), 3.56 (m, 2H), 3.28 (m, 2H), 3.18 (m, 1H), 2.86 (m, 1H), 2.74 (m, 1H), 2.59-2.48 (m, 8H), 2.39 (m, 1H), 2.21 (m, 2H), 2.09 (m, 1H), 1.81 (m, 2H), 1.64-1.55 (m, 3H), 1.06 (d, 3H, J=6.0 Hz), 0.92 (d, 3H, J=5.5 Hz).

EXAMPLE 9

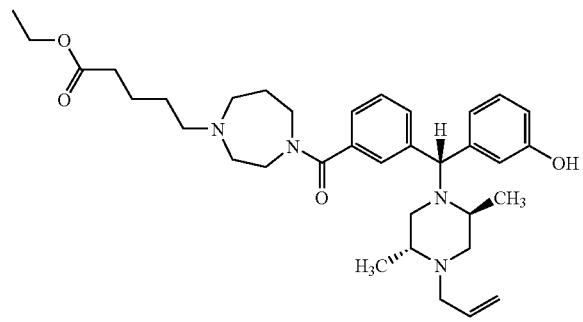

5-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-pentanoic acid ethyl ester Sodium carbonate (2.12 g) was added to the solution of homopiperazine (10.0 g; 5 eq.) and ethyl 5-bromovalerate (4.18 g; 1 eq.) in CH$_3$CN (120 mL). The reaction was stirred at room temperature for 6 h. The reaction mixture was filtered thru a celite pad. The filtrate was concentrated. The remaining residual was dissolved in CHCl$_3$ (120 mL), washed by H$_2$O (50 mL×3) and brine (50 mL×1), dried by Na$_2$SO4 and concentrated to give 5-[1,4]diazepan-1-yl-pentanoic acid ethyl ester (4.0 g), which was carried on for the next step without further purification. $^1$H NMR (300 MHz, CDCl$_3$) δ 4.09 (q, 2H, J=7.0 Hz), 2.90 (m, 4H), 2.63 (m, 4H), 2.47 (t, 2H, J=7.0 Hz), 2.29 (t, 2H, J=7.0 Hz), 2.07 (bs, 1H), 1.73 (m, 2H), 1.60 (m, 2H), 1.48 (m, 2H), 1.22 (t, 3H, J=7.0 Hz).

Thionyl chloride (1.26 g) was added to the cloudy mixture of Acid A (4.04 g) in CH$_2$Cl$_2$ (200 mL) at room temperature. The reaction was stirred at room temperature for 75 minutes while it was opened to air via a drying tube. The reaction solution became clear light-brown solution. The acid chloride solution was transferred into an additional funnel and then slowly added to a round-bottom flask containing 5-[1,4]diazepan-1-yl-pentanoic acid ethyl ester (2.06 g) and N,N-diisopropylethylamine (2.75 g) in CH$_2$Cl$_2$ (100 mL) at 0° C. The reaction system was opened to air via a drying tube. After the addition of acid chloride solution, the cooling ice bath was removed and the reaction was stirred at room temperature for overnight. The reaction was quenched by the addition of water (150 mL). Saturated NaHCO$_3$ solution was used to neutralize the water layer to pH≅8. The CH$_2$Cl$_2$ layer and water layer were separated. The water layer was extracted by CH$_2$Cl$_2$ (150 mL×3). The CH$_2$Cl$_2$ layers were combined, washed by H$_2$O (150 mL×2) and saturated NaCl solution (150 mL×1), dried by Na$_2$SO$_4$ and concentrated to give crude product (2.6 g), which was purified by silica gel chromatography conducted on CombiFlash™ Sq 16× (gradient: 100% CH$_2$Cl$_2$ to 10% MeOH in CH$_2$Cl$_2$) to give 5-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-pentanoic acid ethyl ester (1.20 g; 23%). $^1$H NMR (300 MHz, CDCl$_3$) δ 7.52 (m, 1H), 7.37-7.22 (m, 3H), 7.08 (m, 1H), 6.60 (m, 3H), 5.87 (m, 1H), 5.19 (m, 3H), 4.12 (q, 2H, J=7.0 Hz), 3.71 (m, 2H), 3.38 (m, 3H), 2.92-2.78 (m, 3H), 2.66-2.48 (m, 7H), 2.41 (m, 1H), 2.31 (m, 2H), 2.15 (dd, 1H, J=10.0, 10.0 Hz), 1.96 (m, 2H), 1.74 (m, 1H), 1.67-1.44 (m, 4H), 1.25 (t, 3H, J=7.0 Hz), 1.14 (d, 3H, J=5.5 Hz), 0.99 (d, 3H, J=6.0 Hz).

EXAMPLE 10

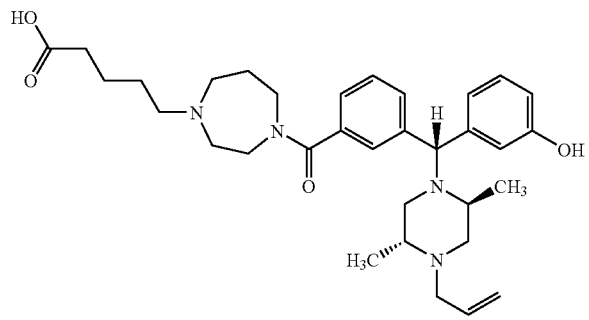

5-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-pentanoic acid To the compound of Example 9 (335 mg) in THF (4 mL) was added 1N NaOH solution (3.0 mL). The reaction was stirred at room temperature for overnight. The reaction solution was neutralized by the addition of 1 N HCl solution (3.0 mL). The mixture was put under rotary evaporator for the removal of THF. The remaining water layer was diluted by water (5 mL). The water layer was extracted by n-butanol (6 mL×3). The combined n-butanol layer was washed by water (5 mL×2) and concentrated to give crude product (225 mg), which was purified by silica gel chromatography conducted on CombiFlash™ Sq 16× (gradient: 100% $CH_2Cl_2$ to 30% MeOH in $CH_2Cl_2$) to give 5-(4-{3-[(R)-((2S,5R)-4-allyl-2,5-dimethyl-piperazin-1-yl)-(3-hydroxy-phenyl)-methyl]-benzoyl}-[1,4]diazepan-1-yl)-pentanoic acid (217 mg; 68%). $^1$H NMR (300 MHz, DMSO-d$_6$) δ 9.36 (bs, 1H), 8.31 (s, 1H), 7.35 (m, 3H), 7.18 (m, 1H), 7.12 (dd, 1H, J=8.0, 8.0 Hz), 6.66 (m, 3H), 5.78 (m, 1H), 5.19-5.00 (m, 3H), 3.56 (m, 2H), 3.30 (m, 2H), 3.19 (m, 1H), 2.86 (m, 1H), 2.72 (m, 2H), 2.59-2.49 (m, 7H), 2.37 (m, 1H), 2.20 (m, 2H), 2.07 (m, 1H), 1.83 (m, 2H), 1.65 (m, 1H), 1.50-1.35 (m, 4H), 1.07 (d, 3H, J=6.0 Hz), 0.92 (d, 3H, J=5.5 Hz).

EXAMPLE 11

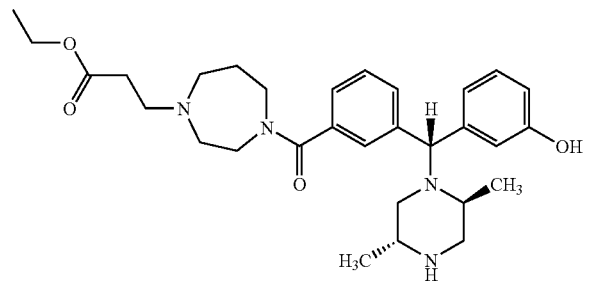

3-(4-{3-[(R)-((2S,5R)-2,5-dimethyl-piperazin-1-yl)-(3-hydroxy-phenyl)-methyl]-benzoyl}-[1,4]diazepan-1-yl)-propionic acid ethyl ester Bis(dibenzylideneacetone)palladium (247 mg) was added to the solution of 1,4-bis(diphenylphosphino)butane (148 mg) in THF (4 mL) under nitrogen at room temperature for 10 minutes. The resulting Pd-catalyst was transferred to the compound of Example 3 (2.42 g) and thiosalicylic acid (1.06 g) in THF (25 mL) via a syringe. The reaction was stirred under nitrogen at room temperature for overnight. The reaction mixture was concentrated. EtOAc (45 mL) was added to the remaining residual, followed by the addition of 1N aqueous HCl (70 mL). The EtOAc layer and acidic water layer were separated. The acidic water layer was extracted by EtOAc (30 mL×2). The acidic water layer was neutralized by saturated NaHCO$_3$ solution to pH≅8 and then extracted by n-butanol (60 mL×3). The combined n-butanol layer was washed by water (30 mL×1) and concentrated to give crude product 3-(4-{3-[(R)-((2S,5R)-2,5-dimethyl-piperazin-1-yl)-(3-hydroxy-phenyl)-methyl]-benzoyl}-[1,4]diazepan-1-yl)-propionic acid ethyl ester (2.2 g; 98%). $^1$H NMR (300 MHz, CD$_3$OD) δ 7.55 (m, 1H), 7.42 (m, 2H), 7.29 (d, 1H, J=7.5 Hz), 7.23 (dd, 1H, J=7.5, 7.5 Hz), 6.77 (m, 2H), 6.69 (s, 1H), 4.13 (m, 2H), 3.70 (m, 2H), 3.42 (m, 3H), 3.02-2.72 (m, 7H), 2.64-2.42 (m, 5H), 2.10 (m, 1H), 1.91 (m, 2H), 1.71 (m, 1H), 1.32 (d, 3H, J=6.0 Hz), 1.25 (m, 6H).

EXAMPLE 12

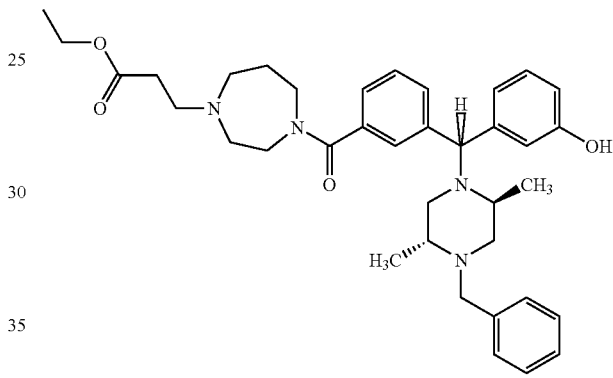

3-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-propionic acid ethyl ester The compound of Example 11 (560 mg), benzaldehyde (227.4 mg) and acetic acid (128.6 mg) in DMF was stirred under nitrogen at room temperature for 30 minutes. Na(OAc)$_3$BH (568 mg) was added to the solution. The reaction was stirred under nitrogen at room temperature for overnight. The reaction was quenched by the addition of saturated NH4Cl solution (1 mL), followed by the addition of H2O (80 mL) for the attempt of making organic product crashed out of water layer. The solution was cloudy but no solid was formed. The solution was extracted by EtOAc (40 mL×3). The combined organic layer was washed by water (50 mL×2) and brine (50 mL×1), dried by Na$_2$SO4 and concentrated to give crude product (466 mg), which was purified by silica gel chromatography conducted on CombiFlash™ Sq 16× (gradient: 100% $CH_2Cl_2$ to 10% MeOH in $CH_2Cl_2$) to give 3-(4-{3-[(R)-((2S,5R)-4-benzyl-2,5-dimethyl-piperazin-1-yl)-(3-hydroxy-phenyl)-methyl]-benzoyl}-[1,4]diazepan-1-yl)-propionic acid ethyl ester as white solid (290 mg; 44%). $^1$H NMR (300 MHz, CDCl$_3$) δ 7.59-7.45 (m, 1H), 7.40-7.22 (m, 8H), 7.13 (dd, 1H, J=7.0, 7.0 Hz), 6.71 (m, 3H), 5.08 (s, 1H), 4.16 (q, 2H, J=7.0 Hz), 3.98 (m, 1H), 3.70 (m, 2H), 3.35 (m, 2H), 3.25 (m, 1H), 2.84 (m, 3H), 2.66 (m, 6H), 2.47 (m, 3H), 2.11

(m, 2H), 1.93 (m, 1H), 1.70 (m, 1H), 1.27 (t, 3H, J=7.0 Hz), 1.13 (bs, 3H), 1.06 (d, 3H, J=5.5 Hz).

EXAMPLE 13

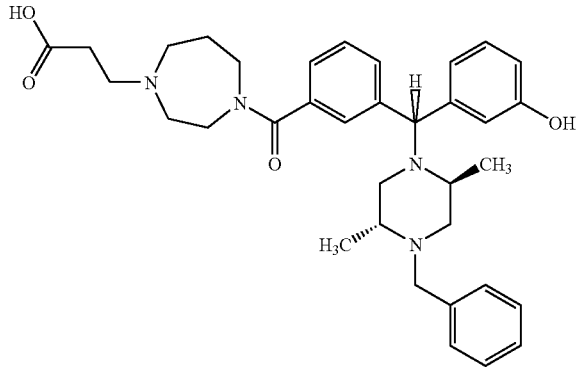

3-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-propionic acid To the compound of Example 12 (215 mg) in THF (4 mL) was added 1N NaOH solution (1 mL). The reaction was stirred at room temperature for overnight. The reaction solution was neutralized by the addition of 1 N HCl solution (1 mL). The mixture was put under rotary evaporator for the removal of THF. The remaining water layer was diluted by water (3 mL). The water layer was extracted by n-butanol (5 mL×3). The combined n-butanol layer was washed by water (5 mL×2) and concentrated to give crude product (200 mg), which was purified by silica gel chromatography conducted on CombiFlash™ Sq 16× (gradient: 100% $CH_2Cl_2$ to 30% MeOH in $CH_2Cl_2$) to give 3-(4-{3-[(R)-((2S,5R)-4-benzyl-2,5-dimethyl-piperazin-1-yl)-(3-hydroxy-phenyl)-methyl]-benzoyl }-[1,4]diazepan-1-yl)-propionic acid (133 mg; 65%). $^1$H NMR (300 MHz, DMSO-$d_6$) δ 9.36 (s, 1H), 7.36-7.17 (m, 9H), 7.12 (dd, 1H, J=7.5, 7.5 Hz), 6.67 (m, 3H), 4.97 (s, 1H), 3.76 (m, 1H), 3.57 (m, 2H), 3.42-3.16 (m, 3H), 2.75 (m, 2H), 2.69-2.49 (m, 8H), 2.37 (m, 1H), 2.31 (m, 1H), 1.98 (m, 1H), 1.90 (m, 1H), 1.79 (m, 1H), 1.63 (m, 1H), 1.01 (m, 6H).

EXAMPLE 14

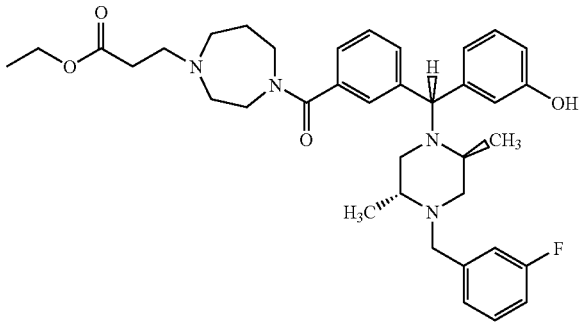

3-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-propionic acid ethyl ester The solution of 3-(4-{3-[(R)-((2S,5R)-2,5-Dimethyl-piperazin-1-yl)-(3-hydroxy-methyl)-benzoyl}-[1,4]diazepan-1-yl)-propionic acid ethyl ester (288 mg; Example 11), 3-fluorobenzaldehyde (137 mg) and acetic acid (66 mg) in DMF (3 mL) was stirred under nitrogen at room temperature for 20 minutes, followed by the addition of Na(OAc)$_3$BH (292 mg). The reaction was stirred under nitrogen at room temperature for overnight. The reaction was quenched by the addition of $H_2O$ (4 mL). The solution was neutralized by sat. NaHCO3 solution to pH≅7. The solution was extracted by EtOAc (5 mL×3). The combined organic layer was washed by water (5 mL×2) and brine (5 mL×1), dried by $Na_2SO_4$ and concentrated to give crude product (300 mg), which was purified by silica gel chromatography conducted on CombiFlash™ Sq 16× (gradient: 100% $CH_2Cl_2$ to 10% MeOH in $CH_2Cl_2$) to give 3-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-propionic acid ethyl ester as white solid (120 mg; 35%). $^1$H NMR (300 MHz, CDCl$_3$) δ 7.59-7.48 (m, 1H), 7.40-7.22 (m, 4H), 7.16-7.04 (m, 3H), 6.92 (m, 1H), 6.72 (m, 3H), 5.04 (bs, 1H), 4.15 (q, J=7.0 Hz, 2H), 3.92 (m, 1H), 3.77 (m, 1H), 3.71 (m, 1H), 3.43 (m, 1H), 3.35 (m, 1H), 3.24 (m, 1H), 2.94-2.81 (m, 3H), 2.72-2.44 (m, 9H), 2.05 (m, 2H), 1.96 (m, 1H), 1.75 (bs, 1H), 1.26 (t, J=7.0 Hz, 3H), 1.06 (m, 6H).

EXAMPLE 15

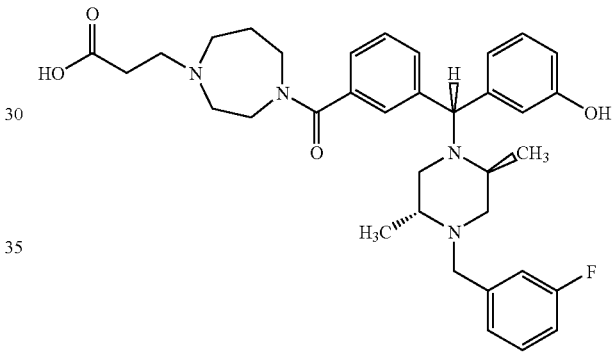

3-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-propionic acid The mixture of 3-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-propionic acid ethyl ester (800 mg, Example 14), THF (10 mL) and 1 N NaOH solution (6 mL) was stirred at room temperature for overnight. The reaction solution was neutralized by the addition of 1 N HCl solution (6 mL). The mixture was dried under rotary evaporator. For the complete removal of water, $CH_3OH$ (25 mL) was added to the flask containing the desired product and the resulting solution was dried by rotary evaporator. The process of adding CH3OH and drying CH3OH was repeated one more time. Ethanol (20 mL) was added to the residual remained in the flask. Solid (NaCl) was seen in the ethanol solution. The mixture was filtered thru a fritted filter. The solid was resined by ethanol (15 mL). The filtrate was concentrated to give crude product, which was purified by reverse phase C-18 column chromatography conducted on CombiFlash™ Sq 16× (gradient: 100% water to 100% methanol) to give 3-(4-{3-[(R)-[(2S,5R)-4-(3-fluoro-benzyl)-2,5-dimethyl-piperazin-1-yl]-(3-hydroxy-phenyl)-methyl]-benzoyl}-[1,4]diazepan-1-yl)-propionic acid (320 mg; 42%). $^1$H NMR (300 MHz, CD$_3$OD) δ 7.61 (m, 1H), 7.50-7.39 (m, 2H), 7.32 (m, 2H), 7.20-7.08 (m, 3H), 6.98 (m, 1H), 6.73 (m, 3H), 5.16 (s, 1H), 3.99-3.92 (m, 2H), 3.60 (bs, 1H), 3.50 (m, 2H), 3.35 (m, 2H), 3.23 (m, 3H), 3.08 (m, 1H), 2.99 (m, 1H), 2.75-2.66 (m, 4H), 2.54 (m, 1H), 2.46 (m, 1H), 2.17-1.99 (m, 4H), 1.13 (m, 6H).

The following homopiperazine derivatives were synthesized by similar methods described for above homopiperazine derivatives.

EXAMPLE 16

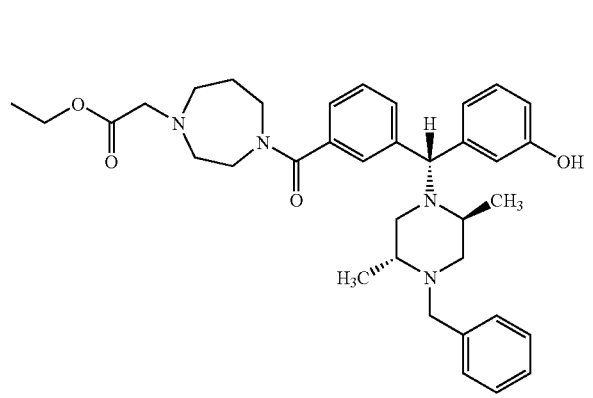

(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-acetic acid ethyl ester $^1$H NMR (300 MHz, CD$_3$OD) δ 7.53-7.25 (m, 9H), 7.17 (dd, J=8.0, 8.0 Hz, 1H), 6.71 (d, J=8.0 Hz, 2H), 6.65 (s, 1H), 5.21 (s, 1H), 4.16 (m, 2H), 4.06 (d, J=13.0 Hz, 1H), 3.80-3.68 (m, 2H), 3.43 (m, 5H), 2.94 (m, 1H), 2.85-2.67 (m, 6H), 2.62 (m, 1H), 2.20 (m, 1H), 2.05 (m, 1H), 1.93 (m, 1H), 1.74 (m, 1H), 1.25 (m, 3H), 1.18 (d, J=5.0 Hz, 3H), 1.13 (d, J=6.0 Hz, 3H).

EXAMPLE 17

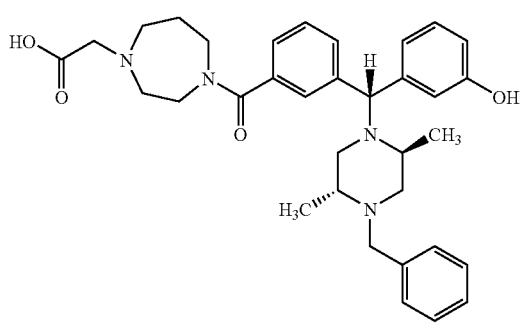

(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-acetic acid $^1$H NMR (300 MHz, CD$_3$OD) δ 7.59 (d, J=7.0 Hz, 1H), 7.49-7.36 (m, 8H), 7.20 (dd, J=8.0, 8.0 Hz, 1H), 6.74 (m, 3H), 5.27 (s, 1H), 4.45 (d, J=12.5 Hz, 1H), 3.93 (m, 2H), 3.74 (m, 2H), 3.57 (m, 2H), 3.37 (m, 6H), 3.01 (d, J=10.0 Hz, 1H), 2.91 (d, J=12.5 Hz, 1H), 2.75 (m, 2H), 2.26 (m, 2H), 2.12 (bs, 1H), 1.39 (d, J=6.5 Hz, 3H), 1.18 (d, J=5.5 Hz, 3H).

EXAMPLE 18

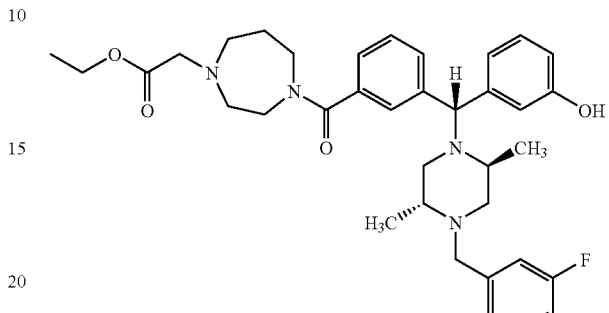

(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-acetic acid ethyl ester $^1$H NMR (300 MHz, CDCl$_3$) δ 7.54-7.13 (m, 6H), 7.05 (m, 2H), 6.91 (m, 1H), 6.74 (m, 3H), 5.04 (m, 1H), 4.19 (q, J=7.0 Hz, 2H), 3.82 (m, 3H), 3.38 (m, 3H), 3.22 (m, 1H), 2.95 (m, 1H), 2.84 (m, 1H), 2.76-2.61 (m, 7H), 2.02 (m, 3H), 1.75 (m, 1H), 1.28 (m, 3H), 1.07 (m, 6H).

EXAMPLE 19

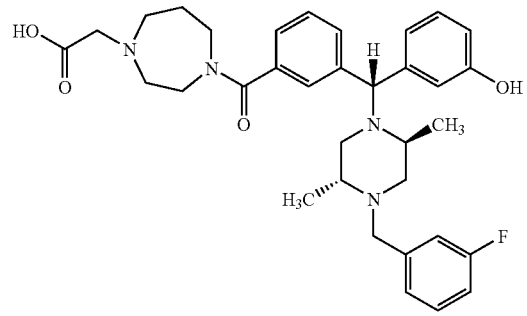

(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-acetic acid $^1$H NMR (300 MHz, CD$_3$OD) δ 7.50 (m, 2H), 7.39-7.24 (m, 3H), 7.12 (m, 3H), 6.96 (m, 1H), 6.70 (m, 3H), 5.13 (s, 1H), 3.91 (d, J=13.0, 1H), 3.75 (m, 2H), 3.44 (m, 2H), 3.27 (d, J=13.0 Hz, 1H), 3.13 (m, 2H), 2.89 (m, 1H), 2.77 (m, 1H), 2.71-2.58 (m, 6H), 2.03 (m, 3H), 1.78 (m, 1H), 1.12 (m, 6H).

EXAMPLE 20

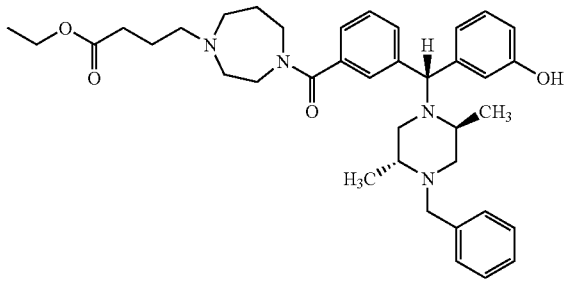

4-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-butyric acid ethyl ester ¹H NMR (300 MHz, CDCl₃) δ 7.54 (m, 1H), 7.37-7.23 (m, 8H), 7.12 (m, 1H), 6.67 (m, 3H), 5.06 (s, 1H), 4.14 (q, J=7.0 Hz, 2H), 3.95 (m, 1H), 3.72 (m, 2H), 3.47 (m, 1H), 3.36 (m, 1H), 3.24 (m, 1H), 2.84-2.48 (m, 10H), 2.33 (m, 2H), 2.02 (m, 3H), 1.79 (m, 3H), 1.26 (t, J=7.0 Hz, 3H), 1.10 (m, 3H), 1.05 (d, J=6.0 Hz, 3H).

EXAMPLE 21

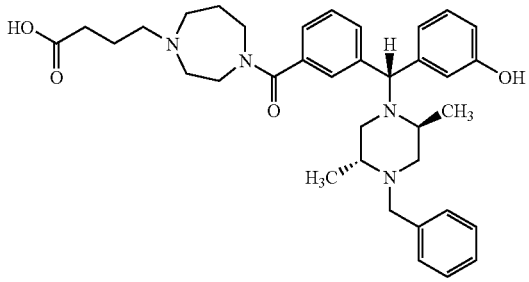

4-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-butyric acid ¹H NMR (300 MHz, CD₃OD) δ 7.60 (m, 1H), 7.49-7.27 (m, 8H), 7.18 (m, 1H), 6.71 (m, 3H), 5.21 (bs, 1H), 4.01 (m, 1H), 3.90 (m, 1H), 3.60 (m, 1H), 3.50 (m, 2H), 3.34 (m, 2H), 3.16 (m, 2H), 3.05 (m, 1H), 2.94 (m, 1H), 2.88 (m, 1H), 2.70 (m, 4H), 2.48 (m, 1H), 2.41 (m, 1H), 2.15 (m, 2H), 2.04 (m, 2H), 1.86 (m, 2H), 1.14 (m, 6H).

EXAMPLE 22

(ARD759)

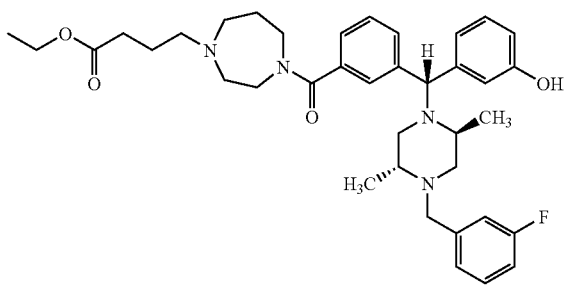

4-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-butyric acid ethyl ester ¹H NMR (300 MHz, CDCl₃) δ 7.57 (m, 1H), 7.36-7.20 (m, 5H), 7.15 (m, 1H), 7.05 (m, 2H), 6.91 (m, 1H), 6.72 (m, 2H), 5.04 (bs, 1H), 4.15 (q, J=7.0 Hz, 2H), 3.87 (m, 1H), 3.74 (m, 2H), 3.48 (m, 1H), 3.35 (m, 1H), 3.21 (m, 1H), 2.85 (m, 1H), 2.70-2.51 (m, 9H), 2.33 (m, 2H), 2.01 (m, 3H), 1.79 (m, 3H), 1.27 (t, J=7.0 Hz, 3H), 1.07 (m, 6H).

EXAMPLE 23

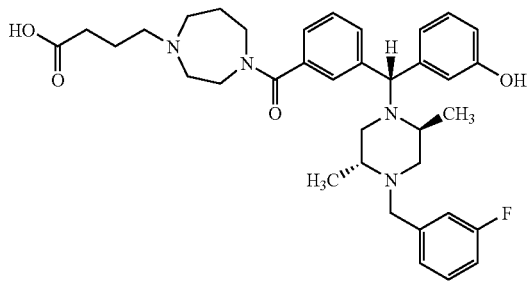

4-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-butyric acid ¹H NMR (300 MHz, CD₃OD) δ 7.62 (m, 1H), 7.49-7.28 (m, 4H), 7.20-7.07 (m, 3H), 6.98 (m, 1H), 6.73 (m, 3H), 5.16 (bs, 1H), 3.94 (m, 2H), 3.61 (m, 1H), 3.51 (m, 2H), 3.32 (m, 2H), 3.19 (m, 2H), 3.08 (m, 2H), 2.93 (m, 1H), 2.70 (m, 4H), 2.46 (m, 2H), 2.07 (m, 4H), 1.87 (m, 2H), 1.13 (m, 6H).

EXAMPLE 24

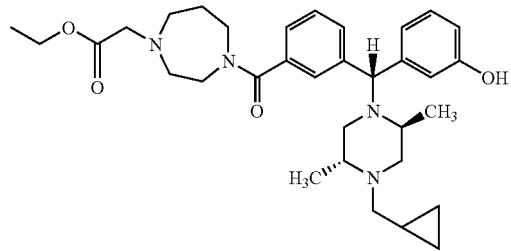

(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-acetic acid ethyl ester ¹H NMR (300 MHz, CD₃OD) δ 7.53 (m, 1H), 7.44 (m, 2H), 7.33 (m, 1H), 7.26 (m, 1H), 6.78 (m, 2H), 6.66 (s, 1H), 5.50 (s, 1H), 4.17 (m, 2H), 3.73 (m, 3H), 3.45 (m, 4H), 3.19-2.96 (m, 6H), 2.85 (m, 4H), 2.20 (m, 1H), 1.95 (m, 1H), 1.79 (m, 1H), 1.41 (d, 3H, J=5.5 Hz), 1.26 (m, 6H), 1.12 (m, 1H), 0.77 (m, 2H), 0.43 (m, 2H).

EXAMPLE 25

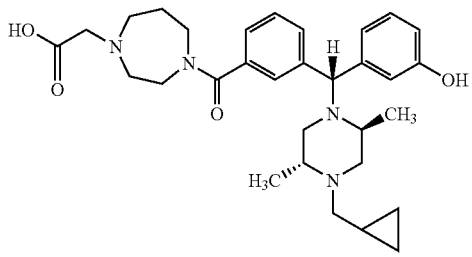

(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-acetic acid $^1$H NMR (300 MHz, CD$_3$OD) δ 7.62 (d, 1H, J=7.0 Hz), 7.44 (m, 3H), 7.22 (dd, 1H, J=7.5, 7.5 Hz), 6.78 (m, 3H), 5.38 (s, 1H), 3.98 (s, 1H), 3.79-3.37 (m, 10H), 3.08 (m, 3H), 2.96(m, 2H), 2.35-2.13 (m, 4H), 1.33 (m, 6H), 1.14(m, 1H), 0.74 (m, 2H), 0.46 (m, 2H).

EXAMPLE 26

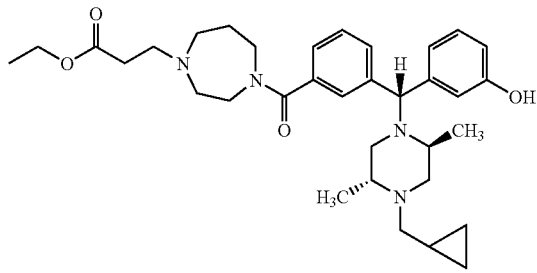

3-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-propionic acid ethyl ester $^1$H NMR (300 MHz, CD$_3$OD) δ 7.56 (m, 1H), 7.44 (m, 2H), 7.33 (m, 1H), 7.26 (m, 1H), 6.79 (m, 2H), 6.66 (s, 1H), 5.50 (s, 1H), 4.14 (m, 2H), 3.80 (m, 1H), 3.73 (m, 2H), 3.46 (m, 3H), 3.20-2.72 (m, 11H), 2.63 (m, 1H), 2.52 (m, 1H), 2.19 (m, 1H), 1.96 (m, 1H), 1.84 (m, 1H), 1.41 (m, 3H), 1.25 (m, 6H), 1.11 (m, 1H), 0.77 (m, 2H), 0.43 (m, 2H).

EXAMPLE 27

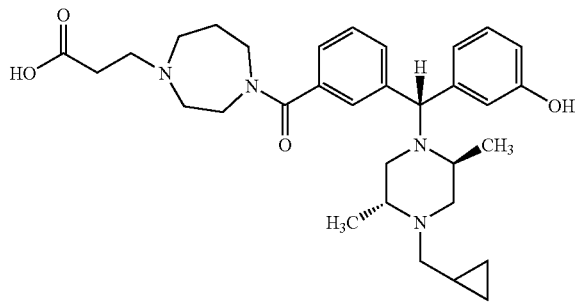

3-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-propionic acid $^1$H NMR (300 MHz, DMSO-d$_6$) δ 9.51 (s, 1H), 7.35 (m, 3H), 7.24 (m, 1H), 7.17 (m, 1H), 6.70 (m, 3H), 5.28 (s, 1H), 3.67 (m, 1H), 3.57 (m, 1H), 3.47-3.29 (m, 3H), 2.95-2.77 (m, 12H), 2.52 (m, 1H), 2.40 (m, 1H), 2.15 (m, 1H), 1.81 (m, 2H), 1.22 (d, 3H, J=5.0 Hz), 1.16 (m, 3H), 1.05 (m, 1H), 0.58 (m, 2H), 0.33 (m, 2H).

EXAMPLE 28

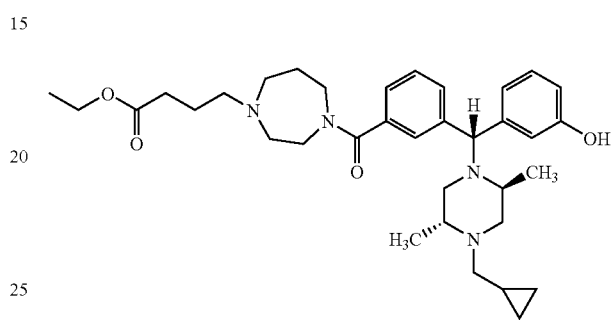

4-(4-{3-[(R)-((2S,5R)-4-Cyclopropylmethyl-2,5-dimethyl-piperazin-1-yl)-(3-methyl]-benzoyl}-[1,4] diazepan-1-yl)-butyric acid ethyl ester $^1$H NMR (300 MHz, CDCl$_3$) δ 0.15(s, 2H), 0.55(t, J=6.5 Hz, 2H), 0.89(m, 1H), 1.01 (d, J=6.0 Hz, 3H), 1.17(d, J=6.0 Hz, 3H), 1.25(t, J=7.00 Hz, 3H), 1.75(m, 3H), 1.93(s, 2H), 2.12 (m, 1H), 2.27-2.78(m, 13H), 3.12(m, 1H), 3.36(m, 2H), 3.72(m, 2H), 4.11 (q, J=7.00 Hz, 2H), 5.19(s, 1H), 6.61-6.65 (m, 3H), 7.10(m, 1H), 7.23-7.53(m, 4H).

EXAMPLE 29

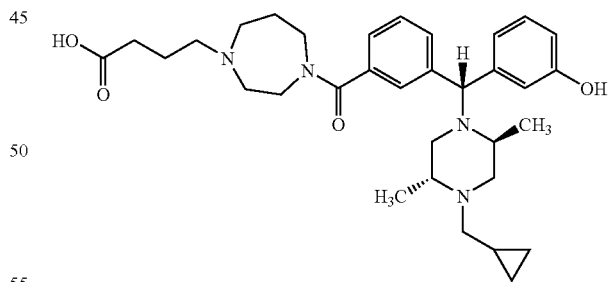

4-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-butyric acid $^1$H NMR (300 MHz, DMSO-d$_6$) δ 7.35 (m, 3H), 7.17 (m, 1H), 7.12 (m, 1H), 6.65 (m, 3H), 5.04 (s, 1H), 3.56 (m, 2H), 3.28 (m, 2H), 2.88 (m, 1H), 2.68 (m, 1H), 2.60-2.42 (m, 7H), 2.36 (m, 2H), 2.23-2.07 (m, 4H), 1.77 (m, 2H), 1.61 (m, 3H), 1.09 (d, 3H, J=6.0 Hz), 0.87 (d, 3H, J=6.0 Hz), 0.75 (m, 1H), 0.39 (m, 2H), 0.18 (m, 2H).

EXAMPLE 30

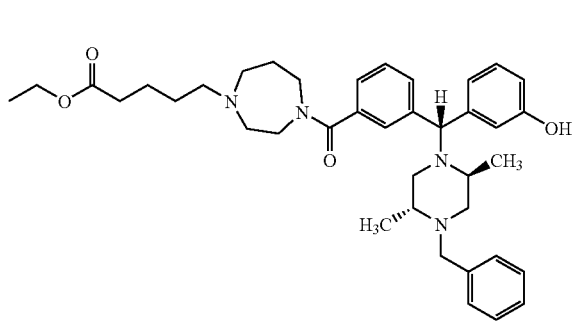

5-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-pentanoic acid ethyl ester $^1$H NMR (300 MHz, CDCl$_3$) δ 7.52 (m, 1H), 7.29 (m, 8H), 7.11 (m, 1H), 6.68 (m, 2H), 6.61 (s, 1H), 5.07 (s, 1H), 4.13 (q, 2H, J=7.0 Hz), 3.97 (d, 1H, J=12.5 Hz), 3.79-3.65 (m, 2H), 3.44 (m, 1H), 3.38 (m, 1H), 3.21 (d, 1H, J=12.5 Hz), 2.86 (s, 1H), 2.71-2.44 (m, 9H), 2.32 (m, 2H), 2.02 (m, 3H), 1.82 (m, 1H), 1.60 (m, 3H), 1.48 (m, 1H), 1.25 (t, 3H, J=7.0 Hz), 1.10 (d, 3H, J=5.0 Hz), 1.05 (d, 3H, J=6.0 Hz).

EXAMPLE 31

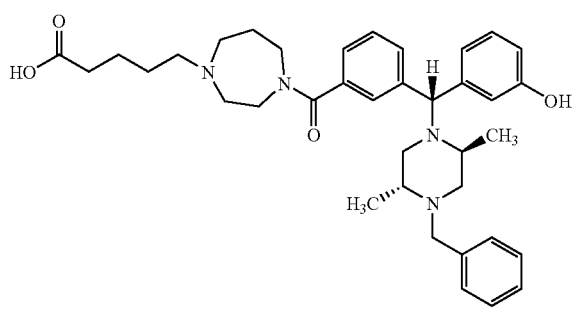

5-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-pentanoic acid $^1$H NMR (300 MHz, CD$_3$OD) δ 7.58 (m, 1H), 7.46-7.30 (m, 8H), 7.18 (dd, 1H, J=7.5, 7.5 Hz), 6.70 (m, 3H), 5.21 (s, 1H), 4.06 (m, 1H), 3.87 (m, 1H), 3.74 (m, 1H), 3.55-3.37 (m, 3H), 3.19 (m, 1H), 3.01-2.61 (m, 9H), 2.21 (m, 3H), 2.06 (m, 2H), 1.96 (m, 1H), 1.64 (m, 4H), 1.19 (m, 3H), 1.13 (d, 3H, J=6.0 Hz).

EXAMPLE 32

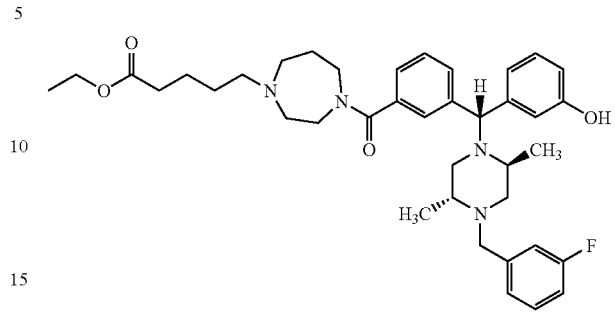

5-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-pentanoic acid ethyl ester $^1$H NMR (300 MHz, CDCl$_3$) δ 7.58 (m, 1H), 7.35-7.20 (m, 4H), 7.13 (dd, 1H, J=7.5, 7.5 Hz) 7.07 (m, 2H), 6.90 (ddd, 1H, J=8.5, 8.5, 2.0 Hz), 6.71 (m, 2H), 6.64 (s, 1H), 5.06 (s, 1H), 4.13 (q, 2H, J=7.0 Hz), 3.89 (d, 1H, J=13.5 Hz), 3.73 (m, 2H), 3.45 (m, 1H), 3.38 (m, 1H), 3.18 (d, 1H, J=13.5 Hz), 2.89 (m, 1H), 2.70-2.47 (m, 9H), 2.32 (m, 2H), 2.01 (m, 3H), 1.86 (m, 1H), 1.61 (m, 3H), 1.50 (m, 1H), 1.26 (t, 3H, J=7.0 Hz), 1.07 (m, 6H).

EXAMPLE 33

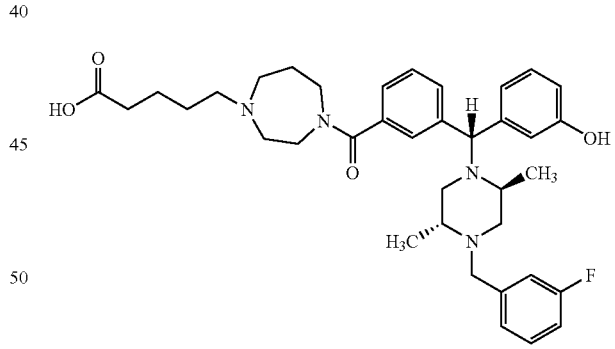

5-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-pentanoic acid $^1$H NMR (300 MHz, CD$_3$OD) δ 7.61 (m, 1H), 7.43 (m, 2H), 7.31 (m, 2H), 7.13 (m, 3H), 6.98 (m, 1H), 6.72 (m, 3H), 5.16 (s, 1H), 3.93 (m, 2H), 3.74 (m, 1H), 3.58 (m, 1H), 3.49 (m, 1H), 3.36 (m, 1H), 3.24 (m, 1H), 3.06 (m, 2H), 2.91 (m, 2H), 2.70 (m, 5H), 2.28 (m, 2H), 2.07 (m, 4H), 1.65 (m, 4H), 1.12 (m, 6H).

EXAMPLE 34

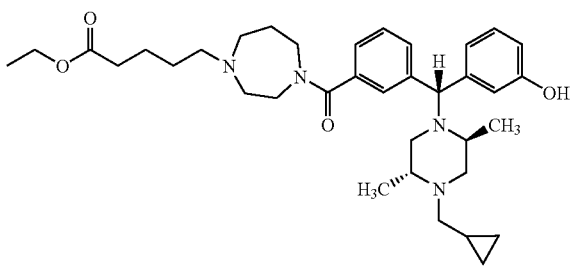

5-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-pentanoic acid ethyl ester ¹H NMR (300 MHz, CDCl₃) δ 7.57-7.39 (m, 2H), 7.35-7.23 (m, 2H), 7.08 (m, 1H), 6.69 (m, 3H), 5.21 (s, 1H), 4.13 (q, 2H, J=7.0 Hz), 3.70 (m, 2H), 3.38 (m, 2H), 3.10 (m, 1H), 2.77 (m, 1H), 2.70-2.47 (m, 8H), 2.40 (m, 1H), 2.33-2.22 (m, 3H), 2.10 (m, 1H), 1.95 (m, 2H), 1.71 (m, 1H), 1.61 (m, 2H),

EXAMPLE 35

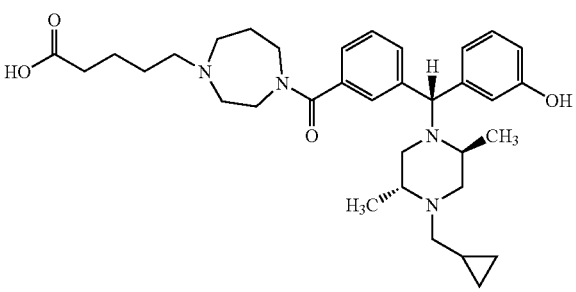

5-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-pentanoic acid ¹H NMR (300 MHz, CD₃OD) δ 7.58 (m, 1H), 7.43 (m, 2H), 7.31 (m, 1H), 7.21 (t, 1H, J=7.5 Hz), 6.76 (m, 2H), 6.69 (s, 1H), 5.32 (s, 1H), 3.82 (m, 1H), 3.72 (m, 1H), 3.43 (m, 3H), 3.06 (m, 2H), 2.94-2.56 (m, 10H), 2.21 (m, 2H), 2.13 (m, 1H), 2.01 (m, 1H), 1.87 (m, 1H), 1.60 (m, 4H), 1.31 (d, 3H, J=6.0 Hz), 1.15 (m, 3H), 0.99 (m, 1H), 0.65 (m, 2H), 0.29 (m, 2H).

EXAMPLE 36

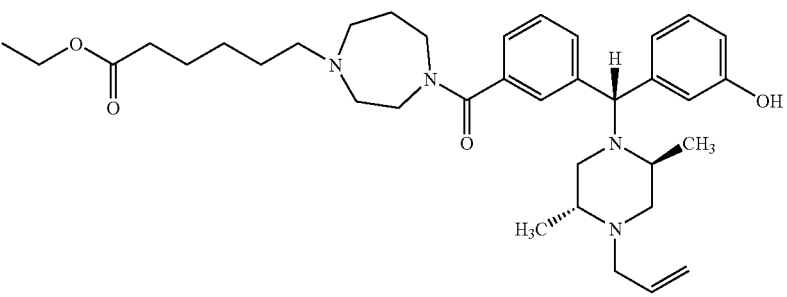

6-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-hexanoic acid ethyl ester ¹H NMR (300 MHz, CDCl₃) δ 0.96(d, J=6.0 Hz, 3H), 1.13(d, J=6.0, 3H), 1.24(t. J=7.0 Hz, 3H), 1.30 (m, 2H), 1.45 (m, 2H), 1.58-1.72(m, 3H), 1.93 (m, 2H), 2.11 (t, J10.5 Hz, 1H), 2.29 (t, J=7.5 Hz, 2H), 2.35-2.62 (m, 8H), 2.76-2.85 (m, 3H), 3.37(m, 3H), 3.73 (m, 2H), 4.11 (q, J=7.0 Hz, 2H), 5.17-5.20(m, 3H), 5.85 (m, 1H), 6.53-6.61(m, 3H), 7.07 (t, J=8.0 Hz, 1H), 7.22-7.38(m, 3H), 7.51 (m, 1H). 1.49 (m, 2H), 1.25 (t, 3H, J=7.0 Hz), 1.20 (d, 3H, J=6.0 Hz), 0.98 (d, 3H, J=6.0 Hz), 0.87 (m, 1H), 0.52 (m, 2H), 0.11 (m, 2H).

EXAMPLE 37

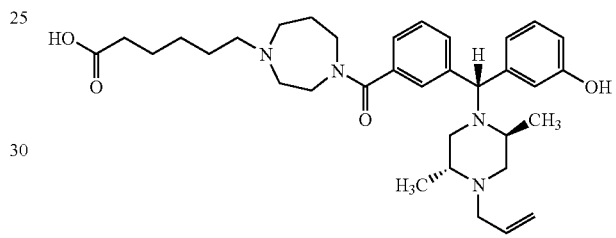

6-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-hexanoic acid ¹H NMR (300 MHz, CD₃OD) δ 7.59 (m, 1H), 7.42 (m, 2H), 7.30 (m, 1H), 7.20 (dd, 1H, J=8.0, 8.0 Hz), 6.74 (m, 2H), 6.66 (s, 1H), 5.90 (m, 1H), 5.33 (m, 3H), 3.84 (m, 1H), 3.73 (m, 1H), 3.51 (m, 3H), 3.11 (m, 2H), 2.95 (m, 3H), 2.78 (m, 5H), 2.62 (m, 1H), 2.39 (m, 1H), 2.22 (m, 2H), 2.02 (m, 2H), 1.91 (m, 1H), 1.63 (m, 3H), 1.53 (m, 1H), 1.37 (m, 2H), 1.24 (d, 3H, J=6.0 Hz), 1.10 (m, 3H).

EXAMPLE 38

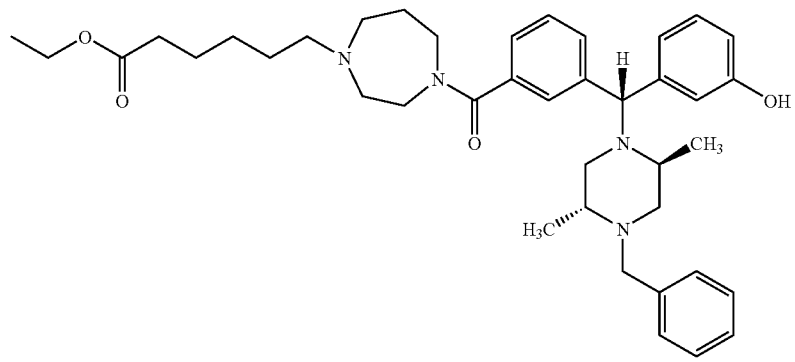

6-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-hexanoic acid ethyl ester $^1$H NMR (300 MHz, CDCl$_3$) δ 1.04 (s, 3H), 1.06 (s, 3H), 1.25 (t, J=7.0 Hz, 3H), 1.30 (m, 2H), 1.34-1.49 (m, 2H), 1.59-1.70 (m. 3H), 1.94-2.04(m, 3H), 2.30 (t, J=7.5 Hz, 2H), 2.35-2.69 (m, 9H), 2.77 (s, 1H), 3.12 (d, J=13.5 Hz, 1H), 3.36(m, 2H), 3.74 (m, 2H), 3.92 (d, J=13.5 Hz, 1H), 4.12 (q, J=7.0 Hz, 2H), 5.08 (s, 1H), 6.58 (s, 1H), 6.70 (m, 2H), 7.09-7.59 (m, 10H).

EXAMPLE 39

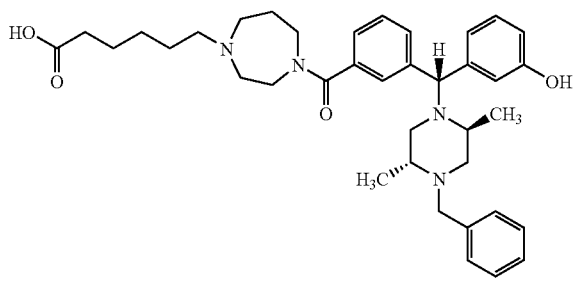

6-(4-{3-[(R)-((2S,5R)-4-Benzyl-2,5-dimethyl-piperazin-1-yl)-(3-hydroxy-phenyl)-methyl]-benzoyl}-[1,4]diazepan-1-yl)-hexanoic acid $^1$H NMR (300 MHz, CD$_3$OD) δ 7.59 (m, 2H), 7.45-7.30 (m, 7H), 7.18 (dd, 1H, J=8.0, 8.0 Hz), 6.73 (m, 2H), 6.66 (s, 1H), 5.21 (s, 1H), 4.07 (m, 1H), 3.85 (m, 1H), 3.73 (m, 1H), 3.54-3.38 (m, 3H), 3.15 (m, 1H), 2.96 (m, 1H), 2.91-2.62 (m, 8H), 2.23 (m, 3H), 2.06 (m, 2H), 1.93 (m, 1H), 1.61 (m, 4H), 1.38 (m, 2H), 1.19 (m, 3H), 1.13 (d, 3H, J=6.5 Hz).

EXAMPLE 40

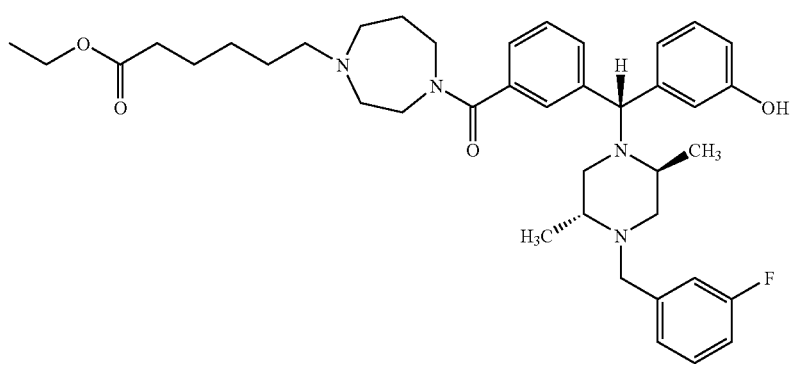

43

6-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-hexanoic acid ethyl ester

$^1$H NMR (300 MHz, CDCl$_3$) δ 1.05(s, 3H), 1.07 (s, 3H), 1.25 (t, J=7.0 Hz, 3H), 1.29-1.48 (m, 4H), 1.59-1.71 (m, 3H), 1.92-2.02 (m, 3H), 2.30 (t, J=7.5 Hz, 2H), 2.36-2.67 (m, 9H), 2.77 (s, 1H), 3.12 (d, J=13.5 Hz, 1H), 3.36 (m, 2H), 3.73 (m, 2H), 3.86 (d, J=13.5, 1H), 4.12 (q, J=7.0 Hz, 2H), 5.06 (s, 1H), 6.60 (s, 1H), 6.68 (d, J=7.5 Hz, 2H), 6.89 (m, 1H), 7.00-7.38 (m, 7H), 7.55 (m, 1H).

EXAMPLE 41

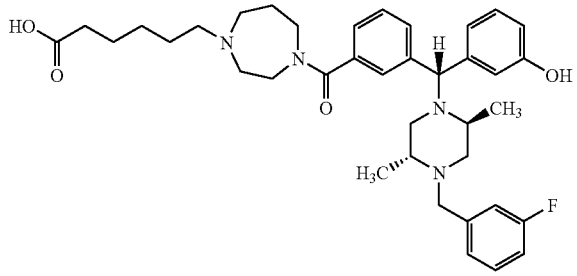

6-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-hexanoic acid

$^1$H NMR (300 MHz, CD$_3$OD) δ 7.60 (m, 1H), 7.42 (m, 2H), 7.31 (m, 2H), 7.13 (m, 3H), 6.98 (m, 1H), 6.72 (m, 3H), 5.16 (s, 1H), 3.96 (m, 1H), 3.86 (m, 1H), 3.74 (m, 1H), 3.55 (m, 1H), 3.48 (m, 1H), 3.35 (m, 1H), 3.18 (m, 1H), 3.00 (m, 2H), 2.89 (m, 2H), 2.70 (m, 5H), 2.24 (m, 2H), 2.14-1.95 (m, 4H), 1.63 (m, 4H), 1.38 (m, 2H), 1.13 (m, 6H).

EXAMPLE 42

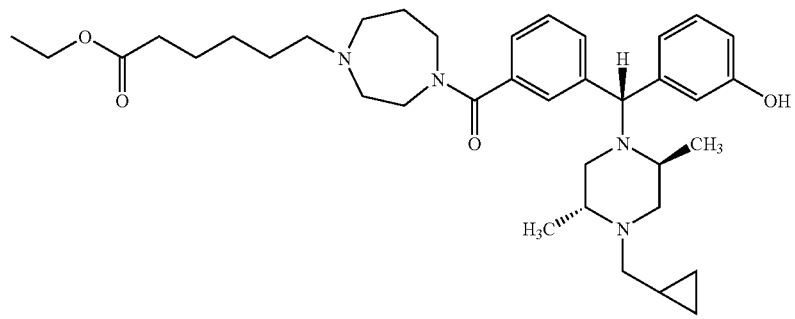

44

6-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-hexanoic acid ethyl ester

$^1$H NMR (300 MHz, CDCl$_3$) δ 0.10 (d, J=4.5 Hz, 2H), 0.51 (t, J=8.0 Hz, 2H), 0.86 (m, 1H), 0.96 (d, J=6.0 Hz, 3H), 1.18 (d, J=6.0 Hz, 3H), 1.25 (t, J=7.0 Hz, 3H), 1.30 (m, 2H), 1.45 (m, 2H), 1.61 (m, 2H), 1.71 (m, 2H), 1.93 (m, 2H), 2.09 (m, 1H), 2.29 (t, J=7.5 H, 2H), 2.35-2.65(m, 9H), 2.76 (s, 1H), 3.08 (d, J=11.0 Hz, 1H), 3.37 (m, 2H), 3.73 (m, 2H), 4.11 (q, J=7.0 Hz, 2H), 5.21 (s, 1H), 6.57 (m, 3H), 7.05-7.54 (m, 5H).

EXAMPLE 43

6-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-hexanoic acid

$^1$H NMR (300 MHz, CD$_3$OD) δ 7.58 (m, 1H), 7.42 (m, 2H), 7.32 (m, 1H), 7.22 (dd, 1H, J=8.0, 8.0 Hz), 6.76 (m, 2H), 6.68 (s, 1H), 5.34 (s, 1H), 3.80 (m, 1H), 3.72 (m, 1H), 3.44 (m, 2H), 3.12-2.56 (m, 11H), 2.54 (m, 1H), 2.18 (m, 4H), 1.99 (m, 1H), 1.85 (m, 1H), 1.58 (m, 4H), 1.35 (m, 5H), 1.17 (m, 3H), 1.00 (m, 1H), 0.67 (m, 2H), 0.30 (m, 2H).

EXAMPLE 44

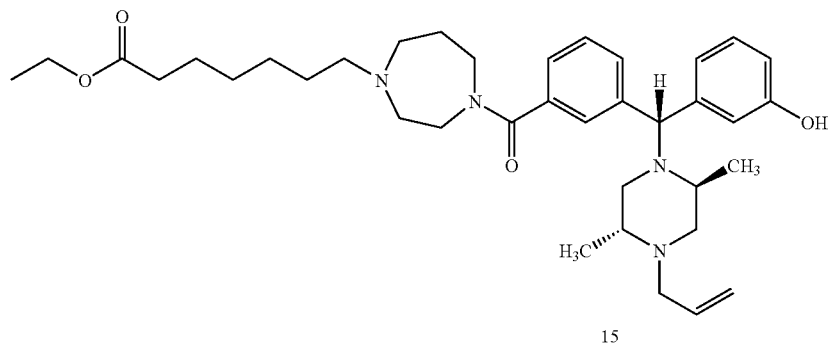

7-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-heptanoic acid ethyl ester $^1$H NMR (300 MHz, CDCl$_3$) δ 0.97 (d, J=6.0 Hz, 3H), 1.14 (d, J=6.0 Hz, 3H), 1.25 (t, J=7.0 Hz, 3H), 1.31 (m, 4H), 1.43 (m, 2H), 1.60 (m, 2H), 1.72 (m, 1H), 1.94 (m, 2H), 2.12 (t, J=10.5 Hz, 1H), 2.29 (t, J=7.5 Hz, 2H), 2.35-2.66 (m, 8H), 2.77-2.88 (m, 3H), 3.37 (m, 3H), 3.73 (m, 2H), 4.11 (q, J=7.0 Hz, 2H), 5.17-5.21 (m, 3H), 5.85 (m, 1H), 6.54 (s, 1H), 6.60 (m, 2H), 7.08 (t, J=7.5 Hz, 1H), 7.22-7.38 (m, 3H), 7.52 (t, J=9.0 Hz, 1H).

EXAMPLE 45

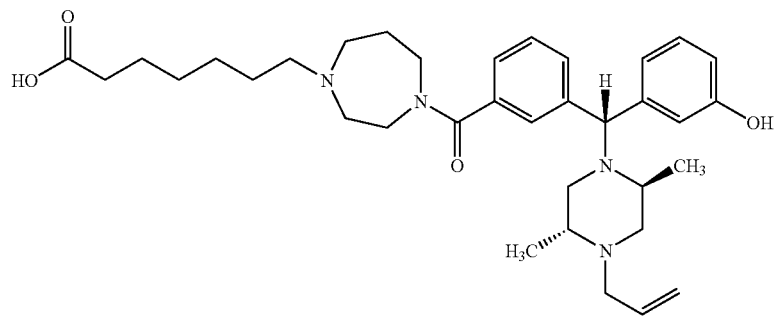

7-(4-{3-[(R)-((2S,5R)-4-Allyl-2,5-dimethyl-piperazin-1-yl)-(3-hydroxy-phenyl)-methyl]-benzoyl}-[1,4]diazepan-1-yl)-heptanoic acid $^1$H NMR (300 MHz, CD$_3$OD) δ 7.59 (m, 1H), 7.42 (m, 2H), 7.30 (m, 1H), 7.20 (dd, 1H, J=8.0, 8.0 Hz), 6.74 (m, 2H), 6.66 (s, 1H), 5.90 (m, 1H), 5.33 (m, 3H), 3.84 (m, 1H), 3.73 (m, 1H), 3.51 (m, 3H), 3.13 (m, 2H), 2.93 (m, 2H), 2.76 (m, 6H), 2.60 (m, 1H), 2.39 (m, 1H), 2.21 (m, 2H), 2.02 (m, 2H), 1.91 (m, 1H), 1.57 (m, 4H), 1.37 (m, 4H), 1.24 (d, 3H, J=6.5 Hz), 1.09 (m, 3H).

EXAMPLE 46

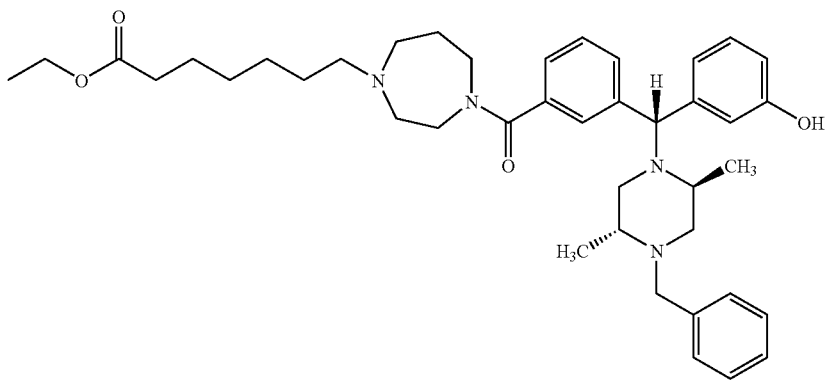

7-(4-{3-[(R)-((2S,5R)-4-Benzyl-2,5-dimethyl-piper-azin-1-yl)-(3-hydroxy-phenyl)-methyl]-benzoyl}-[1,4]diazepan-1-yl)-heptanoic acid ethyl ester $^1$H NMR (300 MHz, CDCl$_3$) δ: 1.05 (s, 3H), 1.07 (s, 3H), 1.25 (t, J=7.0 Hz, 3H), 1.30-1.46(m, 4H), 1.58-1.71 (m, 4H), 1.93-2.02 (m, 4H), 2.30 (t, J=7.32 Hz, 2H), 2.37-2.69 (m, 9H), 2.78 (s, 1H), 3.14 (d, J=9.3 Hz, 1H), 3.36 (m, 2H), 3.73 (t, J=6.1 Hz, 2H), 3.91 (d, J=10.0 Hz, 1H), 4.12 (q, J=7.0 Hz, 2H), 5.08 (s. 1H), 6.61(s. 1H), 6.70 (m. 2H), 7.11-7.38 (m, 9H), 7.54 (t, J=11.5 Hz, 1H).

EXAMPLE 47

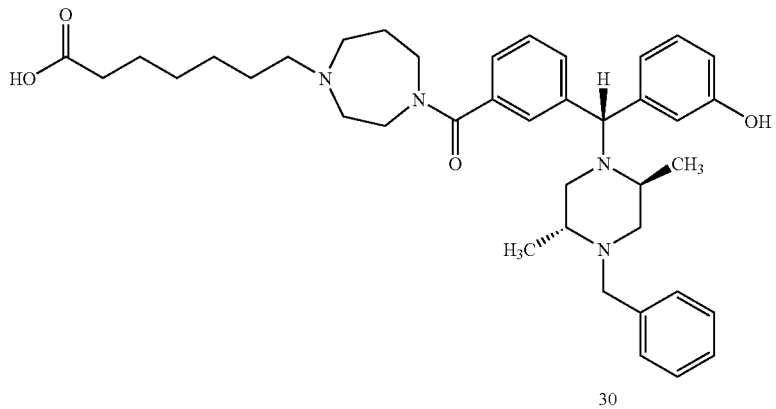

7-(4-{3-[(R)-((2S,5R)-4-Benzyl-2,5-dimethyl-piper-azin-1-yl)-(3-hydroxy-phenyl)-methyl]-benzoyl}-[1,4]diazepan-1-yl)-heptanoic acid $^1$H NMR (300 MHz, CD$_3$OD) δ 7.58 (m, 1H), 7.36 (m, 8H), 7.18 (dd, 1H, J=8.0, 8.0 Hz), 6.73 (m, 2H), 6.66 (s, 1H), 5.21 (s, 1H), 4.05 (m, 1H), 3.84 (m, 1H), 3.73 (m, 1H), 3.45 (m, 3H), 3.13 (m, 1H), 2.94 (m, 2H), 2.84-2.60 (m, 7H), 2.19 (m, 3H), 2.06 (m, 2H), 1.93 (m, 1H), 1.58 (m, 4H), 1.37 (m, 4H), 1.18 (m, 3H), 1.13 (d, 3H, J=6.0 Hz).

EXAMPLE 48

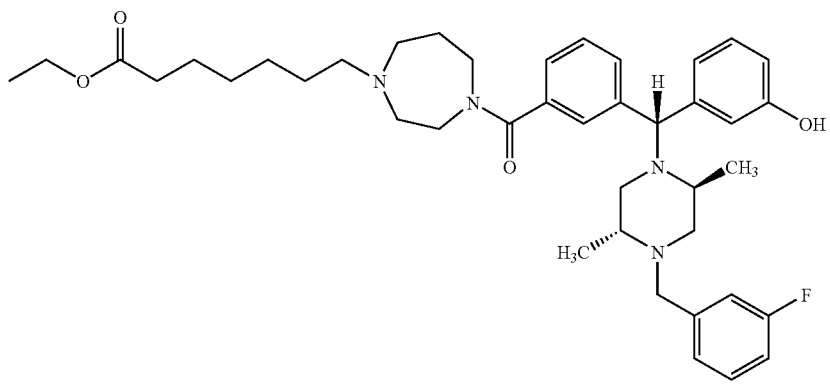

7-(4-{3-[(R)-[(2S,5R)-4-(3-Fluoro-benzyl)-2,5-dim-ethyl-piperazin-1-yl]-(3-hydroxy-phenyl)-methyl]-benzoyl}-[1,4]diazepan-1-yl)-heptanoic acid ethyl ester $^1$H NMR (300 MHz, CDCl$_3$) δ 1.06 (s, 3H), 1.08 (s, 3H), 1.25 (t, J=7.0 Hz, 3H), 1.30 (m, 2H), 1.41-1.46 (m, 2H), 1.58-1.71 (m, 4H), 1.93-2.03 (m, 4H), 2.30 (t, J=7.5 Hz. 2H), 2.37-2.68 (m, 9H), 2.78 (s, 1H), 3.14 (d, J=10.0 Hz, 1H), 3.36 (m, 2H), 3.73 (m, 2H), 3.85 (d, J=12.5 Hz, 1H), 4.12 (q, J=7.0 Hz, 2H), 5.07 (s, 1H), 6.64 (s, 1H), 6.72 (t, J=8.0 Hz, 2H), 6.90 (t, J=8.0 Hz, 1H), 7.01-7.38 (m, 7H), 7.54 (t, J=10.0 Hz, 1H).

EXAMPLE 49

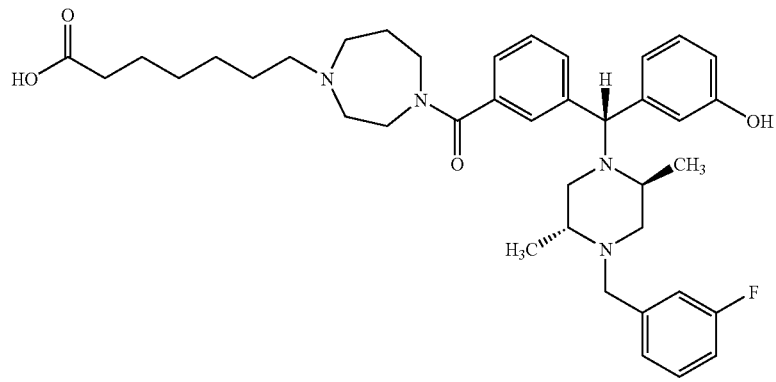

7-(4-{3-[(R)-[(2S,5R)-4-(3-Fluoro-benzyl)-2,5-dimethyl-piperazin-1-yl]-(3-hydroxy-phenyl)-methyl]-benzoyl}-[1,4]diazepan-1-yl)-heptanoic acid $^1$H NMR (300 MHz, CD$_3$OD) δ 7.59 (m, 1H), 7.42 (m, 2H), 7.29 (m, 2H), 7.13 (m, 3H), 6.98 (m, 1H), 6.72 (m, 3H), 5.16 (s, 1H), 3.95 (m, 1H), 3.86 (m, 1H), 3.73 (m, 1H), 3.55 (m, 1H), 3.47 (m, 1H), 3.35 (m, 1H), 3.18 (m, 1H), 3.00 (m, 2H), 2.86 (m, 2H), 2.69 (m, 5H), 2.23 (m, 2H), 2.07 (m, 3H), 1.95 (m, 1H), 1.63 (m, 4H), 1.38 (m, 4H), 1.13 (6H).

EXAMPLE 50

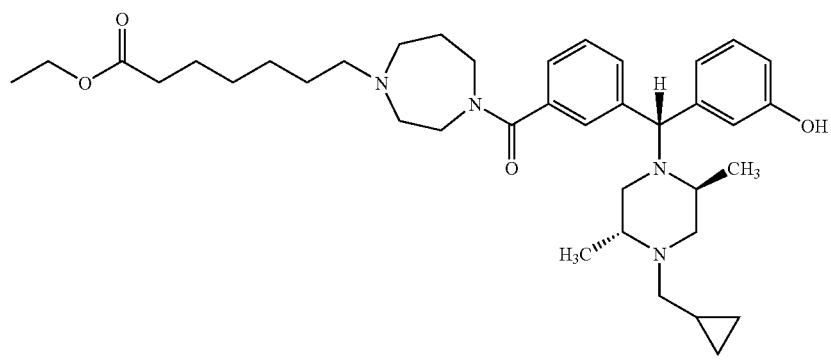

7-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-heptanoic acid ethyl ester $^1$H NMR (300 MHz, CDCl$_3$) δ 0.11 (d, J=4.5 Hz, 2H), 0.52 (t, J=8.0 Hz, 2H), 0.87 (m, 1H), 0.97 (d, J=5.95 Hz, 3H), 1.18 (d, J=5.79 Hz, 3H), 1.25 (t, J=7.16 Hz, 3H), 1.29-1.46 (m, 6H), 1.60 (m, 2H), 1.73 (m, 2H), 1.95 (m, 2H), 2.09 (m, 1H), 2.29 (t, J=7.5 Hz, 2H), 2.37-2.69 (m, 9H), 2.78 (s, 1H), 3.09 (d, J=11.5 Hz, 1H), 3.37 (m, 2H), 3.73 (m, 2H), 4.11 (q, J=7.0 Hz, 2H), 5.20 (s, 1H), 6.61 (m, 3H), 7.08 (t, J=8.0 Hz, 1H), 7.23-7.39 (m, 3H), 7.51 (t, J=8.5 Hz, 1H).

EXAMPLE 51

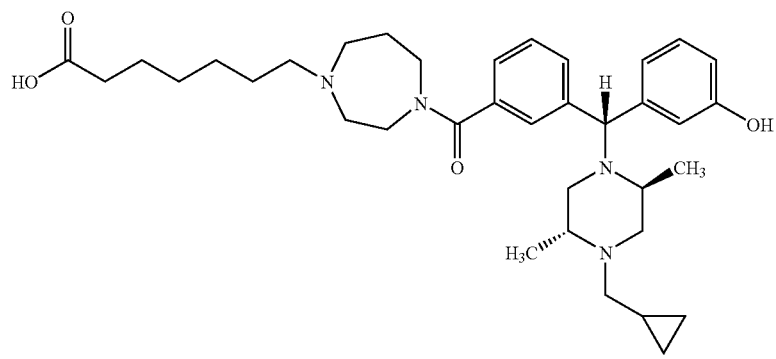

7-(4-{3-[(R)-((2S,5R)-4-Cyclopropylmethyl-2,5-dimethyl-piperazin-1-yl)-(3-hydroxy-phenyl)-methyl]-benzoyl}-[1,4]diazepan-1-yl)-heptanoic acid $^1$H NMR (300 MHz, CD$_3$OD) δ 7.58 (m, 1H), 7.42 (m, 2H), 7.31 (m, 1H), 7.21 (dd, 1H, J=8.0, 8.0 Hz), 6.76 (m, 2H), 6.68 (s, 1H), 5.32 (m, 1H), 3.79 (m, 1H), 3.72 (m, 1H), 3.43 (m, 2H), 3.12-2.74 (m, 10H), 2.68 (m, 2H), 2.52 (m, 1H), 2.15 (m, 3H), 1.98 (m, 1H), 1.83 (m, 1H), 1.60 (m, 3H), 1.48 (m, 1H), 1.33 (7H), 1.16 (m, 3H), 1.00 (m, 1H), 0.64 (m, 2H), 0.30 (m, 2H).

EXAMPLE 52

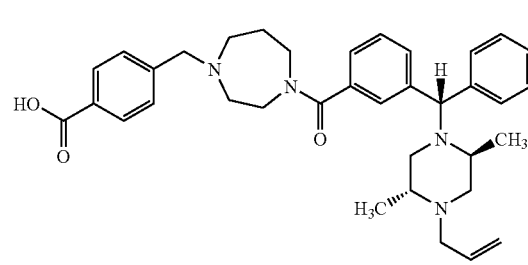

4-(4-{3-[(R)-((2S,5R)-4-Allyl-2,5-dimethyl-piperazin-1-yl)-(3-hydroxy-phenyl)-methyl]-benzoyl}-[1,4]diazepan-1-ylmethyl)-benzoic acid $^1$H NMR (300 MHz, CD$_3$OD) δ 7.92 (m, 2H), 7.53 (m, 1H), 7.41 (m, 3H), 7.30 (m, 2H), 7.17 (m, 1H), 6.72 (m, 3H), 5.91 (m, 1H), 5.42 (m, 2H), 5.26 (m, 1H), 3.79-3.62 (m, 3H), 3.44 (m, 2H), 3.31 (m, 1H), 3.13 (m, 1H), 2.98 (m, 1H), 2.87 (m, 1H), 2.82-2.77 (m, 4H), 2.66-2.58 (m, 4H), 2.11 (m, 1H), 1.95 (m, 1H), 1.75 (m, 1H), 1.24 (m, 3H), 1.15 (m, 3H).

EXAMPLE 53

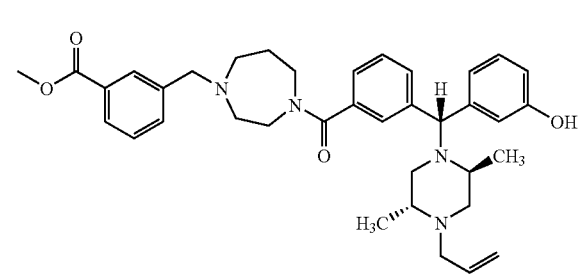

3-(4-{3-[(R)-((2S,5R)-4-Allyl-2,5-dimethyl-piperazin-1-yl)-(3-hydroxy-phenyl)-methyl]-benzoyl}-[1,4]diazepan-1-ylmethyl)-benzoic acid methyl ester NMR (300 MHz, CDCl$_3$) δ: 0.98 (s, 3H), 1.13 (s, 3H), 1.71 (s, 1H), 1.95 (m, 2H), 2.16(t, J=10.0 Hz, 1H), 2.53 (m, 4H), 2.68 (s, 2H), 2.78-2.94 (m, 3H), 3.42 (m, 3H), 3.59(s, 1H), 3.67 (s. 1H), 3.73 (m, 2H), 3.91 (s, 3H), 5.17 (m, 3H), 5.85 (m, 1H), 6.62(m, 3H), 7.07 (m, 1H), 7.26-7.42 (m, 4H), 7.48 (m, 2H), 7.92 (m, 2H).

EXAMPLE 54

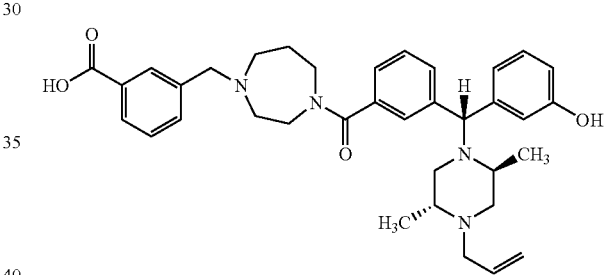

3-(4-{3-[(R)-((2S,5R)-4-Allyl-2,5-dimethyl-piperazin-1-yl)-(3-hydroxy-phenyl)-methyl]-benzoyl}-[1,4]diazepan-1-ylmethyl)-benzoic acid $^1$H NMR (300 MHz, CD$_3$OD) δ 7.92 (m, 2H), 7.52 (m, 2H), 7.38 (m, 3H), 7.29 (m, 1H), 7.16 (m, 1H), 6.72 (m, 3H), 5.91 (m, 1H), 5.43 (m, 2H), 5.25 (m, 1H), 3.72 (m, 5H), 3.43 (m, 2H), 3.31 (m, 1H), 3.15 (m, 1H), 2.98-2.78 (m, 5H), 2.62 (m, 3H), 2.12 (m, 1H), 1.97 (m, 1H), 1.77 (m, 1H), 1.24 (m, 3H), 1.15 (m, 3H).

EXAMPLE 55

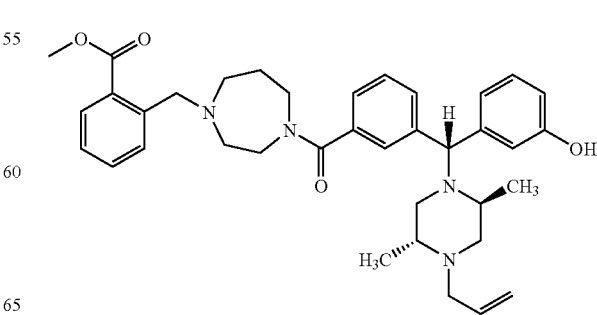

2-(4-{3-[(R)-((2S,5R)-4-Allyl-2,5-dimethyl-piperazin-1-yl)-(3-hydroxy-phenyl)-methyl]-benzoyl}-[1,4]diazepan-1-ylmethyl)-benzoic acid methyl ester NMR (300 MHz, CDCl₃) δ: 0.96 (s, 3H), 1.13 (s, 3H), 1.64 (s, 2H), 1.91 (m, 2H), 2.11 (t, J=9.5 Hz. 1H), 2.44-2.62 (m, 6H), 2.75-2.87 (m, 3H), 3.36 (s, 3H), 3.70 (m, 2H), 3.79 (d, J=10.0 Hz, 1H), 3.87 (s, 3H), 5.15 (s, 2H), 5.20 (s, 1H), 5.85 (m, 1H), 6.61 (m, 3H), 7.08 (t, J=7.5 Hz, 1H), 7.24-7.55 (m, 7H), 7.67 (d, J=7.32 Hz, 1H).

EXAMPLE 56

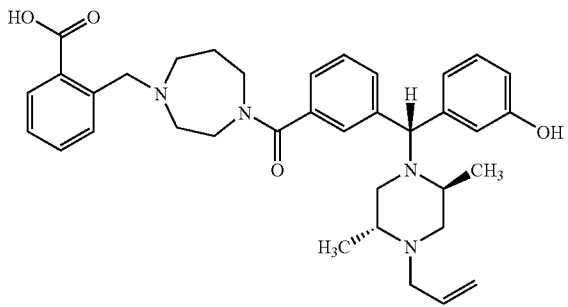

2-(4-{3-[(R)-((2S,5R)-4-Allyl-2,5-dimethyl-piperazin-1-yl)-(3-hydroxy-phenyl)-methyl]-benzoyl}-[1,4]diazepan-1-ylmethyl)-benzoic acid ¹H NMR (300 MHz, CD₃OD) δ 7.92 (m, 1H), 7.59 (m, 1H), 7.42 (m, 6H), 7.17 (dd, 1H, J=8.0, 8.0 Hz), 6.69 (m, 3H), 5.87 (m, 1H), 5.24 (m, 3H), 4.24 (m, 2H), 3.89 (m, 2H), 3.62 (m, 1H), 3.51 (m, 1H), 3.42 (m, 1H), 3.31 (m, 1H), 3.21 (m, 2H), 3.06 (m, 1H), 2.95 (m, 1H), 2.87 (m, 1H), 2.64 (m, 3H), 2.23 (m, 1H), 2.10 (m, 1H), 1.95 (m, 2H), 1.21 (d, 3H, J=6.0 Hz), 1.01 (d, 3H, J=6.0).

Piperazine Derivatives

EXAMPLE 57

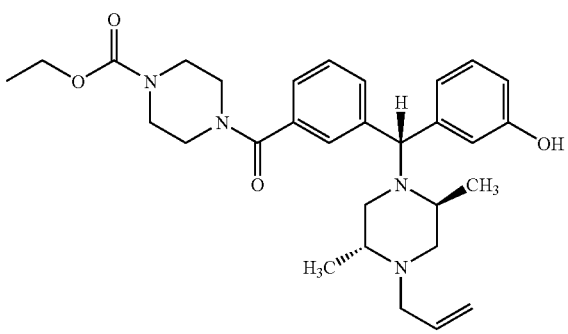

4-{3-[(R)-((2S,5R)-4-Allyl-2,5-dimethylpiperazin-1-yl)(3-hydroxy-phenyl)methyl]benzoyl}piperazine-1-carboxylic acid ethyl ester Acid A (2.00 g, 5.26 mmol) was weighed in a 250 mL, 3-necked round bottom flask and stirred under nitrogen in 150 mL of dichloromethane. A calcium chloride drying tube was placed on the flask. Thionyl chloride (0.54 mL, 7.36 mmol) was added to the cloudy mixture, followed by the addition of 2 drops of DMF. The mixture was stirred at room temperature for an hour and became a clear light brown solution.

The resulting acid chloride was poured into an addition funnel with a drying tube, which was fitted on the top of a round bottom flask containing ethyl 1-piperazine-carboxylate (4.62 mL, 31.54 mmol, 6 equiv.) and triethylamine (2.20 mL, 15.77 mmol) in 100 mL of dichloromethane. The acid chloride was added dropwise via the addition funnel to the amine solution over 1 hour. The mixture solution was allowed to stir at room temperature overnight. Water (200 mL) and saturated sodium hydrogencarbonate (100 mL) were added to the reaction solution and the two layers were separated. The water layer was extracted with dichloromethane (150 mL×3). The combined organic layer was washed with water (200 mL×3) and saturated sodium chloride solution (200 mL), dried over sodium sulfate, and the solvent was removed under vacuum. The crude material (4.85 g) was obtained as a dark pink liquid and was chromatographed on a Biotage silica gel column (32-63 μm, 60 A, cartridge Lot#40M1464-1) eluting first with dichloromethane to remove the less polar contaminant, then with 5% methanol in dichloromethane. The desired fractions were combined and the solvent was removed under reduced pressure to give 1.44 g (52%) of 4-{3-[(R)-((2S,5R)-4-allyl-2,5-dimethyl-piperazin-1-yl)(3-hydroxyphenyl)methyl]benzoyl}piperazine-1-carboxylic acid ethyl ester as a light yellow solid.

¹H NMR (300 MHz, d₆-DMSO): ☐ 0.90-0.92 (d, J=5.9 Hz, 3H); 1.04-1.06 (d, J=6.1 Hz, 3H); 1.14-1.19 (t, 3H), 1.78-1.84 (dd, 1H); 2.03-2.09 (dd, 1H); 2.26-2.29 (m, 1H); 2.48-2.53 (m, 4H); 2.68-2.71 (dd, 1H); 2.78-2.85 (dd, 1H); 3.12-3.18 (dd, 1H); 3.33-3.55 (m, 6H); 4.00-4.07 (q, 2H); 4.99 (s, 1H); 5.05-5.17 (m, 2H); 5.72-5.80 (m, 1H); 6.63-6.69 (m, 3H); 7.09-7.14 (m, 1H); 7.21-7.24 (m, 1H); 7.34-7.46 (m, 3H); 9.34 (s, 1H). Calculated for C₃₀H₄₀N₄O₄.0.60CH₃OH: C, 68.08; H, 7.92; N, 10.38. Found: C, 67.96; H, 7.78; N, 10.74.

EXAMPLE 58

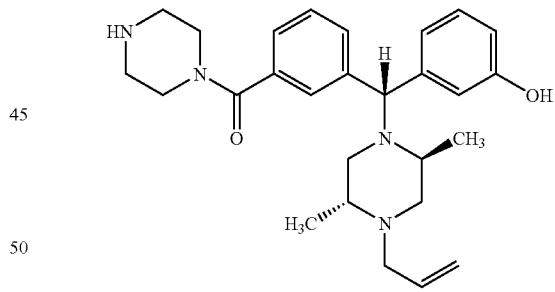

{3-[(R)-((2S,5R)-4-Allyl-2,5-dimethyl-piperazin-1-yl)-(3-hydroxy-phenyl)-methyl]-phenyl}-piperazin-1-yl-methanone The title compound was made by a procedure identical to that of Example 57 with 3.00 g of Acid A (7.38 mmol) and 4.08 g of piperazine (47.3 mmol, 6 equiv.) to give 2.46 g (74%) of desired compound as a yellow solid. ¹H NMR (300 MHz, DMSO-d₆): ☐ 0.90-0.92 (d, J=5.9 Hz, 3H); 1.04-1.06 (d, J=6.1 Hz, 3H); 1.80-1.82 (m, 1H); 2.02-2.08 (dd, 1H); 2.48-2.71 (m, 10H); 2.77-2.84 (dd, 1H); 3.14-3.47 (m, 3H); 4.59 (s, 1H); 4.98 (s, 1H); 5.05-5.17 (dd, 2H); 5.69-5.82 (m, 1H); 6.63-6.68 (m, 3H); 7.07-7.19 (m, 2H); 7.31-7.42 (m, 3H); 9.36 (s, 1H). Calculated for $C_{27}H_{36}N_4O_4 \cdot 0.38 CH_2Cl_2 \cdot 0.10 CH_3OH$: C, 68.18; H, 7.74; N, 11.57. Found: C, 68.68; H, 7.75; N, 11.56.

EXAMPLE 59

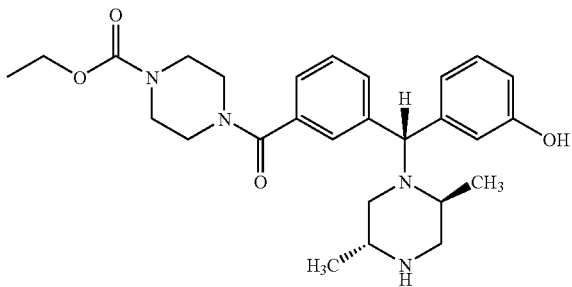

4-{3-[(R)-((2S,5R)-2,5-dimethyl-piperazin-1-yl)-(3-hydroxy-phenyl)-methyl]-benzoyl}-piperazine-1-carboxylic acid ethyl ester The allyl portion of the compound of Example 57 (5.76 g, 11.1 mmol) was removed using tris(triphenylphosphine)rhodium (I) chloride (1.18 g, 1.27 mmol) as follows. The reaction mixture in acetonitrile (80 mL) and water (20 mL) was heated under a gentle reflux and the solvent was allowed to distill off slowly. An additional volume of acetonitrile/water (4:1, 100 mL) was added with a rate such as to maintain a steady distillation. After the addition of solvent was completed, the distillation was continued until the volume was reduced to approximately 50 mL. The cooled solution was concentrated under reduced pressure. The residual dark brown solid was purified by chromatography on Biotage silica gel column (32-63 μm, 60 A, cartridge Lot#40S1614-1) eluting first with dichloromethane to remove the less polar contaminant, then using 5% methanol in dichloromethane with 1 mL of 50% NH4OH, then 10% methanol in dichloromethane. The desired fractions were combined and the solvent was removed under reduced pressure. The amine 4-{3-[(R)-((2S,5R)-2,5-dimethyl-piperazin-1-yl)-(3-hydroxy-phenyl)-methyl]-benzoyl}-piperazine-1-carboxylic acid ethyl ester was obtained as a yellow solid (3.88 g, 73%).

EXAMPLE 60

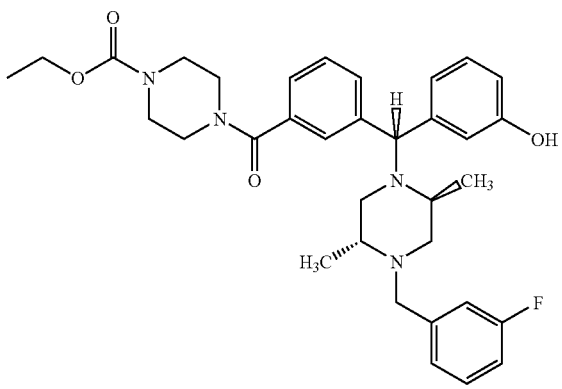

4-{3-[(R)-[(2S,5R)-4-(3-Fluorobenzyl)-2,5-dimethylpiperazin-1-yl]-(3-hydroxyphenyl)methyl]benzoyl}piperazine-1-carboxylic acid ethyl ester The above free amine (1.0 g, 2.08 mmol, Example 59) and 3-fluorobenzaldehyde (0.52 g, 4.16 mmol) were placed in a 50 mL flask and sealed under nitrogen. Tetrahydrofuran (30 mL) and 0.26 mL of acetic acid (4.58 mmol, 2.20 equiv.) were added. The reaction was stirred at room temperature for 20 minutes, and then sodium triacetoxyborohydride (1.10 g, 5.20 mmol) was added and stirred overnight. The reaction solution was concentrated under reduced pressure. The residue was partitioned between ethyl acetate (50 mL) and saturated sodium hydrogencarbonate (25 mL). The organic layer was washed with brine, dried over $Na_2SO_4$ and concentrated under reduced pressure. The residual dark brown oil (1.68 g) was purified by chromatography on Biotage silica gel column (32-63 μm, 60 A, cartridge Lot#40S1614-1) eluting first with dichloromethane to remove the less polar contaminant, then using 2.5% methanol in dichloromethane. The desired fractions were combined and the solvent was removed under reduced pressure. 0.96 g of 4-{3-[(R)-[(2S,5R)-4-(3-fluorobenzyl)-2,5-dimethyl-piperazin-1-yl]-(3-hydroxy-phenyl)-methyl]-benzoyl}-piperazine-1-carboxylic acid ethyl ester was obtained as a light yellow solid. $^1$H NMR (300 MHz, d$_6$-DMSO): ☐ 1.01-1.03 (d, J=5.8 Hz, 6H); 1.14-1.19 (t, 3H), 1.90-2.02 (m, 2H); 2.48 (s, 4H); 2.58-2.67 (m, 4H); 3.33-3.54 (m, 5H); 3.71-3.76 (dd, 1H); 4.00-4.07 (q, 2H); 4.94 (s, 1H); 6.62-6.72 (m, 3H); 6.98-7.14 (m, 4H); 7.21-7.48 (m, 5H); 9.35 (s, 1H). Calculated for $C_{34}H_{41}FN_4O_4 \cdot 0.17\ CH_2Cl_2$: C, 68.04; H, 6.91; N, 9.29; F, 3.15. Found: C, 68.02; H, 6.92; N, 9.24; F, 3.28.

EXAMPLE 61

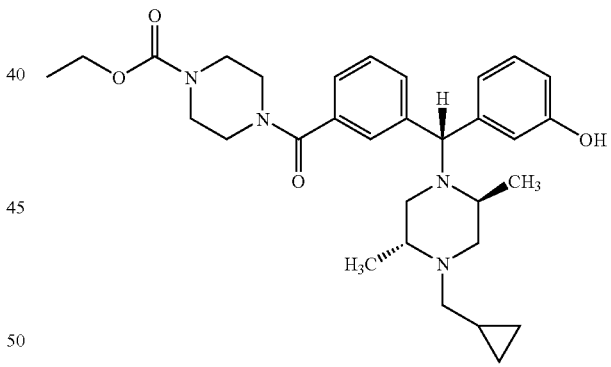

4-{3-[(R)-((2S,5R)-4-cyclopropyl-methyl-2,5-dimethyl-piperazin-1-yl)-(3-hydroxy-phenyl)-methyl]-benzoyl}-piperazine-1-carboxylic acid ethyl ester The title compound was made by a procedure identical to that of Example 60 using 4-{3-[(R)-[(2S,5R)-2,5-dimethyl-piperazin-1-yl]-(3-hydroxy-phenyl)-methyl]-benzoyl}-piperazine-1-carboxylic acid ethyl ester with 0.23 g of cyclopropanecarboxaldehyde (3.33 mmol, 2 equiv.) to give 0.30 g of the desired product as a light pink solid. $^1$H NMR (300 MHz, d$_6$-DMSO): ☐ 0.02 (m, 2H); 0.38-0.41 (d, 2H); 0.75 (m, 1H); 0.86-0.88 (d, J=5.6 Hz, 3H); 1.08-1.10 (d, J=5.8 Hz, 3H); 1.14-1.18 (t, 3H); 1.75-1.81 (t, 1H); 2.07-2.21 (m, 2H); 2.31-2.37 (m, 1H); 2.48-2.51 (m, 6H); 2.87-2.90 (dd, 1H); 3.34-

3.53 (m, 5H); 3.99-4.06 (q, 2H); 5.03 (s, 1H); 6.63-6.67 (m, 3H); 7.10-7.15 (t, 1H); 7.22-7.24 (dd, 1H); 7.35-7.39 (m, 2H); 7.43-7.46 (dd, 1H); 9.34 (s, 1H). Calculated for $C_{31}H_{42}N_4O_4 \cdot 0.25\ CH_2Cl_2$: C, 67.52; H, 7.71; N, 10.08. Found: C, 67.52; H, 7.82; N, 10.07.

EXAMPLE 62

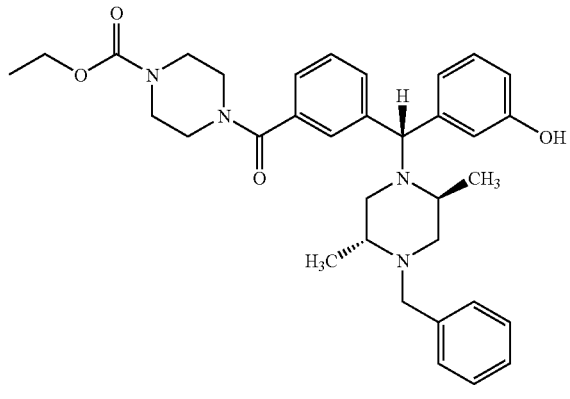

4-{3-[(R)-((2S,5R)-4-Benzyl-2,5-dimethyl-piperazin-1-yl)-(3-hydroxy-phenyl)-methyl]-benzoyl}-piperazine-1-carboxylic acid ethyl ester The title compound was made by a procedure identical to that of Example 60 using 1.0 g of 4-{3-[(R)-((2S,5R)-2,5-dimethyl-piperazin-1-yl)-(3-hydroxy-phenyl)-methyl]-benzoyl}-piperazine-1-carboxylic acid ethyl ester and 0.44 g of benzaldehyde (4.16 mmol, 2 equiv.) to give 0.42 g of the title compound as a light pink solid. $^1H$ NMR (300 MHz, $d_6$-DMSO): □ 1.00-1.01 (d, J=5.5 Hz, 6H); 1.14-1.19 (t, 3H), 1.56-2.00 (m, 2H); 2.48 (s, 4H); 2.56-2.65 (m, 4H); 3.39-3.51 (m, 5H); 3.72-3.76 (dd, 1H); 4.00-4.07 (q, 2H); 4.96 (s, 1H); 6.62-6.70 (m, 3H); 7.09-7.63 (m, 10H); 9.37 (s, 1H). Calculated for $C_{34}H_{42}N_4O_4 \cdot 0.44\ CH_2Cl_2$: C, 68.02; H, 7.11; N, 9.21. Found: C, 68.00; H, 7.20; N, 9.12.

EXAMPLE 63

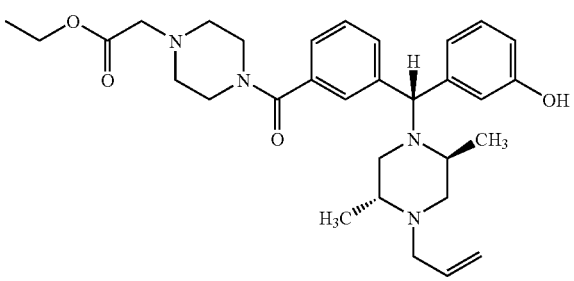

(4-{3-[(R)-((2S,5R)-4-Allyl-2,5-dimethyl-piperazin-1-yl)-(3-hydroxy-phenyl)-methyl]-benzoyl}-piperazin-1-yl)-acetic acid ethyl ester Piperazin-1-yl-acetic acid ethyl ester was made by the nucleophilic substitution between piperazine (5.0 g, 58.05 mmol) and ethyl bromoacetate (1.94 g, 11.61 mmol) in 60 mL of acetonitrile in the presence of sodium carbonate (6.15 g, 58.05 mmol). The crude yield was about 65%.

The title compound was made by a procedure identical to that of Example 57 with 2.75 g of Acid A and 1.25 g of piperazin-1-yl-acetic acid ethyl ester (7.26 mmol). The desired compound was obtained as a yellow solid (2.09 g, 54%). $^1H$ NMR (300 MHz, $d_6$-DMSO): □ 0.89-0.91 (d, J=5.6 Hz, 3H); 1.04-1.06 (d, J=5.9 Hz, 3H); 1.14-1.19 (t, 3H), 1.80-1.83 (dd, 1H); 2.04-2.10 (dd, 1H); 2.48-2.52 (m, 5H); 2.68-2.71 (dd, 1H); 2.79-2.86 (dd, 1H); 3.14-3.15 (dd, 1H); 3.24 (s, 2H); 3.33-3.56 (m, 6H); 4.03-4.10 (q, 2H); 4.99 (s, 1H); 5.06-5.17 (dd, 2H); 5.70-5.83 (m, 1H); 6.63-6.67 (m, 3H); 7.08-7.20 (m, 2H); 7.31-7.40 (m, 3H); 9.33 (s, 1H). Calculated for $C_{31}H_{42}N_4O_4 \cdot 0.60\ CH_3OH$: C, 68.52; H, 8.08; N, 10.11. Found: C, 68.33; H, 7.88; N, 10.32.

EXAMPLE 64

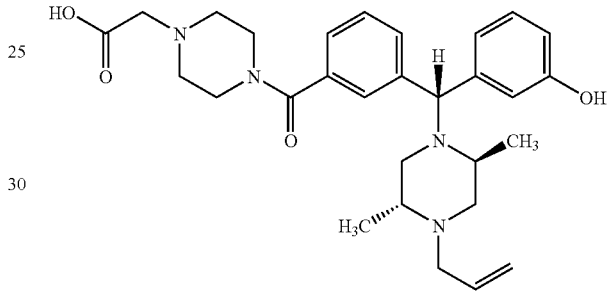

(4-{3-[(R)-((2S,5R)-4-Allyl-2,5-dimethyl-piperazin-1-yl)-(3-hydroxy-phenyl)-methyl]-benzoyl}-piperazin-1-yl)-acetic acid The ester of Example 63 (0.45 g) was hydrolyzed with 2.10 mL of 1N NaOH solution in 3 mL of ethanol at room temperature. The reaction mixture was evaporated to dryness, 2 mL of water was added, and the resulting solution was extracted with 2×2 mL of EtOAc/Et$_2$O to remove impurities. Hydrochloric acid (1.0 N, 2.10 mL) was added dropwise followed by several drops of 0.1 N HCl to obtain a pH of 6.0-6.5. The water layer was lyophilized overnight. The crude white solid was dissolved in isopropanol, filtered to remove sodium chloride, and evaporated to dryness. The resulting white solid was redissolved in water, lyophilized overnight, and dried in a vacuum oven (30 mm Hg, 40° C.). The desired compound (4-{3-[(R)-((2S,5R)-4-allyl-2,5-dimethyl-piperazin-1-yl)-(3-hydroxy-phenyl)-methyl]-benzoyl}-piperazin-1-yl)-acetic acid (290 mg) was obtained with a yield of 68%. $^1H$ NMR (300 MHz, $d_6$-DMSO): □ 0.92-0.94 (d, J=4.8 Hz, 3H); 1.05-1.07 (d, J=5.3 Hz, 3H); 1.80-1.83 (m, 1H); 2.04-2.12 (m, 1H); 2.48-2.54 (m, 5H); 2.72-2.75 (dd, 1H); 2.87-2.90 (m, 1H); 3.15 (s, 2H); 3.23-3.57 (m, 8H); 5.00 (s, 1H); 5.09-5.20 (m, 2H); 5.77-5.79 (m, 1H); 6.64-6.66 (m, 3H); 7.09-7.21 (m, 2H); 7.32-7.38 (m, 3H); 9.39 (s, 1H). Calculated for $C_{29}H_{38}N_4O_4 \cdot 0.85\ HCl \cdot 0.80\ H_2O$: C, 63.10; H, 7.39; N, 10.15. Found: C, 63.15; H, 7.37; N, 9.83.

EXAMPLE 65

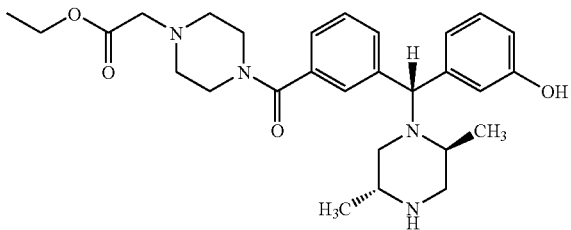

(4-{3-[(R)-((2S,5R)-2,5-dimethyl-piperazin-1-yl)-(3-hydroxy-phenyl)-methyl]-benzoyl}-piperazin-1-yl)-acetic acid ethyl ester The allyl portion of the compound of Example 63 (6.97 g, 13.0 mmol) was removed using tris(triphenylphosphine)rhodium (I) chloride (1.39 g, 1.50 mmol) as follows. The reaction mixture in acetonitrile (80 mL) and water (20 mL) was heated under a gentle reflux and the solvent was allowed to distill off slowly. An additional volume of acetonitrile/water (4:1, 100 mL) was added with a rate such as to maintain a steady distillation. After the addition of solvent was completed, the distillation was continued until the volume was reduced to approximately 50 mL. The cooled solution was concentrated under reduced pressure. The residual dark brown solid was purified by chromatography on a Biotage silica gel column (32-63 μm, 60 A, cartridge Lot#40S1614-1) eluting first with dichloromethane to remove the less polar contaminant, then using 5% methanol in dichloromethane with 1 mL of 50% NH4OH, then 10% methanol in dichloromethane. The desired fractions were combined and the solvent was removed under reduced pressure to give (4-{3-[(R)-((2S,5R)-2,5-dimethyl-piperazin-1-yl)-(3-hydroxy-phenyl)-methyl]-benzoyl}-piperazin-1-yl)-acetic acid ethyl ester as a light yellow solid (4.68 g, 73%).

EXAMPLE 66

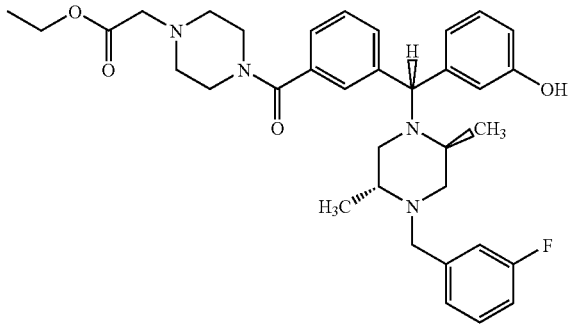

(4-{3-[(R)-[(2S,5R)-4-(3-Fluoro-benzyl)-2,5-dimethyl-piperazin-1-yl]-(3-hydroxy-phenyl)-methyl]-benzoyl}-piperazin-1-yl)-acetic acid ethyl ester The above free amine (1.23 g, 2.49 mmol, Example 65) and 3-fluorobenzaldehyde (0.62 g, 4.98 mmol) were placed in a 100 mL flask and sealed under nitrogen. Tetrahydrofuran (40 mL) and 0.31 mL of acetic acid (5.47 mmol, 2.20 equiv.) was added. The reaction was stirred at room temperature for 20 minutes, and then sodium triacetoxyborohydride (1.32 g, 6.22 mmol) was added and stirred overnight. The reaction solution was concentrated under reduced pressure. The residue was partitioned between ethyl acetate (50 mL) and saturated sodium hydrogencarbonate (25 mL). The organic layer was washed with brine, dried over $Na_2SO_4$ and concentrated under reduced pressure. The residual dark brown oil (2.01 g) was purified by chromatography on a Biotage column (SiO2-F Flash Cartridge, 8 g, 32-63 μm, 60 A) eluting first with dichloromethane to remove the less polar contaminant, then using 2.5% methanol in dichloromethane. The desired fractions were combined and the solvent was removed under reduced pressure. The title product (4-{3-[(R)-[(2S,5R)-4-(3-fluoro-benzyl)-2,5-dimethyl-piperazin-1-yl]-(3-hydroxy-phenyl)-methyl]-benzoyl}-piperazin-1-yl)-acetic acid ethyl ester was obtained as a light yellow solid (0.75 g, 50%). $^1$H NMR (300 MHz, $d_6$-DMSO): □ 0.81-1.01 (m, 6H); 1.14-1.19 (t, 3H), 1.89-2.01 (m, 2H); 2.48 (s, 4H); 2.57-2.66 (m, 4H); 3.24 (s, 2H); 3.29-3.36 (m, 4H); 3.50-3.56 (m, 1H); 3.71-3.76 (dd, 1H); 4.03-4.10 (q, 2H); 4.94 (s, 1H); 6.62-6.71 (m, 3H); 6.97-7.19 (m, 4H); 7.29-7.43 (m, 5H); 9.35 (s, 1H). Calculated for $C_{35}H_{43}FN_4O_4$·0.12 $CH_2Cl_2$: C, 68.82; H, 7.11; N, 9.14; F, 3.10. Found: C, 68.85; H, 7.17; N, 9.11; F, 3.18.

EXAMPLE 67

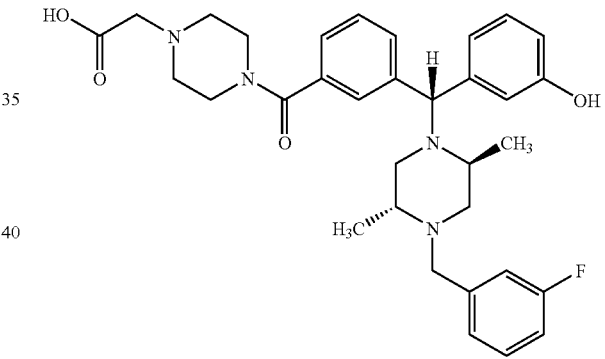

(4-{3-[(R)-[(2S,5R)-4-(3-Fluoro-benzyl)-2,5-dimethyl-piperazin-1-yl]-(3-hydroxy-phenyl)-methyl]-benzoyl}-piperazin-1-yl)-acetic acid The ester of Example 66 (0.45 g) was hydrolyzed with 1.87 mL of 1 N NaOH solution in 4 mL of tetrahydrofuran. The reaction mixture was evaporated to dryness, 2 mL of water was added, and the resulting solution was extracted with 2×2 mL of EtOAc/Et$_2$O to remove impurities. Hydrochloric acid (1.0 N, 1.87 mL) was added dropwise to precipitate the product. The pale yellow gel was collected by filtration, washed with cold water, and dried in a vacuum oven (30 mm Hg, 40° C.) overnight. The title compound (325 mg, 75%) was obtained as a light yellow solid. $^1$H NMR (300 MHz, $d_6$-DMSO): □ 1.00-1.06 (d, J=5.1 Hz, 6H); 1.91-2.02 (m, 2H); 2.48 (s, 4H); 2.57-2.66 (m, 4H); 3.15 (s, 2H); 3.30-3.76 (m, 7H); 4.93 (s, 1H); 6.62-6.71 (m, 3H); 6.98-7.20 (m, 4H); 7.27-7.43 (m, 5H); 9.35 (s, 1H). Calculated for $C_{33}H_{39}FN_4O_4$ 0.43 HCl 1.10 $H_2O$: C, 64.96; H, 6.88; N, 9.18; F, 3.11. Found: C, 64.98; H, 6.88; N, 8.82; F, 3.32.

EXAMPLE 68

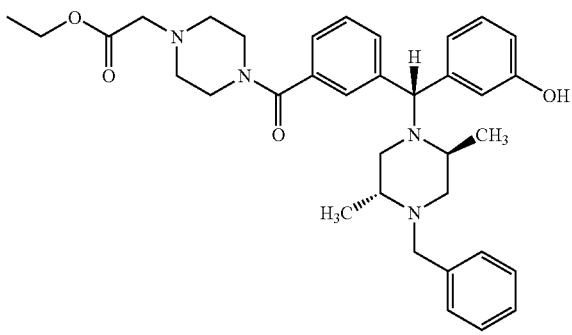

(4-{3-[(R)-((2S,5R)-4-Benzyl-2,5-dimethyl-piperazin-1-yl)-(3-hydroxy-phenyl)-methyl]-benzoyl}-piperazin-1-yl)-acetic acid ethyl ester The title compound was made by a procedure identical to that of Example 66 with 1.50 g of (4-{3-[(R)-((2S,5R)-2,5-dimethyl-piperazin-1-yl)-(3-hydroxy-phenyl)-methyl]-benzoyl}-piperazin-1-yl)-acetic acid ethyl ester (3.03 mmol) and 0.64 g of benzaldehyde (6.07 mmol) to give 0.61 g (34%) of the desired compound as a light yellow solid. $^1$H NMR (300 MHz, $d_6$-DMSO): ☐ 1.00-1.02 (d, J=4.7 Hz, 6H); 1.15-1.19 (t, 3H), 1.87-2.00 (m, 2H); 2.48-2.65 (m, 8H); 3.25 (s, 2H); 3.36-3.57 (m, 5H); 3.73-3.77 (dd, 1H); 4.03-4.10 (q, 2H); 4.96 (s, 1H); 6.62-6.69 (m, 3H); 7.08-7.42 (m, 10H); 9.35 (s, 1H). Calculated for $C_{35}H_{44}N_4O_4 \cdot 0.16\ CH_2Cl_2$: C, 70.58; H, 7.47; N, 9.36. Found: C, 70.57; H, 7.52; N, 9.39.

EXAMPLE 69

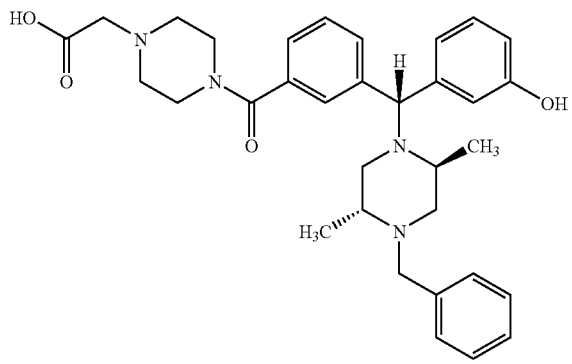

(4-{3-[(R)-((2S,5R)-4-Benzyl-2,5-dimethyl-piperazin-1-yl)-(3-hydroxy-phenyl)-methyl]-benzoyl}-piperazin-1-yl)-acetic acid The ester of Example 68 (0.26 g) was hydrolyzed with 1.11 mL of 1N NaOH solution in 3 mL of tetrahydrofuran. The reaction mixture was evaporated to dryness, 2 mL of water was added, and the resulting solution was extracted with 2×2 mL of EtOAc/Et$_2$O to remove impurities. Hydrochloric acid (1.0 N, 1.11 mL) was added dropwise to neutralize the solution. The water layer was lyophilized overnight and the residue was dried in a vacuum oven (30 mmHg, 40° C.). The title compound (200 mg, 82%) was obtained as a white solid. $^1$H NMR (300 MHz, $d_6$-DMSO): ☐ 0.99-1.01 (d, J=5.3 Hz, 6H); 1.89-1.99 (m, 2H); 2.48-2.64 (m, 8H); 3.14 (s, 2H); 3.20-3.76 (m, 7H); 4.95 (s, 1H); 6.62-6.69 (t, 3H); 7.08-7.42 (m, 10H); 9.35 (s, 1H). MS: 557.2 (M+1, 80%), 423.2 (55%), 209.1 (100%). Calculated for $C_{33}H_{40}N_4O_4$ 0.24 HCl 1.80 H$_2$O: C, 66.29; H. 7.39; N, 9.37; Cl, 1.42. Found: C, 66.32; H, 7.13; N, 8.90; Cl, 1.41.

EXAMPLE 70

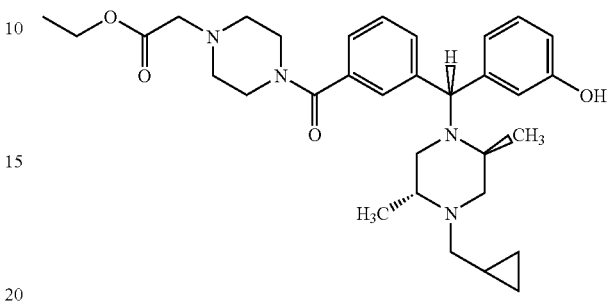

(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-acetic acid ethyl ester The title compound was made by a procedure identical to that of Example 66 except that a shorter reaction time (2 hours) was used to combine 1.50 g of (4-{3-[(R)-((2S,5R)-2,5-dimethyl-piperazin-1-yl)-(3-hydroxy-phenyl)-methyl]-benzoyl}-piperazin-1-yl)-acetic acid ethyl ester (3.03 mmol) and 0.43 g of cyclopropanecarboxaldehyde (6.07 mmol, 2 equiv.) to give 0.73 g (44%) of the title compound as a white solid. $^1$H NMR (300 MHz, $d_6$-DMSO): ☐ 0.02-0.03 (t, 2H); 0.38-0.41 (d, J=7.7 Hz, 2H); 0.73-0.75 (m, 1H); 0.85-0.87 (d, J=5.8 Hz, 3H); 1.07-1.09 (d, J=6.0 Hz, 3H); 1.14-1.19 (t, 3H), 1.76-1.79 (m, 1H); 2.07-2.20 (ddd, 2H); 2.30-2.36 (dd, 1H); 2.48-2.51 (m, 6H); 2.86-2.89 (dd, 1H); 3.24 (s, 2H); 3.37-3.59 (m, 5H); 4.02-4.09 (q, 2H); 5.03 (s, 1H); 6.62-6.66 (m, 3H); 7.09-7.20 (m, 2H); 7.32-7.37 (m, 3H); 9.35 (s, 1H). Calculated for $C_{32}H_{44}N_4O_4 \cdot 0.20\ CH_2Cl_2$: C, 68.37; H, 7.91; N, 9.90. Found: C, 68.38; H, 7.97; N, 9.91.

EXAMPLE 71

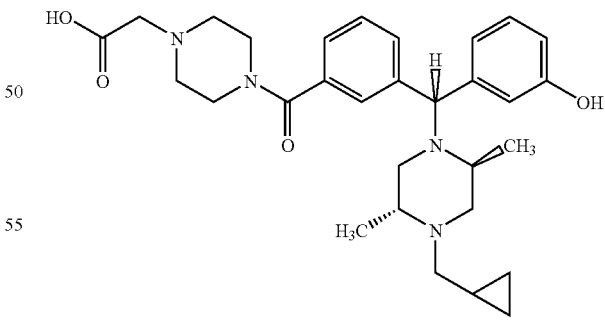

4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-acetic acid The ester of Example 70 (0.42 g) was hydrolyzed with 1.91 mL of 1N NaOH solution in 4 mL of tetrahydrofuran. The reaction mixture was evaporated to dryness, 2 mL of water was added, and the resulting solution was extracted with 2×4 mL of EtOAc/Et$_2$O to remove impurities. Hydrochloric acid (1.0 N, 1.91 mL) was added dropwise followed by several drops of 0.1 N HCl to adjust pH to 6.0-6.5. The water layer was lyophilized overnight. The crude white solid was dissolved in isopropanol and filtered to remove sodium chloride. The filtrate was redissolved in water, lyophilized overnight, and dried in a vacuum oven (30 mm Hg, 40° C.). The desired product (220 mg, 55%) was obtained as a white solid. $^1$H NMR (300 MHz, d$_6$-DMSO): ☐ 0.10 (s, 2H); 0.43-0.46 (d, J=7.9 Hz, 2H); 0.82-0.85 (m, 1H); 0.94-0.96 (d, J=6.1 Hz, 3H); 1.11-1.13 (d, J=5.5 Hz, 3H); 1.80-1.89 (m, 1H); 2.48-2.71 (m, 9H); 3.02-3.28 (m, 1H); 3.15 (s, 2H); 3.30-3.75 (m, 6H); 5.07 (s, 1H); 6.65-6.68 (m, 3H); 7.11-7.22 (m, 2H); 7.33-7.41 (m, 3H); 9.37 (s, 1H). MS: 521.1 (M+1, 20%), 353.2 (90%), 209.1 (100%). Calculated for C$_{30}$H$_{40}$N$_4$O$_4$.0.41 HCl 2.50 H$_2$O: C, 62.06; H, 7.88; N, 9.65; Cl, 2.50. Found: C, 62.00; H, 7.70; N, 9.20; Cl, 2.51.

EXAMPLE 72

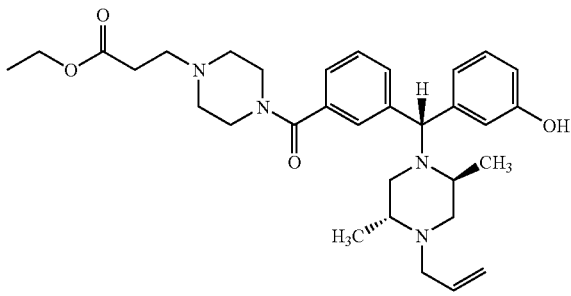

3-(4-{3-[(R)-((2S,5R)-4-Allyl-2,5-dimethyl-piperazin-1-yl)-(3-hydroxy-phenyl)-methyl]-benzoyl}-piperazin-1-yl)-propionic acid ethyl ester 3-Piperazin-1-yl-propionic acid ethyl ester was made by nucleophilic substitution between piperazine (5.0 g, 58.05 mmol) and ethyl 3-bromopropionate (2.10 g, 11.61 mmol) in 60 mL of acetonitrile in the presence of sodium carbonate (6.15 g, 58.05 mmol). The crude yield was about 65%.

The title compound was made by a procedure identical to that of Example 57 with 2.66 g of Acid A and 1.30 g of 3-piperazin-1-yl-propionic acid ethyl ester (6.98 mmol) to give 1.21 g of product as a yellow solid. $^1$H NMR (300 MHz, d$_6$-DMSO): ☐ 0.90-0.92 (d, J=5.8 Hz, 3H); 1.04-1.06 (d, J=6.1 Hz, 3H); 1.13-1.18 (t, 3H), 1.77-1.83 (dd, 1H); 2.04-2.10 (dd, 1H); 2.32-2.59 (m, 9H); 2.68-2.71 (dd, 1H); 2.79-2.86 (dd, 1H); 3.14-3.53 (m, 7H); 4.00-4.05 (q, 2H); 4.99 (s, 1H); 5.06-5.17 (dd, 2H); 5.72-5.81 (m, 1H); 6.63-6.68 (m, 3H); 7.09-7.20 (m, 2H); 7.31-7.41 (m, 3H); 9.33 (s, 1H). Calculated for C$_{32}$H$_{44}$N$_4$O$_4$.0.60 CH$_3$OH: C, 68.94; H, 8.23; N, 9.86. Found: C, 68.88; H, 8.10; N, 10.05.

EXAMPLE 73

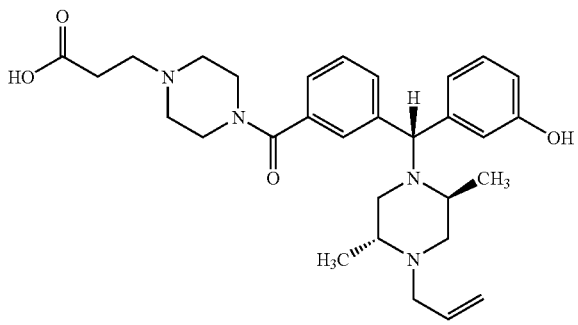

3-(4-{3-[(R)-((2S,5R)-4-Allyl-2,5-dimethyl-piperazin-1-yl)-(3-hydroxy-phenyl)-methyl]-benzoyl}-piperazin-1-yl)-propionic acid The ester of Example 72 (0.37 g) was hydrolyzed with 1.69 mL of 1 N NaOH solution in 2 mL of tetrahydrofuran. The reaction mixture was evaporated to dryness, 2 mL of water was added, and the resulting solution was extracted with 2×4 mL of EtOAc/Et$_2$O to remove impurities. Hydrochloric acid (1.0 N, 1.69 mL) was added dropwise followed by several drops of 0.1N HCl to adjust pH to 6.0-6.5. The water layer was lyophilized overnight. The white solid was redissolved in isopropanol and filtered to remove sodium chloride and solvent was removed under vacuum. The residue was redissolved in water, lyophilized overnight, and dried in a vacuum oven (30 mmHg, 40° C.) to give 210 mg (60%) of white solid. $^1$H NMR (300 MHz, d$_6$-DMSO): ☐ 0.90-0.92 (d, J=5.8 Hz, 3H); 1.07-1.09 (d, J=5.2 Hz, 3H); 1.80-1.89 (m, 1H); 2.36-2.57 (m, 11H); 2.78-2.82 (dd, 1H); 3.02-3.45 (m, 8H); 5.02 (s, 1H); 5.14-5.25 (dd, 2H); 5.79-5.82 (m, 1H); 6.64-6.66 (m, 3H); 7.10-7.21 (m, 2H); 7.33-7.39 (m, 3H); 9.40 (s, 1H). Calculated for C$_{30}$H$_{40}$N$_4$O$_4$.1.10 HCl 1.40 H$_2$O: C, 61.49; H, 7.55; N, 9.56. Found: C, 61.42; H, 7.55; N, 9.58.

EXAMPLE 74

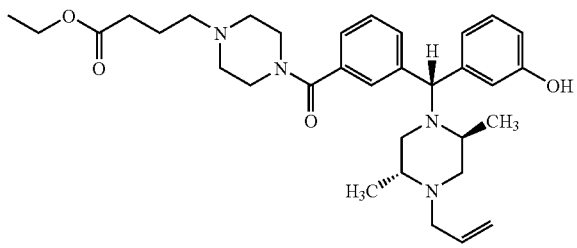

(4-{3-[(R)-((2S,5R)-4-Allyl-2,5-dimethyl-piperazin-1-yl)-(3-hydroxy-phenyl)-methyl]-benzoyl}-piperazin-1-yl)-butyric acid ethyl ester 4-Piperazin-1-yl-butyric acid ethyl ester was made by nucleophilic substitution between piperazine (22.08 g, 256.33 mmol) and ethyl 4-bromobutyrate (10 g, 51.27 mmol) in 250 mL of acetonitrile in the presence of sodium carbonate (27.16 g, 256.33 mmol). The crude yield was about 69%.

The title compound was made by a procedure identical to that of Example 57 with 10 g of Acid A and 7.06 g of 4-piperazin-1-yl-butyric acid ethyl ester (35.25 mmol, 1.34 equiv.) to give the product as a yellow solid. $^1$H NMR (300 MHz, $d_6$-DMSO): ☐ 0.90-0.92 (d, J=5.9 Hz, 3H); 1.04-1.06 (d, J=6.1 Hz, 3H); 1.13-1.17 (t, 3H), 1.63-1.70 (m, 2H); 1.77-1.79 (m, 1H); 2.03-2.09 (dd, 1H); 2.25-2.30 (m, 7H); 2.48-2.52 (m, 4H); 2.67-2.71 (dd, 1H); 2.79-2.86 (dd, 1H); 3.12-3.52 (m, 5H); 3.98-4.05 (q, 2H); 4.99 (s, 1H); 5.06-5.17 (dd, 2H); 5.72-5.81 (m, 1H); 6.63-6.67 (m, 3H); 7.09-7.20 (m, 2H); 7.31-7.40 (m, 3H); 9.37 (s, 1H). Calculated for $C_{33}H_{46}N_4O_4 \cdot 0.66$ $CH_3OH$ $0.10$ $CH_2Cl_2$: C, 68.45; H, 8.31; N, 9.46. Found: C, 68.44; H, 8.32; N, 9.74.

EXAMPLE 75

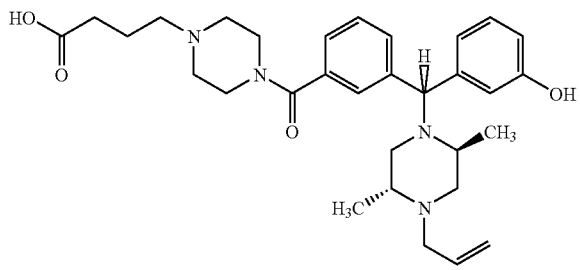

(4-{3-[(R)-((2S,5R)-4-Allyl-2,5-dimethyl-piperazin-1-yl)-(3-hydroxy-phenyl)-methyl]-benzoyl}-piperazin-1-yl)-butyric acid The ester of Example 74 (0.45 g) was hydrolyzed with 2.00 mL of 1N NaOH solution in 3 mL of ethanol. The reaction mixture was evaporated to dryness, 2 mL of water was added, and the resulting solution was extracted with 2×4 mL of EtOAc/Et$_2$O to remove impurities. Hydrochloric acid (1.0 N, 2.00 mL) was added dropwise followed by several drops of 0.1 N HCl to adjust pH to 6.0-6.5. The water layer was lyophilized overnight. The residue was redissolved in isopropanol, filtered to remove sodium chloride, and concentrated under reduced pressure. The product was redissolved in water, lyophilized overnight, and dried in a vacuum oven (30 mm Hg, 40° C.) to give 320 mg (82%) of white solid. $^1$H NMR (300 MHz, $d_6$-DMSO): ☐ 0.89-0.92 (d, J=6.1 Hz, 3H); 1.01-1.03 (d, J=6.1 Hz, 3H); 1.04-1.06 (t, 3H), 1.21-1.63 (m, 2H); 1.66-1.84 (m, 1H); 2.03-2.14 (m, 4H); 2.23-2.28 (m, 4H); 2.45-2.52 (m, 4H); 2.67-2.71 (dd, 1H); 2.78-2.85 (dd, 1H); 3.14-3.79 (m, 6H); 4.99 (s, 1H); 5.06-5.17 (dd, 2H); 5.72-5.82 (m, 1H); 6.62-6.67 (m, 3H); 7.09-7.20 (m, 2H); 7.31-7.43 (m, 3H); 9.37 (s, 1H). MS: 535.0 (M+1, 70%), 209.3 (80%), 176.1 (100%), 153.3 (70%). Calculated for $C_{31}H_{42}N_4O_4 \cdot 1.25$ HCl $0.45$ H2O: C, 63.28; H, 7.56; N, 9.52. Found: C, 63.28; H, 7.57; N, 9.56.

EXAMPLE 76

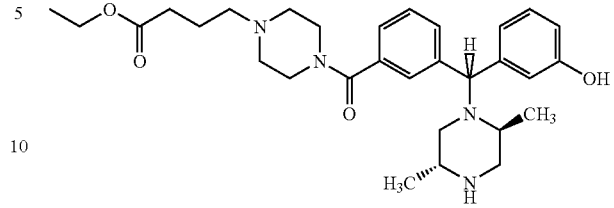

(4-{3-[(R)-((2S,5R)-2,5-dimethyl-piperazin-1-yl)-(3-hydroxy-phenyl)-methyl]-benzoyl}-piperazin-1-yl)-butyric acid ethyl ester The allyl portion of the compound of Example 74 (8.08 g, 14.4 mmol) was removed using tris(triphenylphosphine)rhodium (I) chloride (1.53 g, 1.65 mmol). The reaction mixture in acetonitrile (80 mL) and water (20 mL) was heated under a gentle reflux and the solvent was allowed to distil off slowly. Additional acetonitrile/water (4:1, 100 mL) was added at a rate such as to maintain a steady distillation. After the addition of solvent was completed, the distillation was continued until the volume was reduced to approximately 50 mL. The cooled solution was concentrated under reduced pressure. The residual dark brown solid was purified by chromatography on Biotage silica gel column (32-63 μm, 60 A, cartridge Lot#40S1614-1) eluting first with dichloromethane to remove the less polar contaminant, then using 5% methanol in dichloromethane with 1 mL of 50% NH4OH, then 10% methanol in dichloromethane. The desired fractions were combined and the solvent was removed under reduced pressure. The amine (4-{3-[(R)-((2S,5R)-2,5-dimethyl-piperazin-1-yl)-(3-hydroxy-phenyl)-methyl]-benzoyl}-piperazin-1-yl)-butyric acid ethyl ester (5.55 g, 74%) was obtained as a light yellow solid.

EXAMPLE 77

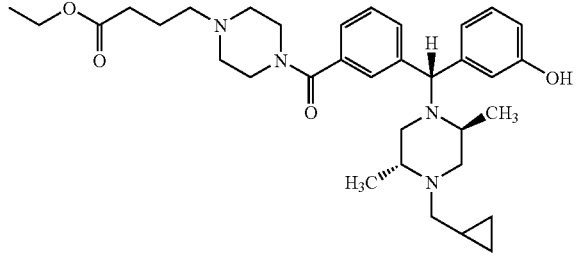

4-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-butyric acid ethyl ester The above free amine (1.50 g, 2.97 mmol, Example 76) and cyclopropanecarboxaldehyde (0.40 g, 5.74 mmol) were placed in a 100 mL flask and sealed under nitrogen. Tetrahydrofuran (40 mL) and 0.38 mL of acetic acid (6.31 mmol, 2.20 equiv.) were added. The reaction was stirred at room temperature for 20 minutes, and then sodium triacetoxyborohydride (1.52 g, 7.17 mmol) was added and stirred overnight. The reaction solution was concentrated under reduced pressure. The residue was partitioned between ethyl acetate (50 mL) and saturated sodium hydrogencarbonate (25 mL). The organic layer was washed with brine, dried over $Na_2SO_4$, and concentrated under reduced pressure. The residual dark brown oil (2.03 g) was purified by chromatography on a Biotage column (SiO2-F Flash Cartridge, 8 g, 32-63 μm, 60 A) eluting first with dichloromethane to remove the less polar contaminant, then using 2.5% methanol in dichloromethane. The desired fractions were combined and the solvent was removed under reduced pressure to give 0.32 g of the title compound as a light yellow solid. $^1$H NMR (300 MHz, $d_6$-DMSO): □ 0.01-0.05 (m, 2H); 0.38-0.41 (d, J=7.4 Hz, 2H); 0.73-0.75 (m, 1H); 0.86-0.88 (d, J=5.9 Hz, 3H); 1.08-1.10 (d, J=6.1 Hz, 3H); 1.13-1.16 (t, 3H), 1.61-1.70 (m, 2H); 1.73-1.80 (m, 1H); 2.07-2.32 (m, 8H); 2.48-2.49 (m, 5H); 2.86-2.89 (dd, 1H); 3.24-3.32 (m, 4H); 3.53-3.56 (m, 1H); 3.99-4.06 (q, 2H); 5.04 (s, 1H); 6.62-6.66 (m, 3H); 7.10-7.20 (m, 2H); 7.32-7.41 (m, 3H); 9.33 (s, 1H). MS: 576.0 (M, 40%), 409.0 (80%), 209.0 (100%). Calculated for $C_{34}H_{48}N_4O_4 \cdot 0.13\ CH_2Cl_2$: C, 69.74; H, 8.28; N, 9.53. Found: C, 69.71; H, 8.37; N, 9.66.

EXAMPLE 78

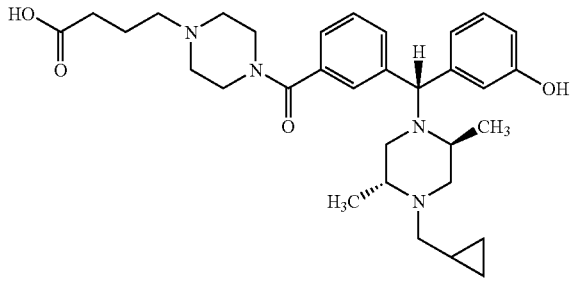

4-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-butyric acid The compound of Example 77 (0.48 g) was hydrolized with 2.08 mL of 1 N NaOH solution in 4 mL of tetrahydrofuran. The reaction mixture was evaporated to dryness, 2 mL of water was added, and the resulting solution was extracted with 2×4 mL of EtOAc/$Et_2O$ to remove impurities. Hydrochloric acid (1.0 N, 2.08 mL) was added dropwise followed by several drops of 0.1N HCl to adjust pH to 6.0-6.5, and the aqueous solution was lyophilized overnight. The residue was redissolved in isopropanol and the solution was filtered to remove sodium chloride. Solvent was removed under vacuum. The residue was redissolved in water, lyophilized overnight, and dried in a vacuum oven (30 mmHg, 40° C.) to give 300 mg (66%) of white solid.

$^1$H NMR (300 MHz, $d_6$-DMSO): □ 0.01-0.09 (m, 2H); 0.42-0.45 (d, J=7.6 Hz, 2H); 0.80-0.82 (m, 1H); 0.93-0.94 (d, J=4.9 Hz, 3H); 1.11-1.12 (d, J=5.6 Hz, 3H); 1.60-1.67 (m, 2H); 1.85-1.89 (m, 1H); 2.19-2.57 (m, 13H); 3.01-3.54 (m, 7H); 5.07 (s, 1H); 6.64-6.68 (m, 3H); 7.11-7.21 (m, 2H); 7.33-7.42 (m, 3H); 9.37 (s, 1H). MS: 549.2 (M+1, 80%), 395.2 (80%), 209.2 (100%) 153.3 (95%). Calculated for $C_{32}H_{44}N_4O_4 \cdot 0.30\ HCl\ 1.80\ H_2O$: C, 64.91; H, 8.15; N, 9.46; Cl, 1.80. Found: C, 64.94; H, 8.09; N, 9.46; Cl, 1.84.

EXAMPLE 79

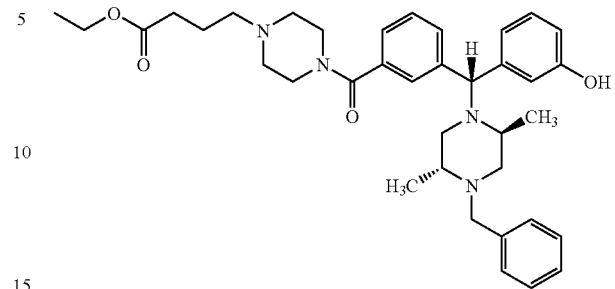

4-(4-{3-[(R)-((2S,5R)-4-Benzyl-2,5-dimethyl-piperazin-1-yl)-(3-hydroxy-phenyl)-methyl]-benzoyl}-piperazin-1-yl)-butyric acid ethyl ester The title compound was made by a procedure identical to that of Example 77 with 1.50 g of (4-{3-[(R)-((2S,5R)-2,5-dimethyl-piperazin-1-yl)-(3-hydroxy-phenyl)-methyl]-benzoyl}-piperazin-1-yl)-butyric acid ethyl ester (2.97 mmol) and 0.61 g of benzaldehyde (5.74 mmol) to give 1.05 g of product as a light yellow solid. $^1$H NMR (300 MHz, $d_6$-DMSO): □ 1.00-1.03 (d, J=4.7 Hz, 6H); 1.13-1.18 (t, 3H), 1.62-1.71 (m, 2H); 1.88-2.05 (m, 2H); 2.25-2.31 (m, 7H); 2.48-2.65 (m, 6H); 3.20-3.32 (m, 3H); 3.54-3.56 (m, 1H); 3.73-3.77 (dd, 1H); 3.99-4.06 (q, 2H); 4.96 (s, 1H); 6.63-6.69 (m, 3H); 7.09-7.43 (m, 10H); 9.33 (s, 1H). MS: 613.0 (M+1, 40%), 409.0 (90%), 209.1 (100%). Calculated for $C_{37}H_{48}N_4O_4 \cdot 0.10\ CH_2Cl_2$: C, 71.72; H. 7.82; N, 9.02. Found: C, 71.72; H, 7.88; N, 9.00.

EXAMPLE 80

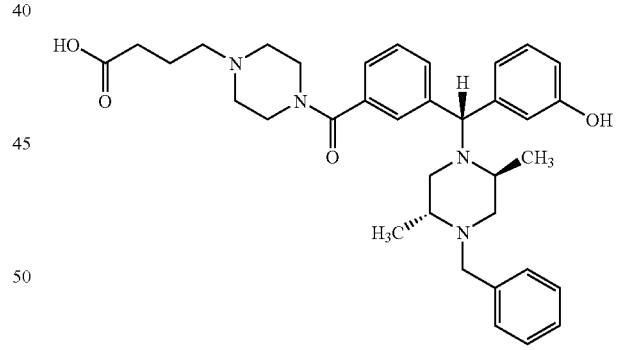

4-(4-{3-[(R)-((2S,5R)-4-Benzyl-2,5-dimethyl-piperazin-1-yl)-(3-hydroxy-phenyl)-methyl]-benzoyl}-piperazin-1-yl)-butyric acid The ester of Example 79 (0.61 g) was hydrolyzed with 2.49 mL of 1 N NaOH solution in 5 mL of tetrahydrofuran. The reaction mixture was evaporated to dryness, 2 mL of water was added, and the resulting solution was extracted with 2×4 mL of $Et_2O$ to remove impurities. Hydrochloric acid (1.0 N, 2.49 mL) was added dropwise to neutralize the solution, which was lyophilized overnight and dried in a vacuum oven (30 mm Hg, 40° C.) to give 270 mg (46%) of the title compound as a white solid. $^1$H NMR (300 MHz, d$_6$-DMSO): ☐ 1.00-1.03 (m, 6H); 1.63-1.71 (m, 2H); 1.89-1.96 (m, 2H); 2.21-2.28 (m, 7H); 2.48-2.65 (m, 6H); 3.24-3.54 (m, 5H); 3.72-3.77 (dd, 1H); 4.96 (s, 1H); 6.64-6.66 (m, 3H); 7.09-7.40 (m, 10H); 9.35 (s, 1H). MS: 585.3 (M+1, 80%), 209.1 (100%). Calculated for C$_{35}$H$_{44}$N$_4$O$_4$ 0.87 H2O: C, 70.01; H, 7.68; N, 9.33. Found: C, 70.01; H, 7.58; N, 9.19.

EXAMPLE 81

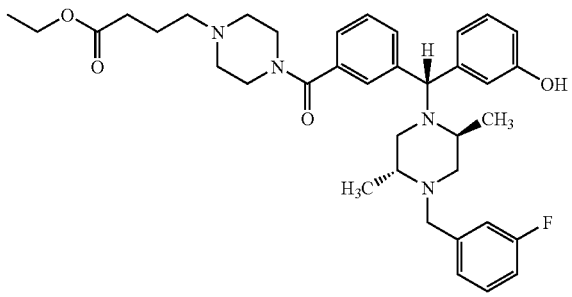

4-(4-{3-[(R)-((2S,5R)-4-(3-Fluorobenzyl)-2,5-dimethyl-piperazin-1-yl)-(3-hydroxy-phenyl)-methyl]-benzoyl}-piperazin-1-yl)-butyric acid ethyl ester The title compound was made by a procedure identical to that of Example 77 with 1.50 g of (4-{3-[(R)-((2S,5R)-2,5-dimethyl-piperazin-1-yl)-(3-hydroxy-phenyl)-methyl]-benzoyl}-piperazin-1-yl)-butyric acid ethyl ester (2.97 mmol) and 0.71 g of 3-Fluorobenzaldehyde (5.74 mmol) to give 1.07 g of product as a yellow solid. $^1$H NMR (300 MHz, d$_6$-DMSO): ☐ 1.01-1.03 (d, J=5.6 Hz, 6H); 1.13-1.18 (t, 3H); 1.62-1.71 (m, 2H); 1.90-2.02 (m, 2H); 2.25-2.31 (m, 7H); 2.48-2.66 (m, 6H); 3.25-3.33 (m, 3H); 3.54-3.56 (m, 1H); 3.72-3.76 (dd, 1H); 3.99-4.06 (q, 2H); 4.94 (s, 1H); 6.62-6.71 (m, 3H); 6.97-7.43 (m, 10H); 9.34 (s, 1H). MS: 629.0 (M−1, 30%), 409.0 (95%), 209.0 (100%). Calculated for C$_{37}$H$_{47}$FN$_4$O$_4$·0.11 CH$_2$Cl$_2$: C, 69.63; H, 7.44; N, 8.75; F, 2.97. Found: C, 69.66; H, 7.50; N, 8.73; F, 2.71.

EXAMPLE 82

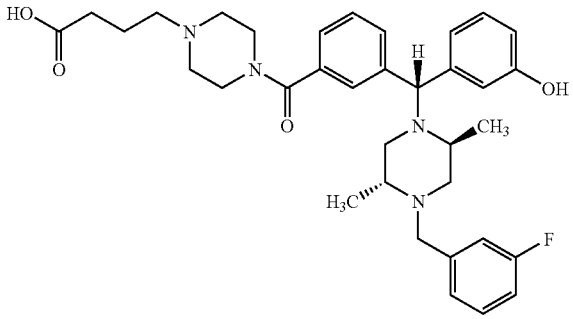

4-(4-{3-[(R)-((2S,5R)-4-(3-Fluorobenzyl)-2,5-dimethyl-piperazin-1-yl)-(3-hydroxy-phenyl)-methyl]-benzoyl}-piperazin-1-yl)-butyric acid The ester of Example 81 (0.69 g) was hydrolyzed with 2.73 mL of 1N NaOH solution in 5 mL of tetrahydrofuran. The reaction mixture was evaporated to dryness, 2 mL of water was added, and the resulting solution was extracted with 2×4 mL of Et$_2$O to remove impurities. Hydrochloric acid (1.0 N, 2.73 mL) was added dropwise to precipitate product. A yellow gel was formed, collected by filtration, washed with cold water, and dried in a vacuum oven (30 mm Hg, 40° C.) to give 520 mg (79%) of the title compound as a yellow solid. $^1$H NMR (300 MHz, d$_6$-DMSO): ☐ 1.00-1.03 (m, 6H); 1.63-1.71 (m, 2H); 1.91-1.98 (m, 2H); 2.18-2.27 (m, 7H); 2.48-2.65 (m, 6H); 3.25-3.76 (m, 6H); 4.94 (s, 1H); 6.64-6.66 (m, 3H); 7.01-7.42 (m, 9H); 9.35 (s, 1H). MS: 603.1 (M+1, 40%), 209.1 (100%). Calculated for C$_{35}$H$_{43}$FN$_4$O$_4$ 1.55 H$_2$O: C, 66.66; H, 7.37; N, 8.88; F, 3.01. Found: C, 66.65; H, 7.12; N, 8.76; F, 2.96.

EXAMPLE 83

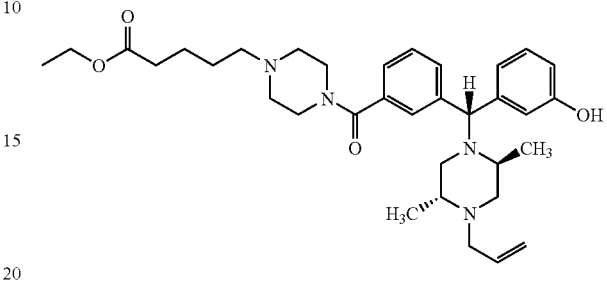

5-(4-{3-[(R)-((2S,5R)-4-Allyl-2,5-dimethyl-piperazin-1-yl)-(3-hydroxy-phenyl)-methyl]-benzoyl}-piperazin-1-yl)-pentanoic acid ethyl ester 5-Piperazin-1-yl-pentanoic acid ethyl ester was made by nucleophilic substitution between piperazine (20.60 g, 239.1 mmol) and ethyl 5-bromovalerate (10.0 g, 47.8 mmol) in 250 mL of acetonitrile in the presence of sodium carbonate (25.35 g, 239.1 mmol). The crude yield was about 65%.

The title compound was made by a procedure identical to the method of Example 57 with 10 g of Acid A and 8.44 g of 5-piperazin-1-yl-pentanoic acid ethyl ester (39.38 mmol, 1.44 equiv.) to give 670 mg of product as a light yellow solid. $^1$H NMR (300 MHz, d$_6$-DMSO): ☐ 0.90-0.92 (d, J=5.6 Hz, 3H); 1.04-1.06 (d, J=6.1 Hz, 3H); 1.12-1.17 (t, 3H); 1.40-1.56 (m, 5H); 1.78-1.84 (dd, 1H); 2.03-2.09 (dd, 1H); 2.25-2.30 (m, 6H); 2.48-2.52 (m, 4H); 2.68-2.71 (dd, 1H); 2.78-2.85 (dd, 1H); 3.14-3.60 (m, 5H); 3.98-4.05 (q, 2H); 4.99 (s, 1H); 5.06-5.17 (dd, 2H); 5.72-5.80 (m, 1H); 6.63-6.67 (m, 3H); 7.09-7.12 (t, 1H); 7.21-7.24 (dd, 1H); 7.34-7.40 (m, 3H); 9.36 (s, 1H). Calculated for C$_{34}$H$_{48}$N$_4$O$_4$·0.50 CH$_3$OH: C, 69.90; H, 8.50; N, 9.45. Found: C, 69.92; H, 8.41; N, 9.62.

EXAMPLE 84

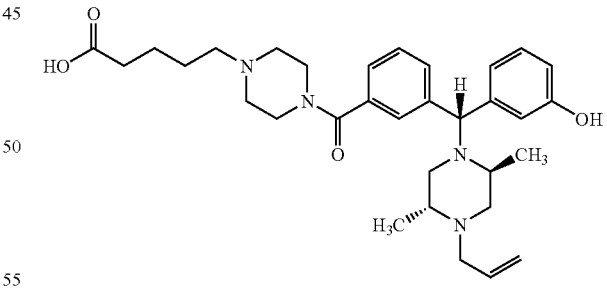

5-(4-{3-[(R)-((2S,5R)-4-Allyl-2,5-dimethyl-piperazin-1-yl)-(3-hydroxy-phenyl)-methyl]-benzoyl}-piperazin-1-yl)-pentanoic acid The ester of Example 83 (0.93 g) was hydrolyzed with 4.03 mL of 1 N NaOH solution in 5 mL of ethanol. The reaction mixture was evaporated to dryness, 2 mL of water was added, and the resulting solution was extracted with 2×4 mL of EtOAc/Et$_2$O to remove impurities. Hydrochloric acid (1.0 N, 4.03 mL) was added dropwise followed by several drops of 0.1 N HCl to adjust pH to 6.0-6.5. The water layer was extracted by n-butanol (6 mL×3). The combined n-butanol layer was washed by water (10 mL), concentrated to give a yellow oil which was redissolved in acetone, concentrated under reduced pressure, redissolved in water, lyophilized overnight, and dried in a vacuum oven (30 mm Hg, 40° C.) to give 90 mg of the title compound.

$^1$H NMR (300 MHz, d$_6$-DMSO): ☐ 0.99 (s, 3H); 1.08-1.09 (d, J=5.6 Hz, 3H); 1.35-1.55 (m, 5H); 1.80-1.96 (m, 2H); 2.18-2.60 (m, 8H); 2.84-2.86 (m, 1H); 3.02-3.04 (m, 1H); 3.04-3.90 (m, 8H); 5.03 (s, 1H); 5.20-5.32 (dd, 2H); 5.70-5.90 (m, 1H); 6.65-6.67 (m, 3H); 7.10-7.15 (t, 1H); 7.19-7.21 (dd, 1H); 7.33-7.42 (m, 3H); 9.39 (s, 1H). MS: 549.1 (M+1, 100%), 169.2 (100%). Calculated for $C_{32}H_{44}N_4O_4$·0.90 HCl 1.60 H$_2$O: C, 62.97; H, 7.94; N, 9.18. Found: C, 62.97; H, 7.94; N, 8.97.

EXAMPLE 85

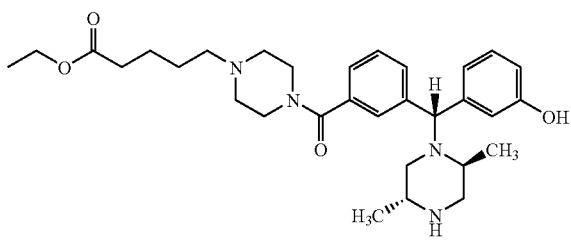

5-(4-{3-[(R)-((2S,5R)-2,5-dimethyl-piperazin-1-yl)-(3-hydroxy-phenyl)-methyl]-benzoyl}-piperazin-1-yl)-pentanoic acid ethyl ester The allyl portion of the compound of Example 83 (3.99 g, 6.92 mmol) was removed using tris(triphenylphosphine)rhodium (I) chloride (0.74 g, 0.80 mmol). The reaction mixture in acetonitrile (80 mL) and water (20 mL) was heated under a gentle reflux and the solvent was allowed to distill off slowly. Additional acetonitrile/water (4:1, 100 mL) was added with a rate such as to maintain a steady distillation. After the addition of solvent was completed, the distillation was continued until the volume was reduced to approximately 50 mL. The cooled solution was concentrated under reduced pressure. The amine 5-(4-{3-[(R)-((2S,5R)-2,5-dimethyl-piperazin-1-yl)-(3-hydroxy-phenyl)-methyl]-benzoyl}-piperazin-1-yl)-pentanoic acid ethyl ester was obtained as 4.66 g of a dark brown solid.

EXAMPLE 86

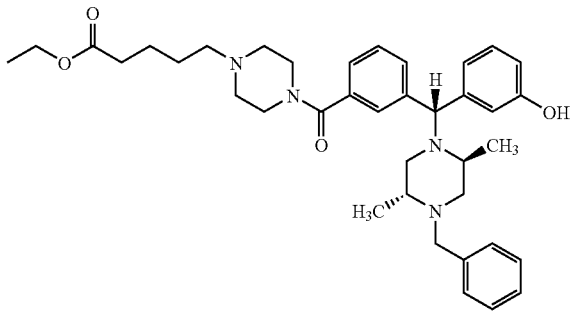

5-(4-{3-[(R)-[(2S,5R)-4-Benzyl-2,5-dimethyl-piperazin-1-yl]-(3-hydroxy-phenyl)-methyl]-benzoyl}-piperazin-1-yl)-pentanoic acid ethyl ester The above free amine (1.50 g, 2.79 mmol, Example 85) and benzaldehyde (0.59 g, 5.59 mmol) were placed in a 100 mL flask and sealed under nitrogen. Tetrahydrofuran (40 mL) and 0.35 mL of acetic acid (6.15 mmol, 2.20 equiv.) were added. The reaction was stirred at room temperature for 20 minutes, and then sodium triacetoxyborohydride (1.48 g, 6.99 mmol) was added and stirred overnight. The reaction solution was concentrated under reduced pressure. The residue was partitioned between ethyl acetate (50 mL) and saturated sodium hydrogencarbonate (25 mL). The organic layer was washed with brine, dried over Na$_2$SO$_4$ and concentrated under reduced pressure. The residual dark brown oil (1.86 g) was purified by chromatography on Biotage column (SiO2-F Flash Cartridge, 8 g, 32-63 μm, 60 A) eluting first with dichloromethane to remove the less polar contaminant, then using 2.5% methanol in dichloromethane. The desired fractions were combined and the solvent was removed under reduced pressure. The title compound (0.60 g was obtained as a yellow solid. $^1$H NMR (300 MHz, d$_6$-DMSO): ☐ 1.01-1.03 (m, 6H); 1.12-1.16 (t, 3H), 1.40-1.54 (m, 4H); 1.89-1.99 (m, 2H); 2.26-2.30 (m, 7H); 2.48-2.65 (m, 6H); 2.97-3.45 (m, 3H); 3.54-3.56 (m, 1H); 3.73-3.77 (dd, 1H); 3.98-4.05 (q, 2H); 4.96 (s, 1H); 6.63-6.69 (m, 3H); 7.00-7.42 (m, 10H); 9.35 (s, 1H). MS: 627.1 (M+1, 50%), 209.2 (100%). Calculated for $C_{38}H_{50}N_4O_4$·0.18 CH$_2$Cl$_2$: C, 71.42; H, 7.90; N, 8.73. Found: C, 71.41; H, 7.91; N, 8.69.

EXAMPLE 87

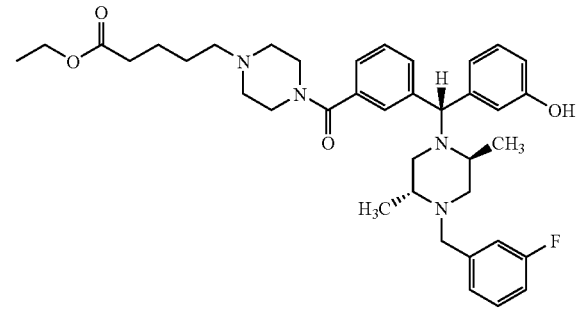

5-(4-{3-[(R)-((2S,5R)-4-(3-Fluorobenzyl)-2,5-dimethyl-piperazin-1-yl)-(3-hydroxy-phenyl)-methyl]-benzoyl}-piperazin-1-yl)-pentanoic acid ethyl ester The title compound was made by a procedure identical to that of Example 86 with 1.50 g of (4-{3-[(R)-((2S,5R)-2,5-dimethyl-piperazin-1-yl)-(3-hydroxy-phenyl)-methyl]-benzoyl}-piperazin-1-yl)-pentanoic acid ethyl ester (2.79 mmol) and 0.69 g of 3-fluorobenzaldehyde (5.59 mmol) to give 0.58 g of product as a yellow solid. $^1$H NMR (300 MHz, d$_6$-DMSO): ☐ 1.01-1.02 (d, J=5.6 Hz, 6H); 1.12-1.17 (t, 3H), 1.40-1.56 (m, 4H); 1.89-2.02 (m, 2H); 2.24-2.30 (m, 7H); 2.48-2.66 (m, 6H); 3.25-3.45 (m, 3H); 3.54-3.56 (m, 1H); 3.71-3.76 (dd, 1H); 3.98-4.05 (q, 2H); 4.94 (s, 1H); 6.62-6.71 (m, 3H); 6.98-7.43 (m, 9H); 9.35 (s, 1H). MS: 643.8 (M−1, 20%), 423.1 (90%), 209.1 (100%). Calculated for $C_{38}H_{49}FN_4O_4$·0.15 CH$_2$Cl$_2$: C, 69.68; H, 7.56; N, 8.52; F, 2.89. Found: C, 69.69; H, 7.55; N, 8.49; F, 3.05.

EXAMPLE 88

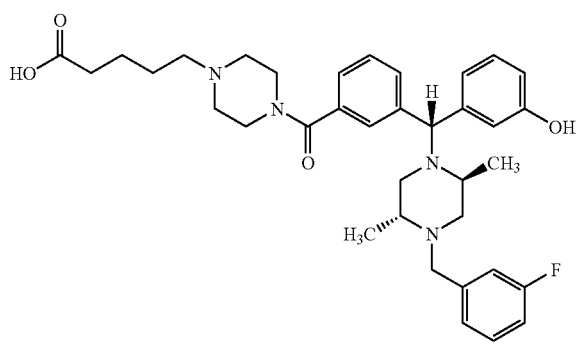

5-(4-{3-[(R)-((2S,5R)-4-(3-Fluorobenzyl)-2,5-dimethyl-piperazin-1-yl)-(3-hydroxy-phenyl)-methyl]-benzoyl}-piperazin-1-yl)-pentanoic acid The ester of Example 87 (0.26 g) was hydrolyzed with 1.00 mL of 1 N NaOH solution in 4 mL of tetrahydrofuran. The reaction mixture was evaporated to dryness, 2 mL of water was added, and the resulting solution was extracted with 2×4 mL of Et$_2$O to remove impurities Hydrochloric acid (1.0 N, 1.00 mL) was added dropwise to precipitate product, which was collected by filtration, washed with water, and dried in a vacuum oven (30 mm Hg, 40° C.) to give 312 mg of a yellow solid. $^1$H NMR (300 MHz, d$_6$-DMSO): □ 1.01-1.03 (d, J=5.6 Hz, 6H); 1.44-1.49 (m, 4H); 1.89-2.02 (m, 2H); 2.18-2.27 (m, 7H); 2.48-2.67 (m, 6H); 3.30-3.40 (m, 4H); 3.54-3.56 (m, 1H); 3.72-3.76 (dd, 1H); 4.94 (s, 1H); 6.62-6.71 (m, 3H); 6.98-7.43 (m, 9H); 9.34 (s, 1H). MS: 617.1 (M+1, 60%), 209.1 (100%). Calculated for C$_{36}$H$_{45}$FN$_4$O$_4$ 1.48 H2O: C, 67.20; H, 7.51; N, 8.71; F, 2.95. Found: C, 67.21; H, 7.29; N, 8.33; F, 3.02.

EXAMPLE 89

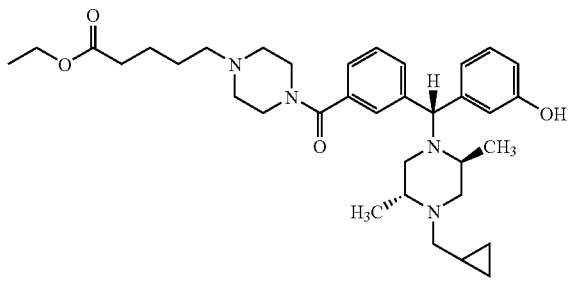

5-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-pentanoic acid ethyl ester The title compound was made by a procedure identical to that of Example 86 with 1.50 g of (4-{3-[(R)-((2S,5R)-2,5-Dimethyl-piperazin-1-yl)-(3-hydroxy-phenyl)-methyl]-benzoyl}-piperazin-1-yl)-pentanoic acid ethyl ester (2.79 mmol) and 0.39 g of Cyclopropanecarboxaldehyde (5.59 mmol) to give 0.66 g of product as a yellow solid. $^1$H NMR (300 MHz, d$_6$-DMSO): □ 0.01-0.03 (m, 2H); 0.38-0.41 (d, J=7.4 Hz, 2H); 0.73-0.75 (m, 1H); 0.86-0.88 (d, J=5.8 Hz, 3H); 1.08-1.10 (d, J=6.1 Hz, 3H); 1.12-1.17 (t, 3H); 1.40-1.53 (m, 4H); 1.73-1.80 (m, 1H); 2.07-2.30 (m, 8H); 2.48-2.62 (m, 5H); 2.86-2.89 (dd, 1H); 3.12-3.34 (m, 5H); 3.98-4.06 (q, 2H); 5.04 (s, 1H); 6.62-6.66 (m, 3H); 7.10-7.15 (t, 1H); 7.18-7.20 (dd, 1H); 7.32-7.40 (m, 3H); 9.34 (s, 1H). MS: 591.0 (M+1, 70%), 423.2(55%), 209.1(100%). Calculated for C$_{35}$H$_{50}$N$_4$O$_4$.0.17 CH$_2$Cl$_2$: C, 69.79; H, 8.38; N, 9.26. Found: C, 69.79; H, 8.49; N, 9.25.

EXAMPLE 90

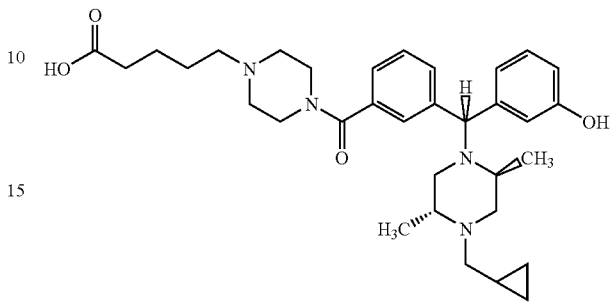

5-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-pentanoic acid The ester of Example 89 (0.34 g) was hydrolyzed with 1.44 mL of 1 N NaOH solution in 4 mL of tetrahydrofuran. The reaction mixture was evaporated to dryness, 2 mL of water was added, and the resulting solution was extracted with 2×4 mL of EtOAc/Et$_2$O to remove impurities. Hydrochloric acid (1.0 N, 1.44 mL) was added dropwise to precipitate product, which was collected by filtration, washed with water and dried in a vacuum oven (30 mm Hg, 40° C.) to give 160 mg (49%) of a light yellow solid. $^1$H NMR (300 MHz, d$_6$-DMSO): □ 0.01-0.02 (m, 2H); 0.38-0.41 (d, J=7.4 Hz, 2H); 0.73-0.75 (m, 1H); 0.86-0.88 (d, J=5.9 Hz, 3H); 1.07-1.09 (d, J=6.1 Hz, 3H); 1.42-1.46 (m, 4H); 1.74-1.80 (m, 1H); 2.10-2.33 (m, 8H); 2.48-2.61 (m, 5H); 2.88-2.91 (dd, 1H); 3.25-3.54 (m, 6H); 5.04 (s, 1H); 6.60-6.66 (m, 3H); 7.10-7.15 (t, 1H); 7.17-7.20 (dd, 1H); 7.31-7.39 (m, 3H); 9.34 (s, 1H). MS: 563.1 (M+1, 50%), 209.1 (100%). Calculated for C$_{33}$H$_{46}$N$_4$O$_4$.1.52 H2O: C, 67.16; H, 8.38; N, 9.49. Found: C, 67.17; H, 8.12; N, 9.31.

EXAMPLE 91

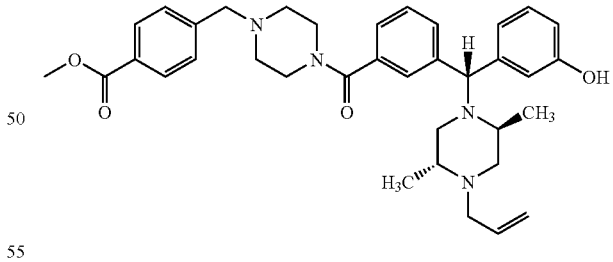

4-(4-{3-[(R)-((2S,5R)-4-Allyl-2,5-dimethyl-piperazin-1-yl)-(3-hydroxy-phenyl)-methyl]-benzoyl}-piperazin-1-ylmethyl)-benzoic acid methyl ester 4-Piperazin-1-ylmethylbenzoic acid methyl ester was made by the nucleophilic substitution between piperazine (18.80 g, 218.3 mmol, 5 equiv.) and methyl 4-(bromomethyl)benzoate (10.0 g, 43.6 mmol) in 60 mL of acetonitrile in the presence of sodium carbonate (23.18 g, 218.3 mmol).

The title compound was made by a procedure identical to that of Example 57 with 4.69 g of Acid A and 2.89 g of 4-piperazin-1-ylmethyl-benzoic acid methyl ester (12.34 mmol) to give 0.84 g of pure compound as a light yellow solid. $^1$H NMR (300 MHz, d$_6$-DMSO): □ 0.87-0.89 (d, J=6.0 Hz, 3H); 1.04-1.06 (d, J=6.1 Hz, 3H); 1.78-1.82 (m, 1H); 2.02-2.05 (dd, 1H); 2.36-2.39 (m, 1H); 2.48-2.53 (m, 4H); 2.67-2.71 (dd, 1H); 2.78-2.87 (dd, 1H); 3.14-3.18 (dd, 1H); 3.35-3.49 (m, 6H); 3.56 (s, 2H); 3.82 (s, 3H); 4.99 (s, 1H); 5.06-5.18 (dd, 2H); 5.70-5.83 (m, 1H); 6.63-6.65 (m, 3H); 7.08-7.13 (t, 1H); 7.18-7.20 (d, J=7.0 Hz, 1H); 7.31-7.46 (m, 5H); 7.90-7.93 (d, J=8.2 Hz, 2H); 9.34 (s, 1H). Calculated for C$_{36}$H$_{44}$N$_4$O$_4$.1.00 CH$_3$OH: C, 70.67; H, 7.69; N, 8.91. Found: C, 70.57; H, 7.34; N, 9.06.

EXAMPLE 92

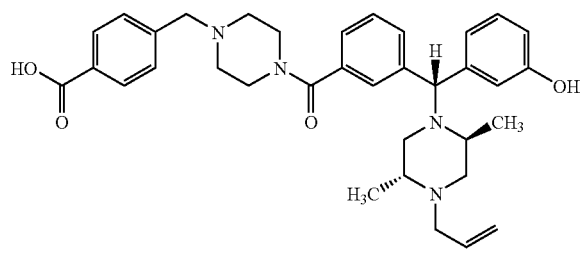

4-(4-{3-[(R)-((2S,5R)-4-Allyl-2,5-dimethyl-piperazin-1-yl)-(3-hydroxy-phenyl)-methyl]-benzoyl}-piperazin-1-ylmethyl)-benzoic acid The ester of Example 91 (0.55 g) was hydrolyzed with 2.30 mL of 1 N NaOH solution in 3 mL of tetrahydrofuran. The reaction mixture was evaporated to dryness, 2 mL of water was added, and the resulting solution was extracted with 2×4 mL of EtOAc/Et$_2$O to remove impurities. Hydrochloric acid (1.0 N, 2.30 mL) was added dropwise to precipitate product. A light yellow gel was formed during the neutralization, collected by filtration, washed by cold water and dried in a vacuum oven (30 mm Hg, 40° C.) overnight to give 210 mg (39%) of the title compound. $^1$H NMR (300 MHz, d$_6$-DMSO): □ 0.87-0.89 (d, J=6.0 Hz, 3H); 1.04-1.06 (d, J=6.1 Hz, 3H); 1.78-1.82 (m, 1H); 2.02-2.05 (dd, 1H); 2.36-2.53 (m, 5H); 2.67-2.71 (m, 1H); 2.78-2.87 (m, 1H); 3.14-3.90 (m, 10H); 4.99-5.25 (m, 3H); 5.70-5.89 (m, 1H); 6.60-6.75 (m, 3H); 7.08-7.55 (m, 7H); 7.90-7.93 (m, 2H); 9.36 (s, 1H). Calculated for C$_{35}$H$_{42}$N$_4$O$_4$.2.00 H$_2$O: C, 67.94; H, 7.49; N, 9.05. Found: C, 67.95; H, 7.34; N, 9.04.

EXAMPLE 93

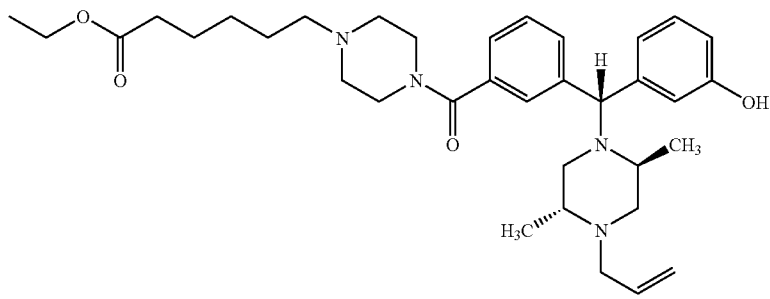

6-(4-{3-[(R)-((2S,5R)-4-Allyl-2,5-dimethyl-piperazin-1-yl)-(3-hydroxy-phenyl)-methyl]-benzoyl}-piperazin-1-yl)-hexanoic acid ethyl ester 6-Piperazin-1-yl-hexanoic acid ethyl ester was made by the nucleophilic substitution between piperazine (19.31 g, 224.1 mmol) and ethyl 6-bromohexanoate (10.0 g, 44.8 mmol) in 250 mL of acetonitrile in the presence of sodium carbonate (23.75 g, 224.1 mmol). The crude yield was about 92%.

The title compound was made by a procedure identical to that of Example 57 with 12 g of Acid A and 9.39 g of 6-piperazin-1-yl-hexanoic acid ethyl ester (41.1 mmol, 1.30 equiv.) to give 12.49 g (67%) of desired product as a yellow solid. $^1$H NMR (300 MHz, d$_6$-DMSO): □ 0.90-0.92 (d, J=6.0 Hz, 3H); 1.05-1.07 (d, J=6.1 Hz, 3H); 1.13-1.17 (t, 3H), 1.23-1.30 (m, 2H); 1.35-1.42 (m, 2H); 1.45-1.54 (m, 2H); 1.78-1.84 (dd, 1H); 2.04-2.10 (dd, 1H); 2.19-2.28 (m, 6H); 2.48-2.52 (m, 4H); 2.68-2.71 (dd, 1H); 2.79-2.86 (dd, 1H); 3.12-3.19 (dd, 1H); 3.31-3.53 (m, 4H); 3.99-4.06 (q, 2H); 5.00 (s, 1H); 5.06-5.17 (dd, 2H); 5.73-5.78 (m, 1H); 6.63-6.68 (m, 3H); 7.09-7.14 (t, 1H); 7.17-7.20 (dd, 1H); 7.31-7.41 (m, 3H); 9.31 (s, 1H). MS: 591.2 (M+1, 30%), 437.3 (40%), 153.2 (100%). Calculated for C$_{35}$H$_{50}$N$_4$O$_4$.0.60 CH$_3$OH: C, 70.09; H, 8.66; N, 9.18. Found: C, 70.11; H, 8.72; N, 9.23.

EXAMPLE 94

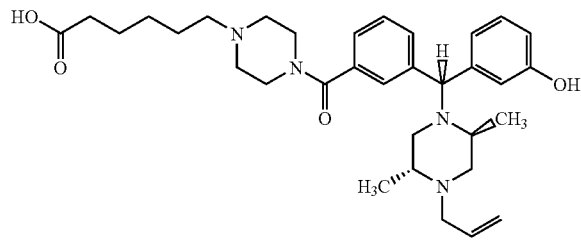

6-(4-{3-[(R)-((2S,5R)-4-Allyl-2,5-dimethyl-piperazin-1-yl)-(3-hydroxy-phenyl)-methyl]-benzoyl}-piperazin-1-yl)-hexanoic acid The ester of Example 93 (0.54 g) was hydrolyzed with 2.29 mL of 1 N NaOH solution in 5 mL of tetrahydrofuran. The reaction mixture was evaporated to dryness, 2 mL of water was added, and the resulting solution was extracted with 2×4 mL of EtOAc/Et$_2$O to remove impurities. Hydrochloric acid (1.0 N, 2.29 mL) was added dropwise followed by several drops of 0.1 N HCl to adjust pH to 6.0-6.5. The water layer was lyophilized overnight. The residue was redissolved in isopropanol, filtered to remove sodium chloride, and concentrated under reduced pressure. The residue was redissolved in water, lyophilized overnight, and dried in a vacuum oven (30 mm Hg, 40° C.) to give 500 mg (97%) of the title compound as a white solid. $^1$H NMR (300 MHz, d$_6$-DMSO): ☐ 0.90-0.92 (d, J=5.8 Hz, 3H); 1.05-1.07 (d, J=6.0 Hz, 3H); 1.24-1.29 (m, 2H); 1.37-1.53 (m, 4H); 1.77-1.84 (dd, 1H); 2.04-2.11 (dd, 1H); 2.15-2.27 (m, 7H); 2.48-2.52 (m, 4H); 2.69-2.72 (dd, 1H); 2.80-2.87 (dd, 1H); 3.01-3.54 (m, 6H); 5.00 (s, 1H); 5.06-5.18 (dd, 2H); 5.70-5.81 (m, 1H); 6.63-6.67 (m, 3H); 7.09-7.14 (t, 1H); 7.18-7.20 (dd, 1H); 7.31-7.41 (m, 3H); 9.35 (s, 1H). MS: 563.3 (M+1, 100%), 409.3 (60%), 209.2 (100%), 153.2 (85%). Calculated for C$_{33}$H$_{46}$N$_4$O$_4$.0.11 HCl 1.55 H$_2$O: C, 66.65; H, 8.34; N, 9.42; Cl, 0.66. Found: C, 66.65; H, 8.34; N, 9.30; Cl, 0.69.

EXAMPLE 95

6-(4-{3-[(R)-((2S,5R)-2,5-dimethyl-piperazin-1-yl)-(3-hydroxy-phenyl)-methyl]-benzoyl}-piperazin-1-yl)-hexanoic acid ethyl ester The allyl portion of the compound of Example 93 (11.60 g, 19.63 mmol) was removed using tris(triphenylphosphine)rhodium (I) chloride (2.09 g, 2.26 mmol). The reaction mixture in acetonitrile (144 mL) and water (36 mL) was heated under a gentle reflux and the solvent was allowed to distil off slowly. Additional acetonitrile/water (4:1, 180 mL) was added with a rate such as to maintain a steady distillation. After the addition of solvent was completed, the distillation was continued until the volume was reduced to approximately 50 mL. The cooled solution was concentrated under reduced pressure. The residual dark brown solid was purified by chromatography on Biotage silica gel column (32-63 μm, 60 A, cartridge Lot#40S1614-1) eluting first with dichloromethane to remove the less polar contaminant, then using 5% methanol in dichloromethane with 1 mL of 50% NH4OH, then 10% methanol in dichloromethane. The desired fractions were combined and the solvent was removed under reduced pressure. The amine 6-(4-{3-[(R)-((2S,5R)-2,5-dimethyl-piperazin-1-yl)-(3-hydroxy-phenyl)-methyl]-benzoyl}-piperazin-1-yl)-hexanoic acid ethyl ester was obtained as 7.37 g (68%) of a yellow solid.

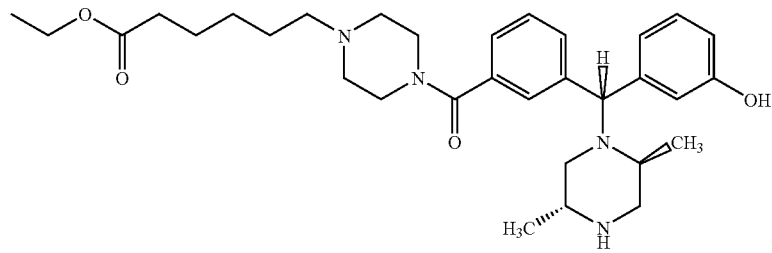

EXAMPLE 96

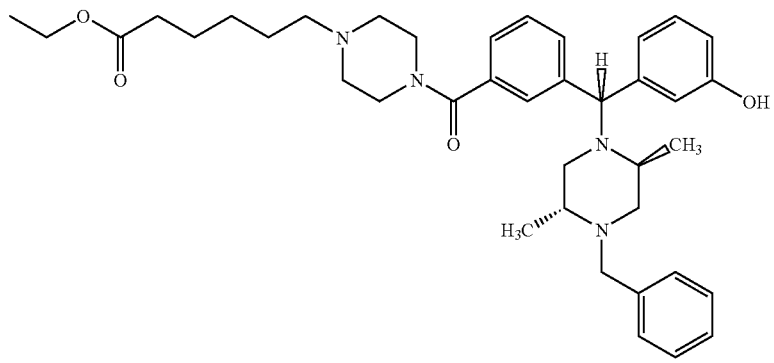

6-(4-{3-[(R)-((2S,5R)-4-Benzyl-2,5-dimethyl-piperazin-1-yl)-(3-hydroxy-phenyl)-methyl]-benzoyl}-piperazin-1-yl)-hexanoic acid ethyl ester The above free amine (1.50 g, 2.72 mmol, Example 95) and benzaldehyde (0.58 g, 5.5 mmol) were placed in a 100 mL flask and sealed under nitrogen. Tetrahydrofuran (40 mL) and 0.34 mL of acetic acid (5.99 mmol, 2.20 equiv.) was added. The reaction was stirred at room temperature for 20 minutes, and then sodium triacetoxyborohydride (1.44 g, 6.81 mmol) was added and stirred overnight. The reaction solution was concentrated under reduced pressure and partitioned between ethyl acetate (60 mL) and saturated sodium hydrogencarbonate (30 mL). The organic layer was washed with brine, dried over $Na_2SO_4$ and concentrated under reduced pressure. The residual dark brown oil (2.23 g) was purified by chromatography on a Biotage column (SiO2-F Flash Cartridge, 8 g, 32-6 μm, 60 A) eluting first with dichloromethane to remove the less polar contaminant, then using 2.5% methanol in dichloromethane. The desired fractions were combined and the solvent was removed under reduced pressure. The title compound was obtained as 1.10 g of a yellow solid. $^1$H NMR (300 MHz, $d_6$-DMSO): ☐ 1.00-1.02 (m, 6H); 1.12-1.17 (t, 3H), 1.25-1.30 (m, 2H); 1.35-1.56 (m, 4H); 1.89-2.00 (m, 2H); 2.23-2.28 (m, 7H); 2.48-2.65 (m, 6H); 3.19-3.33 (m, 3H); 3.54-3.56 (m, 1H); 3.73-3.78 (dd, 1H); 3.98-4.05 (q, 2H); 4.96 (s, 1H); 6.63-6.69 (m, 3H); 7.08-7.42 (m, 10H); 9.34 (s, 1H). MS: 641.1 (M+1, 55%), 437.2 (65%), 209.1 (80%), 203.2 (100%). Calculated for $C_{39}H_{52}N_4O_4$·0.10 $CH_2Cl_2$: C, 72.32; H, 8.10; N, 8.63. Found: C, 72.29; H, 8.12; N, 8.61.

EXAMPLE 97

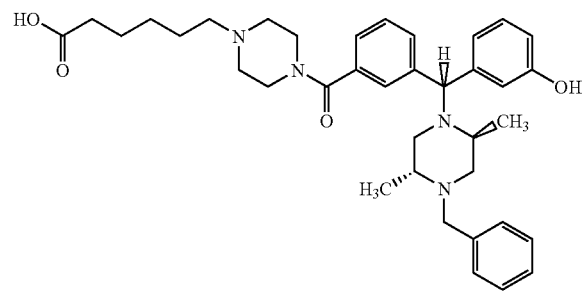

6-(4-{3-[(R)-((2S,5R)-4-Benzyl-2,5-dimethyl-piperazin-1-yl)-(3-hydroxy-phenyl)-methyl]-benzoyl}-piperazin-1-yl)-hexanoic acid The ester of Example 96 (0.75 g) was hydrolyzed with 2.93 mL of 1 N NaOH solution in 5 mL of tetrahydrofuran. The reaction mixture was evaporated to dryness, 2 mL of water was added, and the resulting solution was extracted with 2×4 mL of $Et_2O$ to remove impurities. Hydrochloric (1.0 N, 2.93 mL) was added dropwise followed by several drops of 0.1 N HCl to adjust pH to 6.0-6.5. A yellow gel precipitated during neutralization, which was collected by filtration, washed with water, and dried in a vacuum oven (30 mm Hg, 40° C.) overnight to give 570 mg (79%) of the title compound. $^1$H NMR (300 MHz, $d_6$-DMSO): ☐ 1.00-1.02 (m, 6H); 1.25-1.30 (m, 2H); 1.35-1.56 (m, 4H); 1.89-2.00 (m, 2H); 2.23-2.28 (m, 7H); 2.48-2.65 (m, 6H); 3.19-3.73 (m, 6H); 4.96 (s, 1H); 6.63-6.69 (m, 3H); 7.08-7.55 (m, 10H); 9.35 (s, 1H). MS: 613.0 (M+1, 45%), 409.1 (35%), 203.2 (100%). Calculated for $C_{37}H_{48}N_4O_4$·0.60 $H_2O$: C, 71.26; H, 7.95; N, 8.98. Found: C, 71.22; H, 7.78; N, 8.78.

EXAMPLE 98

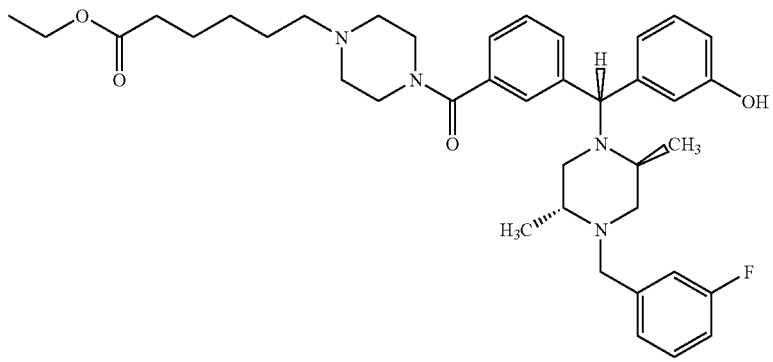

6-(4-{3-[(R)-((2S,5R)-4-(3-Fluorobenzyl)-2,5-dimethyl-piperazin-1-yl)-(3-hydroxy-phenyl)-methyl]-benzoyl}-piperazin-1-yl)-hexanoic acid ethyl ester The title compound was made by a procedure identical to that of Example 96 with 1.50 g of 6-(4-{3-[(R)-((2S,5R)-2,5-dimethyl-piperazin-1-yl)-(3-hydroxy-phenyl)-methyl]-benzoyl}-piperazin-1-yl)-hexanoic acid ethyl ester (2.72 mmol) and 0.68 g of 3-fluorobenzaldehyde (5.5 mmol) to give 0.97 g of desired compound as a light yellow solid. $^1$H NMR (300 MHz, $d_6$-DMSO): ☐ 1.01-1.03 (d, J=5.8 Hz, 6H); 1.12-1.17 (t, 3H), 1.22-1.29 (m, 2H); 1.35-1.56 (m, 4H); 1.90-2.02 (m, 2H); 2.23-2.33 (m, 7H); 2.48-2.66 (m, 6H); 3.25-3.33 (m, 3H); 3.54-3.56 (m, 1H); 3.72-3.76 (dd, 1H); 3.98-4.05 (q, 2H); 4.95 (s, 1H); 6.62-6.71 (m, 3H); 6.97-7.43 (m, 9); 9.34 (s, 1H). MS: 659.0 (M+1, 80%), 437.2(85%), 221.2(100%), 209.1(70%). Calculated for $C_{39}H_{51}FN_4O_4$ 0.11 $CH_2Cl_2$: C, 70.30; H, 7.73; N, 8.38; F, 2.84. Found: C, 70.32; H, 7.78; N, 8.41; F, 3.00.

EXAMPLE 99

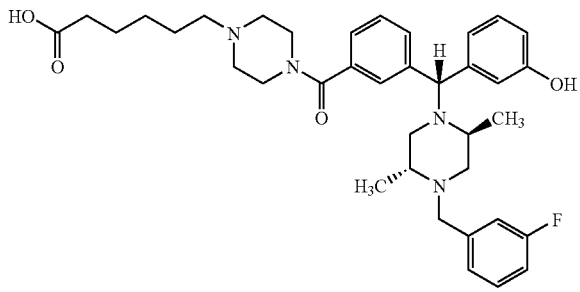

6-(4-{3-[(R)-((2S,5R)-4-(3-Fluorobenzyl)-2,5-dimethyl-piperazin-1-yl)-(3-hydroxy-phenyl)-methyl]-benzoyl}-piperazin-1-yl)-hexanoic acid The ester of Example 98 (0.62 g) was hydrolyzed with 2.35 mL of 1 N NaOH solution in 5 mL of tetrahydrofuran. The reaction mixture was evaporated to dryness, 2 mL of water was added, and the resulting solution was extracted with 2×4 mL of Et$_2$O to remove impurities. Hydrochloric acid (1.0 N, 2.35 mL) was added dropwise to neutralize the solution. A white gel was formed during neutralization, which was collected by filtration, washed with water, and dried in a vacuum oven (30 mm Hg, 40° C.) overnight to give 500 mg (84%) of the title compound as a white solid. $^1$H NMR (300 MHz, d$_6$-DMSO): ☐ 1.01-1.02 (d, J=4.3 Hz, 6H); 1.25-1.29 (m, 2H); 1.40-1.51 (m, 4H); 1.91-1.98 (m, 2H); 2.16-2.25 (m, 7H); 2.48-2.66 (m, 6H); 3.33-3.55 (m, 5H); 3.72-3.76 (dd, 1H); 4.94 (s, 1H); 6.63-6.70 (m, 3H); 6.98-7.43 (m, 9H); 9.36 (s, 1H); MS: 630.9 (M+1, 50%), 409.1 (40%), 221.1 (100%), 109.0 (70%). Calculated for C$_{37}$H$_{47}$FN$_4$O$_4$ 1.50 H$_2$O: C, 67.56; H, 7.66; N, 8.52; F, 2.89. Found: C, 67.56; H, 7.29; N, 8.37; F, 2.98.

EXAMPLE 100

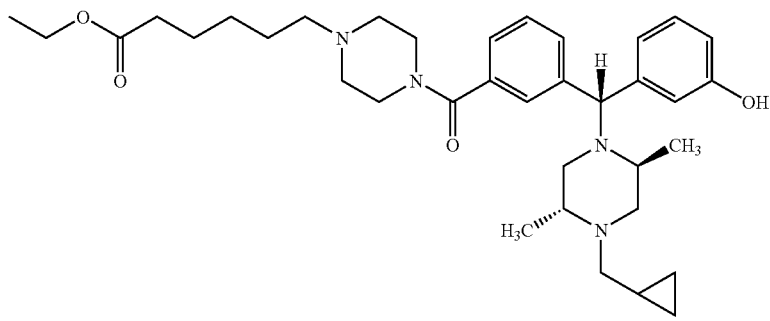

6-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-hexanoic acid ethyl ester The title compound was made by a procedure identical to that of Example 96 with 1.50 g of 6-(4-{3-[(R)-((2S,5 R)-2,5-dimethyl-piperazin-1-yl)-(3-hydroxy-phenyl)-methyl]-benzoyl}-piperazin-1-yl)-hexanoic acid ethyl ester (2.72 mmol) and 0.38 g of cyclopropanecarboxaldehyde (5.5 mmol) to give 0.63 g of desired compound as a white solid. $^1$H NMR (300 MHz, d$_6$-DMSO): ☐ 0.02-0.03 (m, 2H); 0.38-0.41 (d, J=7.7 Hz, 2H); 0.73-0.75 (m, 1H); 0.86-0.88 (d, J=5.7 Hz, 3H); 1.08-1.10 (d, J=6.0 Hz, 3H); 1.12-1.17 (t, 3H), 1.21-1.28 (m, 2H); 1.37-1.55 (m, 4H); 1.73-1.80 (m, 1H); 2.07-2.33 (m, 8H); 2.48-2.62 (m, 5H); 2.86-2.89 (dd, 1H); 3.27-3.33 (m, 4H); 3.53-3.56 (m, 1H); 3.98-4.05 (q, 2H); 5.04 (s, 1H); 6.62-6.66 (m, 3H); 7.10-7.15 (t, 1H); 7.18-7.20 (dd, 1H); 7.32-7.40 (m, 3H); 9.34 (s, 1H). MS: 604.9 (M+1, 70%), 437.1 (50%), 209.1 (75%), 167.1 (100%). Calculated for C$_{36}$H$_{52}$N$_4$O$_4$ 0.08 CH$_2$Cl$_2$: C, 70.85; H, 8.60; N, 9.16. Found: C, 70.89; H, 8.65; N, 8.86.

EXAMPLE 101

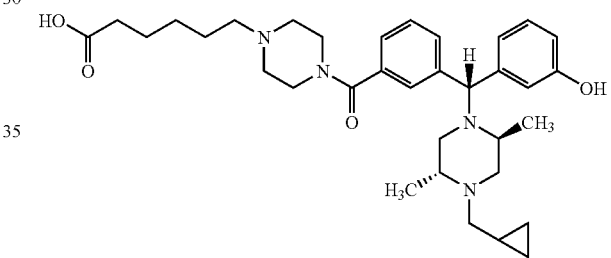

6-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-hexanoic acid The ester of Example 100 (0.30 g) was hydrolyzed with 1.24 mL of 1 N NaOH solution in 5 mL of tetrahydrofuran. The reaction mixture was evaporated to dryness, 2 mL of water was added, and the resulting solution was extracted with 2×4 mL of Et₂O to remove impurities. Hydrochloric acid (1.0 N, 1.24 mL) was added dropwise followed by several drops of 0.1 N HCl to adjust pH to 6.0-6.5. The water layer was lyophilized overnight. The residue was redissolved in isopropanol, filtered to remove sodium chloride, and concentrated under reduced pressure. The residue was redissolved in water, lyophilized overnight, and dried in a vacuum oven (30 mm Hg, 40° C.) to give 250 mg (87%) of the title compound. ¹H NMR (300 MHz, d₆-DMSO): ☐ 0.02-0.03 (m, 2H); 0.38-0.41 (d, 2H); 0.73-0.75 (m, 1H); 1.01-1.02 (d, J=5.8 Hz, 3H); 1.16-1.50 (m, 9H); 1.89-2.62 (m, 15H); 3.02-3.54 (m, 6H); 5.14 (s, 1H); 6.62-6.67 (m, 3H); 7.12-7.22 (m, 2H); 7.32-7.39 (m, 3H); 9.42 (s, 1H). MS: 577.2 (M+1, 70%), 409.2 (25%), 209.1 (40%), 149.1 (100%). Calculated for $C_{34}H_{48}N_4O_4$ 0.53 $CH_2Cl_2$ 1.60 $H_2O$: C, 65.35; H, 8.34; N, 8.97; Cl, 3.01. Found: C, 65.37; H, 8.27; N, 8.78; Cl, 3.01.

The following piperazine derivatives were synthesized by similar methods described for above piperazine derivatives.

EXAMPLE 102

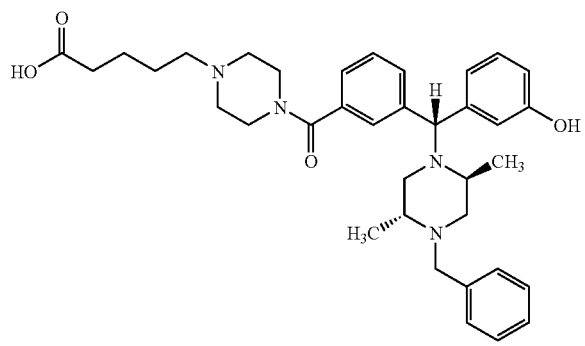

5-(4-{3-[(R)-((2S,5R)-4-benzyl-2,5-dimethyl-piperazin-1-yl)-(3-hydroxy-phenyl)-methyl]-benzoyl}-piperazin-1-yl)-pentanoic acid ¹H NMR (300 MHz, d₆-DMSO): ☐ 1.01-1.03 (m, 6H); 1.38-1.56 (m, 4H); 1.81-2.00 (m, 2H); 2.20-2.40 (m, 7H); 2.40-2.71 (m, 6H); 2.97-3.50 (m, 3H); 3.54-3.60 (m, 1H); 3.73-3.77 (dd, J=12.1 Hz, 1H); 4.96 (s, 1H); 6.65-6.69 (m, 3H); 7.08-7.42 (m, 10H); 9.38 (s, 1H). Calculated for $C_{36}H_{46}N_4O_4$ 0.37 HCl 1.00 $H_2O$: C, 68.60; H, 7.74; N, 8.89; Cl, 2.08. Found: C, 68.62; H, 7.64; N, 8.49; Cl, 2.10.

EXAMPLE 103

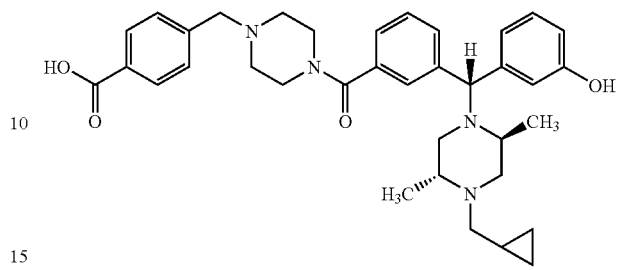

4-(4-{3-[(R)-((2S,5R)-4-Cyclopropylmethyl-2,5-dimethyl-piperazin-1-yl)-(3-hydroxy-phenyl)-methyl]-benzoyl}-piperazin-1-ylmethyl)-benzoic acid ¹H NMR (300 MHz, d₆-DMSO): ☐ 0.07 (s, 2H), 0.42 (s, 2H), 0.82-0.99 (m, 4H); 0.99-1.02 (m, 3H); 1.75-1.84 (m, 1H); 2.01-2.78 (m, 7H); 2.78-2.96 (m, 1H); 3.01-3.90 (m, 10H); 5.05 (s, 1H); 6.50-6.75 (m, 3H); 7.03-7.60 (m, 7H); 7.80-8.01 (m, 2H); 9.36 (s, 1H). MS: 597.2 (M+1, 100%), 209.2 (100%). Calculated for $C_{36}H_{44}N_4O_4$ 0.15 HCl 1.55 $H_2O$: C, 68.62; H, 7.56; N, 8.89; Cl, 0.84. Found: C, 68.63; H, 7.45; N, 8.87; Cl, 0.81.

EXAMPLE 104

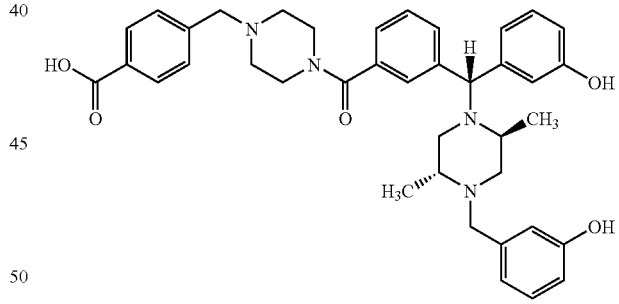

4-(4-{3-[(R)-[(2S,5R)-4-(3-Hydroxy-benzyl)-2,5-dimethyl-piperazin-1-yl]-(3-hydroxy-phenyl)-methyl]-benzoyl}-piperazin-1-ylmethyl)-benzoic acid ¹H NMR (300 MHz, d₆-DMSO): ☐ 1.07-1.27 (m, 6H); 1.75-1.98 (m, 2H); 2.02-3.00 (m, 6H); 3.00-3.75 (m, 10H); 5.09 (s, 1H); 6.61-6.82 (m, 6H); 7.04-7.44 (m, 8H); 7.89-7.91 (d, J=8.0 Hz, 2H); 9.28 (s, 1H); 9.44 (s, 1H); 9.74 (s, 1H). MS: 649.8 (M+1, 68%), 209.1 (100%). Calculated for $C_{39}H_{44}N_4O_5$ 0.32 HCl 1.65 $H_2O$: C, 67.87; H, 6.95; N, 8.12; Cl, 1.64. Found: C, 67.81; H, 6.80; N, 7.92; Cl, 1.65.

EXAMPLE 105

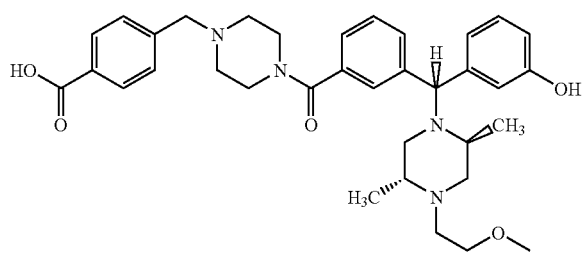

4-[4-(3-{(R)-(3-Hydroxy-phenyl)-[(2S,5R)-4-(2-methoxy-ethyl)-2,5-dimethyl-piperazin-1-yl]-methyl}-benzoyl)-piperazin-1-ylmethyl]-benzoic acid $^1$H NMR (300 MHz, d$_6$-DMSO): 0.86-0.88 (d, J=5.5 Hz, 3H); 1.04-1.06 (d, J=5.8 Hz, 3H); 1.15-1.21 (m, 1H); 1.77 (s, 3H); 2.13-2.16 (m, 1H); 2.31-2.60 (m, 7H); 2.60-2.68 (m, 1H); 2.76-2.79 (d, J=8.9 Hz, 1H); 2.80-3.90 (m, 10H); 4.98 (s, 1H); 6.63-6.66 (m, 3H); 7.07-7.19 (m, 4H); 7.32-7.40 (m, 3H); 7.77-7.79 (d, J=7.6 Hz, 2H); 9.33 (s, 1H). MS: 601.1 (M+1, 90%), 176.1 (100%) Calculated for C$_{35}$H$_{44}$N$_4$O$_5$ 0.11 HCl 3.00 H$_2$0: C, 63.81; H, 7.67; N, 8.50; Cl, 0.59. Found: C, 63.89; H, 7.23; N, 8.11; Cl, 0.51.

EXAMPLE 106

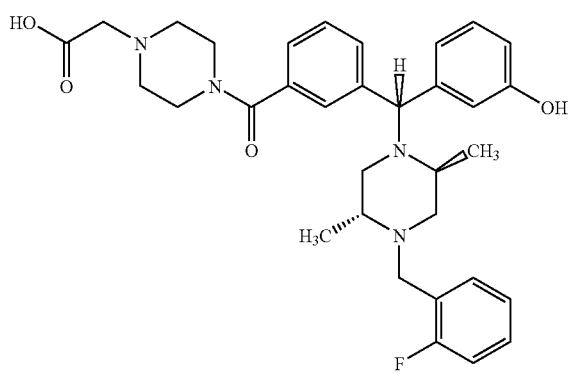

(4-{3-[(R)-((2S,5R)-4-(2-Fluoro-benzyl)-2,5-dimethyl-piperazin-1-yl)-(3-hydroxy-phenyl)-methyl]-benzoyl}-piperazin-1-yl)-acetic acid $^1$H NMR (300 MHz, d$_6$-DMSO): ☐ 0.83-1.21 (m, 6H); 1.86-2.00 (m, 2H); 2.48 (s, 4H); 2.54-2.64 (m, 4H); 3.13 (s, 2H); 3.45-3.76 (m, 7H); 4.96 (s, 1H); 6.62-6.71 (m, 3H); 7.11-7.35 (m, 9H); 9.37 (s, 1H). Calculated for C$_{33}$H$_{39}$FN$_4$O$_4$ 1.68 H$_2$O: C, 65.52; H, 7.06; N, 9.26; F, 3.14. Found: C, 65.52; H, 6.71; N, 9.11; F, 3.11.

EXAMPLE 107

[4-(4-{3-[(R)-((2S,5R)-4-Allyl-2,5-dimethyl-piperazin-1-yl)-(3-hydroxy-phenyl)-methyl]-benzoyl}-piperazin-1-ylmethyl)-indol-1-yl]-acetic acid $^1$H NMR (300 MHz, d$_6$-DMSO): ☐ 0.81-1.00 (m, 3H); 1.05-1.07 (d, J=5.7 Hz, 3H); 1.78-1.82 (m, 1H); 2.03-2.20 (m, 1H); 2.20-2.63 (m, 7H); 2.65-2.80 (m, 1H); 2.80-3.00 (m, 1H); 3.00-3.71 (m, 8H); 4.95-5.21 (m, 5H); 5.70-5.89 (m, 1H); 6.56-6.70 (m, 4H); 6.94-7.37 (m, 9H); 9.34 (s, 1H). MS: 636.1 (M+1, 90%), 188.1 (100%). Calculated for C$_{38}$H$_{45}$N$_5$O$_4$ 0.09 HCl 1.05 H$_2$O: C, 69.36; H, 7.23; N, 10.64; Cl, 0.48. Found: C, 69.36; H, 7.15; N, 10.51; Cl, 0.49.

EXAMPLE 108

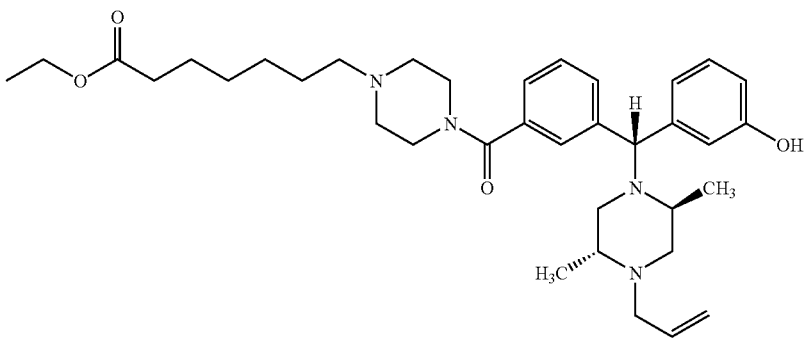

7-(4-{3-[(R)-((2S,5R)-4-Allyl-2,5-dimethyl-piperazin-1-yl)-(3-hydroxy-phenyl)-methyl]-benzoyl}-piperazin-1-yl)-heptanoic acid ethyl ester ¹H NMR (300 MHz, d₆-DMSO): ☐ 0.89-0.91 (d, J=5.8 Hz, 3H); 1.04-1.06 (d, J=6.1 Hz, 3H); 1.12-1.17 (t, 3H), 1.24-1.30 (m, 2H); 1.38-1.41 (m, 2H); 1.46-1.51 (m, 2H); 1.77-1.83 (dd, 1H); 2.03-2.09 (dd, 1H); 2.16-2.40 (m, 9H); 2.48-2.52 (m, 4H); 2.68-2.71 (dd, 1H); 2.78-2.85 (dd, 1H); 3.14-3.19 (dd, 1H); 3.21-3.55 (m, 4H); 3.98-4.05 (q, 2H); 5.00 (s, 1H); 5.05-5.17 (dd, 2H); 5.72-5.81 (m, 1H); 6.63-6.67 (m, 3H); 7.09-7.17 (m, 2H); 7.31-7.41 (m, 3H); 9.35 (s, 1H). MS: 605.1 (M+1, 65%), 451.3 (85%), 153.2 (100%). Calculated for $C_{36}H_{52}N_4O_4$ 0.11 $CH_2Cl_2$: C, 70.62; H, 8.57; N, 9.12. Found: C, 70.64; H, 8.75; N, 9.12.

EXAMPLE 109

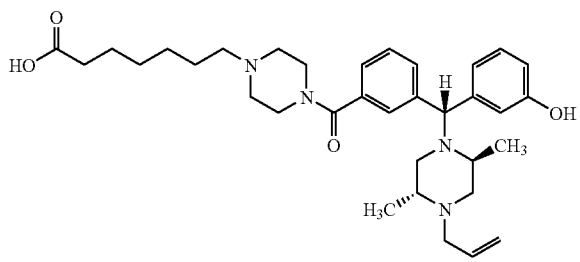

7-(4-{3-[(R)-((2S,5R)-4-Allyl-2,5-dimethyl-piperazin-1-yl)-(3-hydroxy-phenyl)-methyl]-benzoyl}-piperazin-1-yl)-heptanoic acid ¹H NMR (300 MHz, d₆-DMSO): ☐ 0.95-1.08 (m, 6H); 1.24-1.30 (m, 2H); 1.38-1.46 (m, 4H); 1.85-1.95 (m, 1H); 2.14-2.56 (m, 14H); 2.70-3.00 (m, 2H); 3.03-3.55 (m, 6H); 5.03 (s, 1H); 5.05-5.27 (m, 2H); 5.72-5.89 (m, 1H); 6.64-6.66 (m, 3H); 7.10-7.21 (m, 2H); 7.32-7.41 (m, 3H); 9.36 (s, 1H). MS: 563.3 (M+1, 100%), 409.3 (60%), 209.2 (100%), 153.2 (85%). Calculated for $C_{34}H_{48}N_4O_4$ 0.32 HCl 1.25 $H_2O$: C, 66.84; H, 8.38; N, 9.17; Cl, 1.86. Found: C, 66.83; H, 8.34; N, 9.17; Cl, 1.88.

EXAMPLE 110

7-(4-{3-[(R)-((2S,5R)-4-Benzyl-2,5-dimethyl-piperazin-1-yl)-(3-hydroxy-phenyl)-methyl]-benzoyl}-piperazin-1-yl)-heptanoic acid ethyl ester ¹H NMR (300 MHz, d₆-DMSO): ☐ 0.90-1.01 (m, 6H); 1.12-1.16 (t, 3H); 1.24-1.30 (m, 2H); 1.39-1.49 (m, 4H); 1.88-1.99 (m, 2H); 2.22-2.39 (m, 9H); 2.48-2.65 (m, 6H); 3.19-3.34 (m, 3H); 3.41-3.60 (m, 1H); 3.73-3.77 (d, J=13.8 Hz, 1H); 3.98-4.05 (q, 2H); 4.96 (s, 1H); 6.63-6.69 (m, 3H); 7.08-7.42 (m, 10H); 9.35 (s, 1H). Calculated for $C_{40}H_{54}N_4O_4$ 0.35 MeOH: C, 72.76; H, 8.38; N, 8.41. Found: C, 72.75; H, 8.34; N, 8.49.

EXAMPLE 111

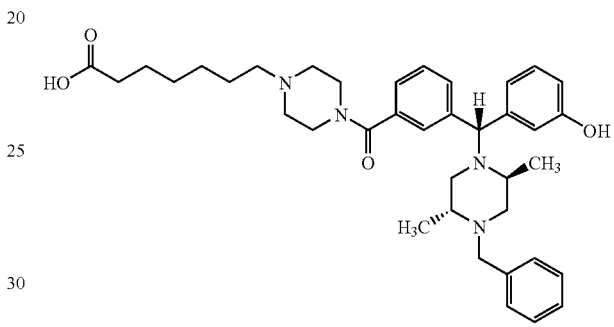

7-(4-{3-[(R)-((2S,5R)-4-Benzyl-2,5-dimethyl-piperazin-1-yl)-(3-hydroxy-phenyl)-methyl]-benzoyl}-piperazin-1-yl)-heptanoic acid ¹H NMR (300 MHz, d₆-DMSO): ☐ 0.99-1.09 (m, 6H); 1.24-1.30 (m, 2H); 1.39-1.47 (m, 4H); 1.89-1.97 (m, 2H); 2.14-2.39 (m, 9H); 2.48-2.65 (m, 6H); 3.20-3.40 (m, 4H); 3.40-3.62 (m, 1H); 3.74-3.78 (d, J=12.1 Hz, 1H); 4.97 (s, 1H); 6.63-6.69 (m, 3H); 7.08-7.43 (m, 10H); 9.35 (s, 1H). MS: 627.2 (M+1, 75%), 423.2 (78%), 209.2 (100%). Calculated for $C_{38}H_{50}N_4O_4$ 0.89 $H_2O$: C, 71.00; H, 8.12; N, 8.72. Found: C, 71.00; H, 7.94; N, 8.57.

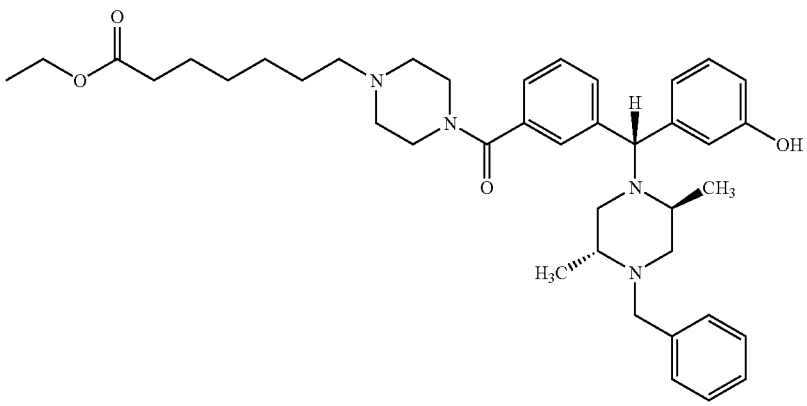

EXAMPLE 112

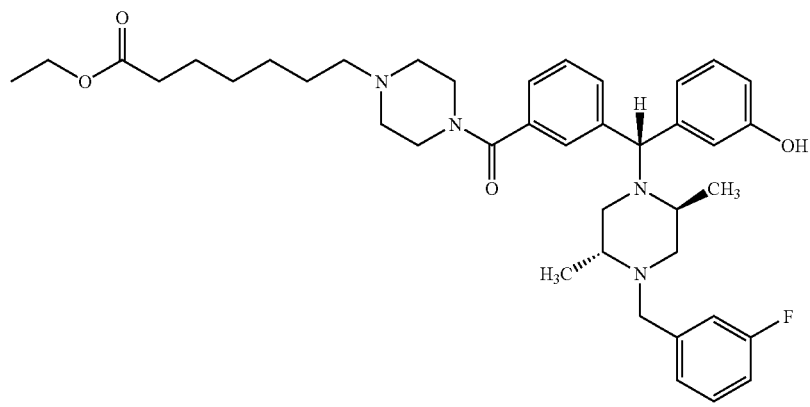

7-(4-{3-[(R)-[(2S,5R)-4-(3-Fluoro-benzyl)-2,5-dimethyl-piperazin-1-yl]-(3-hydroxy-phenyl)-methyl]-benzoyl}-piperazin-1-yl)-heptanoic acid ethyl ester $^1$H NMR (300 MHz, d$_6$-DMSO): ☐ 0.93-1.02 (m, 6H); 1.12-1.16 (t, 3H); 1.24-1.30 (m, 2H); 1.38-1.51 (m, 4H); 1.89-2.02 (m, 2H); 2.22-2.33 (m, 9H); 2.48-2.66 (m, 6H); 3.25-3.33 (m, 3H); 3.41-3.60 (m, 1H); 3.72-3.76 (d, J=13.8 Hz, 1H); 3.98-4.05 (q, 2H); 4.94 (s, 1H); 6.62-6.71 (m, 3H); 6.98-7.19 (m, 5H); 7.27-7.43 (m, 4H); 9.34 (s, 1H). MS 673.1 (M+1, 50%), 451.3 (90%), 209.2 (80%). Calculated for C$_{40}$H$_{53}$FN$_4$O$_4$ 0.22 MeOH: C, 71.05; H, 7.99; N, 8.24; F, 2.79. Found: C, 71.04; H, 7.90; N, 8.29; F, 2.73.

EXAMPLE 113

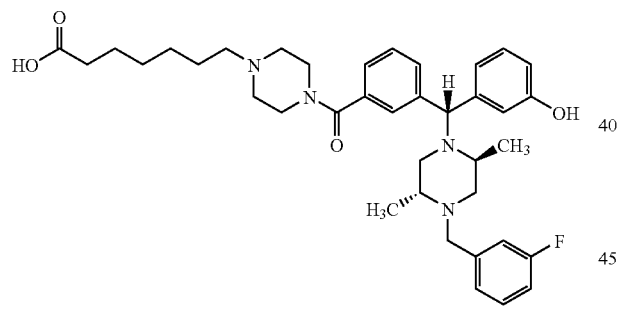

7-(4-{3-[(R)-[(2S,5R)-4-(3-Fluoro-benzyl)-2,5-dimethyl-piperazin-1-yl]-(3-hydroxy-phenyl-methyl]-benzoyl}-piperazin-1-yl)-heptanoic acid $^1$H NMR (300 MHz, d$_6$-DMSO): ☐ 0.95-1.02 (m, 6H); 1.24-1.35 (m, 2H); 1.35-1.51 (m, 4H); 1.93-2.01 (m, 2H); 2.14-2.40 (m, 9H); 2.40-2.66 (m, 6H); 3.25-3.55 (m, 5H); 3.71-3.76 (d, J=12.8 Hz, 1H); 4.94 (s, 1H); 6.63-6.70 (m, 3H); 6.98-7.19 (m, 5H); 7.27-7.43 (m, 4H); 9.34 (s, 1H). MS: 645.8 (M+1, 85%), 423.2 (90%), 176.0 (100%). Calculated for C$_{38}$H$_{49}$FN$_4$O$_4$ 0.66 H$_2$O: C, 69.50; H, 7.72; N, 8.53; F, 2.89. Found: C, 69.50; H, 7.48; N, 8.48; F, 2.92.

EXAMPLE 114

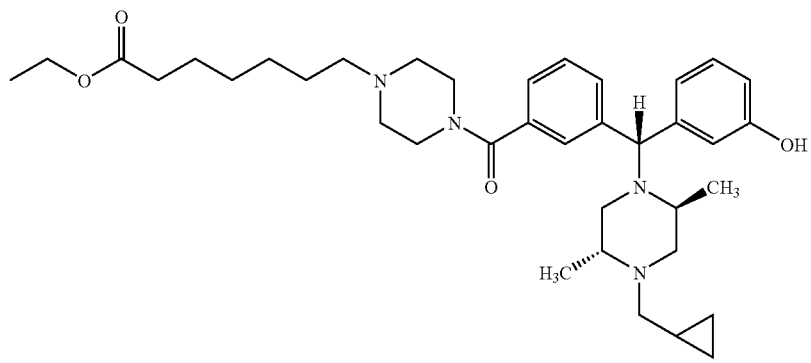

7-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-heptanoic acid ethyl ester $^1$H NMR (300 MHz, d$_6$-DMSO): ☐ 0.02-0.03 (m, 2H), 0.38-0.41 (m, 2H), 0.70-0.80 (m, 1H); 0.80-0.96 (m, 3H); 1.08-1.10 (d, J=5.9 Hz, 3H); 1.12-1.17 (t, 3H); 1.24-1.30 (m, 2H); 1.34-1.51 (m, 4H); 1.74-1.79 (m, 1H); 2.07-2.40 (m, 10H); 2.40-2.62 (m, 5H); 2.86-2.89 (d, J=9.5 Hz, 1H); 3.26-3.40 (m, 3H); 3.40-3.60 (m, 2H); 3.98-4.05 (q, 2H); 5.04 (s, 1H); 6.62-6.66 (m, 3H); 7.09-7.20 (m, 2H); 7.31-7.40 (m, 3H); 9.33 (s, 1H). Calculated for C$_{37}$H$_{54}$N$_4$O$_4$ 0.09 CH$_2$Cl$_2$: C, 71.11; H, 8.72; N, 8.94. Found: C, 71.13; H, 8.76; N, 8.97.

EXAMPLE 115

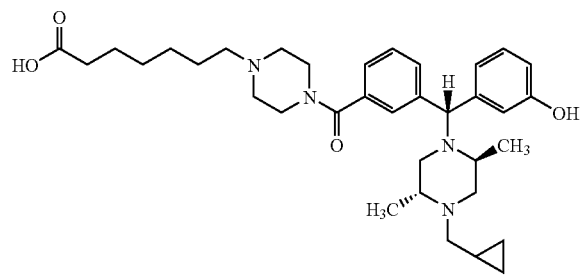

7-(4-{3-[(R)-((2S,5R)-4-Cyclopropylmethyl-2,5-dimethyl-piperazin-1-yl)-(3-hydroxy-phenyl)-methyl]-benzoyl}-piperazin-1-yl)-heptanoic acid $^1$H NMR (300 MHz, d$_6$-DMSO): ☐ 0.08-0.20 (m, 2H), 0.42-0.44 (m, 2H), 0.75-0.85 (m, 1H); 0.91-0.93 (m, 3H); 1.10-1.12 (d, J=5.7 Hz, 3H); 1.24-1.30 (m, 2H); 1.30-1.50 (m, 4H); 1.74-1.89 (m, 1H); 2.14-2.27 (m, 10H); 2.27-2.62 (m, 5H); 2.86-3.10 (m, 1H); 3.10-3.60 (m, 6H); 5.08 (s, 1H); 6.63-6.68 (m, 3H); 7.11-7.21 (m, 2H); 7.32-7.41 (m, 31H); 9.38 (s, 1H). MS: 591.2 (M+1, 100%), 209.1 (90%). Calculated for C$_{35}$H$_{50}$N$_4$O$_4$ 0.23 HCl 1.12 H$_2$O: C, 67.87; H, 8.54; N, 9.05; Cl, 1.32. Found: C, 67.88; H, 8.51; N, 8.86; Cl, 1.31.

EXAMPLE 116

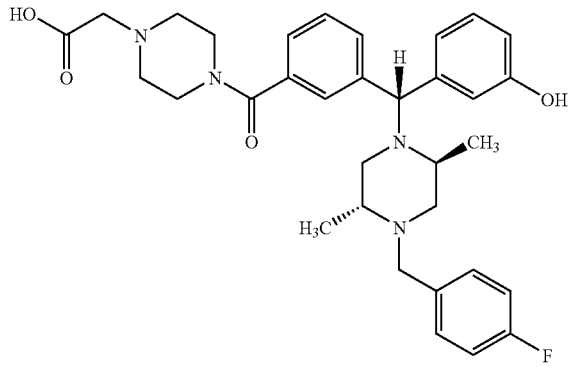

(4-{3-[(R)-[(2S,5R)-4-(4-Fluoro-benzyl)-2,5-dimethyl-piperazin-1-yl]-(3-hydroxy-phenyl)-methyl]-benzoyl}-piperazin-1-yl)-acetic acid $^1$H NMR (300 MHz, d$_6$-DMSO): ☐ 1.01 (s, 6H); 1.88-1.96 (m, 2H); 2.48 (s, 4H); 2.55-2.60 (m, 4H); 3.16 (s, 2H); 3.43-3.69 (m, 7H); 4.95 (s, 1H); 6.62-6.69 (m, 3H); 7.05-7.20 (m, 4H); 7.28-7.40 (m, 5H); 9.38 (s, 1H). Calculated for C$_{33}$H$_{39}$FN$_4$O$_4$ 0.45 H$_2$O: C, 68.01; H, 6.90; N, 9.61; F, 3.26. Found: C, 68.02; H, 6.75; N, 9.41; F, 3.32.

EXAMPLE 117

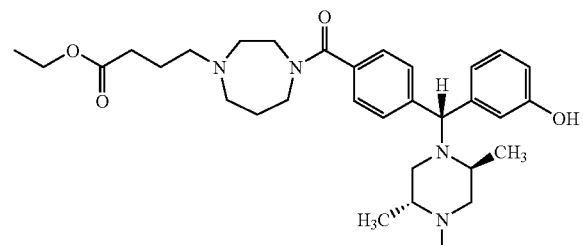

4-(4-{4-[(R)-((2S,5R)-4-Allyl-2,5-dimethylpiperazin-1-yl)(3-hydroxyphenyl)methyl]-benzoyl}[1,4]diazepan-1-yl)butyric acid ethyl ester Thionyl chloride (0.93 g) was added to the cloudy mixture of Acid B (2.13 g) in CH$_2$Cl$_2$ (150 mL) at room temperature. The reaction was stirred for 2 h while it was opened to air via a drying tube. At the end of 2 h, the reaction solution still had solid floating in the solution. Additional thionyl chloride (653 mg) was added to the reaction solution. The reaction was stirred for another 1 h. (Solid was still floating in the reaction solution.) The acid chloride solution was transferred into an addition funnel and then slowly added to a round-bottom flask containing 4-[1,4]diazepan-1-yl-butyric acid ethyl ester (1.2 g; cf. Example 7) and diisopropylethylamine (2.89 g) in CH$_2$Cl$_2$ (100 mL) at room temperature. The reaction was stirred at room temperature overnight while it was opened to air via a drying tube. The reaction was quenched by the addition of water (150 mL). Saturated NaHCO$_3$ solution was used to neutralize the water layer to pH≅8. The CH$_2$Cl$_2$ layer and water layer were separated. The water layer was extracted by CH$_2$Cl$_2$ (150 mL×3). The CH$_2$Cl$_2$ layers were combined, washed by H$_2$O (150 mL×2) and saturated NaCl solution (150 mL×1), dried over Na$_2$SO$_4$, and concentrated to give crude product (2.5 g), which was purified by silica gel chromatography conducted on CombiFlash™ Sq 16×(gradient: 100% CH$_2$Cl$_2$ to 10% MeOH in CH$_2$Cl$_2$) to give 4-(4-{4-[(R)-((2S,5R)-4-allyl-2,5-dimethylpiperazin-1-yl)(3-hydroxyphenyl)methyl]benzoyl}[1,4]diazepan-1-yl)butyric acid ethyl ester (752 mg; 23%). $^1$H NMR (300 MHz, CDCl$_3$) δ 7.40 (d, 2H, J=7.5 Hz), 7.27 (d, 2H, J=7.5 Hz), 7.09 (dd, 1H, J=8.0, 8.0 Hz), 6.63 (m, 3H), 5.88 (m, 1H), 5.27-5.12 (m, 3H), 4.09 (m, 2H), 3.73 (m, 2H), 3.43 (m, 3H), 2.98-2.79 (m, 3H), 2.67-2.42 (m, 8H), 2.30 (m, 2H), 2.19 (m, 1H), 2.02 (m, 1H), 1.93 (m, 1H), 1.75 (m, 3H), 1.22 (m, 3H), 1.13 (d, 3H, J=6.0 Hz), 1.03 (d, 3H, J=6.0 Hz).

EXAMPLE 118

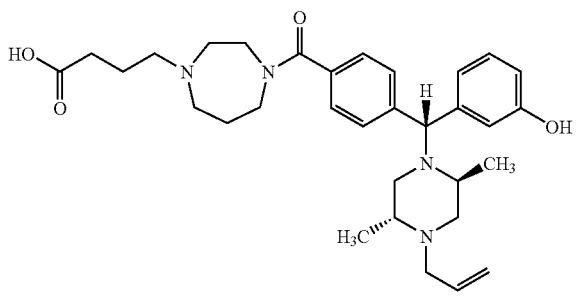

4-(4-{4-[(R)-((2S,5R)-4-Allyl-2,5-dimethylpiper-azin-1-yl)(3-hydroxy-phenyl)methyl]benzoyl)}[1,4]diazepan-1-yl)butyric acid To the compound of Example 117 (330 mg) in THF (5 mL) was added 1N NaOH solution (3 mL). The reaction was stirred at room temperature overnight. The reaction solution was neutralized by the addition of 1 N HCl solution (3 mL). The organic solvent was removed under vacuum. The remaining water layer was diluted by water (4 mL). The water layer was extracted by n-butanol (10 mL×3). The combined n-butanol layer was washed by water (10 mL×2) and concentrated to give crude product (245 mg), which was purified by silica gel chromatography conducted on CombiFlash™ Sq 16×(gradient: 100% $CH_2Cl_2$ to 30% MeOH in $CH_2Cl_2$) to give 4-(4-{4-[(R)-((2S,5R)-4-allyl-2,5-dimethylpiperazin-1-yl)(3-hydroxy-phenyl)methyl]benzoyl}[1,4]diazepan-1-yl)butyric acid (180 mg; 57%). $^1$H NMR (300 MHz, DMSO-$d_6$) δ 9.36 (bs, 1H), 8.31 (s, 1H), 7.40 (d, 2H, J=7.5 Hz), 7.30 (d, 2H, J=7.5 Hz), 7.12 (dd, 1H, J=8.0, 8.0 Hz), 6.66 (m, 3H), 5.78 (m, 1H), 5.20-4.97 (m, 3H), 3.59 (m, 2H), 3.47-3.34 (m, 2H), 3.18 (m, 1H), 2.86 (m, 1H), 2.73 (m, 2H), 2.60-2.49 (m, 7H), 2.42 (m, 1H), 2.21 (m, 2H), 2.10 (m, 1H), 1.83 (m, 2H), 1.69-1.55 (m, 3H), 1.06 (d, 3H, J=6.0 Hz), 0.94 (d, 3H, J=5.5 Hz).

Piperidine Derivatives

EXAMPLE 119

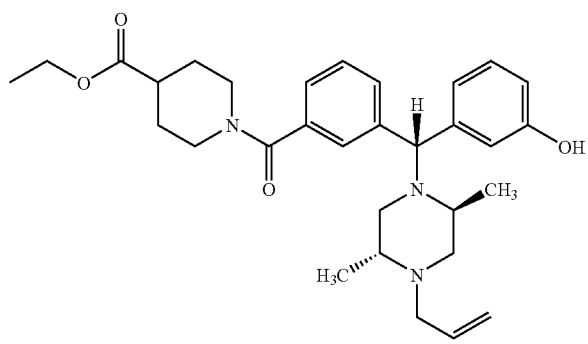

1-{3-[(R)-((2S,5R)-4-Allyl-2,5-dimethylpiperazin-1-yl)-(3-hydroxy-phenyl)methyl]benzoyl}piperidine-4-carboxylic acid ethyl ester Thionyl chloride (2.64 g, 22.2 mmol) was added to the cloudy mixture of Acid A (6.03 g) in $CH_2Cl_2$ (186 mL) at room temperature. The reaction was stirred at room temperature for 60 minutes under a drying tube. The reaction solution became clear. The acid chloride solution was transferred into an additional funnel and then slowly added to a round bottom flask containing ethyl isonipecotate (2.49 g, 15.86 mmol) and triethylamine (4.01 g) in $CH_2Cl_2$ (85 mL) at room temperature. The reaction was stirred at room temperature overnight under a drying tube. Water (200 mL) was added, followed by the addition of saturated $NaHCO_3$ solution to neutralize the water layer to pH≅8. The $CH_2Cl_2$ layer and water layer were separated. The water layer was extracted by $CH_2Cl_2$ (40 mL×2). The combined $CH_2Cl_2$ layer was washed with $H_2O$ (70 mL×3) and brine (70 mL×1), dried over $Na_2SO_4$ and concentrated to give crude product, which was purified by silica gel chromatography conducted on CombiFlash™ Sq 16×(gradient: 100% $CH_2Cl_2$ to 10% MeOH in $CH_2Cl_2$) to give 1-{3-[(R)-((2S,5R)-4-allyl-2,5-dimethyl-piperazin-1-yl)-(3-hydroxy-phenyl)methyl]benzoyl}-piperidine-4-carboxylic acid ethyl ester (5.2 g; 63%). $^1$H NMR (300 MHz, CDCl3) δ 7.46 (m, 2H), 7.28 (m, 2H), 7.07 (dd, J=8.0, 8.0 Hz, 1H), 6.60 (m, 3H), 5.91 (m, 1H), 5.20 (m, 3H), 4.50 (m, 1H), 4.15 (q, J=7.0 Hz, 2H), 3.70 (m, 1H), 3.44 (m, 1H), 3.05-2.84 (m, 4H), 2.70 (m, 1H), 2.56 (m, 3H), 2.20 (m, 1H), 2.01 (m, 1H), 1.73 (m, 4H), 1.26 (t, J=7.0 Hz, 3H), 1.16 (d, J=6.0 Hz, 3H), 1.04 (d, J=6.0 Hz, 3H).

EXAMPLE 120

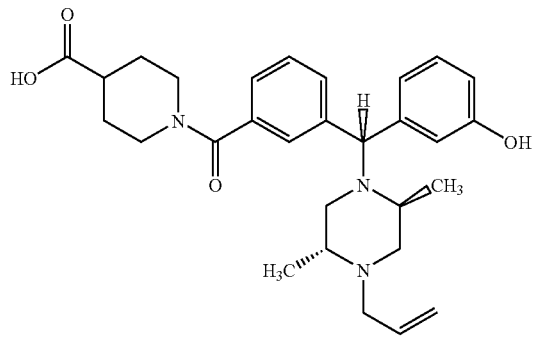

1-{3-[(R)-((2S,5R)-4-Allyl-2,5-dimethyl-piperazin-1-yl)-(3-hydroxy-phenyl)-methyl]-benzoyl}-piperidine-4-carboxylic acid To a solution of 1-{3-[(R)-((2S,5R)-4-allyl-2,5-dimethyl-piperazin-1-yl)-(3-hydroxy-phenyl)-methyl]-benzoyl}-piperidine-4-carboxylic acid ethyl ester (512 mg, Example 119) in THF (5 mL) was added 1 N NaOH solution (4 mL). The reaction was stirred at room temperature overnight. The reaction solution was neutralized by the addition of 1 N HCl solution (4 mL). The reaction solution was concentrated to dryness under vacuum to give crude product, which was subjected to reverse phase C-18 column chromatography conducted on CombiFlash™ Sq 16×(gradient: 100% $H_2O$ to 100% MeOH) to give 1-{3-[(R)-((2S,5R)-4-allyl-2,5-dimethyl-piperazin-1-yl)-(3-hydroxy-phenyl)-methyl]-benzoyl}-piperidine-4-carboxylic acid (445 mg; 92%). $^1$H NMR (300 MHz, $CD_3OD$) δ 7.52-7.37 (m, 3H), 7.28 (m, 1H), 7.19 (dd, J=8.0, 8.0 Hz, 1H), 6.72 (m, 3H), 5.93 (m, 1H), 5.45 (m, 2H), 5.30 (s, 1H), 4.48 (m, 1H), 3.69 (m, 2H), 3.39 (m, 1H), 3.19-2.99 (m, 4H), 2.79 (m, 2H), 2.65 (m, 1H), 2.47 (m, 1H), 2.13 (m, 1H), 1.98 (m, 1H), 1.79 (m, 1H), 1.64 (m, 2H), 1.27 (d, J=6.0 Hz, 3H), 1.20 (d, J=6.5 Hz, 3H).

EXAMPLE 121

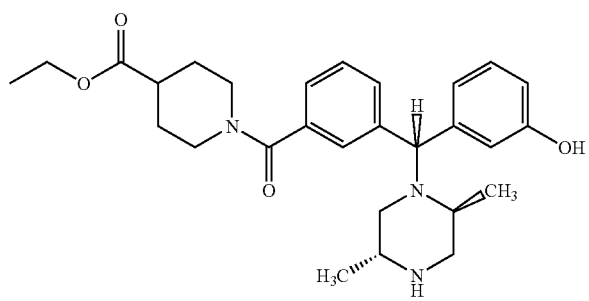

1-{3-[(R)-((2S,5R)-2,5-Dimethyl-piperazin-1-yl)-(3-hydroxy-phenyl)-methyl]-benzoyl}-piperidine-4-carboxylic acid ethyl ester Bis(dibenzylideneacetone)palladium (398 mg) was added to a solution of 1,4-bis(diphenylphosphino)butane (295 mg) in THF (7.3 mL) under nitrogen at room temperature for 10 minutes. The resulting Pd-catalyst was transferred to the solution of 1-{3-[(R)-((2S,5R)-4-allyl-2,5-dimethyl-piperazin-1-yl)-(3-hydroxy-phenyl)-methyl]-benzoyl}-piperidine-4-carboxylic acid ethyl ester (3.6 g, Ex. 58) and thiosalicylic acid (1.71 g) in THF (40 mL) via a syringe. The reaction was stirred under nitrogen at room temperature for overnight. The reaction mixture was concentrated under vacuum. EtOAc (75 mL) was added to the residue, followed by the addition of 1 N aqueous HCl (110 mL). The EtOAc layer and acidic water layer were separated. The acidic water layer was extracted with EtOAc (50 mL×2). The acidic water layer was neutralized with saturated NaHCO₃ solution to pH≅8 and then extracted with n-butanol (75 mL×3). The combined n-butanol layer was washed with water (60 mL) and concentrated to give crude product, 1-{3-[(R)-((2S,5R)-2,5-dimethyl-piperazin-1-yl)-(3-hydroxy-phenyl)-methyl]-benzoyl}-piperidine-4-carboxylic acid ethyl ester (3.0 g). ¹H NMR (300 MHz, CD₃OD) δ 7.55-7.37 (m, 3H), 7.27 (m, 1H), 7.18 (dd, J=8.0, 8.0, 1H), 6.71 (m, 2H), 6.61 (s, 1H), 5.36 (s, 1H), 4.44 (m, 1H), 4.14 (q, J=7.0 Hz, 2H), 3.68 (m, 1H), 3.08 (m, 2H), 2.89 (m, 2H), 2.65 (m, 2H), 2.46 (m, 1H), 2.00 (m, 1H), 1.84 (m, 1H), 1.76-1.45 (m, 3H), 1.25 (t, J=7.0 Hz, 3H), 1.21 (d, J=6.0 Hz, 3H), 0.96 (d, J=6.5, 3H).

EXAMPLE 122

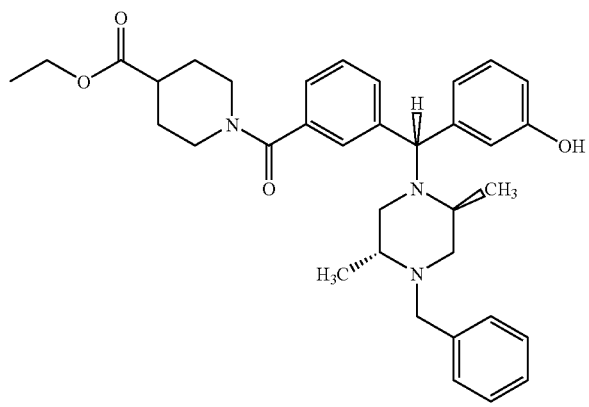

1-{3-[(R)-((2S,5R)-4-Benzyl-2,5-dimethyl-piperazin-1-yl)-(3-hydroxy-phenyl)-methyl]-benzoyl}-piperidine-4-carboxylic acid ethyl ester Sodium triacetoxyborohydride (1.083 g) was added to a mixture of 1-{3-[(R)-((2S,5R)-2,5-dimethyl-piperazin-1-yl)-(3-hydroxy-phenyl)-methyl]-benzoyl}-piperidine-4-carboxylic acid ethyl ester (981 mg, Example 121), benzaldehyde (434.1 mg) and acetic acid (245.6 mg) in dimethylformamide (15 mL). The reaction was stirred under nitrogen at room temperature for 2 hours. The reaction was quenched by the addition of saturated NH₄Cl solution (2 mL), followed by the addition of H₂O (10 mL). The resulting solution was diluted with 120 mL of H₂O which caused precipitation of product. The solution was neutralized with saturated NaHCO₃ solution to pH=7 to precipitate additional product. The mixture was filtered thru a celite pad. The collected solid was rinsed with water (35 mL×2). The solid was dissolved with EtOAc (50 mL) and then eluted through the celite pad. The filtrate (EtOAc solution) was washed with H₂O (15 mL×2) and brine (15 mL×1), dried over Na₂SO₄ and concentrated to give crude product, which was purified by silica gel chromatography conducted on CombiFlash™ Sq 16×(gradient: 100% CH₂Cl₂ to 10% MeOH in CH₂Cl₂) to give 1-{3-[(R)-((2S,5R)-4-benzyl-2,5-dimethyl-piperazin-1-yl)-(3-hydroxy-phenyl)-methyl]-benzoyl}-piperidine-4-carboxylic acid ethyl ester as pink solid (570 mg; 49%). ¹H NMR (300 MHz, CDCl3) δ 7.47 (m, 3H), 7.26 (m, 6H), 7.07 (dd, J=8.0, 8.0 Hz, 1H), 6.60 (m, 2H), 6.54 (s, 1H), 5.04 (s, 1H), 4.50 (m, 1H), 4.16 (q, J=7.0 Hz, 2H), 3.98 (d, J=13.0 Hz, 1H), 3.69 (m, 1H), 3.18 (d, J=13.0 Hz, 1H), 3.02 (m, 2H), 2.70-2.52 (m, 5H), 2.00 (m, 3H), 1.73 (m, 31H), 1.26 (t, J=7.0 Hz, 3H), 1.10 (d, J=6.0 Hz, 3H), 1.02 (d, J=6.3 Hz, 3H).

EXAMPLE 123

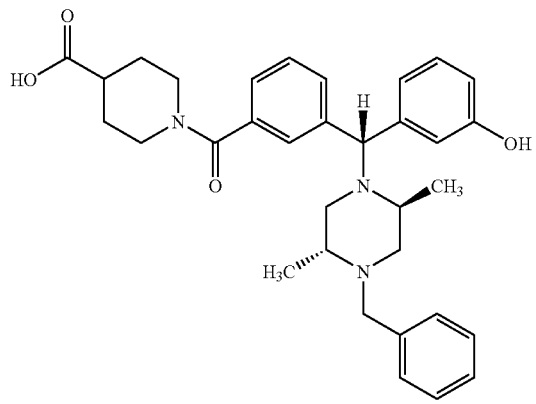

1-{3-[(R)-((2S,5R)-4-Benzyl-2,5-dimethyl-piperazin-1-yl)-(3-hydroxy-phenyl)-methyl]-benzoyl}-piperidine-4-carboxylic acid To a solution of 1-{3-[(R)-((2S,5R)-4-benzyl-2,5-dimethyl-piperazin-1-yl)-(3-hydroxy-phenyl)-methyl]-benzoyl}-piperidine-4-carboxylic acid ethyl ester (365 mg, Example 122) in THF (4 mL) was added 1N NaOH solution (3 mL). The reaction was stirred at room temperature overnight. The reaction solution was neutralized by the addition of 1 N HCl solution (3 mL). The resulting solution was concentrated under vacuum to give crude product, which was subjected to reverse phase C-18 column chromatography conducted on CombiFlash™ Sq 16×(gradient: 100% H₂O to 100% MeOH) to give 1-{3-[(R)-((2S,5R)-4-benzyl-2,5-dimethyl-piperazin-1-yl)-(3-hydroxy-phenyl)-methyl]-benzoyl}-piperidine-4-carboxylic acid (228 mg; 66%). ¹H NMR (300 MHz, CD₃OD) δ 7.49 (m, 2H), 7.38 (m, 6H), 7.28 (m, 1H), 7.18 (dd, J=8.0, 8.0 Hz, 1H), 6.73 (m, 2H), 6.67 (s, 1H), 5.26 (s, 1H), 4.48 (m, 1H), 4.27 (d, J=13.0 Hz, 1H), 3.66 (m, 2H), 3.13 (m, 1H), 3.01 (m, 2H), 2.85 (m, 2H), 2.68 (m, 1H), 2.49 (m, 2H), 2.13 (dd, J=10.5, 10.5 Hz, 1H), 2.00 (m, 1H), 1.82 (m, 1H), 1.65 (m, 2H), 1.28 (d, J=6.5 Hz, 3H), 1.17 (d, J=6.0 Hz, 3H).

EXAMPLE 124

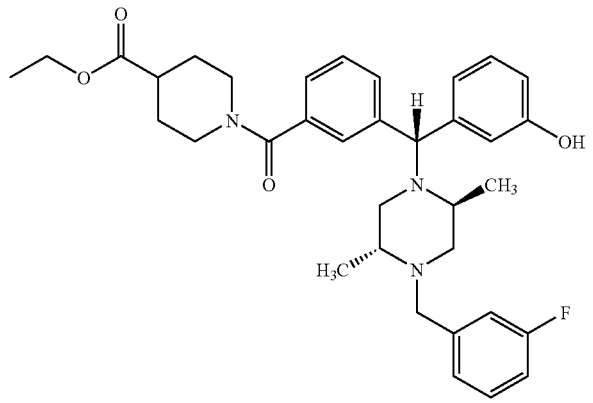

1-{3-[(R)-[(2S,5R)-4-(3-Fluoro-benzyl)-2,5-dimethyl-piperazin-1-yl]-(3-hydroxy-phenyl)-methyl]-benzoyl}-piperidine-4-carboxylic acid ethyl ester Sodium triacetoxyborohydride (1.012 g) was added to a mixture of 1-{3-[(R)-((2S,5R)-2,5-dimethyl-piperazin-1-yl)-(3-hydroxy-phenyl)-methyl]-benzoyl}-piperidine-4-carboxylic acid ethyl ester (916 mg, Example 121), 3-fluorobenzaldehyde (474 mg) and acetic acid (229.4 mg) in dimethylformamide (15 mL). The reaction was stirred under nitrogen at room temperature for 2 hours. The reaction was quenched by the addition of saturated NH$_4$Cl solution (2 mL), followed by the addition of H$_2$O (10 mL). The resulting solution was diluted with 120 mL of H$_2$O to precipitate product. The solution was neutralized with saturated NaHCO$_3$ solution to pH=7 to produce additional precipitate. The mixture was filtered thru a celite pad. The collected solid was rinsed by water (35 mL×2). The solid was dissolved in EtOAc (50 mL) and then eluted from the celite pad. The filtrate (EtOAc solution) was washed with H$_2$O (15 mL×2) and brine (15 mL×1), dried over Na$_2$SO$_4$ and concentrated to give crude product, which was purified by silica gel chromatography conducted on CombiFlash™ Sq 16×(gradient: 100% CH$_2$Cl$_2$ to 10% MeOH in CH$_2$Cl$_2$) to give 1-{3-[(R)-[(2S,5R)-4-(3-fluoro-benzyl)-2,5-dimethyl-piperazin-1-yl]-(3-hydroxy-phenyl)-methyl]-benzoyl}-piperidine-4-carboxylic acid ethyl ester as light pink solid (675 mg; 60%). $^1$H NMR (300 MHz, CDCl3) δ 7.47 (m, 2H), 7.25 (m, 3H), 7.06 (m, 3H), 6.90 (m, 1H), 6.64 (m, 3H), 5.03 (s, 1H), 4.50 (m, 1H), 4.15 (q, J=7.0 Hz, 2H), 3.91 (d, J=13.5 Hz, 1H), 3.70 (m, 1H), 3.18 (d, J=13.5 Hz, 1H), 3.02 (m, 2H), 2.60 (m, 5H), 2.01 (m, 3H), 1.72 (m, 3H), 1.26 (t, J=7.0 Hz, 3H), 1.05 (m, 6H).

EXAMPLE 125

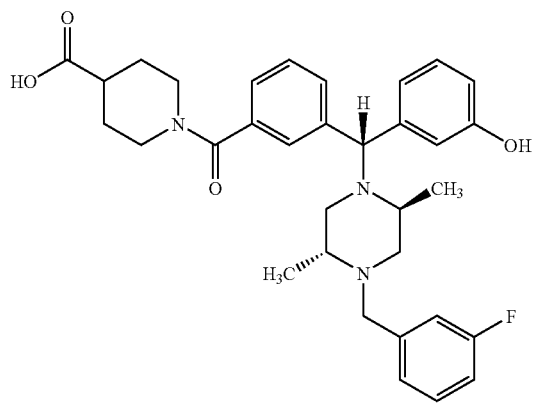

1-{3-[(R)-[(2S,5R)-4-(3-Fluoro-benzyl)-2,5-dimethyl-piperazin-1-yl]-(3-hydroxyphenyl)-methyl]-benzoyl}-piperidine-4-carboxylic acid To a solution of 1-{3-[(R)-[(2S,5R)-4-(3-fluoro-benzyl)-2,5-dimethyl-piperazin-1-yl]-hydroxy-phenyl)-methyl]-benzoyl}-piperidine-4-carboxylic acid ethyl ester (463 mg, Example 124) in THF (4 mL) was added 1N NaOH solution (3 mL). The reaction was stirred at room temperature overnight. The reaction solution was neutralized by the addition of 1 N HCl solution (3 mL). The resulting solution was concentrated under vacuum to give crude product, which was subjected to reverse phase C-18 column chromatography conducted on CombiFlash™ Sq 16×(gradient: 100% H$_2$O to 100% MeOH) to give 1-{3-[(R)-[(2S,5R)-4-(3-fluoro-benzyl)-2,5-dimethyl-piperazin-1-yl]-(3-hydroxyphenyl)-methyl]-benzoyl}-piperidine-4-carboxylic acid (183 mg; 41%). $^1$H NMR (300 MHz, CD$_3$OD) δ 7.48 (m, 2H), 7.37 (m, 2H), 7.27 (m, 1H), 7.16 (m, 3H), 7.04 (m, 1H), 6.71 (m, 3H), 5.21 (s, 1H), 4.47 (m, 1H), 4.13 (d, J=13.5 Hz, 1H), 3.66 (m, 1H), 3.51 (d, J=13.5 Hz, 1H), 3.09 (m, 2H), 2.81 (m, 3H), 2.68 (m, 1H), 2.55 (m, 1H), 2.30 (m, 1H), 2.06 (m, 2H), 1.83 (m, 1H), 1.65 (m, 2H), 1.21 (d, J=6.0 Hz, 3H), 1.15 (d, J=6.5 Hz, 3H).

Examples 126-133 were synthesized by similar methods described for above piperidine derivatives.

EXAMPLE 126

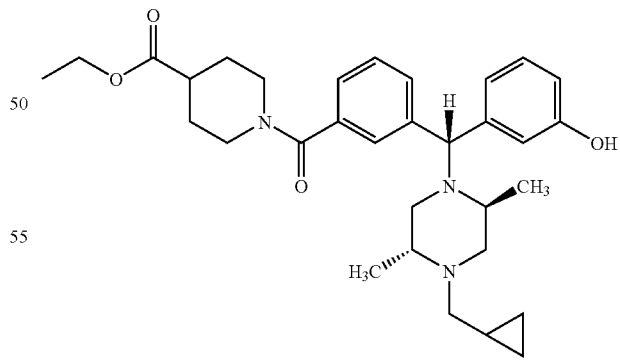

1-{3-[(R)-((1S,4R)-4-Cyclopropylmethyl-2,5-dimethyl-piperazin-1-yl]-(3-hydroxy-phenyl)-methyl]-benzoyl}-piperidine-4-carboxylic acid ethyl ester $^1$H NMR (300 MHz, CDCl$_3$) δ 7.41 (s, 1H), 7.26 (m, 3H), 7.08 (dd, 1H, J=8.0, 8.0 Hz), 6.82 (m, 2H), 6.60 (m, 1H), 5.24

(s, 1H), 4.49 (m, 1H), 4.14 (q, 2H, J=7.0 Hz), 3.66 (m, 1H), 3.44 (m, 1H), 3.29-2.88 (m, 7H), 2.77 (m, 2H), 2.56 (m, 1H), 2.00 (m, 1H), 1.50-1.88 (m, 3H), 1.31 (m, 3H), 1.25 (t, 3H, J=7.0 Hz), 1.21 (m, 4H), 0.74 (m, 2H), 0.35 (m, 2H).

EXAMPLE 127

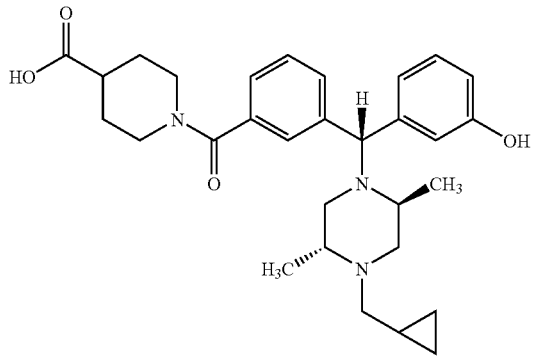

1-{3-[(R)-((1S,4R)-4-Cyclopropylmethyl-2,5-dimethyl-piperazin-1-yl)-(3-hydroxy-phenyl)-methyl]-benzoyl}-piperidine-4-carboxylic acid $^1$H NMR (300 MHz, CD$_3$OD) δ 7.56 (m, 1H), 7.43 (m, 2H), 7.30 (m, 1H), 7.22 (dd, 1H, J=8.0, 8.0 Hz), 6.74 (m, 3H), 5.36 (s, 1H), 4.52 (m, 1H), 3.67 (m, 1H), 3.56 (d, 1H, J=9.5 Hz), 3.31 (m, 1H), 3.08-2.88 (m, 7H), 2.43 (m, 1H), 2.19 (m, 1H), 1.98 (m, 1H), 1.77 (m, 1H), 1.65 (m, 2H), 1.35 (d, 3H, J=6.0 Hz), 1.22 (d, 3H, J=6.0 Hz), 1.05 (m, 1H), 0.72 (m, 2H), 0.37 (m, 2H).

EXAMPLE 128

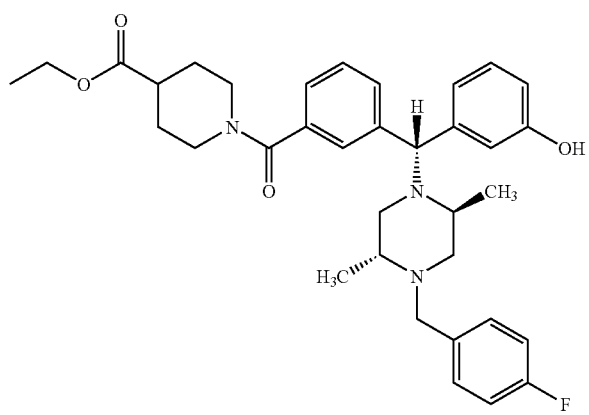

1-{3-[(R)-[(2S,5R)-4-(4-Fluoro-benzyl)-2,5-dimethyl-piperazin-1-yl]-(3-hydroxy-phenyl)-methyl]-benzoyl}-piperidine-4-carboxylic acid ethyl ester $^1$H NMR (300MHz, CDCl$_3$) δ: 1.06 (m, 6H), 1.26 (t, J=7.0 Hz, 3H), 1.79 (m, 3H), 1.84-2.00 (m, 3H), 2.52-2.66(m, 5H), 3.02 (m, 2H), 3.11 (d, J=13.0 Hz, 1H), 3.71 (bs, 1H), 3.87 (d, J=13.0 Hz, 1H), 4.15 (q, J=7.0 Hz, 2H), 4.50 (bs, 1H), 505 (s, 1H), 6.60-6.68 (m, 3H), 6.96 (t, J=8.5 Hz, 2H), 7.09 (t, J=8.0 Hz, 1H), 7.22-7.33 (m, 4H), 7.44 (s, 1H), 7.48 (m, 1H).

EXAMPLE 129

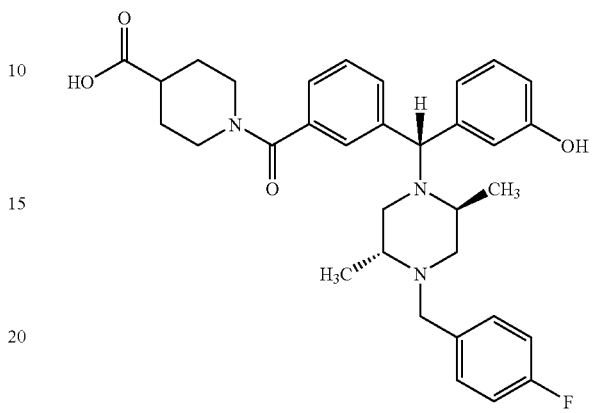

1-{3-[(R)-[(2S,5R)-4-(4-Fluoro-benzyl)-2,5-dimethyl-piperazin-1-yl]-(3-hydroxy-phenyl)-methyl]-benzoyl}-piperidine-4-carboxylic acid $^1$H NMR (300 MHz, CD$_3$OD) δ 7.51-7.37 (m, 5H), 7.28 (m, 1H), 7.21-7.09 (m, 3H), 6.71 (m, 3H), 5.26 (s, 1H), 4.46 (m, 1H), 4.26 (m, 1H), 3.67 (m, 2H), 3.08 (m, 3H), 2.86 (m, 2H), 2.69 (m, 1H), 2.56 (m, 1H), 2.46 (m, 1H), 2.14 (dd, 1H, J=11.0, 11.0 Hz), 2.00 (m, 1H), 1.83 (m, 1H), 1.63 (m, 2H), 1.28 (d, 31H, J=6.5 Hz), 1.18 (d, 31H, J=6.5 Hz).

EXAMPLE 130

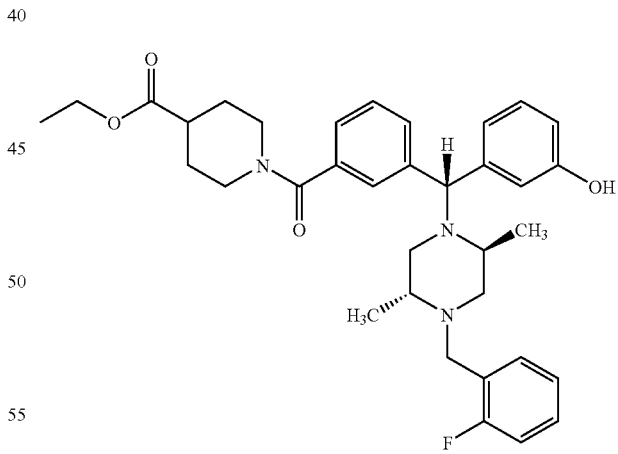

1-{3-[(R)-[(2S,5R)-4-(2-Fluoro-benzyl)-2,5-dimethyl-piperazin-1-yl]-(3-hydroxy-phenyl)-methyl]-benzoyl}-piperidine-4-carboxylic acid ethyl ester $^1$H NMR (300 MHz, CDCl$_3$) δ 1.07 (m, 6H), 1.27 (t, J=7.0 Hz, 3H), 1.73 (m, 3H), 1.92-2.10 (m, 3H), 2.52-2.61 (m, 4H), 2.70 (d, J=11.0 Hz, 1H), 3.02 (m, 2H), 3.31 (d, J=13.5 Hz, 1H), 3.71 (bs, 1H), 3.88 (d, J=13.5 Hz, 1H), 4.15 (t, J=7.0 Hz, 2H), 4.50 (bs, 1H), 5.06 (s, 1H), 6.51-6.68(m, 3H), 7.00 (m, 1H), 7.06-7.22 (m, 4H), 7.28-7.39 (m, 2H), 7.42 (s, 1H), 7.49 (m, 1H).

EXAMPLE 131

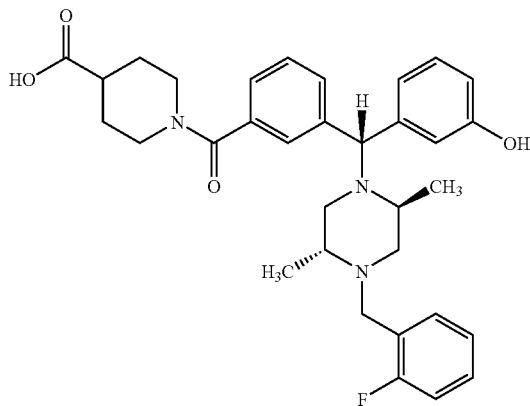

1-{3-[(R)-[(2S,5R)-4-(2-Fluoro-benzyl)-2,5-dimethyl-piperazin-1-yl]-(3-hydroxy-phenyl)-methyl]-benzoyl}-piperidine-4-carboxylic acid $^1$H NMR (300 MHz, CD$_3$OD) δ 7.49-7.31 (m, 5H), 7.27 (m, 1H), 7.14 (m, 3H), 6.70 (m, 3H), 5.24 (s, 1H), 4.46 (m, 1H), 4.10 (d, 1H, J=13.5 Hz), 3.65 (m, 1H), 3.63 (d, 1H, J=13.5 Hz), 3.08 (m, 2H), 2.88-2.73 (m, 3H), 2.65 (m, 1H), 2.55 (m, 1H), 2.32 (dd, 1H, J=10.0, 10.0 Hz), 2.05 (m, 2H), 1.83 (m, 1H), 1.66 (m, 2H), 1.21 (d, 3H, J=6.5 Hz), 1.16 (d, 3H, J=6.5 Hz).

EXAMPLE 132

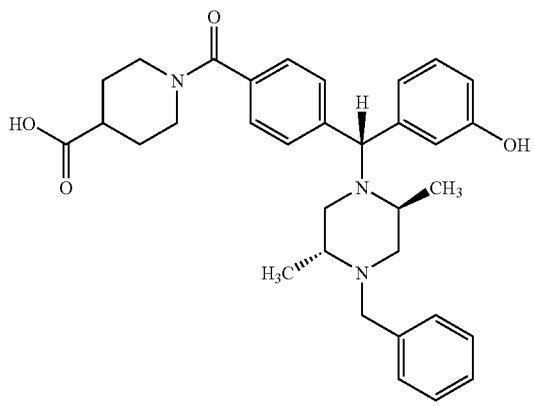

1-{4-[(R)-((2S,5R)-4-Benzyl-2,5-dimethyl-piperazin-1-yl)-(3-hydroxy-phenyl)-methyl]-benzoyl}-piperidine-4-carboxylic acid $^1$H NMR (300 MHz, CD$_3$OD) δ 7.51 (d, 2H, J=8.0 Hz), 7.37 (m, 7H), 7.18 (dd, 1H, J=8.0, 8.0 Hz), 6.71 (m, 3H), 5.23 (s, 1H), 4.48 (m, 1H), 4.25 (d, 1H, J=13.0 Hz), 3.73 (m, 1H), 3.66 (d, 1H, J=13.0 Hz), 3.15 (m, 1H), 3.00 (m, 2H), 2.85 (m, 2H), 2.70 (m, 1H), 2.52 (m, 1H), 2.44 (m, 1H), 2.14 (dd, 1H, J=12.5, 9.0 Hz), 1.99 (m, 1H), 1.81 (m, 1H), 1.66 (m, 2H), 1.29 (d, 3H, J=6.5 Hz), 1.16 (d, 3H, J=6.0 Hz).

EXAMPLE 133

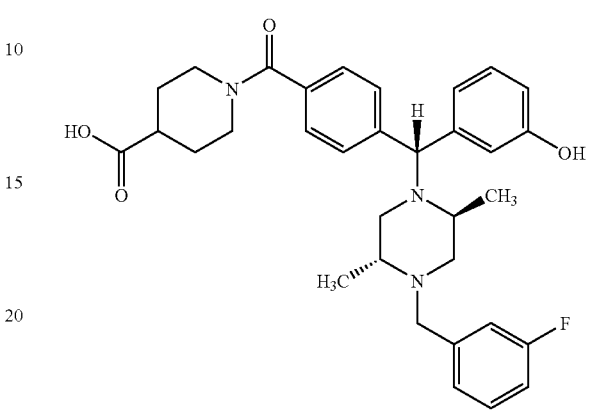

1-{4-[(R)-[(2S,5R)-4-(3-Fluoro-benzyl)-2,5-dimethyl-piperazin-1-yl]-(3-hydroxy-phenyl)-methyl]-benzoyl}-piperidine-4-carboxylic acid $^1$H NMR (300 MHz, CD$_3$OD) δ 7.55-7.26 (m, 5H), 7.15 (m, 3H), 7.03 (ddd, 1H, J=8.5, 8.0 2.5 Hz), 6.71 (m, 3H), 5.16 (s, 1H), 4.45 (m, 1H), 4.07 (d, 1H, J=13.5 Hz), 3.72 (m, 1H), 3.48 (d, 1H, J=13.5 Hz), 3.15 (m, 1H), 3.06 (m, 1H), 2.90-2.69 (m, 4H), 2.57 (m, 1H), 2.25 (m, 1H), 2.06 (m, 2H), 1.84 (m, 1H), 1.67 (m, 2H), 1.20 (d, 3H, J=6.5 Hz), 1.15 (d, 3H, J=6.5 Hz).

EXAMPLE 134

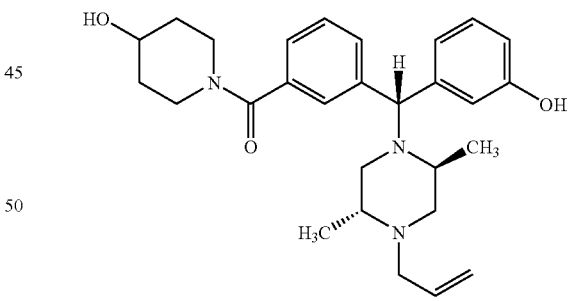

{3-[(R)-((2S,5R)-4-Allyl-2,5-dimethyl-piperazin-1-yl)-(3-hydroxy-phenyl)-methyl]-phenyl}-(4-hydroxy-piperidin-1-yl)-methanone The title compound was synthesized from Acid A and 4-hydroxypiperidine by following the similar method described in Example 119.

$^1$H NMR (300 MHz, DMSO-d$_6$) δ 9.33 (s, 1H), 7.37 (m, 3H), 7.18 (d, 1H, J=7.0 Hz), 7.12 (dd, 1H, J=8.0, 8.0 Hz), 6.66 (m, 3H), 5.77 (m, 1H), 5.12 (m, 2H), 4.98 (s, 1H), 4.78 (d, 1H, J=4.0 Hz), 3.95 (m, 1H), 3.70 (m, 1H), 3.43 (m, 1H), 3.15 (m,

3H), 2.83 (m, 1H), 2.70 (m, 1H), 2.55 (m, 3H), 2.07 (m, 1H), 1.82 (m, 1H), 1.70 (m, 2H), 1.30 (m, 2H), 1.06 (d, 3H, J=6.0 Hz), 0.92 (d, 3H, J=6.0 Hz).

EXAMPLE 135

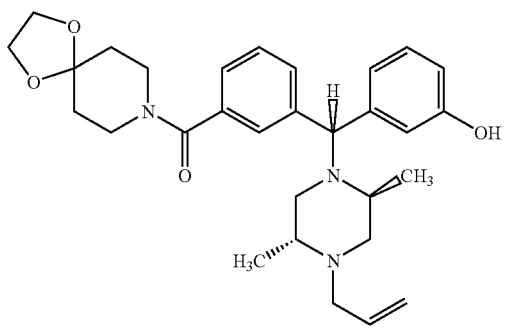

{3-[(R)-((2S,5R)-4-allyl-2,5-dimethyl-1-piperazinyl) (3-hydroxyphenyl)methyl]-phenyl}-(1,4-dioxa-8-azaspiro[4,5]dec-8-yl)methanone A 250 mL 3-necked round bottom flask equipped with a magnetic stir bar, a condenser topped with a nitrogen outlet, a stopper, and a rubber septum was flushed with nitrogen and charged with 24.38 g (50 mmol, 1 eq) of 3-[(R)-((2S,5R)-4-allyl-2,5-dimethyl-1-piperazinyl)(3-hydroxyphenyl)methyl]-N-(3-fluorophenyl)-N-methylbenzamide {DPI-3290; U.S. Pat. No. 5,574,159, Example 16}, 7.5 mL (58.5 mmol, 1.17 eq) of 1,4-dioxa-8-azaspiro-[4.5]decane, and 100 mL of anhydrous tetrahydrofuran. While stirring briskly, 55 mL (110 mmol, 2.2 eq) of 2.0 M isopropylmagnesium chloride in THF was added by syringe over 5 minutes. A vigorous, exothermic reaction ensued. After addition was completed, a heating mantle was attached and the reaction was heated to reflux for 4 hours. The reaction was cooled to room temperature overnight under nitrogen. The reaction was quenched by careful addition of 15 mL of saturated aqueous NH$_4$Cl solution and stirred vigorously for 30 minutes. Approximately 15 g of anhydrous magnesium sulfate was added and the mixture was filtered, rinsing the solids with THF (2×25 mL). The filtrate was concentrated in vacuo and the residue was partitioned between 100 mL ethyl acetate and water. The aqueous solution was adjusted to pH=8-9 using saturated sodium bicarbonate solution. The layers were separated and the organic phase was washed with water and then brine. The organic extract was dried over sodium sulfate/magnesium sulfate and the solvent was removed in vacuo, leaving 31.85 g of crude product as an amber-colored foam. Chromatography of this material on ~300 g of silica gel eluting with dichloromethane/ethyl acetate with 2% ammonium hydroxide yielded 23.93 g (91.5%) of {3-[(R)-((2S,5R)-4-allyl-2,5-dimethyl-1-piperazinyl)(3-hydroxyphenyl)methyl]-phenyl}-(1,4-dioxa-8-azaspiro[4.5]dec-8-yl)methanone as an off-white foam. Calculated for $C_{30}H_{39}N_3O_4$ 0.1 $CH_2Cl_2$ 0.1 $C_4H_8O_2$: %C, 70.05; H, 7.71; N, 8.04. Found: %C, 69.95; H, 7.80; N, 8.05. $^1$H NMR (300 MHz, CDCl$_3$): □□□□d, J=7.6 Hz, 1H), 7.45 (s, 1H), 7.33-7.23 (m, 2H), 7.05 (t, J=7.7 Hz, 1H), 6.56 (t, J=8.3 Hz, 2H), 6.53 (s, 1H), 5.95-5.82 (m, 1H), 5.21 (d, J=9.3 Hz, 1H), 5.16 (s, 2H), 3.97 (s, 4H), 3.82 (br s, 2H), 3.45-3.38 (m, 3H), 2.90-2.80 (m, 2H), 2.63-2.45 (m, 3H), 2.13 (dd, J=1.1, 10.9 Hz, 1H), 1.91 (dd, J=1.0, 11.2 Hz, 1H), 1.78 (br s, 2H), 1.60 (br s, 2H), 1.14 (d, J=6.0 Hz, 3H), 0.99 (d, J=6.1 Hz, 3H).

Alternate Method: The piperidone ketal described above may also be prepared by making the acid chloride of Acid A (e.g. see Example 1) and reacting it with 1.2 equivalents of 1,4-dioxa-8-azaspiro-[4.5]decane and 1 equivalent of triethylamine. Purification can be accomplished as above.

EXAMPLE 136

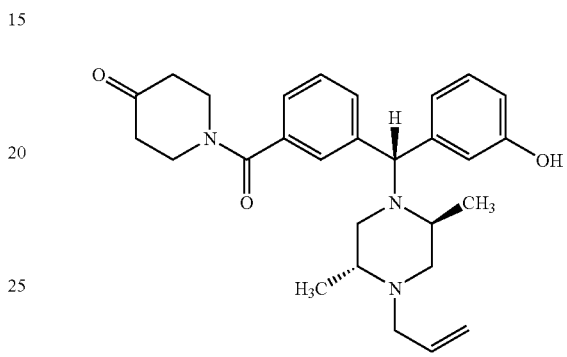

1-{3-[(R)-((2S,5R)-4-allyl-2,5-dimethyl-1-piperazinyl)(3-hydroxyphenyl)-methyl]-benzoyl}-4-piperidinone The ketal of the preceding product, Example 135, was hydrolyzed as follows. A 500 mL round bottom flask equipped with a magnetic stir bar was charged with 21.40 g (40.9 mmol) of {3-[(R)-((2S,5R)-4-allyl-2,5-dimethyl-1-piperazinyl)(3-hydroxy-phenyl)methyl]phenyl}-(1,4-dioxa-8-azaspiro[4.5]dec-8-yl)methanone, 180 mL ethanol, and 60 mL 10 N aqueous sulfuric acid. The reaction was stirred at room temperature for 20 hours and concentrated under reduced pressure. The residue was partitioned between 150 mL dichloromethane and water, and the aqueous solution was adjusted to pH=8-9 using 50% aqueous NaOH. The layers were separated and the aqueous phase was washed with dichloromethane (2×30 mL). The combined organic extracts were dried over sodium sulfate/magnesium sulfate and the solvent was removed in vacuo, leaving 20.25 g of crude product as a light yellow, viscous oil. Chromatography of this material on ~100 g of silica gel eluting with dichloromethane/ethyl acetate with 2% ammonium hydroxide yielded 15.30 g (81%) of 1-{3-[(R)-((2S,5R)-4-allyl-2,5-dimethyl-1-piperazinyl)(3-hydroxyphenyl)-methyl]-benzoyl}-4-piperidinone as an off-white solid. This material contained 12-13% (as estimated by NMR) of the starting ketal, and was difficult to purify further without significant loss of material. $^1$H NMR (300 MHz, CDCl$_3$): □□□□d, J=6.9 Hz, 1H), 7.45 (s, 1H), 7.40-7.32 (m, 2H), 7.10 (t, J=7.8 Hz, 1H), 6.61 (t, J=7.8 Hz, 2H), 6.56 (s, 1H), 5.94-5.81 (m, 1H), 5.21 (d, J=7.8 Hz, 2H), 5.17 (s, 1H), 3.8 (v br s, 4H), 3.42 (dd, J=5.1, 13.5 Hz, 1H), 2.89-2.82 (m, 2H), 2.62-2.38 (m, 7H), 2.13 (dd, J=1, 10 Hz, 1H), 1.93 (dd, J=1, 9.5 Hz, 1H), 1.17 (d, J=5.9 Hz, 3H), 1.00 (d, J=6.1 Hz, 3H).

EXAMPLE 137

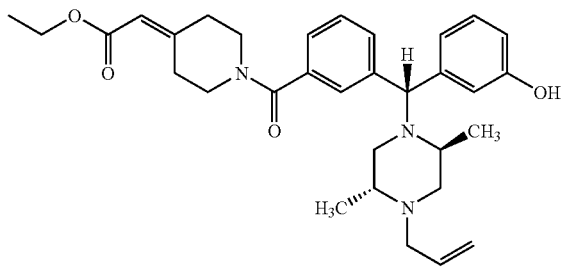

(1-{3-[(R)-((2S,5R)-4-allyl-2,5-dimethyl-1-piperazinyl)(3-hydroxyphenyl)methyl]-benzoyl}-4-piperidinylidene)acetic acid ethyl ester A 100 mL round bottom flask equipped with a magnetic stir bar was flushed with nitrogen and charged with 2.31 g (5 mmol, 1 eq) of 1-{3-[(R)-((2S,5R)-4-allyl-2,5-dimethyl-1-piperazinyl)(3-hydroxyphenyl)-methyl]-benzoyl}-4-piperidinone, 1.5 mL (7.5 mmol, 1.5 eq) of triethyl phosphonoacetate, and 15 mL of anhydrous tetrahydrofuran. While stirring briskly, a total of 10.5 mL (10.5 mmol, 2.1 eq) of 1.0 M lithium bis(trimethylsilyl)amide in THF was added by syringe. The reaction was stirred overnight at room temperature under nitrogen, quenched by the addition of 2 mL of saturated aqueous NH$_4$Cl solution, and stirred vigorously for 15 minutes. The reaction was concentrated in vacuo and the residue was partitioned between ethyl acetate and water. The aqueous solution was adjusted to pH=8-9 using saturated sodium bicarbonate solution. The layers were separated and the organic phase was washed with water and then brine. The organic extract was dried over sodium sulfate/magnesium sulfate and the solvent was removed in vacuo, leaving 2.81 g of crude product as a viscous, amber-colored oil. Chromatography of this material on a pre-packed 4×7 cm Biotage® silica gel cartridge, eluting with dichloromethane/ethyl acetate with 2% ammonium hydroxide, yielded 1.63 g (60%) of (1-{3-[(R)-((2S,5R)-4-allyl-2,5-dimethyl-1-piperazinyl)(3-hydroxyphenyl)methyl]-benzoyl}-4-piperidinylidene)acetic acid ethyl ester as an off-white foam. Calculated for C$_{32}$H$_{41}$N$_3$O$_4$ 0.08 CH$_2$Cl$_2$: %C, 71.55; H, 7.70; N, 7.80. Found: %C, 71.58; H, 7.75; N, 7.76. $^1$H NMR (300 MHz, CDCl$_3$): ☐☐☐☐d, J=6.8 Hz, 1H), 7.43 (s, 1H), 7.36-7.26 (m, 2H), 7.11 (t, J=7.7 Hz, 1H), 6.63 (t, J=8.7 Hz, 2H), 6.57 (s, 1H), 5.94-5.80 (m, 1H), 5.75 (br s, 1H), 5.21-5.14 (m, 3H), 4.15 (q, J=7.1 Hz, 2H), 3.84 (br s, 1H), 3.74 (br s, 1H), 3.40 (dd, J=5.5, 13.9 Hz, 1H, overlapping br s, 2H), 3.05-2.80 (m, 4H), 2.62-2.42 (m, 4H), 2.21 (brs, 1H), 2.13 (dd, J=1.1,9.8 Hz, 1H), 1.92 (dd, J=1, 10 Hz, 1H), 1.65 (br s, 2H), 1.28 (t, J=7.1 Hz, 3H), 1.16 (d, J=6.0 Hz, 3H), 1.00 (d, J=6.1 Hz, 3H).

EXAMPLE 138

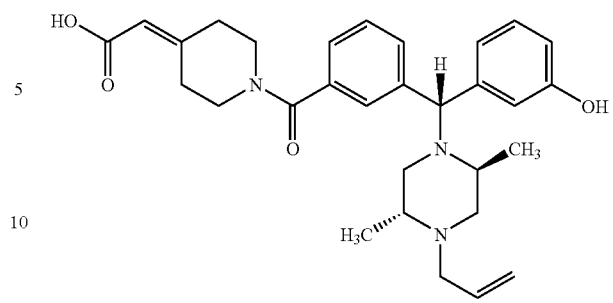

(1-{3-[(R)-((2S,5R)-4-allyl-2,5-dimethyl-1-piperazinyl)(3-hydroxyphenyl)methyl]-benzoyl}-4-piperidinylidene)acetic acid The preceding ester, Example 137, was hydrolyzed as follows. A 50 mL round bottom flask equipped with a magnetic stir bar was charged with 0.64 g (1.2 mmol, 1 eq) of (1-{3-[(R)-((2S,5R)-4-allyl-2,5-dimethyl-1-piperazinyl)(3-hydroxyphenyl)methyl]-benzoyl}-4-piperidinylidene)acetic acid ethyl ester, 5.0 mL ethanol, and 3.0 mL (6 mmol, 5 eq) of 2 N aqueous NaOH solution. The reaction was stirred at room temperature for 3 days and neutralized with 3.0 mL (6 mmol, 5 eq) of 2 N aqueous sulfuric acid. After stirring for 30 minutes, the reaction was filtered to remove the sodium sulfate and the solvent was removed in vacuo. The residue was dissolved in 5 mL of ethanol and filtered through a 0.2 ☐m polypropylene membrane. The filtrate was concentrated in vacuo, leaving an off-white solid. This material was dissolved in 8 mL of water, filtered through a 0.2 ☐m polypropylene membrane, and lyophilized to give (1-{3-[(R)-((2S,5R)-4-allyl-2,5-dimethyl-1-piperazinyl)(3-hydroxyphenyl)methyl]-benzoyl}-4-piperidinylidene)acetic acid as a fluffy, white solid, 0.598 g. Calculated for C$_{30}$H$_{37}$N$_3$O$_4$ 0.25 H$_2$SO$_4$ 2.0 H$_2$O: %C, 63.87; H, 7.41; N, 7.45. Found: %C, 64.03; H, 7.31; N, 7.42. $^1$H NMR (300 MHz, D$_2$O with ~0.1 N NaOD): ☐☐☐☐brd, J=7.6 Hz, 1H), 7.30-7.25 (m, 2H), 7.14 (d, J=7.2 Hz, 1H), 6.93 (t, J=7.7 Hz, 1H), 6.46-6.37 (m, 2H), 6.29 (d, J=7.3 Hz, 1H), 5.77-5.66 (m, 1H), 5.61 (d, J=13.3 Hz, 1H), 5.10 (d, J=8.3 Hz, 1H), 5.07 (s, 2H), 3.72-3.51 (m, 2H), 3.26-3.22 (m, 3H), 2.76-2.21 (series of m, 8H), 2.02 (brt, 2H), 1.91 (brt, 1H, 0.96 (d, J=6.1 Hz, 3H), 0.82 (d, J=6.1 Hz, 3H).

EXAMPLE 139

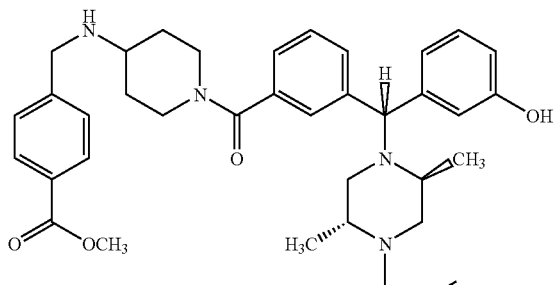

4-[(1-{3-[(R)-((2S,5 R)-4aAllyl-2,5-dimethyl-1-piperazinyl)(3-hydroxyphenyl)-methyl]-benzoyl}-4-piperidinylamino)methyl]benzoic acid methyl ester A 100 mL round bottom flask equipped with a magnetic stir bar was flushed with nitrogen and charged with 1.85 g (4 mmol, 1 eq) of 1-{3-[(R)-((2S,5R)-4-allyl-2,5-dimethyl-1-piperazinyl)(3-hydroxyphenyl)-methyl]-benzoyl}-4-piperidinone (Example 136), 0.81 g (4 mmol, 1 eq) of methyl 4-(aminomethyl)benzoate hydrochloride, 0.23 g (4.1 mmol, 1.02 eq) of potassium hydroxide, and 12 mL of methanol. The reaction was stirred vigorously at room temperature under nitrogen for 30 minutes. A solution of 0.25 g (4 mmol, 1 eq) of sodium cyanoborohydride in 3 mL of methanol was added and the reaction was stirred overnight. The reaction was quenched by careful addition of 1 mL of saturated aqueous $NH_4Cl$ solution and stirred vigorously for 30 minutes and concentrated in vacuo. The residue was partitioned between 50 mL dichloromethane and water, and the aqueous solution was adjusted to pH=8-9 using saturated sodium bicarbonate solution. The organic layer was separated and dried over sodium sulfate/magnesium sulfate and the solvent was removed in vacuo, leaving 2.42 g of crude product as a viscous, amber-colored oil. Chromatography of this material on a pre-packed 4×15 cm Biotage® silica gel cartridge eluting with dichloromethane/ethyl acetate with 2% ammonium hydroxide yielded 1.54 g (61%) of 4-[(1-{3-[(R)-((2S,5R)-4aAllyl-2,5-dimethyl-1-piperazinyl)(3-hydroxyphenyl)-methyl]-benzoyl}-4-piperidinylamino)methyl]benzoic acid methyl ester as an off-white foam. Calculated for $C_{37}H_{46}N_4O_4$ 0.1 $CH_2Cl_2$ 0.05 EtOAc: %C, 71.83; H, 7.53; N, 8.98. Found: %C, 71.95; H, 7.61; N, 8.96. $^1$H NMR (300 MHz, $CDCl_3$): ▫▫▫d, J=8.4 Hz, 2H), 7.51 (br s, 1H), ▫▫▫d, J=8.2 Hz, 2H), 7.31 (t, J=7.7 Hz, 1H), 7.26-7.22 (m, 2H), 7.09 (t, J=7.7 Hz, 1H), 6.65-6.56 (m, 3H), 5.93-5.80 (m, 1H), 5.20-5.13 (m, 3H), 4.52 (br s, 1H), 3.91 (s, 3H), 3.88 (s, 2H), 3.68 (br s, 1H), 3.38 (br d, 1H), 3.00-2.73 (m, 5H), 2.62-2.44 (m, 3H), 2.12 (br d, J=10 Hz, 1H), 2.01-1.28 (m, 7H), 1.15 (d, J=6.1 Hz, 3H), 0.98 (d, J=6.3 Hz, 3H).

EXAMPLE 140

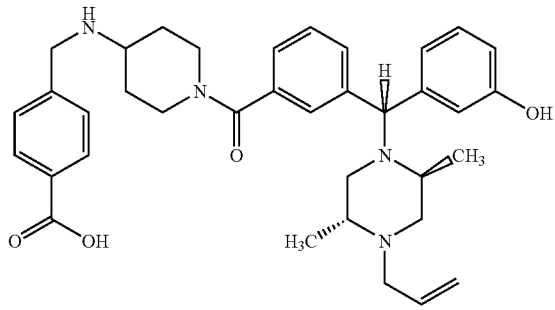

4-[(1-{3-[(R)-((2S,5R)-4-Allyl-2,5-dimethyl-piperazin-1-yl)-(3-hydroxy-phenyl)-methyl]-benzoyl}-piperidin-4-ylamino)-methyl]-benzoic acid The preceding ester, Example 139, was hydrolyzed as follows. A 50 mL round bottom flask equipped with a magnetic stir bar was charged with 0.75 g (1.2 mmol, 1 eq) of 4-[(1-{3-[(R)-((2S,5 R)-4-allyl-2,5-dimethyl-1-piperazinyl)(3-hydroxyphenyl)-methyl]-benzoyl}-4-piperidinylamino)methyl]benzoic acid methyl ester, 5.0 mL methanol, and 3.0 mL (6 mmol, 5 eq) of 2 N aqueous NaOH solution. The reaction was stirred at room temperature for 3 days, and neutralized with 3.0 mL (6 mmol, 5 eq) of 2 N aqueous sulfuric acid. After stirring for 30 minutes, the reaction was filtered to remove the sodium sulfate, and the solvent was removed in vacuo. The residue was dissolved in 5 mL of methanol and filtered through a 0.2 ▫m polypropylene membrane. The filtrate was concentrated in vacuo, leaving an off-white solid. This material was dissolved in 2 mL methanol and 6 mL of water, filtered through a 0.2 ▫m polypropylene membrane, and lyophilized to give 0.693 g of the title compound as a white solid. Calculated for $C_{36}H_{44}N_4O_4$ 0.4 $H_2SO_4$ 0.6 $H_2O$ 0.6 MeOH: %C, 66.00; H, 7.32; N, 8.41. Found: %C, 66.00; H, 7.29; N, 8.46. $^1$H NMR (300 MHz, $D_2O$ with ~0.1 N NaOD): ▫▫▫d, J=8.1 Hz, 2H), ▫▫▫d, J=8.2 Hz, 2H), 7.37-7.18 (m, 3H), 7.09 (d, J=7.1 Hz, 1H), 6.92 (t, J=7.3 Hz, 1H), 6.37 (br d, J=6.0 Hz, 2H), 6.29 (d, J=7.9 Hz, 1H), 5.72-5.64 (m, 1H), 5.06-5.00 (m, 3H), 4.27 (br d, J=11 Hz, 1H), 3.64 (d, J=4.3 Hz, 2H), 3.45 (m, 1H), 3.23-3.16 (m, 1H), 2.88-2.81 (m, 1H), 2.71-2.61 (m, 5H), 2.45 (m, 1H), 2.30 (m, 1H), 2.01 (t, J=11 Hz, 1H), 1.96-1.87 (m, 2H), 1.73-1.62 (m, 1H), 1.22-0.97 (m, 2H), 0.96 (distorted t, 3H), 0.80 (d, J=6.0 Hz, 3H).

EXAMPLE 141

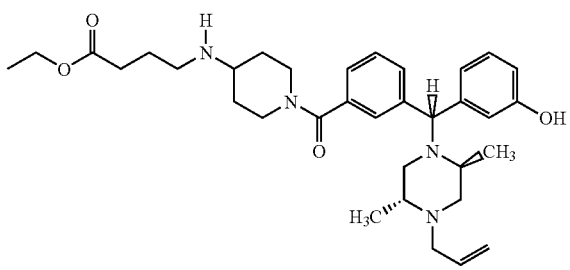

4-(1-{3-[(R)-((2S,5R)-4-Allyl-2,5-dimethyl-piperazin-1-yl)-(3-hydroxy-phenyl)-methyl]-benzoyl}-piperidin-4-ylamino)-butyric acid ethyl ester A 100 mL round bottom flask equipped with a magnetic stir bar was flushed with nitrogen and charged with 2.31 g (5 mmol, 1 eq) of 1-{3-[(R)-((2S,5R)-4-allyl-2,5-dimethyl-1-piperazinyl)(3-hydroxyphenyl)-methyl]-benzoyl}-4-piperidinone (Example 136), 1.41 g (8.4 mmol, 1.68 eq) of ethyl 4-aminobutyrate hydrochloride, 0.47 g (8.4 mmol, 1.68 eq) of potassium hydroxide, and 10 mL of ethanol. The reaction was stirred vigorously at room temperature under nitrogen for 2.5 hours. A solution of 0.32 g (5 mmol, 1 eq) of sodium cyanoborohydride in 5 mL of ethanol was added and the reaction was stirred overnight. The reaction was quenched by careful addition of 1 mL of saturated aqueous $NH_4Cl$ solution and stirred vigorously for 30 minutes and concentrated in vacuo. The residue was partitioned between 50 mL dichloromethane and water, and the aqueous solution was adjusted to pH=8-9 using saturated sodium bicarbonate solution. The organic layer was separated and dried over sodium sulfate/magnesium sulfate and the solvent was removed in vacuo, leaving 2.81 g of crude product as a viscous, amber-colored oil. Chromatography of this material on a pre-packed 4×15 cm Biotage® silica gel cartridge eluting with dichloromethane/ethyl acetate with 2% ammonium hydroxide yielded 1.57 g (53%) of 4-(1-{3-[(R)-((2S,5R)-4-Allyl-2,5-dimethyl-piperazin-1-yl)-(3-hydroxy-phenyl)-methyl]-benzoyl}-piperidin-4-ylamino)-butyric acid ethyl ester as an off-white foam. Calculated for $C_{34}H_{48}N_4O_4$ 0.1 $CH_2Cl_2$: %C, 69.98; H, 8.30; N, 9.57. Found: %C, 70.07; H, 8.39; N, 9.65. $^1$H NMR (300 MHz, CDCl$_3$): ☐☐☐$_1$☐☐$_1$m, 1H), 7.38-7.23 (m, 3H), 7.11 (t, J=7.9 Hz, 1H), 6.68-6.56 (m, 1H), 6.65 (t, J=7.9 Hz, 2H), 5.93-5.80 (m, 1H), 5.21-5.14 (m, 3H), 4.52 (br s, 1H), 4.14 (q, J=7.2 Hz, 2H), 3.67 (m, 1H), 3.36 (br d, 1H), 2.98-2.78 (m, 4H), 2.73-2.55 (m, 5H), 2.46 (m, 1H), 2.37 (t, J=7.2 Hz, 2H), 2.12 (dd, J=1, 9.3 Hz, 1H), 1.92 (m, 1H), 1.79 (quint, J=7.1 Hz, 2H), 1.26 (t, J=7.1 Hz, 3H), 1.15 (br d, J=5.6 Hz, 3H), 0.98 (d, J=6.2 Hz, 3H).

EXAMPLE 142

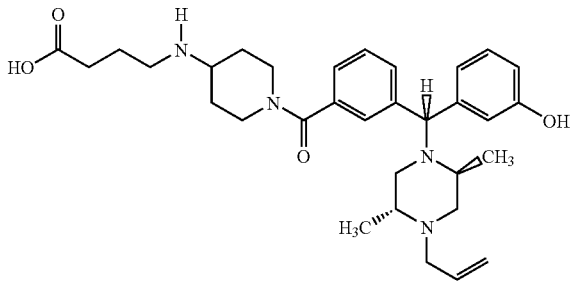

4-(1-{3-[(R)-((2S,5R)-4-Allyl-2,5-dimethyl-piperazin-1-yl)-(3-hydroxy-phenyl)-methyl]-benzoyl}-piperidin-4-ylamino)-butyric acid The preceding ester, Example 141, was hydrolyzed as follows. A 50 mL round bottom flask equipped with a magnetic stir bar was charged with 0.70 g (1.2 mmol, 1 eq) of 4-[(1-{3-[(R)-((2S,5R)-4-allyl-2,5-dimethyl-1-piperazinyl)(3-hydroxyphenyl)-methyl]-benzoyl}-4-piperidinylamino)methyl]butyric acid ethyl ester, 5.0 mL ethanol, and 3.0 mL (6 mmol, 5 eq) of 2 N aqueous NaOH solution. The reaction was stirred at room temperature for 3 days and neutralized with 3.0 mL (6 mmol, 5 eq) of 2 N aqueous sulfuric acid. After stirring for 30 minutes, the reaction was filtered to remove the sodium sulfate, and the solvent was removed in vacuo. The residue was dissolved in 25 mL of dichloromethane and extracted with 2×10 mL of water. The aqueous phase was diluted with 50 mL ethanol and concentrated in vacuo, leaving an off-white solid. This material was dissolved in 8 mL of water, filtered through a 0.2 ☐m polypropylene membrane, and lyophilized to give 0.488 g of the title compound as a white solid. Calculated for C$_{32}$H$_{44}$N$_4$O$_4$ 1.5 H$_2$SO$_4$ 1.5 H$_2$O 0.25 Na$_2$SO$_4$: %C, 50.68; H, 6.65; N, 7.39. Found: %C, 50.73; H, 6.65; N, 7.39. $^1$H NMR (300 MHz, D$_2$O with ~0.1 N NaOD): ☐7.37-7.18 (m, 3H), 7.10 (d, J=7.5 Hz, 1H), 6.92 (t, J=7.0 Hz, 1 H), 6.45-6.36 (m, 2H), 6.28 (t, J=7.0 Hz, 1H), 5.76-5.62 (m, 1H), 5.10-5.04 (m, 3H), 4.27 (br d, J=12.5 Hz, 1H), 3.46 (m, 1H), ☐☐☐dd, J=5.3, 13.4 Hz, 1H), ☐☐$_1$t, J=13 Hz, 1H), 2.79-2.61 (m, 5H), 2.46-2.31 (m, 4H), 2.05-1.98 (m, 3H), 1.96-1.85 (m, 2H), 1.69-1.50 (m, 3H), 1.16-0.92 (m, 2H), 0.95 (distorted t, 3H), 0.81 (d, J=5.8 Hz, 3H).

Proline Derivative

Proline derivatives were synthesized from L-proline methyl ester hydrochloride and Acid A using the similar methods described above.

EXAMPLE 143

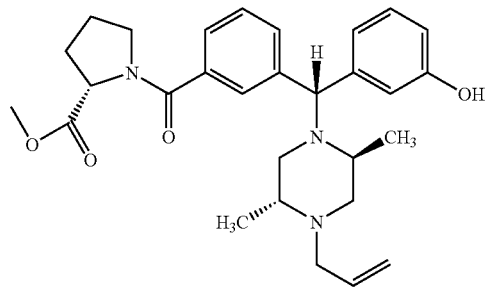

1-{3-[(R)-((2S,5R)-4-Allyl-2,5-dimethyl-piperazin-1-yl)-(3-hydroxy-phenyl)-methyl]-benzoyl}-pyrrolidine-2-carboxylic acid (S)-methyl ester $^1$H NMR (300 MHz, CDCl$_3$) δ 7.63 (s, 1H), 7.49 (d, 1H, J=8.0 Hz), 7.43 (d, 1H, J=8.0 Hz), 7.29 (dd, 1H, J=7.5, 7.5 Hz), 7.07 (m, 1H), 6.54 (m, 3H), 5.88 (m, 1H), 5.19 (m, 3H), 4.64 (dd, 1H, J=5.0, 8.0 Hz), 3.76 (s, 3H), 3.63 (m, 1H), 3.45 (m, 2H), 2.85 (m, 2H), 2.62-2.47 (m, 3H), 2.31 (m, 1H), 2.14 (m, 1H), 2.06-1.84 (m, 4H), 1.15 (d, 3H, J=6.0 Hz), 1.00 (d, 3H, J=6.5 Hz).

EXAMPLE 144

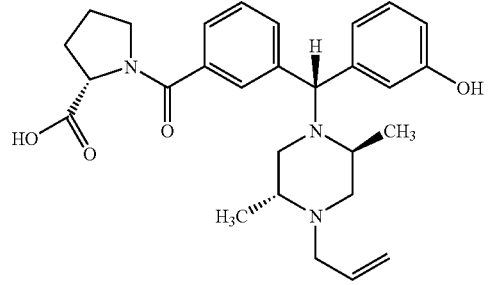

1-{3-[(R)-((2S,5R)-4-Allyl-2,5-dimethyl-piperazin-1-yl)-(3-hydroxy-phenyl)-methyl]-benzoyl}-pyrrolidine-2-carboxylic acid $^1$H NMR (300 MHz, DMSO-d$_6$) δ 9.38 (s, 1H), 7.54-7.18 (m, 4H), 7.13 (dd, 1H, J=8.0, 8.0 Hz), 6.68 (m, 3H), 5.78 (m, 1H), 5.11 (m, 3H), 4.37 (m, 1H), 3.48 (m, 2H), 3.18 (m, 1H), 2.86 (dd, 1H, J=7.0, 14.0 Hz), 2.74 (d, 1H, J=9.0 Hz), 2.53 (m, 3H), 2.25 (m, 1H), 2.11 (m, 1H), 1.84 (m, 4H), 1.08 (d, 3H, J=6.0 Hz), 0.94 (d, 3H, J=6.5 Hz).

EXAMPLE 145

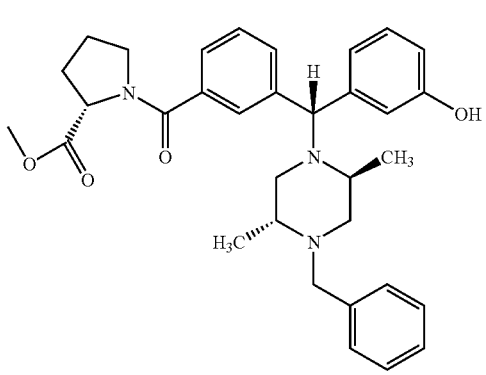

1-{3-[(R)-((2S,5R)-4-Benzyl-2,5-dimethyl-piperazin-1-yl)-(3-hydroxy-phenyl)-methyl]-benzoyl}-pyrrolidine-2-carboxylic acid (S)-methyl ester $^1$H NMR (300 MHz, CDCl$_3$) δ 1.03 (d, J=6.0 Hz, 3H), 1.08 (d, J=6.0 Hz, 3H), 1.86-2.07 (m, 5H), 2.28-2.33 (m, 1H), 2.55-2.70 (m, 4H), 3.14 (d, J=13.5 Hz, 1H), 3.47-3.51 (m, 2H), 3.62-3.65 (m, 1H), 3.75 (s, 2H), 3.93 (d, J=13.5 Hz, 1H), 4.62 (m, 1H), 5.04 (s, 1H), 6.54-6.66 (m, 4H), 7.09 (t, J=8.0 Hz, 1H), 7.22-7.32 (m, 5H), 7.42 (d, J=16.5 Hz, 1H), 7.44 (d, J=16.0 Hz, 1H), 7.65 (s, 1H).

EXAMPLE 146

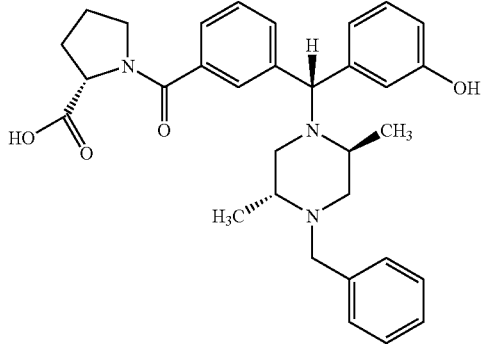

1-{3-[(R)-((2S,5R)-4-Benzyl-2,5-diethyl-piperazin-1-yl)-(3-hydroxy-phenyl)-methyl]-benzoyl}-pyrrolidine-2-carboxylic acid $^1$H NMR (300 MHz, DMSO-d$_6$) δ 12.51 (bs, 1H), 9.37 (s, 1H), 7.56-7.10 (m, 10H), 6.69 (m, 3H), 4.99 (s, 1H), 4.38 (m, 1H), 3.77 (m, 1H), 3.58-3.23 (m, 3H), 2.63 (m, 4H), 2.25 (m, 1H), 2.03-1.80 (m, 5H), 1.04 (m, 6H).

EXAMPLE 147

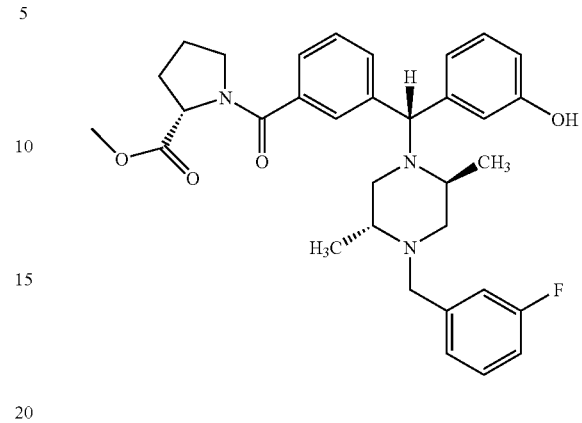

1-{3-[(R)-[(2S,5R)-4-(3-Fluoro-benzyl)-2,5-dimethyl-piperazin-1-yl]-(3-hydroxy-phenyl)-methyl]-benzoyl}-pyrrolidine-2-carboxylic acid (S)-methyl ester $^1$H NMR (300 MHz, DMSO-d$_6$) δ 1.01 (s, 3H), 1.03 (s, 3H), 1.85 (m, 4H), 2.02 (m, 1H), 2.24 (m, 1H), 2.59 (m, 4H), 3.26 (m, 1H), 3.44-3.56 (m, 2H), 3.64 (s, 3H), 3.71 (d, J=14.0 Hz, 1H), 4.44 (m, 1H), 4.95 (s, 1H), 6.62-6.72 (m, 3H), 6.98-7.55 (m, 9H), 9.35 (s, 1H).

EXAMPLE 148

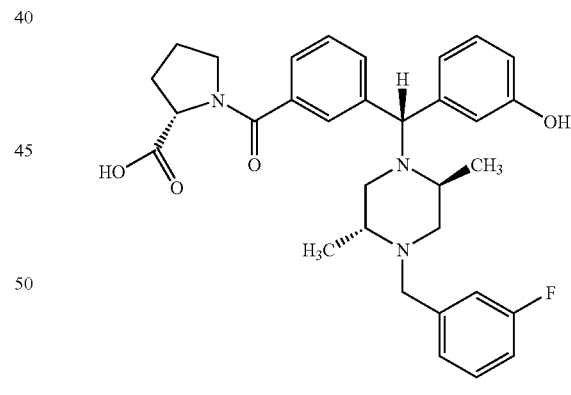

1-{3-[(R)-[(2S,5R)-4-(3-Fluoro-benzyl)-2,5-dimethyl-piperazin-1-yl]-(3-hydroxy-phenyl)-methyl]-benzoyl}-pyrrolidine-2-carboxylic acid $^1$H NMR (300 MHz, DMSO-d$_6$) δ 12.56 (bs, 1H), 9.37 (s, 1H), 7.56-7.27 (m, 5H), 7.20-7.00 (m, 4H), 6.69 (m, 3H), 4.97 (s, 1H), 4.36 (m, 1H), 3.75 (m, 1H), 3.56-3.40 (m, 2H), 3.28 (m, 1H), 2.61 (m, 4H), 2.25 (m, 1H), 2.04-1.80 (m, 5H), 1.04 (m, 6H).

EXAMPLE 149

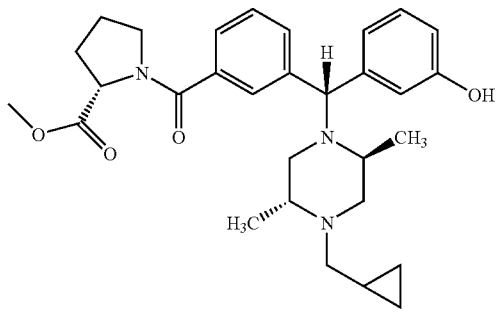

1-{3-[(R)-((2S,5R)-4-Cyclopropylmethyl-2,5-dimethyl-piperazin-1-yl)-(3-hydroxy-phenyl)-methyl]-benzoyl}-pyrrolidine-2-carboxylic acid (S)-methyl ester $^1$H NMR (300 MHz, CDCl$_3$) δ 0.35 (s, 1H), 0.43 (s, 1H), 0.77 (bs, 2H), 1.21 (m, 4H), 1.33 (s, 3H), 1.87-2.05 (m, 4H), 2.31 (m, 2H), 2.75 (m, 4H), 3.11 (bs, 1H), 3.31 (bs, 2H), 3.58 (m, 1H), 3.76 (s, 3H), 4.63 (m, 1H), 5.27 (s, 1H), 6.60 (bs, 1H), 6.82 (bs, 1H), 6.91 (bs, 1H), 7.12 (t, J=8.0 Hz, 1H), 7.30 (m, 2H), 7.43 (m, 1H), 7.61 (s, 1H).

EXAMPLE 150

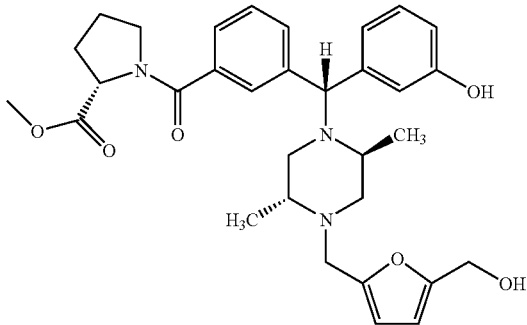

1-{3-[(R)-[(2S,5R)-4-(5-Hydroxymethyl-furan-2-ylmethyl)-2,5-dimethyl-piperazin-1-yl]-(3-hydroxy-phenyl)-methyl]-benzoyl}-pyrrolidine-2-carboxylic acid (S)-methyl ester $^1$H NMR (300 MHz, CDCl$_3$) δ 1.06 (d, J=6.0 Hz, 3H), 1.10 (d, J=6.0 Hz, 3H), 1.88-2.04 (m, 5H), 2.16 (m, 1H), 2.30 (m, 1H), 2.44 (m, 1H), 2.55 (s, 1H), 2.58 (s, 1H), 2.72 (d, J=11.0 Hz, 1H), 3.39 (m, 3H), 3.60 (m, 1H), 3.76 (s, 2H), 3.80 (d, J=14.5Hz, 1H), 4.44 (s, 2H), 4.63 (m, 1H), 5.17 (s, 1H), 6.13 (d, J=3.0 Hz, 1H), 6.19 (d, J=3.0 Hz, 1H), 6.53 (s, 1H), 6.57 (s, 1H), 6.60 (s, 1H), 7.08 (t, J=8.0 Hz, 1H), 7.29(m, 1H), 7.42-7.49 (m, 2H), 7.62 (s, 1H).

Sarcosine Derivatives

Sarcosine derivatives were synthesized from sarcosine ethyl ester hydrochloride and Acid A using similar methods described above.

EXAMPLE 151

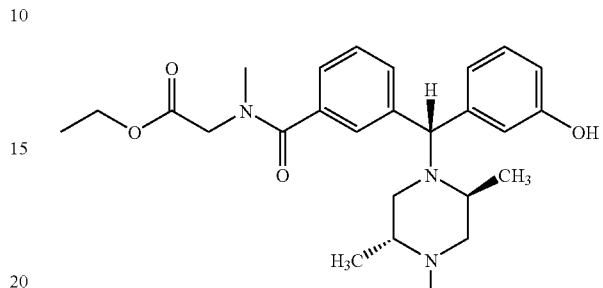

({3-[(R)-((2S,5R)-4-Allyl-2,5-dimethyl-piperazin-1-yl)-(3-hydroxy-phenyl)-methyl]-benzoyl}-methyl-amino)-acetic acid ethyl ester $^1$H NMR (300 MHz, CDCl$_3$) δ 7.48 (m, 2H), 7.27 (m, 2H), 7.06 (dd, 1H, J=8.0, 8.0 Hz), 6.56 (m, 3H), 5.88 (m, 1H), 5.18 (m, 3H), 4.17 (m, 3H), 3.97 (s, 1H), 3.40 (dd, 1H, J=4.5, 14.0 Hz), 3.05 (m, 3H), 2.85 (m, 2H), 2.53 (m, 3H), 2.13 (dd, 1H, J=11.0, 10.0 Hz), 1.93 (dd, 1H, J=9.5, 10.0 Hz), 1.26 (m, 3H), 1.15 (d, 3H, J=5.5 Hz), 1.00 (d, 3H, J=6.5 Hz).

EXAMPLE 152

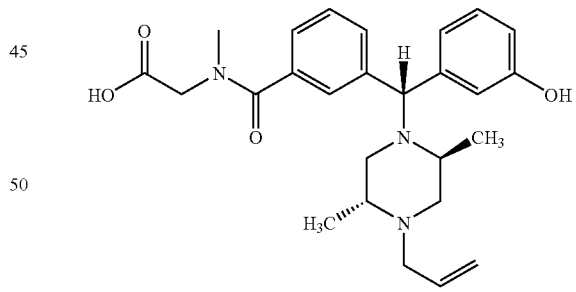

({3-[(R)-((2S,5R)-4-Allyl-2,5-dimethyl-piperazin-1-yl)-(3-hydroxy-phenyl)-methyl]-benzoyl}-methyl-amino)-acetic acid $^1$H NMR (300 MHz, DMSO-d$_6$) δ 9.35 (bs, 1H), 7.45-7.10 (m, 5H), 6.68 (m, 3H), 5.77 (m, 1H), 5.15 (m, 2H), 4.96 (m, 1H), 4.09 (s, 1H), 3.80 (s, 1H), 3.19 (m, 1H), 2.90 (m, 4H), 2.75 (m, 1H), 2.53 (m, 3H), 2.13 (m, 1H), 1.85 (m, 1H), 1.06 (d, 3H, J=5.0 Hz), 0.94 (d, 3H, J=6.0).

EXAMPLE 153

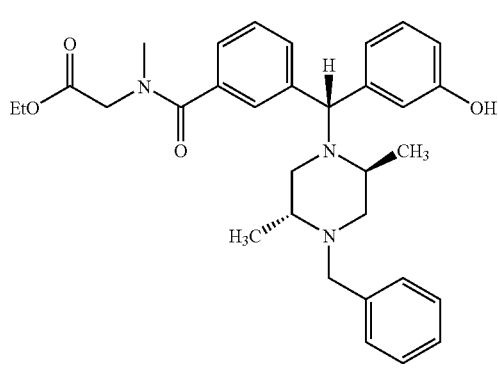

({3-[(R)-((2S,5R)-4-Benzyl-2,5-dimethyl-piperazin-1-yl)-(3-hydroxy-phenyl)-methyl]-benzoyl}-methyl-amino)-acetic acid ethyl ester $^1$H NMR (300 MHz, CDCl$_3$) δ 1.02 (d, J=5.5 Hz, 3H), 1.08 (d, J=6.0 Hz, 3H), 1.29 (m, 3H), 1.96 (m, 2H), 2.05 (s, 1H), 2.55 (m, 3H), 2.66 (d, J=10.5 Hz, 1H), 3.01 (s, 2H), 3.13 (m, 2H), 3.94-3.98 (m, 2H), 4.16 (q, J=7.0 Hz, 2H), 5.05 (s, 1H), 6.5 (d, J=10.0 Hz, 7.09 (t, J=8.0 Hz, 1H), 7.29 (m, 7H), 7.53 (m, 2H).

EXAMPLE 154

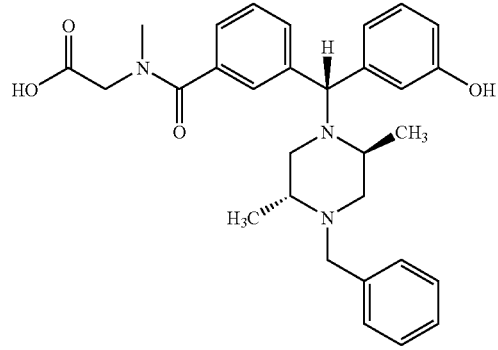

({3-[(R)-((2S,5R)-4-Benzyl-2,5-dimethyl-piperazin-1-yl)-(3-hydroxy-phenyl)-methyl]-benzoyl}methyl-amino)-acetic acid $^1$H NMR (300 MHz, DMSO-d$_6$) δ 9.37 (s, 1H), 7.47-7.10 (m, 10H), 6.68 (m, 3H), 4.95 (m, 1H), 4.12 (s, 1H), 3.88 (s, 1H), 3.78 (d, 1H, J=13.5 Hz), 3.26 (d, 1H, J=14.0 Hz), 2.93 (m, 3H), 2.62 (m, 4H), 2.02 (m, 1H), 1.92 (m, 1H), 1.03 (m, 6H).

EXAMPLE 155

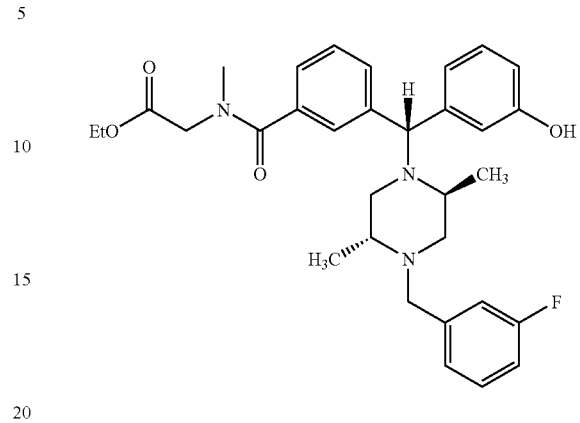

({3-[(R)-[(2S,5R)-4-(3-Fluoro-benzyl)-2,5-dimethyl-piperazin-1-yl]-(3-hydroxy-phenyl)-methyl]-benzoyl}-methyl-amino)-acetic acid ethyl ester $^1$H NMR (300 MHz, CDCl$_3$) δ: 1.04 (s, 3H), 1.06 (s, 3H), 1.29 (m, 3H), 1.97 (m, 3H), 2.60 (m, 4H), 3.01 (s, 2H), 3.15 (m, 2H), 3.86-3.97 (m, 2H), 4.17 (m, 2H), 5.06 (bs, 1H), 6.63 (m, 3H), 6.90 (m, 1H), 6.97-7.33 (m, 6H), 7.54 (m, 2H).

EXAMPLE 156

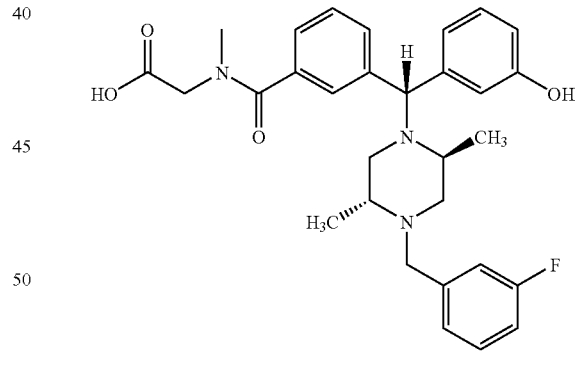

({3-[(R)-[(2S,5R)-4-(3-Fluoro-benzyl)-2,5-dimethyl-piperazin-1-yl]-(3-hydroxy-phenyl)-methyl]-benzoyl}-methyl-amino)-acetic acid $^1$H NMR (300 MHz, DMSO-d$_6$) δ 9.37 (bs, 1H), 7.48-7.22 (m, 5H), 7.07 (m, 4H), 6.69 (m, 3H), 4.93 (m, 1H), 4.12 (s, 1H), 3.89 (s, 1H), 3.76 (d, 1H, J=13.5 Hz), 3.30 (d, 1H, J=13.5 Hz), 2.93 (m, 3H), 2.65 (m, 4H), 2.03 (m, 1H), 1.94 (m, 1H), 1.04 (m, 6H).

EXAMPLE 157

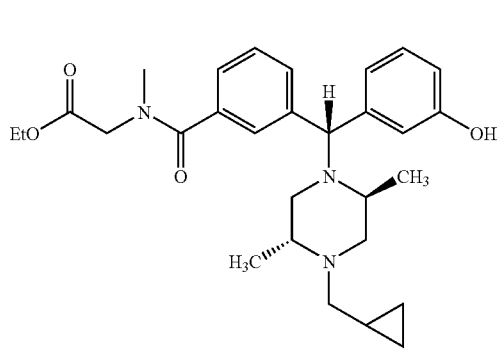

({3-[(R)-((2S,5R)-4-Cyclopropylmethyl-2,5-dimethyl-piperazin-1-yl)-(3-hydroxy-phenyl)-methyl]-benzoyl}-methyl-amino)-acetic acid ethyl ester $^1$H NMR (300 MHz, CDCl$_3$) δ: 0.12 (s, 1H), 0.13 (s, 1H), 0.53 (t, J=8.0 Hz, 2H), 0.86 (m, 1H), 0.99 (d, J=6.0 Hz, 3H), 1.20 (d, J=5.5 Hz, 3H),1.29 (t, J=7.5 Hz, 3H), 2.0 (m, 1H), 2.12 (m, 1H), 2.28 (t, J=10.5 Hz, 1H), 2.54 (m, 2H), 2.68 (m, 2H), 3.01 (s, 2H), 3.15 (m, 2H), 3.97 (s, 1H), 4.17 (m, 2H), 4.24 (m, 1H), 5.23 (m, 1H), 6.59 (m, 3H), 7.09 (t, J=8.0 Hz, 1H), 7.36 (m, 2H), 7.5 (m, 2H).

EXAMPLE 158

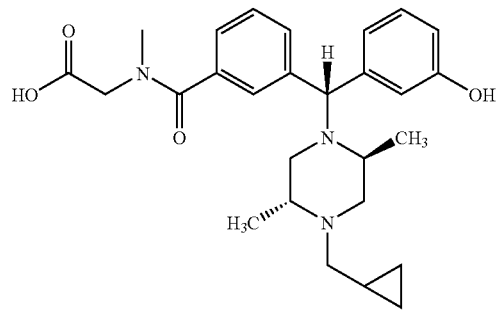

({3-[(R)-((2S,5R)-4-Cyclopropylmethyl-2,5-dimethyl-piperazin-1-yl)-(3-hydroxy-phenyl)-methyl]-benzoyl}-methyl-amino)-acetic acid $^1$H NMR (300 MHz, DMSO-d$_6$) δ 7.46-7.09 (m, 5H), 6.65 (m, 3H), 5.04 (m, 1H), 4.07 (s, 1H), 3.70 (s, 1H), 3.06 (m, 1H), 2.90 (m, 3H), 2.89-2.29 (m, 6H), 1.91 (m, 1H), 1.13 (m, 3H), 0.98 (m, 3H), 0.85 (m, 1H), 0.46 (m, 2H), 0.12 (m, 2H).

EXAMPLE 159

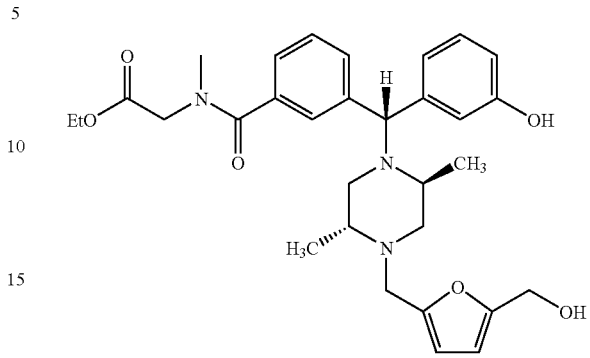

({3-[(R)-[(2S,5R)-4-(5-Hydroxymethyl-furan-2-ylmethyl)-2,5-dimethyl-piperazin-1-yl]-(3-hydroxy-phenyl)-methyl]-benzoyl}-methyl-amino)-acetic acid ethyl ester $^1$H NMR (300 MHz, CDCl$_3$) δ 1.07 (d, J=6.5 Hz, 3H), 1.11 (d, J=5.5 Hz, 3H), 1.23 (t, J=7.0 Hz, 3H), 1.94 (t, J=10.0 Hz, 1H), 2.04 (s, 1H), 2.16 (t, J=10.0 Hz, 1H), 2.47-2.58 (m, 3H), 2.73 (d, J=11.0 Hz, 1H), 3.00 (s, 2H), 3.43 (m, 1H), 3.81 (m, 1H), 3.97 (s, 1H), 4.11 (q, J=7.0 Hz, 2H), 4.18-4.23 (m, 2H), 4.45 (s, 2H), 5.14 (s, 1H), 6.13 (d, J=2.5 Hz, 1H), 6.19 (d, J=3.0 Hz, 1H), 6.5-6.60 (m, 3H), 7.08 (t, J=8.0 Hz, 1H), 7.22-7.33 (m, 2H), 7.42-7.50 (m, 2H).

EXAMPLE 160 (ARD-874)

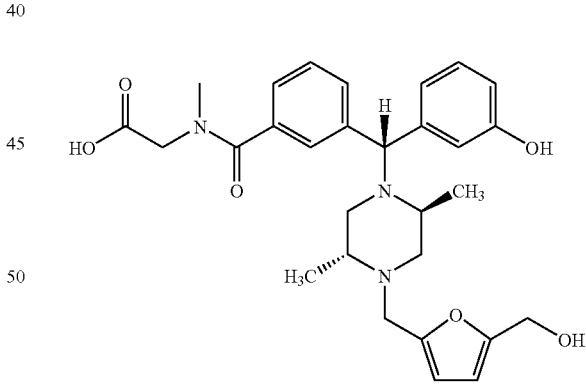

({3-[(R)-[(2S,5R)-4-(5-Hydroxymethyl-furan-2-ylmethyl)-2,5-dimethyl-piperazin-1-yl]-(3-hydroxy-phenyl)-methyl]-benzoyl}-methyl-amino)-acetic acid $^1$H NMR (300 MHz, DMSO-d$_6$) δ 7.44-7.21 (m, 3H), 7.10 (m, 2H), 6.66 (m, 2H), 6.57 (d, 1H, J=8.5 Hz), 6.18 (d, 1H, J=3.0 Hz), 6.15 (d, 1H, J=3.0), 4.98 (m, 1H), 4.33 (s, 2H), 3.96 (s, 1H), 3.64-3.42 (m, 4H), 2.89 (m, 3H), 2.69 (m, 1H), 2.49 (m, 3H), 2.10 (m, 1), 1.79 (m, 1H), 1.02 (m, 6H).

2-(Ethylamino)ethanol Derivatives

EXAMPLE 161

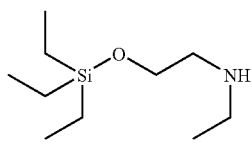

Ethyl-(2-triethylsilanyloxy-ethyl)-amine

Imidazole (18.15 g) was added to the solution of 2-(ethylamino)ethanol (9.14 g) in $CH_2Cl_2$ (200 mL) at room temperature. The mixture was stirred for 10 minutes until all imidazole were dissolved. The solution was cooled in ice bath for 20 minutes. Chlorotriethylsilane (15.46 g) was added to the solution via a syringe. The solution was stirred under nitrogen for overnight, while it was warmed up to room temperature. The reaction solution was washed by $H_2O$ (150 mL×3), brine (150 mL×1), dried by $Na_2SO_4$ and concentrated to give crude ethyl-(2-triethylsilanyloxy-ethyl)-amine (21.94 g), which was used in next step without further purification. $^1H$ NMR (300 MHz, DMSO-$d_6$) ☐ 3.58 (t, 2H, J=6.0 Hz), 2.53 (m, 4H), 1.41 (s, 1H), 0.93 (m, 12H), 0.54 (q, 6H, J=8.0 Hz).

EXAMPLE 162

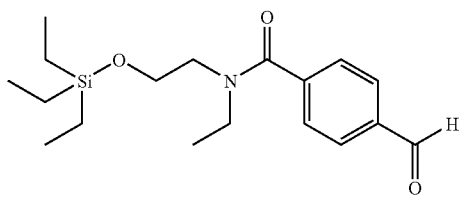

N-Ethyl-4-formyl-N-(2-triethylsilanyloxy-ethyl)-benzamide $SOCl_2$ (4.33 mL) was added to the mixture of 4-carboxybenzaldehyde (8.1 g) in toluene (150 mL), followed by the addition of DMF (0.5 mL). The reaction mixture was refluxed with a drying tube attached to the top of condenser. After being refluxed for 40 minutes, the reaction mixture became clear yellow solution. The reflux was continued for another 30 minutes. The reaction solution was cooled to room temperature and then to 0° C.

The solution of ethyl-(2-triethylsilanyloxy-ethyl)-amine (10.97 g) in $CH_2Cl_2$ (70 mL) was cooled to 0° C. and then added via a syringe to the above acid chloride solution, followed by the addition of $Et_3N$ (8.19 g). The reaction was stirred under nitrogen for overnight, while it was warmed up to room temperature. The reaction mixture was poured into $NaHCO_3$ solution, which was prepared by mixing 1:1=$H_2O$: saturated $NaHCO_3$ solution, followed by the addition of $CH_2Cl_2$ (150 mL). The organic layer was separated by separate funnel, washed by $H_2O$ (120 mL×3) and brine (120 mL×1), dried by $Na_2SO4$ and concentrated to give crude N-ethyl-4-formyl-N-(2-triethylsilanyloxy-ethyl)-benzamide (15.76 g). $^1H$ NMR (300 MHz, CDCl$_3$) ☐ 10.04 (s, 1H), 7.91 (m, 2H), 7.55 (m, 2H), 3.91 (m, 1H), 3.62 (m, 3H), 3.35 (m, 2H), 1.08-1.28 (m, 3H), 0.94 (m, 9H), 0.58 (m, 6H).

EXAMPLE 163

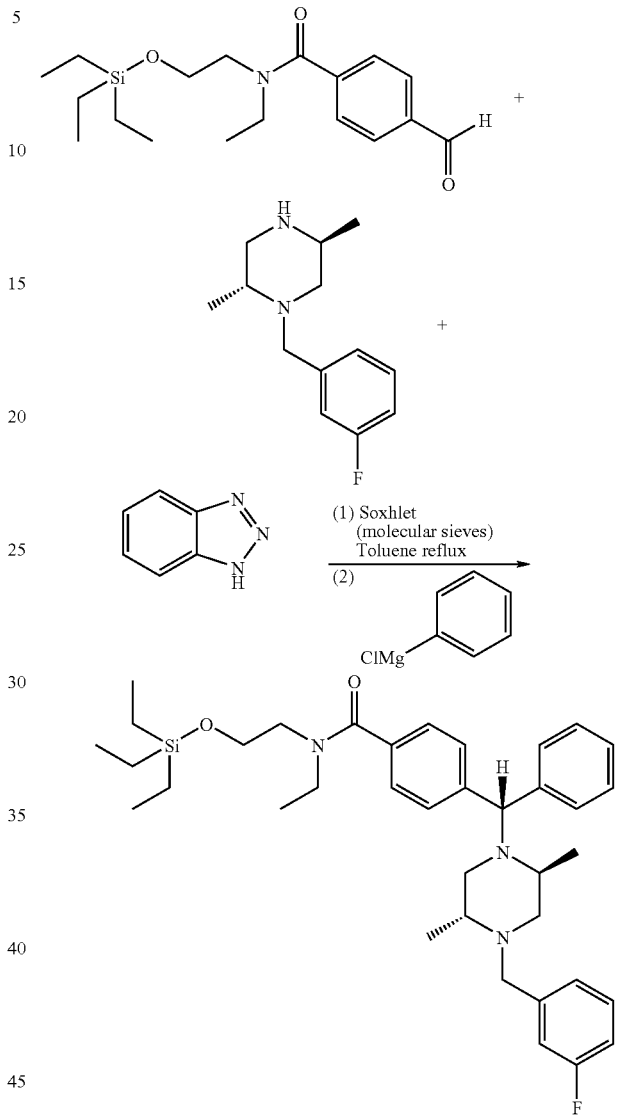

N-Ethyl-4-{(S)-[(2S,5R)-4-(3-fluoro-benzyl)-2,5-dimethyl-piperazin-1-yl]-phenyl-methyl}-N-triethyl-silanyloxy-ethyl)-benzamide The mixture of N-Ethyl-4-formyl-N-(2-triethylsilanyloxy-ethyl)-benzamide (3.58 g), (2R,5S)-1-(3-Fluoro-benzyl)-2,5-dimethyl-piperazine (2.61 g) and benzotriazole (1.4 g) in toluene (200 mL) was refluxed in a 3-neck round-bottom flask equipped with a soxhlet filled with molecule sieve under $N_2$ for 16 h. The reaction solution was cooled to room temperature under $N_2$ and then was added dropwise to the phenylmagnesium bromide (24 mL, 1 M THF solution) via an addition funnel under $N_2$. The reaction was reacted under $N_2$ at room temperature for overnight. The reaction was quenched by the addition of saturated $NH_4Cl$ (6 mL) and $H_2O$ (90 mL). Two scoops of celite were added to the mixture. The resulting mixture was filtered through a celite pad. The reaction flask was rinsed by EtOAc (90 mL×1), which was also filtered through the celite pad.

The celite pad was rinsed by EtOAc (60 mL×1). The filtrate was poured into a separatory funnel. The organic layer and water layer were separated. The water layer was extracted by EtOAc (45 mL×2). The combined organic layer was washed by 5% NaOH solution (90 mL×3), H$_2$O (90 mL×2) and brine (90 mL×1). The organic layer was dried by Na$_2$SO$_4$ and concentrated to give crude product, which was purified by column chromatography to give N-Ethyl-4-{(S)-[(2S,5R)-4-(3-fluoro-benzyl)-2,5-dimethyl-piperazin-1-yl]-phenyl-methyl}-N-(2-triethylsilanyloxy-ethyl)-benzamide (4.5 g, 83%). $^1$H NMR (300 MHz, CDCl$_3$) □ 7.47 (m, 2H), 7.36-7.20 (m, 8H), 7.04 (m, 2H), 6.90 (m, 1H), 5.15 (s, 1H), 3.88 (m, 2H), 3.60 (m, 3H), 3.38 (m, 2H), 3.18 (d, 1H, J=13.5 Hz), 2.67 (m, 2H), 2.56 (m, 2H), 1.93 (m, 1H), 2.02 (m, 1H), 1.09 (m, 9H), 0.96 (m, 9H), 0.62 (m, 3H), 0.51 (m, 3H).

EXAMPLE 164

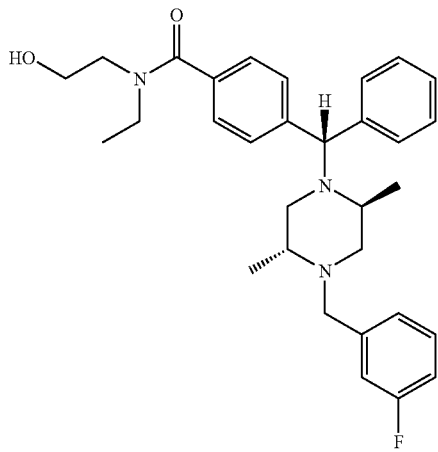

N-Ethyl-4-{(S)-[(2S,5R)-4-(3-fluoro-benzyl)-2,5-dimethyl-piperazin-1-yl]-phenyl-methyl}-N-(2-hydroxy-ethyl)-benzamide Tetrabutylammonium fluoride hydrate (1.83 g) was added to the solution of N-Ethyl-4-{(S)-[(2S,5R)-4-(3-fluoro-benzyl)-2,5-dimethyl-piperazin-1-yl]-phenyl-methyl}-N-(2-triethylsilanyloxy-ethyl)-benzamide (3.6 g) in THF (30 mL). The reaction was stirred at room temperature for 90 minutes. The reaction mixture was concentrated. The residual was dissolved in EtOAc (60 mL). The EtOAc solution was washed by H2O (30 mL×3) and brine (30 mL×1), dried by Na2SO4 and concentrated to give crude product (3.3 g), which was purified to give pure N-Ethyl-4-{(S)-[(2S,5R)-4-(3-fluoro-benzyl)-2,5-dimethyl-piperazin-1-yl]-phenyl-methyl}-N-(2-hydroxy-ethyl)-benzamide (2.76 g; 94%). $^1$H NMR (300 MHz, CDCl$_3$) □ 7.49 (m, 2H), 7.37-7.19 (m, 8H), 7.04 (m, 2H), 6.90 (ddd, 1H, J=8.5, 8.5, 2.0 Hz), 5.16 (s, 1H), 3.87 (m, 3H), 3.69 (m, 2H), 3.36 (m, 2H), 3.18 (d, 1H, J=13.5 Hz), 2.67 (m, 2H), 2.56 (m, 2H), 1.97 (m, 2H), 1.67 (s, 1H), 1.16 (m, 3H), 1.12 (d, 3H, J=6.0 Hz), 1.06 (d, 3H, J=6.5 Hz).

EXAMPLE 165

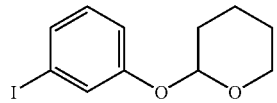

2-(3-Iodo-phenoxy)-tetrahydro-pyran

The solution of 3-iodophenol (70.31 g), PPTS (750 mg) and 3,4-dihydro-2H-pyran (55.68 g) in CH2Cl2 (400 mL) was refluxed under N2 for 3 h. TLC of the reaction solution indicated the presence of starting material, 3-iodophenol. Consequently, more 3,4-dihydro-2H-pyran (30 mL) and PPTS (350 mg) were added to the reaction solution. The reaction was refluxed for another 3 h. After being cooled to room temperature, the reaction solution was washed by saturated NaHCO$_3$ (100 mL×2), H2O (120 mL×3) and brine (120 mL×1), dried by Na2SO4 and concentrated to give crude product, which was purified to give pure 2-(3-Iodo-phenoxy)-tetrahydro-pyran (89.5 g; 92%). $^1$H NMR (300 MHz, CDCl$_3$) □ 7.42 (m, 1H), 7.31 (m, 1H), 7.00 (m, 2H), 5.39 (dd, 1H, J=3.0, 3.0 Hz), 3.87 (m, 1H), 3.61 (m, 1H), 1.97 (m, 1H), 1.84 (m, 2H), 1.65 (m, 3H).

EXAMPLE 166

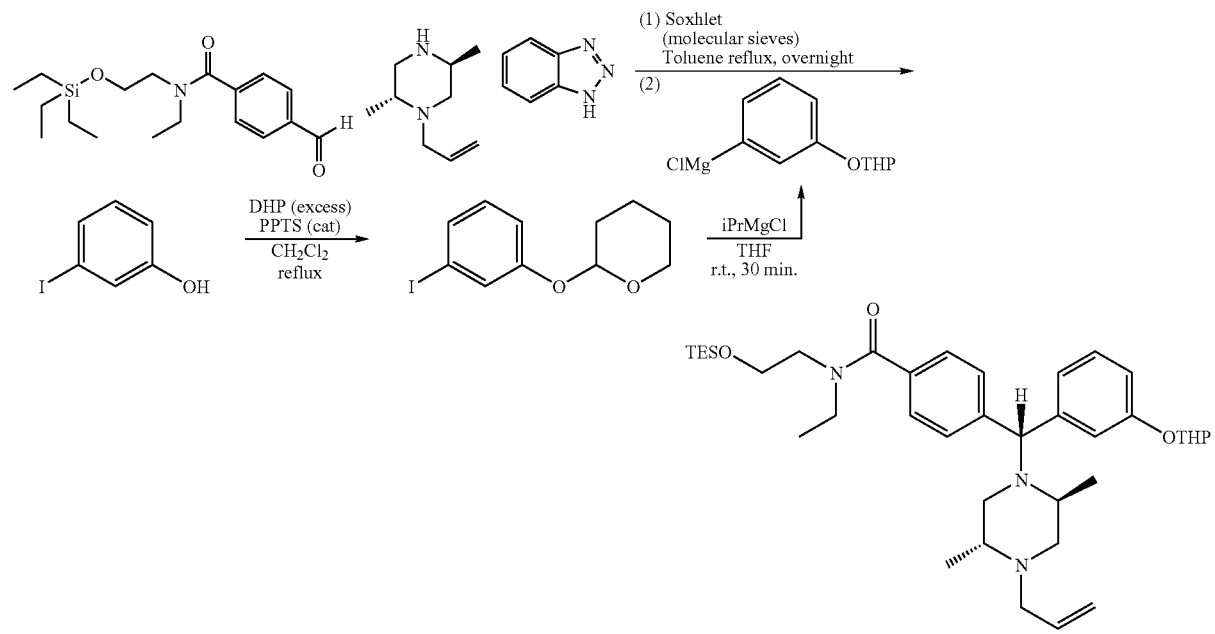

4-{(R)-((2S,5R)-4-Allyl-2,5-dimethyl-piperazin-1-yl)-[3-(tetrahydro-pyran-2-yloxy)-phenyl]-methyl}-N-ethyl-N-(2-triethylsilanyloxy-ethyl)-benzamide The mixture of N-Ethyl-4-formyl-N-(2-triethylsilanyloxy-ethyl)-benzamide (6.06 g), (2R,5S)-1-Allyl-2,5-dimethyl-piperazine (3.06 g) and benzotriazole (2.37 g) in toluene (350 mL) was refluxed in a 3-neck round-bottom flask equipped with a soxhlet filled with molecule sieve under $N_2$ for 16 h. The reaction solution was cooled to room temperature under $N_2$ and then was added dropwise to the Grignard reagent via an addition funnel under $N_2$. The reaction was reacted under $N_2$ at room temperature for overnight. The reaction was quenched by the addition of saturated $NH_4Cl$ (10 mL) and $H_2O$ (150 mL). Two scoops of celite were added to the mixture. The resulting mixture was filtered through a celite pad. The reaction flask was rinsed by EtOAc (150 mL×1), which was also filtered through the celite pad. The celite pad was rinsed by EtOAc (100 mL×1). The filtrate was poured into a separatory funnel. The organic layer and water layer were separated. The water layer was extracted by EtOAc (75 mL×2). The combined organic layer was washed by 5% NaOH solution (150 mL×3), $H_2O$ (150 mL×2) and brine (150 mL×1). The organic layer was dried by $Na_2SO_4$ and concentrated to give crude product, which was purified by column chromatography to give pure 4-{(R)-((2S,5R)-4-Allyl-2,5-dimethyl-piperazin-1-yl)-[3-(tetrahydro-pyran-2-yloxy)-phenyl]-methyl}-N-ethyl-N-(2-triethylsilanyloxy-ethyl)-benzamide (5.3 g; 45%). $^1$H NMR (300 MHz, $CDCl_3$) □ 7.47 (d, 2H, J=8.0 Hz), 7.30 (d, 2H, J=8.0 Hz), 7.22 (dd, 1H, J=8.0, 8.0 Hz), 6.96 (m, 1H), 6.86 (m, 1H), 6.78 (m, 1H), 5.86 (m, 1H), 5.36 (m, 1H), 5.16 (m, 3H), 3.90 (m, 2H), 3.58 (m, 4H), 3.37 (m, 3H), 2.82 (m, 2H), 2.59 (m, 2H), 2.45 (m, 1H), 2.11 (m, 1H), 1.98 (m, 1H), 1.85 (m, 3H), 1.63 (m, 3H), 1.17 (m, 6H), 0.94 (m, 12H), 0.58 (m, 6H).

EXAMPLE 167

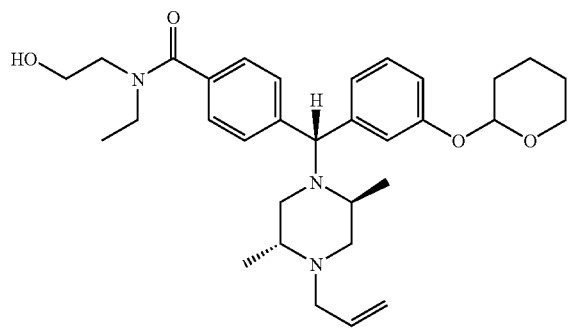

4-{(R)-((2S,5R)-4-Allyl-2,5-dimethyl-piperazin-1-yl)-[3-(tetrahydro-pyran-2-yloxy)-phenyl]-methyl}-N-ethyl-N-(2-hydroxy-ethyl)-benzamide $^1$H NMR (300 MHz, $CDCl_3$) □ 7.49 (d, 2H, J=8.0 Hz), 7.33 (d, 2H, J=8.0 Hz), 7.22 (dd, 1H, J=8.0, 8.0 Hz), 6.96 (m, 1H), 6.85 (m, 1H), 6.77 (m, 1H), 5.85 (m, 1H), 5.35 (m, 1H), 5.23-5.12 (m, 3H), 3.92-3.55 (m, 6H), 3.36 (m, 3H), 2.82 (m, 2H), 2.57 (m, 2H), 2.45 (m, 1H), 2.12 (m, 1H), 1.98 (m, 1H), 1.85 (m, 3H), 1.63 (m, 4H), 1.18 (m, 6H), 0.98 (d, 3H, J=6.0 Hz).

EXAMPLE 168

Compounds of the present invention were evaluated for in vitro opioid receptor affinity in rat brain membranes (μ and δ opioid) and guinea pig cerebellum (κ opioid receptor). Membranes for radioligand binding were prepared from either rat whole brain or guinea pig cerebellum, supplied by Pel-Freeze Biological Inc. (Rogers, Ark.). Tissues were homogenized in 50 mM TRIS (Tris[hydroxymethyl]aminomethane) buffer (pH 7.4) containing 50 ug/ml soybean trypsin inhibitor, 1 mM EDTA (Ethylenediaminetetraacetic acid), and 100 μM PMSF (Phenylmethylsulfonyl fluoride). The homogenized brain tissues were centrifuged at 500×g for 30 minutes (4° C.) to remove large debris. The supernatant was polytronically sonicated for 10 seconds (P.E. setting of 2, 4° C.). Sucrose solution was then added to a final concentration of 0.35 M using a 10 mM TRIS-Sucrose buffer (pH 7.4) and the brain membranes were then centrifuged at 40,000×g for 30 minutes (4° C.). The membrane pellets were then washed twice in 10 mM TRIS buffer (pH 7.4) containing 50 μg/ml soybean trypsin inhibitor, 1 mM EDTA, and 100 μM PMSF.

For human opioid receptors, cell membranes, prepared from HEK-293 cells (Perkin Elmer product # 6110549) that expressed human delta receptor expressed or CHO cells (Perkin Elmer product # 6110535) that expressed human mu opioid receptor, were purchased from Perkin Elmer, Boston, Mass.

Radioligand binding assays were performed in 10 mM TRIS buffer (pH 7.4) containing protease inhibitors of 50 μg/ml soybean trypsin inhibitor, and 100 μM PMSF (for brain membranes preparations only), 1 mM EDTA and 5 or 10 mM $MgCl_2$. Tritium-labeled DAMGO (μ), Deltorphin II (δ), or U69593 (κ) purchased from New England Nuclear were used as ligands in competitive experiments ($2-3\times10^{-10}$ M final concentrations) with non-specific binding defined by $0.5\times 10^{-6}$ M Naloxone (purchased from SIGMA Chemical Co.). All binding assays were run at room temperature for 90 minutes and then terminated by rapid filtration on GF/C glass fiber filters (Whatman, Hillsboro, Oreg.) with 50 mM TRIS buffer (4° C., pH 7.4) employing a Brandel Semi-automatic Cell Harvester (Model M48, Brandel, Gaithersburg, Md.). The filters were washed twice with 50 mM TRIS buffer (4° C., pH 7.4) and the filters were placed in liquid scintillation cocktail and the bound radioactivity counted on a Beckman LS 6500 scintillation counter. The potency of the compounds in inhibiting the binding of radiolabelled DAMGO (μ), Deltorphin II (δ), or U69593 (κ) was determined from full concentration-effect curves. With the computer program Prism (GraphPad Software Inc., San Diego, Calif.) the $IC_{50}$ values were determined using a one-site nonlinear regression analysis of the radioligand binding data. The $IC_{50}$ values were then converted to $K_i$ values using the Cheng-Prusoff equation. (Cheng Y and Prusoff W H (1973) Relationship between the inhibition constant (K1) and the concentration of inhibitor which causes 50 percent inhibition (I50) of a enzymatic reaction. Biochem Pharm 22:3099-3108.)

Further the compounds of formula (1) were evaluated for in vitro opioid receptor activity in various receptor systems, including mouse vas deferens (Mouse Vas Deferens $ED_{50}$), and guinea pig ileum (Guinea Pig Ileum $ED_{50}$). The assay procedures used for such determinations of receptor activity are set out below.

In vitro bioassays: Mouse vasa deferentia (MVD), CD-1 strain, Harlan, Raleigh, N.C.) were removed from mice and suspended between platinum electrodes with 0.5 g of tension in organ bath chambers containing a modified $Mg^{++}$ free Krebs buffer of the following composition (millimolar): NaCl, 117.5; KCl, 4.75; $CaCl_2$, 2.6; $KH_2PO_4$, 1.20; $NaHCO_3$, 24.5; and glucose, 11. The buffer was saturated with 95% $O_2$/5% $CO_2$ and kept at 37° C. Tissues were stimulated at supramaximal voltage with 10-Hz pulse trains for 400-msec.; train interval 10 seconds; and 1.0 msec pulse duration at maximal voltage. Delta receptor activity was determined by adding appropriate concentrations of test compound to organ baths and allowing a maximal response before addition of the next higher concentration. Mu receptor activity was determined in similar fashion, but in the presence of 3 $\square$M TIPP (a highly selective delta antagonist; P. W. Schiller, T. M.-D. Nguyen, G. Weltrowska, B. C. Wilkes, B. J. Marsden, C. Lemieux, and N. N. Chung, *Proc. Natl. Acad. Sci.* 89, 11871 (1992)) and 15 nM nor-BNI (a selective kappa antagonist; P. S. Portoghese, A. W. Lipkowski, and A. E. Takemori, Life Sci. 40, 1287 (1987)).

Intact ileums (about 3 cm length) were removed from guinea pig and suspended with 1 g of tension in a bath chamber as described for the vasa deferentia. The ileums were stimulated with electrical square-wave pulses of 0.1-Hz, 1 msec pulse duration at supramaximal voltage.

The percentage inhibition of the electrically induced muscle contractions was determined for the compounds at varying cumulative concentrations. The $ED_{50}$ values were extrapolated from curves showing the dose concentration plotted against the response (J. A. H. Lord, A. A. Waterfield, J. Hughes, H. W. Kosterlitz, *Nature* 267, 495, (1977)).

EXAMPLE 169

Mouse Seizure-Like Convulsions and antinociception: The central (CNS) effects of the compound were tested with central delta receptor mediated seizure-like convulsions and central mu opioid receptor mediated antinociceptive effects in mice. Male CD-1 mice (Charles River, Raleigh, N.C.) weighing 20-25 g were used to determine the seizure-like convulsion and antinociception activities for compounds.

Each mouse received a single bolus dose of i.v. via the tail vein (10 mg/kg; n=10/dose). They were then observed for seizure-like convulsions for one hour following the treatment. A seizure-like event was recorded if a mouse had uncontrollable clonic (or tonic/clonic) muscle movements that encompassed its entire body, usually followed by a brief cataleptic period. Catalepsy was determined by placing the animal's front paws on a horizontal bar held 2-3 inches from the cage floor. Cataleptic animals made no attempt to remove their paws.

All mice received 10 mg/kg iv dose of compounds were also tested for the antinociceptive activity by a standard tail-pinch assay with an artery clamp. The test was performed by placing the artery clamp on the base of the tail. The clamp remained in place until an escape response occurred (i.e., tail-flick or vocalization or biting) or a maximum time of 20 seconds had elapsed. The normal response time to the pressure from the clamp is less than 1 second. Analgesic compounds like morphine at 4 mg/kg iv dose or fentanyl at 50 $\square$g/kg iv dose will produce an antinociceptive effect with a maximum time of response of 20 seconds.

Tabulated empirical data for compounds of the invention are set out below in Tables 1-6 hereinafter set forth (Table 1=Homopiperazine Derivatives; Table 2=Piperazine Derivatives; Table 3=Piperidine Derivatives; Table 4=Proline Derivatives; Table 5=Sarcosine Derivatives; and Table 6=2-(Ethylamino)ethanol Derivatives).

TABLE 1

Homopiperazine Derivatives

| Homopiperazine Derivatives (7-member ring) | δ | μ | : | MVD (nM) | GPI (nM) | Seiz. | UI | Anti-nociception in tail-pinch assay |
|---|---|---|---|---|---|---|---|---|
| Example 1 | 5.45 (rat) | 1.58 (rat) | 1.93 | 26.27 | | 0% 10 mg/kg IV (mouse TP- 54% MPE; no rat analg.) | | |
| Example 2 | 4.68 (rat) | 1.61 (rat) | 1.6 | 6.07 | | 45% 10 mg/kg IV | | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 5 | 1.35 (rat) | 3.33 (rat) | 4.15 | 1.36 | | 25% 10 mg/kg IV | | |
| Example 6 | 3.53 (rat) | 3.03 (rat) | 12.68 | 4.7 | | 0% 3 mg/kg IV 10% 10 mg/kg IV | 18% 6 mg/kg PO | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 16 | 0.21 | 0.56 | | 2.4 | 526 | 60% 10 mg/kg IV | | |
| Example 17 | | 1.27 | | 1.4 | >1000 | 0% 20 mg/kg IV | | |

TABLE 1-continued
Homopiperazine Derivatives
| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 18 | 5.4 | 2.6 | :: | 13.37 | 760.6 | 20% 10 mg/kg IV | | |
| Example 19 | | 3.1 | | | | | | |
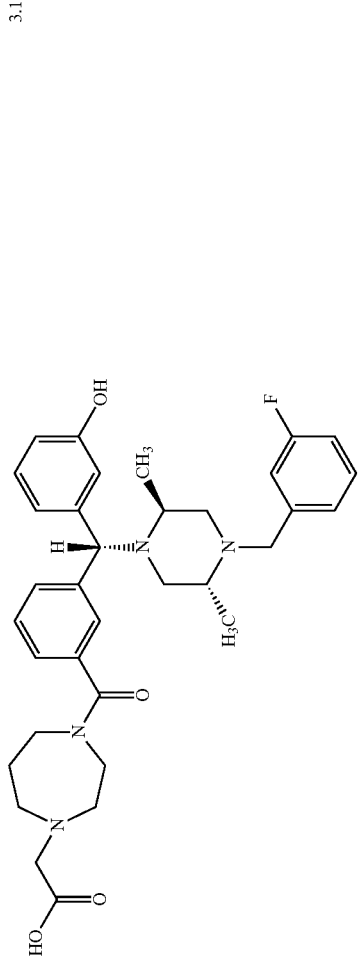

TABLE 1-continued

Homopiperazine Derivatives

| Homopiperazine Derivatives (7-member ring) | δ | μ | : | MVD (nM) | GPI (nM) | Seiz. | UI | Anti-nociception in tail-pinch assay |
|---|---|---|---|---|---|---|---|---|
| Example 24 | 1.9 | 3.9 | | 38.9 | | 0% 20 mg/kg IV | | |
| Example 25 | 6.8 | 33.1 | | 65.2 | | 0% 20 mg/kg IV | | |

TABLE 1-continued
Homopiperazine Derivatives
| Homopiperazine Derivatives (7-member ring) | δ | μ | : | MVD (nM) | GPI (nM) | Seiz. | UI | Antinociception in tail-pinch assay |
|---|---|---|---|---|---|---|---|---|
| Example 3 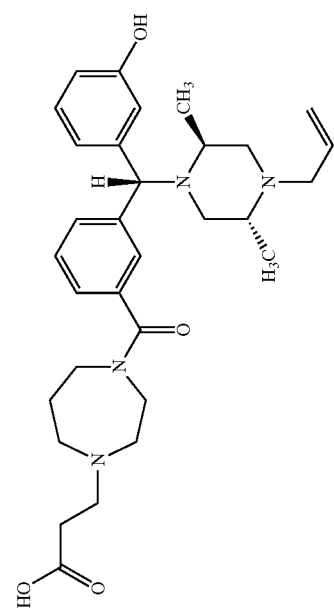 | 0.57 (rat) | 0.55 (rat) | 1.09 | 5.58 | 111.5 | 30% 10 mg/kg IV | | |
| Example 4 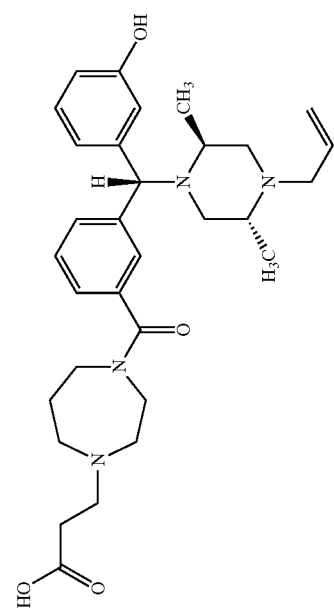 | 3.03 (rat) | 3.89 (rat) | 9.85 | 5.39 | 117.3 | 0% 10 mg/kg IV | | |

TABLE 1-continued
Homopiperazine Derivatives
| Homopiperazine Derivatives (7-member ring) | δ | μ | : | MVD (nM) | GPI (nM) | Seiz. | UI | Antinociception in tail-pinch assay |
|---|---|---|---|---|---|---|---|---|
| 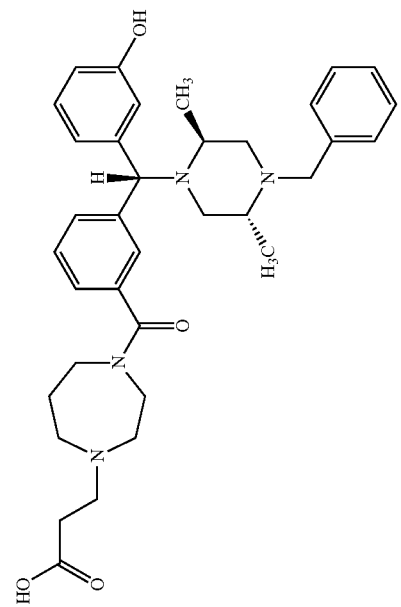<br>Example 12 | 1.2 (rat) | 0.75 (rat) | 2.98 | 1.5 | 835.6 | 80% 10 mg/kg IV (42% MPE mouse TP) | 20% 3 mg/kg PO | |
| Example 13 | 4 (rat) | 3.9 (rat) | 3828 | 0.52 | 52.2 | 0% 200 mg/kg PO 0% 20 mg/kg IV | 18% 3 mg/kg PO 28% 6 mg/kg PO | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 14 | 71 | 4.8 | : | 17.1 | 977.7 | 20% 10 mg/kg IV | 10% 6 mg/kg PO | |
| Example 15 | 4.17 | 7.7 | | 4.0 | 153.8 | 0% 200 mg/kg PO & SC 0% 20 mg/kg IV | 14% 0.1 mg/kg PO 23% 0.2 mg/kg PO | |

TABLE 1-continued
Homopiperazine Derivatives
| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 26 | 121.5 | 2.9 | | 22.6 | 567.3 | 0% 10 mg/kg IV | | |
| Example 27 | 68.99 | 22.3 | | 65.95 | 663.5 | 0% 20 mg/kg IV | 26% 1.0 mg/kg PO | |
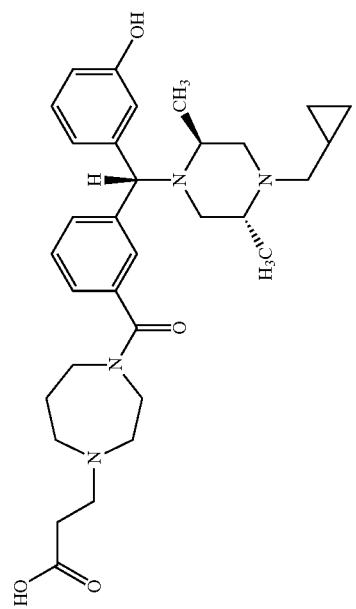

TABLE 1-continued
Homopiperazine Derivatives
| Homopiperazine Derivatives (7-member ring) | δ | μ | : | MVD (nM) | GPI (nM) | Seiz. | UI | Anti-nociception in tail-pinch assay |
|---|---|---|---|---|---|---|---|---|
| Example 7 | 1.66 (rat) | 1.76 (rat) | 1.22 | 22.63 | 198.4 | 0% 10 mg/kg IV | | |
| Example 8 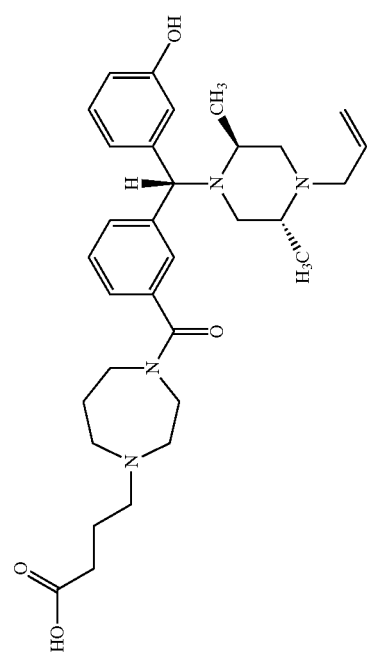 | 2.75 (rat) | 5.57 (rat) | 16.26 | 2.2 | 185.8 | 0% 10 mg/kg IV | 8% 6 mg/kg PO | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 20 | 50.1 | 1.2 | | 10.58 | | 30% 10 mg/kg IV | | |
| Example 21 | 14.8 | 1.9 | | 1.07 | 159 | 0% 10 mg/kg IV | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 22 | 1.7 | 2.3 | : | 29.97 | 1500 | | | |
| Example 23 | 94 | 0.27 | | 6.37 | | 0% 10 mg/kg IV | | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 28 | 10.3 | 3.9 | | 92.52 | | | | |
| Example 29 | 526.9 | 26.5 | | 60.89 | | | | |

TABLE 1-continued
Homopiperazine Derivatives
| Homopiperazine Derivatives (7-member ring) | δ | μ | : | MVD (nM) | GPI (nM) | Seiz. | UI | Anti- nociception in tail-pinch assay |
|---|---|---|---|---|---|---|---|---|
| Example 9 | 2.9 (rat) | 1.25 (rat) | 0.6 | 43.7 | 231 | 0% 10 mg/kg IV | | |
| Example 10 | 6.43 (rat) | 9.0 (rat) | 27.7 | 3.33 | | 0% 10 mg/kg IV 0% 100 mg/kg SC | 21% 6 mg/kg PO | |
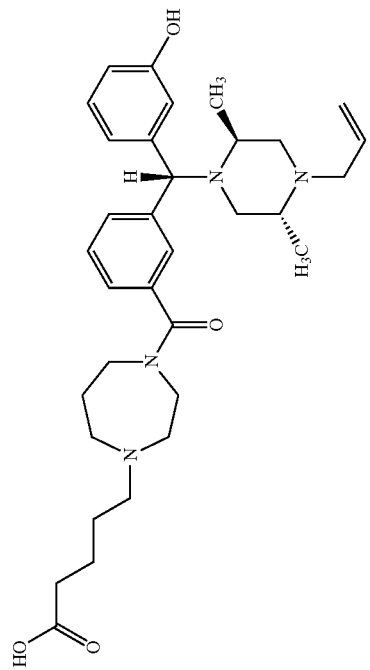

TABLE 1-continued
Homopiperazine Derivatives
| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| 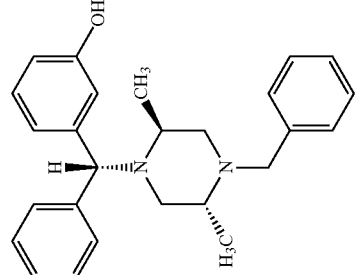<br>Example 30 | 2.6 | 6.3 | | 11.11 | | 25%<br>10 mg/kg<br>IV | | |
| 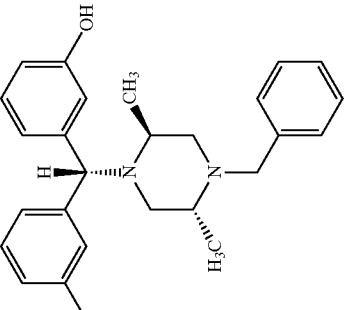<br>Example 31 | 20.4 | 23.5 | | 3.28 | | 0%<br>10 mg/kg<br>IV | | |

TABLE 1-continued
Homopiperazine Derivatives
| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 32 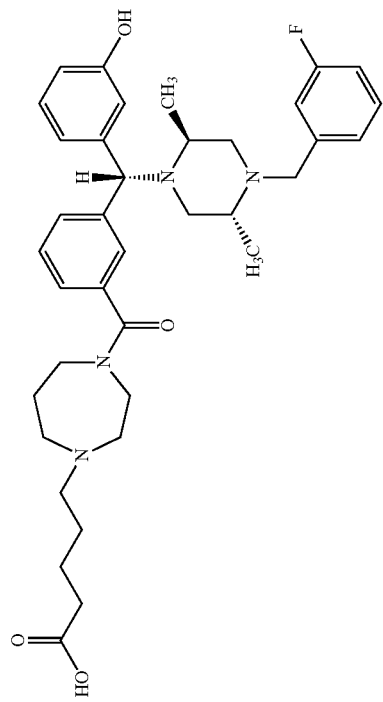 | 6.1 | 15.7 | | 61.5 | | 0% 10 mg/kg IV | | |
| Example 33 | 35.4 | 34.8 | | 14.70 | | 0% 10 mg/kg IV | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 34 | 88.5 | 29.9 | | 115.8 | | | | |
| Example 35 | 62.1 | 557.7 | | 77.51 | | | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 36 | 3.2 | 21.3 | | 43.26 | | | | |
| Example 37 | 5.3 | 89.9 | | 18.98 | | 0% 10 mg/kg IV | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 38 | 3.7 | 23.4 | | 29.63 | | | | |
| Example 39 | 2.8 | 3.9 | | 3.26 | 303.1 | | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 40 | 12.9 | 58.5 | | 155.7 | | | | |
| Example 41 | 25.1 | 222.1 | | 16.19 | | | | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 42 | 23.5 | 9.3 | | 1045 | | | | |
| Example 43 | 5.6 | 20.3 | | 110 | | | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 44 | 3.1 | 3.9 | | 52.29 | | | | |
| Example 45 | 5.6 | 8.3 | | 34.91 | | | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 46 | 2.4 | 3.8 | | 28.6 | | | | |
| Example 47 | 4.9 | 6.3 | | 10.42 | | | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 48 | 13.3 | 7.0 | | 245.4 | | | | |
| Example 49 | 141.3 | 221.6 | | 109.4 | | | | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 50 | 44.3 | 8.0 | | 88.1 | | | | |
| Example 51 | 50.6 | 40.7 | | 339.4 | | | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| ![Example 52 structure] Example 52 | 0.39 | 4.0 | :: | 3.1 | 149.9 | 0% 10 mg/kg IV | 18% 6 mg/kg PO | |
| ![Example 53 structure] Example 53 | | | | 19.55 | | | | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 54 | | 5.5 | | 6.23 | | 0% 10 mg/kg IV | | |
| Example 55 | | | | 21.82 | | | | |

TABLE 1-continued

Homopiperazine Derivatives

| Homopiperazine Derivatives (7-member ring) | δ | μ | κ | MVD (nM) | GPI (nM) | Seiz. | UI | Anti-nociception in tail-pinch assay |
|---|---|---|---|---|---|---|---|---|
| Example 56 | | 1.4 | | 2.20 | | 40% 10 mg/kg IV | | |
| Example 117 | 1.9 (rat) | 2.6 (rat) | 1.2 | 1.44 | 526.5 | 0% 10 mg/kg IV | | |

TABLE 1-continued

Homopiperazine Derivatives

| Homopiperazine Derivatives (7-member ring) | δ | μ | κ | MVD (nM) | GPI (nM) | Seiz. | UI | Antinociception in tail-pinch assay |
|---|---|---|---|---|---|---|---|---|
| Example 118 [structure] | 3.94 (rat) | 16.1 (rat) | 29.18 | 0.95 | 439.2 | 0% 10 mg/kg IV 0% 100 mg/kg SC | | |

TABLE 2

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 57 | 0.81 | 0.80 | | 5.15 | | 40% 10 mg/kg IV | | |
| Example 62 | 2.2 | 1.7 | | 6.78 | | 70% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 60 | 13.1 | 9.8 | | 47.17 | | | | |
| Example 51 | 23.2 | 4.0 | | 38.96 | | | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 58 | 5.1 | 1.1 | | 12.11 | | 0% 10 mg/kg IV | | |
| Example 63 | 0.44 | 0.47 | | 7.71 | | 20% 10 mg/kg IV | | |
| Example 64 | 0.79 | 9.0 | | 5.18 | | 30% 10 mg/kg IV | | |

TABLE 2-continued

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 68 | 0.73 | 1.22 | | 1.91 | 525.7 | 80% 10 mg/kg IV | | |
| Example 69 | 0.54 | 1.36 | | 0.48 | 47.78 | 0% 10 mg/kg IV | | |

TABLE 2-continued
Piperazine Derivatives
| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| 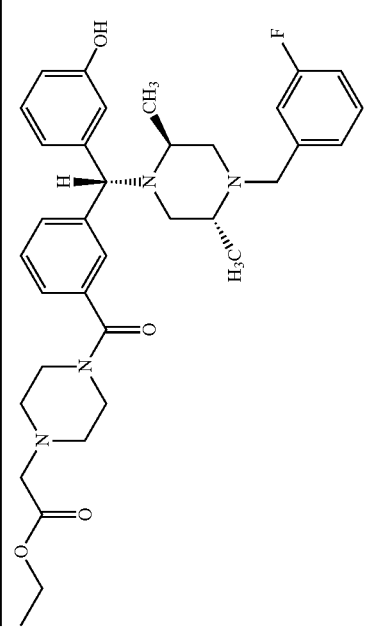<br>Example 66 | 1.3 | 5.05 | | 21.97 | | | | |
| 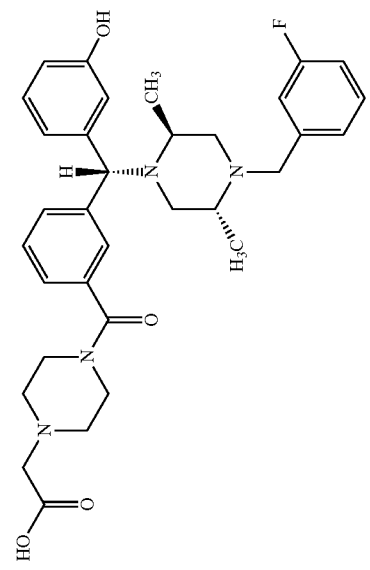<br>Example 67 | | 10.7 | | 2.82 | | 0%<br>10 mg/kg<br>IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 116 | 0.83 | | | 1.95 | | | | |
| Example 70 | 3.5 | 8.7 | | 55.43 | | | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 71 | 6.1 | 81.8 | | 35.85 | | | | |
| Example 106 | | | | | | | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 72 | 0.61 | 2.4 | | 8.03 | | 20% 10 mg/kg IV | | |
| Example 73 | 2.6 | 17.1 | | 2.28 | | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 74 | 122.8 | 1.95 | | 23.32 | | 10% 10 mg/kg IV | | |
| Example 75 | 25.3 | 10.8 | | 4.1 | 178 | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 79 | 3.7 | 1.3 | | 3.95 | | 80% 10 mg/kg IV | | |
| Example 80 | 5.7 | 5.3 | | 0.34 | 103.6 | 0% 10 mg/kg IV | | |

TABLE 2-continued

| Piperazine Derivatives (6-member ring) | Piperazine Derivatives | | | MVD (nM) | GPI (nM) | Seiz. | UI | Anti-nociception in tail-pinch assay |
| --- | --- | --- | --- | --- | --- | --- | --- | --- |
| | δ | μ | κ | | | | | |
| Example 81 | 12.7 | 4.9 | | 44.80 | | | | |
| Example 82 | 31.1 | 13.8 | | 2.65 | | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 77 | 401.9 | 4.4 | | 110.7 | | | | |
| Example 78 | 10.2 | 194 | | 26.65 | | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 83 | 10.7 | 8.9 | | 11.82 | | 30% 10 mg/kg IV | | |
| Example 84 | 13.4 | 57.3 | | 3.76 | 209 | 0% 10 mg/kg IV | | |

TABLE 2-continued

| Piperazine Derivatives (6-member ring) | δ | μ | κ | MVD (nM) | GPI (nM) | Seiz. | UI | Antinociception in tail-pinch assay |
|---|---|---|---|---|---|---|---|---|
| Example 86 | 3.1 | 9.1 | | 12.56 | | 60% 10 mg/kg IV | | |
| Example 102 | | | | | | | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 87 | 10.8 | 21.3 | | 36.22 | | | | |
| Example 88 | 16.9 | 210.7 | | 6.66 | | 0% 10 mg/kg IV | | |

TABLE 2-continued
Piperazine Derivatives
| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| 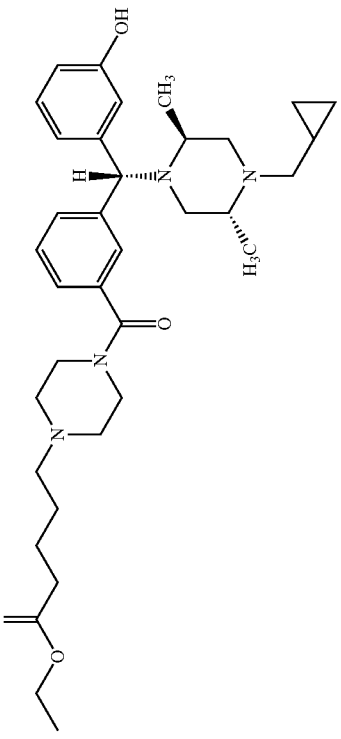 Example 89 | 15.4 | 23.2 | | 92.69 | | | | |
| 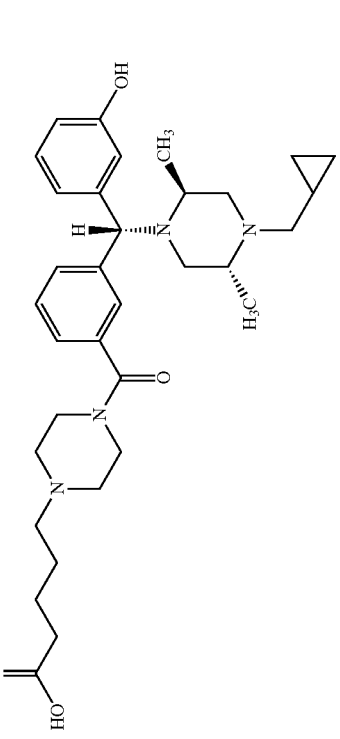 Example 90 | 32.5 | 409.3 | | 46.18 | | | | |

TABLE 2-continued

Piperazine Derivatives

| Piperazine Derivatives (6-member ring) | δ | μ | κ | MVD (nM) | GPI (nM) | Seiz. | UI | Antinociception in tail-pinch assay |
|---|---|---|---|---|---|---|---|---|
| Example 93 | 5.4 | 30.5 | | 58.78 | | | | |
| Example 94 | 2.5 | 64.3 | | 6.07 | | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 96 | 6.9 | 2.0 | | 10.38 | | 60% 10 mg/kg IV | | |
| Example 97 | 1.2 | | | 2.50 | 445.4 | 0% 10 mg/kg IV | | |

TABLE 2-continued

| Piperazine Derivatives (6-member ring) | δ | μ | κ | MVD (nM) | GPI (nM) | Seiz. | UI | Antinociception in tail-pinch assay |
|---|---|---|---|---|---|---|---|---|
| Example 98 | 7.1 | 8.5 | | 101.6 | | | | |
| Example 99 | 15.7 | | | 10.55 | | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 100 | | | | 169.5 | | | | |
| Example 101 | | | | 75.78 | | | | |

TABLE 2-continued
Piperazine Derivatives
| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 108 | | | | 31.68 | | | | |
| Example 109 | 1.9 | | | 7.48 | | 0% 10 mg/kg IV | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 110 | | | | 18.79 | | 70% 10 mg/kg IV | | |
| Example 111 | 0.77 | 8.7 | | 3.82 | | 0% 10 mg/kg IV | | |

TABLE 2-continued
Piperazine Derivatives
| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| 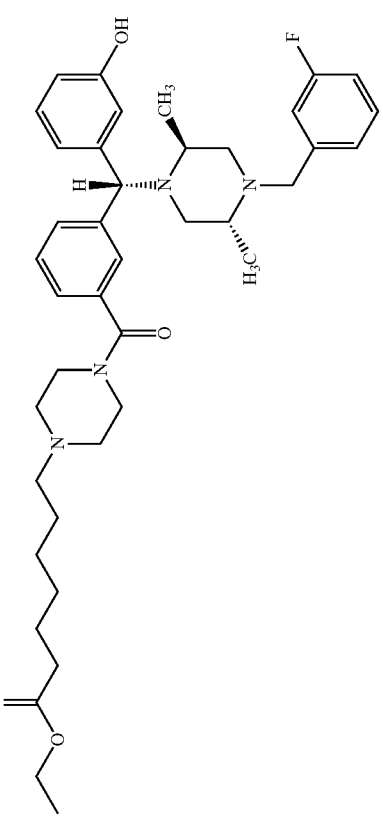 Example 112 | | 5.9 | | 110.9 | | | | |
| 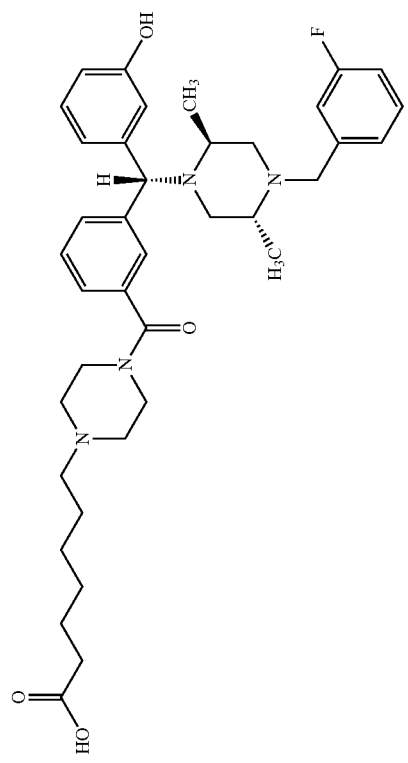 Example 113 | | | | | | | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 114 | | | | 221.3 | | | | |
| Example 115 | 22 | | | 85.85 | | | | |

TABLE 2-continued

Piperazine Derivatives

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 91 | 2.7 | 6.5 | | 23.14 | | 70% 10 mg/kg IV | | |
| Example 92 | 1.7 | 30.7 | | 9.82 | 304 | 0% 10 mg/kg IV | | |

TABLE 2-continued

| Piperazine Derivatives (6-member ring) | δ | μ | κ | MVD (nM) | GPI (nM) | Seiz. | UI | Anti-nociception in tail-pinch assay |
|---|---|---|---|---|---|---|---|---|
| Example 103 | | 84.7 | | 187 | | 0% 60 mg/kg PO | | |
| Example 104 | 0.99 | 19.4 | | 2.06 | | | | |

TABLE 2-continued

Piperazine Derivatives

| Piperazine Derivatives (6-member ring) | δ | μ | κ | MVD (nM) | GPI (nM) | Seiz. | UI | Antinociception in tail-pinch assay |
|---|---|---|---|---|---|---|---|---|
| Example 105 | 32 | 88.6 | | 30.64 | | | | |
| Example 107 | 0.95 | 6.5 | | 3.97 | | | | |

TABLE 3

Piperidine Derivatives

| Piperidine Derivatives | δ | μ | κ | MVD (nM) | GPI (nM) | Seiz. | UI | Anti-nociception in tail-pinch assay |
|---|---|---|---|---|---|---|---|---|
| Example 119 | 2.95 | 0.54 | | 1.96 | 86.3 | 80% 10 mg/kg IV | | |
| Example 120 | | 4.1 | | 2.49 | 48.61 | 10% 10 mg/kg IV | | |
| Example 122 | 4.5 | 1.9 | | 0.82 | 153 | 70% 10 mg/kg IV | | |

TABLE 3-continued

Piperidine Derivatives

| Piperidine Derivatives | δ | μ | κ | MVD (nM) | GPI (nM) | Seiz. | UI | Anti-nociception in tail-pinch assay |
|---|---|---|---|---|---|---|---|---|
| Example 123 | | | | 0.48 | 17.75 | 0% 10 mg/kg IV | | |
| Example 124 | 28.6 | 3.5 | 2.54 | 1678 | | 10% 10 mg/kg IV | | |
| Example 125 | | | | 1.42 | 46.74 | 0% 10 mg/kg IV | | |

TABLE 3-continued

Piperidine Derivatives

| Piperidine Derivatives | δ | μ | κ | MVD (nM) | GPI (nM) | Seiz. | UI | Anti-nociception in tail-pinch assay |
|---|---|---|---|---|---|---|---|---|

Example 128

Example 129

Example 130

TABLE 3-continued

Piperidine Derivatives

| Piperidine Derivatives | δ | μ | κ | MVD (nM) | GPI (nM) | Seiz. | UI | Anti-nociception in tail-pinch assay |
|---|---|---|---|---|---|---|---|---|
| Example 131 | | | | | | | | |
| Example 126 | 3.7 | 1.5 | | 8.64 | 3308 | 10% 10 mg/kg IV | | |
| Example 127 | 4.35 | | | 11.52 | 241.9 | 0% 10 mg/kg IV | | |

TABLE 3-continued
Piperidine Derivatives
| Piperidine Derivatives | δ | μ | κ | MVD (nM) | GPI (nM) | Seiz. | UI | Antinociception in tail-pinch assay |
|---|---|---|---|---|---|---|---|---|
| 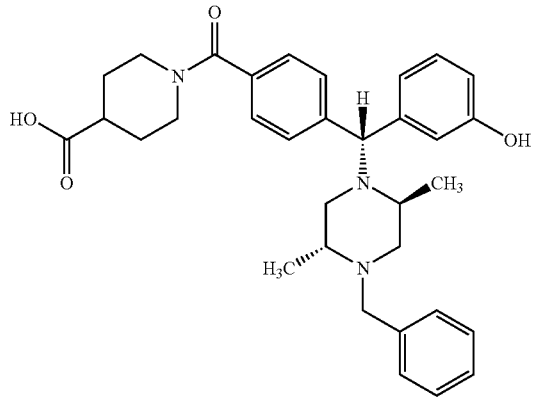<br>Example 132 | | | | | | | | |
| 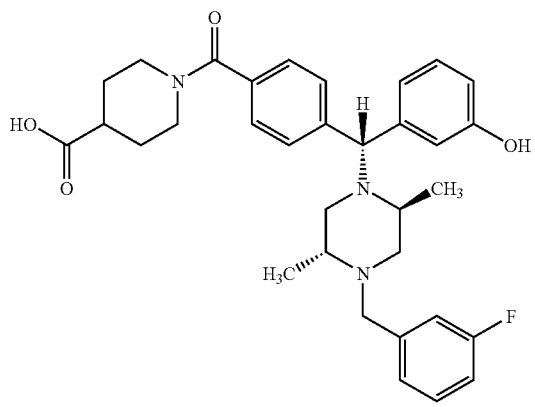<br>Example 133 | | | | | | | | |
| 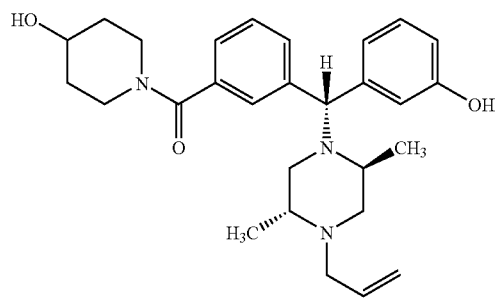<br>Example 134 | 0.36 | 1.1 | 5.44 | 46.67 | | | | 0% 10 mg/kg IV |

TABLE 3-continued

Piperidine Derivatives

| Piperidine Derivatives | δ | μ | κ | MVD (nM) | GPI (nM) Seiz. | UI | Anti-nociception in tail-pinch assay |
|---|---|---|---|---|---|---|---|
| Example 135 | | | | | | | |
| Example 136 | | | | | | | |
| Example 137 | | | | | | | |
| Example 138 | 0.63 | 7.4 | 1.35 | | | | 0% 10 mg/kg IV |

TABLE 3-continued

Piperidine Derivatives

| Piperidine Derivatives | δ | μ | κ | MVD (nM) | GPI (nM) | Seiz. | UI | Anti-nociception in tail-pinch assay |
|---|---|---|---|---|---|---|---|---|
| Example 139 | | | | | | | | |
| Example 140 | | | | 1.2 | 4.6 | 6.74 | | 0% 10 mg/kg IV |
| Example 141 | | | | | | | | |
| Example 142 | | | | 1.7 | 8.7 | 12.51 | | 0% 10 mg/kg IV |

TABLE 4
| Proline Derivatives | δ | μ | κ | MVD (nM) | GPI (nM) | Seiz. | UI | Anti-nociception in tail-pinch assay |
|---|---|---|---|---|---|---|---|---|
| 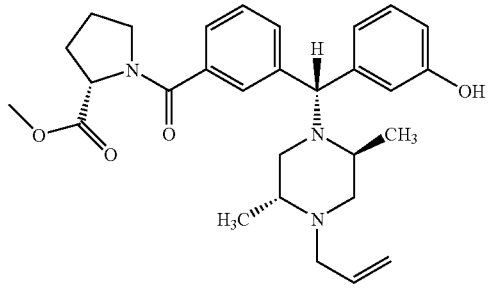<br>Example 143 | 1.5 | 0.50 | | 1.79 | | 10%<br>10 mg/kg<br>IV | | |
| 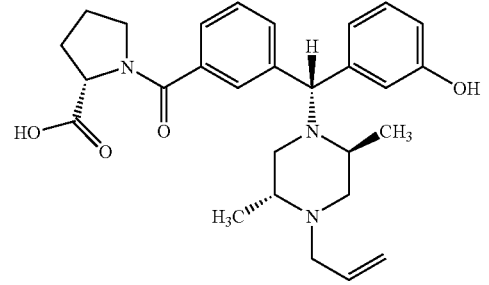<br>Example 144 | 0.62 | | | 1.15 | | 0%<br>10 mg/kg<br>IV | | |
| 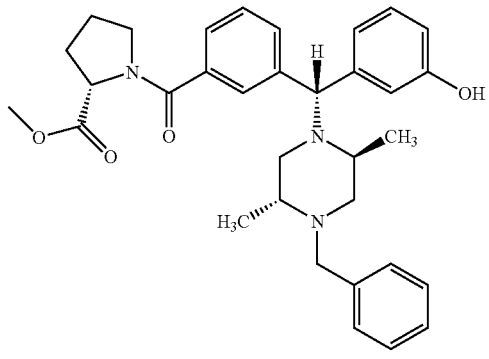<br>Example 145 | | | | | | | | |
| 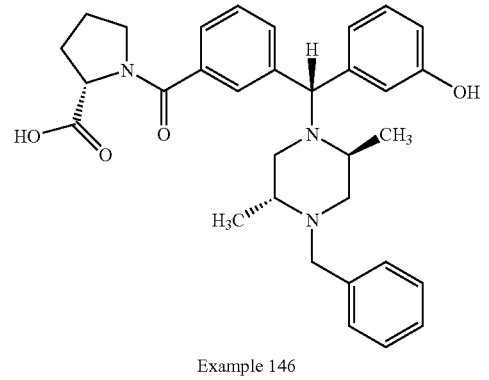<br>Example 146 | | | | | | | | |

TABLE 4-continued

Proline Derivatives

| Proline Derivatives | δ | μ | κ | MVD (nM) | GPI (nM) | Seiz. | UI | Antinociception in tail-pinch assay |
|---|---|---|---|---|---|---|---|---|
| Example 147 | | | | | | | | |
| Example 148 | | | | | | | | |
| Example 149 | | | | | | | | |
| Example 150 | | | | | | | | |

TABLE 5

Sarcosine Derivatives

| Sarcosine Derivatives | δ | μ | κ | MVD (nM) | GPI (nM) | Seiz. | UI | Anti-nociception in tail-pinch assay |
|---|---|---|---|---|---|---|---|---|
| Example 151 | | | | 0.50 | 1.60 | 100% 10 mg/kg IV | | |
| Example 152 | | | | 0.70 | 2.36 | 0% 10 mg/kg IV | | |
| Example 153 | | | | | | | | |
| Example 154 | | | | | | | | |

TABLE 5-continued

Sarcosine Derivatives

| Sarcosine Derivatives | δ | μ | κ | MVD (nM) | GPI (nM) | Seiz. | UI | Anti-nociception in tail-pinch assay |
|---|---|---|---|---|---|---|---|---|

Example 155

Example 156

Example 157

Example 158

TABLE 5-continued

Sarcosine Derivatives

| Sarcosine Derivatives | δ | μ | κ | MVD (nM) | GPI (nM) | Seiz. | UI | Anti-nociception in tail-pinch assay |
|---|---|---|---|---|---|---|---|---|

Example 159

Example 160

TABLE 6

2-(Ethylamino)ethanol Derivatives

| 2-(Ethylamino)ethanol Derivative | δ | μ | κ | MVD (nM) | GPI (nM) | Seiz. | UI | Anti-nociception in tail-pinch assay |
|---|---|---|---|---|---|---|---|---|

Example 164

TABLE 6-continued 2-(Ethylamino)ethanol Derivatives

| 2-(Ethylamino)ethanol Derivative | δ | μ | κ | MVD (nM) | GPI (nM) | Seiz. | UI | Anti-nociception in tail-pinch assay |
|---|---|---|---|---|---|---|---|---|
| Example 167 | | | | | | | | |

The invention claimed is:

1. A compound of the formula

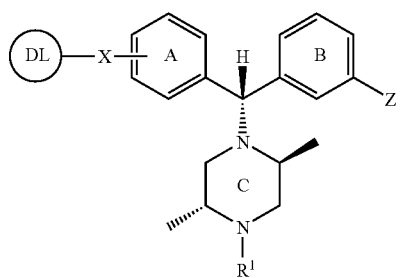

wherein:
Z is H, O(CH$_2$)nCH$_3$, wherein n=0 to 4, or OH;
X is —C=O which is on the meta or para position of the phenyl ring;
DL is a group having a nitrogen that is covalently bonded to the carbon atom of group X;
R$^1$ is C$_1$-C$_6$ alkyl, C$_1$-C$_6$ alkenyl, C$_1$-C$_6$ cycloalkylmethyl, arylalkyl having C$_5$-C$_{10}$ aryl and C$_1$-C$_6$ alkyl moieties, halobenzyl or carboxybenzyl; and wherein the DL is selected from the group consisting of:

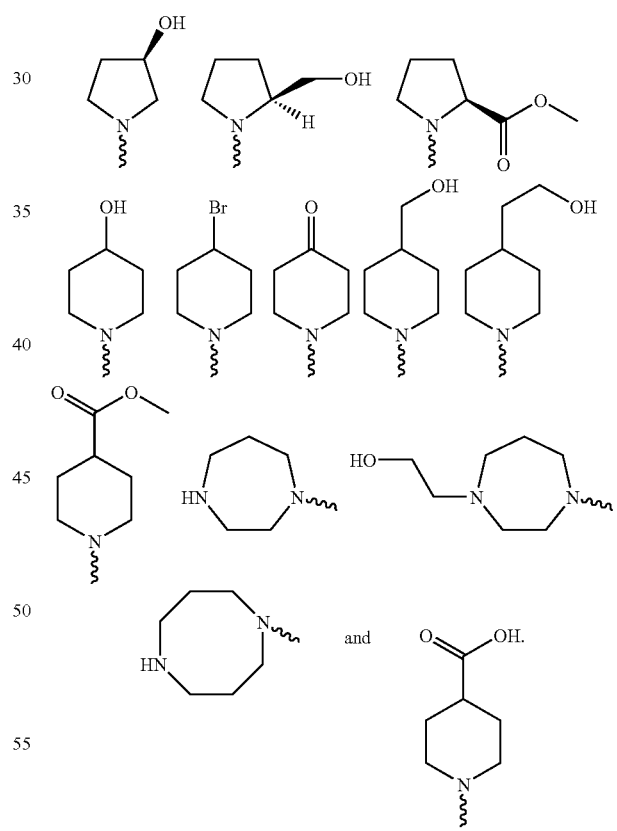

* * * * *